US011248047B2

(12) United States Patent
Morsey et al.

(10) Patent No.: US 11,248,047 B2
(45) Date of Patent: *Feb. 15, 2022

(54) CANINIZED ANTIBODIES

(71) Applicant: Intervet Inc., Madison, NJ (US)

(72) Inventors: Mohamad Morsey, Omaha, NE (US); Yuanzheng Zhang, Edison, NJ (US); Ian Tarpey, St. Ives (GB)

(73) Assignee: Intervet Inc., Summit, NJ (US)

( * ) Notice: Subject to any disclaimer, the term of this patent is extended or adjusted under 35 U.S.C. 154(b) by 221 days.

This patent is subject to a terminal disclaimer.

(21) Appl. No.: 16/130,578

(22) Filed: Sep. 13, 2018

(65) Prior Publication Data

US 2019/0002562 A1   Jan. 3, 2019

Related U.S. Application Data

(62) Division of application No. 15/105,211, filed as application No. PCT/EP2014/078653 on Dec. 19, 2014, now Pat. No. 10,106,607.

(60) Provisional application No. 62/030,812, filed on Jul. 30, 2014, provisional application No. 61/918,847, filed on Dec. 20, 2013, provisional application No. 61/918,946, filed on Dec. 20, 2013.

(51) Int. Cl.
| | |
|---|---|
| *C07K 16/28* | (2006.01) |
| *A61K 39/00* | (2006.01) |
| *A61P 37/04* | (2006.01) |
| *A61K 39/395* | (2006.01) |

(52) U.S. Cl.
CPC .......... *C07K 16/2803* (2013.01); *A61K 39/00* (2013.01); *A61K 39/3955* (2013.01); *A61P 37/04* (2018.01); *C07K 16/2818* (2013.01); *C07K 16/2896* (2013.01); *A61K 2039/55516* (2013.01); *C07K 2317/24* (2013.01); *C07K 2317/34* (2013.01); *C07K 2317/52* (2013.01); *C07K 2317/565* (2013.01); *C07K 2317/76* (2013.01); *C07K 2317/92* (2013.01)

(58) Field of Classification Search
CPC .................. C07K 2317/52; C07K 2317/24
See application file for complete search history.

(56) References Cited

U.S. PATENT DOCUMENTS

| | | | |
|---|---|---|---|
| 6,005,079 A | 12/1999 | Casterman et al. | |
| 6,703,360 B2 | 3/2004 | McCall et al. | |
| 6,808,710 B1 | 10/2004 | Wood et al. | |
| 6,936,704 B1 | 8/2005 | Freeman et al. | |
| 7,038,013 B2 | 5/2006 | Freeman et al. | |
| 7,101,550 B2 | 9/2006 | Wood et al. | |
| 7,105,328 B2 | 9/2006 | Wood et al. | |
| 7,261,890 B2 | 8/2007 | Krah, III et al. | |
| 7,432,059 B2 | 10/2008 | Freeman et al. | |
| 7,595,048 B2 | 9/2009 | Honjo et al. | |
| 7,635,757 B2 | 12/2009 | Freeman et al. | |
| 7,638,492 B2 | 12/2009 | Wood et al. | |
| 7,700,301 B2 | 4/2010 | Wood et al. | |
| 7,709,214 B2 | 5/2010 | Freeman et al. | |
| 7,722,868 B2 | 5/2010 | Freeman et al. | |
| 7,807,158 B2 | 10/2010 | Endl et al. | |
| 8,008,449 B2 | 8/2011 | Korman et al. | |
| 8,337,842 B2 | 12/2012 | Hansen | |
| 8,354,509 B2 | 1/2013 | Carven et al. | |
| 8,569,460 B2 | 10/2013 | Hansen | |
| 8,652,470 B2 | 2/2014 | Hansen | |
| 8,735,553 B1 | 5/2014 | Li et al. | |
| 9,067,999 B1 | 6/2015 | Honjo et al. | |
| 9,580,496 B2 | 2/2017 | Gearing | |
| 9,616,120 B2 | 4/2017 | Hansen | |
| 9,790,280 B2 | 10/2017 | Rue et al. | |
| 9,944,704 B2* | 4/2018 | Morsey | A61K 39/3955 |
| 10,550,194 B2* | 2/2020 | Morsey | A61K 39/00 |
| 2002/0165135 A1 | 11/2002 | McCall et al. | |
| 2007/0003546 A1 | 1/2007 | Lazar et al. | |
| 2007/0148164 A1 | 6/2007 | Farrington et al. | |
| 2010/0203056 A1 | 8/2010 | Irving | |
| 2010/0266617 A1 | 10/2010 | Carven et al. | |
| 2011/0318373 A1 | 12/2011 | Sasikumar et al. | |
| 2012/0039906 A1 | 2/2012 | Olive | |
| 2012/0237522 A1 | 9/2012 | Kang | |
| 2016/0311902 A1 | 10/2016 | Morsey et al. | |
| 2016/0333096 A1 | 11/2016 | Morsey et al. | |

FOREIGN PATENT DOCUMENTS

| | | |
|---|---|---|
| EP | 1537878 B1 | 6/2005 |
| EP | 1836226 B1 | 6/2011 |
| EP | 2705057 B1 | 3/2016 |
| JP | 2014140982 | 1/2016 |
| RU | 2402569 C2 | 10/2010 |

(Continued)

OTHER PUBLICATIONS

Al-Lazikani, Standard Conformations for the Canonical Structures of Immunoglobulins, J. Mol. Biol., 1997, 927-948, 273.

Alegre, A non-activating "humanized" anti-CD3 monoclonal antibody retains immunosuppressive properties in vivo, Transplantation, 1994, 1537-1543, 57.

Amgen vs. Sanofi and Regeneron, Case 17-1480, Document 176, filed Feb. 6, 2018, United States Court of Appeals for the Federal Circuit, Response to Petition for Rehearing En Banc, 27 pages.

Atherton, MJ et al., Cancer immunology and canine malignant melanoma: A comparative review, Veterinary Immunology and Immunopathology, 2016, pp. 15-26, 169.

Barber et al., Restoring function in exhausted CD8 T cells during chronic viral infection, Nature, 2006, pp. 682-687, vol. 439.

(Continued)

*Primary Examiner* — Hong Sang
(74) *Attorney, Agent, or Firm* — Michael D. Davis

(57) ABSTRACT

The present invention discloses caninized antibodies with specific properties. The present invention also discloses caninized murine antibodies against canine PD-1 that have a high binding affinity for canine PD-1. The invention further discloses the use of the caninized antibodies of the present invention in the treatment of cancer in dogs.

16 Claims, 9 Drawing Sheets

Specification includes a Sequence Listing.

(56) References Cited

FOREIGN PATENT DOCUMENTS

| | | |
|---|---|---|
| WO | 9404678 A1 | 3/1994 |
| WO | 9425591 A1 | 11/1994 |
| WO | 1999051642 A1 | 10/1999 |
| WO | 2003042402 A2 | 5/2003 |
| WO | 2004004771 A1 | 1/2004 |
| WO | 2005090407 A1 | 9/2005 |
| WO | 2008083174 A2 | 7/2008 |
| WO | 2008156712 A1 | 12/2008 |
| WO | 2010027488 A2 | 3/2010 |
| WO | 2010077634 A1 | 7/2010 |
| WO | 2010110838 A2 | 9/2010 |
| WO | 2010117448 A2 | 10/2010 |
| WO | 2010117760 A2 | 10/2010 |
| WO | 2012135408 A1 | 10/2012 |
| WO | 2012153121 A1 | 11/2012 |
| WO | 2012153122 A1 | 11/2012 |
| WO | 2012153123 A1 | 11/2012 |
| WO | 2012153126 A1 | 11/2012 |
| WO | 2012158126 A1 | 11/2012 |
| WO | 2013030568 A1 | 3/2013 |
| WO | 2013034900 A1 | 3/2013 |
| WO | 2013054127 A1 | 4/2013 |
| WO | 2013063186 A2 | 5/2013 |
| WO | 2013124666 A1 | 8/2013 |
| WO | 2015091911 A2 | 6/2015 |
| WO | 2015091914 A2 | 6/2015 |
| WO | 2016006241 A1 | 1/2016 |

OTHER PUBLICATIONS

Baudino et al., Crucial Role of aspartic acid at position 265 in the CH2 domain for muri e IgG2a and IgG2b Fc-assiciated effector functions, J. Immunology, 2008, pp. 6664-6669, vol. 181.

Bendig, Mary E., humanization of Rodent Monoclonal Antibodies by CDR Grafting, Methods: A companion to methods in Enzymology, 1993, 83-93, 8.

Bergeron et al., Comparative functional characterization of canine IgG subclasses, Veterinary Immunology and Immunopathology, 2014, pp. 31-41, 157, WO.

Berglund, L et al., The epitope space of the human proteome, Protein Science, 2008, pp. 606-613, 17.

Brown, Blockade of Programmed Death-1 Ligands on Dendritic Cells Enhances T Cell Activation and Cytokine Production, J. Immunol., 2003, pp. 1257-1266, vol. 170.

Chan et al., Therapeutic antibodies for autoimmunity and inflammation, The Journal of Immunology, 2010, pp. 301-316, 10-5, WO.

Chothia et al, Canonical Structures for the Hypervariable Regions of Immunoglobins, J. Mol. Biol., 1987, 901-917, 196.

Chothia et al., Conformations of immunoglobin hypervariable regions, Nature, 1989, 877-883, 342.

Cobbold, et al., The immunology of companion animals: reagents and therapeutic strategies with potential veterinary and human clinical applications, Immunology Today, 1994, pp. 347-353, 15-8.

Colman, Effects of amino acid sequence changes on antibody-antigen interactions, Research Immunology, 1994, 33-36, 145.

Dong et al., Tumor-associated B7-H1 promotes T-cell apoptosis: A potential mechanism of immune evasion, Nature Medicine, 2002, pp. 793-800, vol. 8(8).

Dorai, H et al., Aglycosylated chimeric mouse/human IgG1 antibody retains some effector function, Hybridoma, 1991, pp. 211-217, 10(2).

Esch, et al., Programmed Death 1-Mediated T Cell Exhaustion during Visceral Leishmaniasis Impairs Phagocyte Functioni, The Journal of Immunology, 2013, pp. 5542-5550, 191, WO.

Gearing, DP et al., A fully caninised anti-NGF monoclonal antibody for pain relief in dogs, BMC Veterinary Research, 2013, pp. 1-11, vol. 9 (226), WO.

Geczy, T et. al., Molecular basis for failure of "Atypical" C1 domain of Vav1 to bind diacylglycerol/phorbol ester, The Journal of Biological Chemistry, 2012, pp. 13137-13158, 287(16).

Hutchins, Improved bio distribution, tumor targeting and reduced immunogenicity in mice with a gamma 4 variant of CAMPATH-1H, Proc. Natl. Acad. Sci. USA, 1995, pp. 11980-11984, 92.

Ikebuchi et al., Blockade of bovine PD-1 increases T cell funtion and inhibits bovine leukemia virus expression in B cells in vitro, Veterinary Research, 2013, 1-15, 44-59.

International Search Report for PCT/EP2014/078653 dated Jun. 15, 2015, 20 pages.

International Search Report for PCT/EP2014/078653 dated Jul. 6, 2015, 8 pages.

International Search Report for PCT/EP2014/078655 dated Aug. 13, 2015, 14 pages.

International Search report for PCT/EP2014/078665 dated Jul. 23, 2015, 20 pages.

Iwai, Involvement of PD-L1 on tumor cells in the escape from host immune system and tumor immunotherapy by PD-L1 blockade, Proc. Natl. Acad. Sci. USA, 2002, pp. 12293-12297, vol. 99.

Jackson, et al., In Vitro Antibody Maturation, Improvement of a High Affinity, Neutralizing Antibody Against IL-1Beta, The Journal of Immunology, 1995, pp. 3310-3319, 154, WO.

Kabat, The Structural Basis of Antibody Complementarity, Adv. Prot. Chem., 1978, 1-75, 32.

Kabat, Unusual Distributions of Amino Acids in Complementarity-determining (Hypervriable) Segment of Heavy and Light Chains of Immunoglobulins and Their Possible Roles in Specificity of Antibody-combining Sites, J. Biol. Chem., 1977, 6609-6616, 252.

Khantasup, K et al., Design and generation of humanized single-chain Fv derived from mouse hybridoma for potential targeting application, Monoclonal antibodies, 2015, pp. 404-417, 34(6).

Lin, The PD-1/PD-L1 complex resembles the antigen-binding Fv domains of antibodies and T cell receptors, Proc. Natl. Acad. Sci. USA, 2008, pp. 3011-3016, vol. 105.

Lund et al., J. Immunol., J. Immunol., 1996, pp. 4963-4969, 157.

Lyford-Pike, et al., Evidence for a Role of the PD-1:PD-L1 Pathway in Immune Resistance of HPV-Associated Head and Neck Squamous Cell Carcinoma, Cancer Research, 2012, pp. 1733-1741, 73-6, WO.

McDermott, et al., PD-1 as a potential target in cancer therapy, Cancer Medicine, 2013, pp. 662-673, WO.

McEarchern, Engineered anti-CD70 antibody with multiple effector functions exhibits in vitro and in vivo antitumor activities, Blood, 2007, 1185-1192, 109.

Mimura, Y et al., Glycosylation engineering of therapeutic IgG antibodies: challenges for the safety, functionality and efficacy, Protein Cell, 2018, pp. 47-62, 9(1).

Muyldermans, Recognition of antigens by single-domain antibody fragments: the superfluous luxury of paired domains, Trends Biochem. Sci., 2001, 230-235, 26.

National Service Foundation Award Abstract #1262435, ABI Innovation: Predicting the combined impact of multiple mutations on protein functional adaptation, 2012, 2 pages.

NCBI Reference Sequence: XP_543338.3, Sep. 24, 2013, XP055179334, retrieved from Internet: URL:http://www.ncbi.nlm.nih.gov/protein/XP_543338.

Nomi et al., Clinical Significance and Therapeutic Potential of the Programmed Death-1 Ligand/Programmed Death-1 Pathway in Human Pancreatic Cancer, Clinical Cancer Research, 2007, pp. 2151-2157, vol. 13.

Okazaki, PD-1 and PD-1 ligands: from discovery to clinical application, Int. Immunol., 2007, pp. 813-824, vol. 19.

Paul, WE, Fundamental Immunology, Fundamental Immunolgy, third edition, 1993, 292-295, Third Edition.

Reichmann, Single domain antibodies: comparison of camel VH and camelised human VH domains, J. Immunol. Methods, 1999, 25-38, 231.

Roguin, LP et al., Monoclonal antibodies inducing conformational changes on the antigen molecule, Scandinaavian Journal of Immunology, 2003, pp. 387-394, 58.

Rudikoff, S et al., Single amino acid substitution altering antigen-binding specificity, PNAS, 1982, pp. 1979-1983, 79.

Sazinsky, Aglycosylated immunoglobin G1 variants productively engage activating Fc receptors, Proc. Natl. Acad. Sci., 2008, 20167-20172, 105.

(56) References Cited

OTHER PUBLICATIONS

Shields, High Resolution Mapping of the Binding Site on Human IgG1 for FcyRI, FcyRII, FcyRIII, and FcRn and Design of IgG1 Variants with Improved Binding to the FeyR, J. of Biol. Chem., 2001, 6591-6604, 276-9.

Strome et al., B7-H1 Blockade Augments Adoptive T-Cell Immunotherapy for Squamous Cell Cancinoma, Cancer Research, 2003, pp. 6501-6505, vol. 63.

Tang et al., Cloning and characterization of cDNAs encoding four different canine immunoglobulin Y chains, Veterinary Immunology and Immunopathology, 2001, pp. 259-270, 80.

Tao, MH et al., Role of carbohydrate in the structure and effector functions mediated by the human IgG constant region, The Journal of Immunology, 1989, pp. 2595-2601, 143(8).

Thompson et al., PD-1 Is Expressed by Tumor-Infiltrating Immune Cells and Is Associated with Poor Outcome for Patients with Renal Cell Carcinoma, Clinical Cancer Research, 2007, pp. 1757-1761, vol. 15.

Thompson et al., Tumor B7-H1 Is Associated with Poor Prognosis in Renal Cell Carcinoma Patients with Long-Term Follow-up, Cancer Res., 2006, pp. 3381-3385, vol. 66.

Tsushima et al., Predominant expression of B7-H1 and its immunoregulatory roles in oral squamous cell carcinoma, Oral Oncol., 2006, pp. 268-274, vol. 42.

Tzartos, SJ, Epitope mapping by antibody competition, Methods in Molecular Biology, 1996, pp. 55-66, 66.

Wintterle et al., Expression of the B7-Related Molecule B7-H1 by Glioma Cells: A Potential Mechanism of Immune Paralysis, Cancer Res., 2003, pp. 7462-7467, vol. 63.

Wong, et al., Structural Requirements for a Specificity Switch and for Maintenance of Affinity Using Mutational Analysis of a Phage-Displayed Anti-Arsonate Antibody of Fab Heavy Chain First Complementarity-Determining Region, Journal of Immunology, 1998, pp. 5990-5997, 160, WO.

Zhang et al., Structural and Functional Analysis of the Costimulatory Receptor Programmed Death-1, Immunity, 2004, pp. 337-347, vol. 20.

Diamond, B et al., Somatic mutation of the T15 heavy chain gives rise to an antibody with autoantibody specificity, Proc. Natl. Acad., 1984, pp. 5841-5844, 81.

Folkl, A et al, Feline programmed death and its ligand: Characterization and changes with feline immunodeficiency virus infection, Veterinary Immunology and Immunopathology, 2010, 107-114, 134.

Ohno, S et al., Antigen-binding specificities of antibodies are primarily determined by seven residues of Vh, Proc. Natl. Acad., 1985, pp. 2945-2949, 82.

Roit, A et al., Immunology, Mir, 2000, pp. 9, 110, Translation from English.

Translation of Roit A, et al., Immunology, translation from English, Mir, 2000, pp. 9, 110, 5 pages.

Translation of Yarlin, AA et al., Immunology Principles, Medicine, 1999, pp. 172-174, 5 pages.

Translation of Yarlin, AA, Immunology Principles, Medicine, 1999, pp. 354-358, 8 pages.

Translation of Yeger, L, Clinical Immunology and allergology, Translation from German, Medicine, in three volumes, 1990, vol. 2, pp. 484-485, 5 pages.

Yarlin, AA, Immunology Principles, Medicine, 1999, pp. 172-174.

Yarlin, AA, Immunology Principles, Medicine, 1999, pp. 354-358.

Yeger, L, Clinical Immunology and allergology, Medicine, 1990, pp. 484-485, vol. 2.

Gong, Qian et al., Importance of Cellular Microenvironment and Circulatory Dynamics in B Cell Immunotherapy, The Journal of Immunology, 2005, 817-826, 174.

Lee, Chingwei V. et al., Synthetic anti-BR3 antibodies that mimic BAFF binding and target both human and murine B cells, Blood, 2006, 3103-3111, 108(9).

Miyakawa, Shin et al., Structural and molecular basis for hyperspecificity of RNA aptamer to human immunoglobulin G, RNA, 2008, 1154-1163, 14.

Qing, Jing et al., Antibody-based targeting of FGFR3 in bladder carcinoma and t(4;14)-positive multiple myeloma in mice, The Journal of Clinical Investigation, 2009, 1216-1229, 119(5).

Lux et al, Impact of Immune Complex Size and Glycosylation on IgG Binding to Human Fc gamma Rs, Journal of Immunology, 2013, 4315-4323, 190.

* cited by examiner

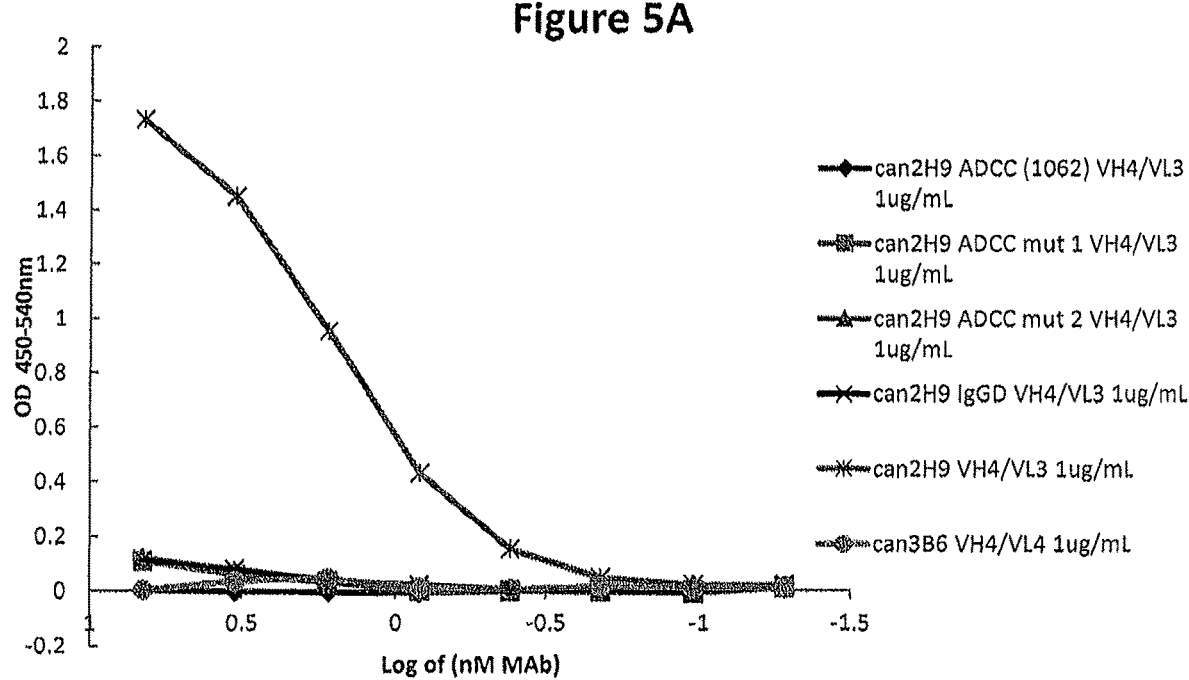

CANINIZED ANTIBODIES

CROSS-REFERENCE TO RELATED APPLICATIONS

This application is a Divisional of U.S. Ser. No. 15/105,211, filled on Jun. 16, 2016, which is a national stage entry under 35 U.S.C. § 371 of PCT/EP2014/078653, filed on Dec. 19, 2014, which claims priority to U.S. Provisional Application No. 62/030,812, filed on Jul. 30, 2014, U.S. Provisional Application No. 61/918,847, filed on Dec. 20, 2013, and U.S. Provisional Application No. 61/918,946, filed on Dec. 20, 2013. The contents of all of which are hereby incorporated by reference in their entireties.

FIELD OF THE INVENTION

The present invention relates to caninized antibodies with specific properties. The present invention also relates to caninized antibodies against canine PD-1 that have specific sequences and a high binding affinity for canine PD-1. The invention further relates to use of the antibodies of the present invention in the treatment of dogs, including cancer treatment.

BACKGROUND OF THE INVENTION

Canine antibodies (also referred to as immunoglobulin G or IgG) are large tetrameric proteins of about 150 Kd. Each IgG protein is composed of two identical light chains of about 25 Kd each, and two identical heavy chains of about 50 Kd each. There are four known IgG heavy chain sub-classes of canine IgG and they are referred to as IgGA, IgGB, IgGC, and IgGD. There are two types of light chains; kappa and lambda chains. Each of the kappa or lambda light chains is composed of one variable domain (VL) and one constant domain (CL). Each of the two heavy chains consists of one variable domain (VH) and three constant domains referred to as CH-1, CH-2, and CH-3. The CH-1 domain is connected to the CH-2 domain via an amino acid sequence referred to as the "hinge" or alternatively as the "hinge region". In humans, IgG exists in one of four subclasses referred to as IgG1, IgG2, IgG3, and IgG4. The subclass of IgG is determined largely by the sequence of the hinge region, which differs among the four subclasses of IgG. The two heavy chains are linked to each other by disulfide bonds and each heavy chain is linked to one of the light chains also through a disulfide bond.

Digestion of IgG antibodies with the enzyme papain breaks the antibody molecule in the hinge region and results in the formation of three fragments. Two of these fragments are identical and each consists of the light chain held together with the VH and CH1 domains of the heavy chain. These fragments are called the "Fab" fragments and they contain the antigen binding sites of the antibody. The third fragment that results from digestion with papain is called the "Fc" and it contains the remainder of the two heavy chains held together by disulfide bonds. The Fc thus contains a dimer consisting of the CH2 and CH3 domain of each of the two heavy chains. While the Fab enables the antibody to bind to its cognate epitope, the Fc enables the antibody to mediate immune effector functions such as antibody dependent cellular cytotoxicity (ADCC), antibody-dependent phagocytosis (ADCP) and complement dependent cytotoxicity (CDC).

It is well known in the art that IgG antibodies mediate effector functions such as ADCC and ADCP through binding of their Fc portion to a family of proteins known as $Fc_\gamma$ receptors, whereas CDC is mediated through the binding of the Fc to the first component of complement, C1q. It is also well known in the art that different IgG sub-classes differ in their capacity to mediate these effector functions. For example, human IgG1 displays strong ADCC and CDC, whereas IgG4 displays a weak to no ADCC and CDC. In addition, methods for identification of which IgG sub-classes display or lack effector functions are well known in the art.

Approaches that rely on use of monoclonal antibodies for therapeutic purposes require the design of fit-for-purpose antibodies or antibody fragments to achieve the desired therapeutic response. For example, some therapeutic approaches for cancer require the therapeutic antibodies to have enhanced effector functions, while others require the effector functions to be significantly reduced or eliminated altogether. Enhancement or elimination of effector functions may be achieved through introduction of one or more amino acid mutations (substitutions) in the Fc portion of the antibody so as to enhance or reduce binding to $Fc_\gamma$ receptors and the first component of complement. There are numerous reports in the prior art describing amino acid substitutions that may be introduced into an antibody molecule in order to modulate its effector functions. For example, Shields et al., [*J. of Biol. Chem.*, 276 (9): 6591-6604 (2001)] disclosed that an asparagine to alanine (N297A) substitution, which result in a non-glycosylated antibody, significantly reduced antibody binding to several $Fc_\gamma$ receptors. Additionally, Shields et al., disclosed that an aspartic acid-to-alanine (D265A) substitution also significantly reduced binding of the antibody to $Fc_\gamma$ receptors. Each of the N297A and D265A substitutions were also shown to significantly impair CDC. There are other similar reports identifying potential substitutions to reduce or eliminate effector function in antibodies [e.g., Sazinsky et al., *Proc.Nat.Acad.Sci.*,105:20167-20172 (2008), Alegre et al., *Transplantation*, 57:1537-1543 (1994), Hutchins et al., *Proc.Nat.Acad.Sci.* 92:11980-11984 (1994), McEarchem et al., *Blood*, 109:1185-1192 (2007)].

An immunoinhibitory receptor that is primarily expressed on activated T and B cells, Programmed Cell Death Receptor 1, also referred to as Programmed Death Receptor 1 (PD-1), is a member of the immunoglobulin superfamily related to CD28 and CTLA-4. PD-1 and like family members are type I transmembrane glycoproteins containing an extracellular Ig Variable-type (V-type) domain that binds its ligands and a cytoplasmic tail that binds signaling molecules. The cytoplasmic tail of PD-1 contains two tyrosine-based signaling motifs, an ITIM (immunoreceptor tyrosine-based inhibition motif) and an ITSM (immunoreceptor tyrosine-based switch motif).

PD-1 attenuates T-cell responses when bound to Programmed Cell Death Ligand 1, also referred to as Programmed Death Ligand 1 (PD-L1), and/or Programmed Cell Death Ligand 2, also referred to as Programmed Death Ligand 2 (PD-L2). The binding of either of these ligands to PD-1 negatively regulates antigen receptor signaling. Blocking the binding of PD-L1 to PD-1 enhances tumor-specific $CD8^+$ T-cell immunity, while aiding the clearance of tumor cells by the immune system. The three-dimensional structure of murine PD-1, as well as the co-crystal structure of mouse PD-1 with human PD-L1 have been reported [Zhang et al., *Immunity* 20: 337-347 (2004); Lin et al., *Proc. Natl. Acad. Sci. USA* 105: 3011-3016 (2008)].

PD-L1 and PD-L2 are type I transmembrane ligands that contain both IgV- and IgC-like domains in the extracellular region along with short cytoplasmic regions with no known signaling motifs. Both PD-L1 and PD-L2 are either constitutively expressed or can be induced in a variety of cell types, including non-hematopoietic tissues as well as various tumor types. PD-L1 is not only expressed on B, T, myeloid and dendritic cells (DCs), but also on peripheral cells, such as microvascular endothelial cells and non-lymphoid organs e.g., heart or lung. In contrast, PD-L2 is only found on macrophages and DCs. The expression pattern of PD-1 ligands suggests that PD-1 plays a role in maintaining peripheral tolerance and may further serve to regulate self-reactive T- and B-cell responses in the periphery.

In any case, it is now abundantly clear that PD-1 plays a critical role in at least certain human cancers, presumably by mediating immune evasion. Accordingly, PD-L1 has been shown to be expressed on a number of mouse and human tumors and is inducible by IFN-γ in the majority of PD-L1 negative tumor cell lines [Iwai et al., *Proc. Natl. Acad. Sci. USA*. 99: 12293-12297 (2002); Strome et al., *Cancer Res.*, 63: 6501-6505 (2003)]. Furthermore, the expression of PD-1 on tumor infiltrating lymphocytes and/or PD-L1 on tumor cells has been identified in a number of primary human tumor biopsies. Such tumor tissues include cancers of the lung, liver, ovary, cervix, skin, colon, glioma, bladder, breast, kidney, esophagus, stomach, oral squamous cell, urothelial cell, and pancreas, as well as tumors of the head and neck [Brown et al., *J. Immunol.* 170: 1257-1266 (2003); Dong et al., *Nat. Med.* 8: 793-800 (2002); Wintterle et al., *Cancer Res.* 63: 7462-7467 (2003); Strome et al., *Cancer Res.*, 63: 6501-6505 (2003); Thompson et al., *Cancer Res.* 66: 3381-5 (2006); Thompson et al., *Clin. Cancer Res.* 13: 1757-1761 (2007); Nomi et al., *Clin.Cancer Res.* 13: 2151-2157. (2007)]. More strikingly, PD-ligand expression on tumor cells has been correlated to poor prognosis of human cancer patients across multiple tumor types [reviewed in Okazaki and Honjo, *Int. Immunol.* 19: 813-824 (2007)].

Moreover, Nomi et al. [*Clin. Cancer Res.* 13: 2151-2157 (2007)] demonstrated the therapeutic efficacy of blocking the binding of PD-L1 to PD-1 in a murine model of aggressive pancreatic cancer through administering either PD-1 or PD-L1 directed antibody. These antibodies effectively promoted tumor reactive CD8+ T cell infiltration into the tumor resulting in the up-regulation of anti-tumor effectors including IFN-γ, granzyme B, and perforin. Similarly, the use of antibodies to block the binding of PD-L1 and PD-1 significantly inhibited tumor growth in a model of mouse squamous cell carcinoma [Tsushima et al., *Oral Oncol.* 42: 268-274 (2006)].

In other studies, transfection of a murine mastocytoma line with PD-L1 led to decreased lysis of the tumor cells when co-cultured with a tumor-specific CTL clone. Lysis was restored when anti-PD-L1 monoclonal antibody was added [Iwai et al., *Proc. Natl. Acad. Sci. U.S.A.* 99: 12293-12297 (2002)]. In vivo, blocking the PD1/PD-L1 interaction was shown to increase the efficacy of adoptive T cell transfer therapy in a mouse tumor model [Strome et al., *Cancer Res.* 63: 6501-6505 (2003)]. Further evidence for the role of PD-1 in cancer treatment comes from experiments performed with PD-1 knockout mice in which PD-L1 expressing myeloma cells grew only in wild-type animals (resulting in tumor growth and associated animal death), but not in PD-1 deficient mice [Iwai Y. et al., *Proc. Natl. Acad. Sci. U.S.A.* 99: 12293-12297 (2002)]. More recently, antibodies against PD-1 (including humanized murine monoclonal antibodies against human PD-1) have shown at least initial success in cancer therapy in humans [see e.g., U.S. Pat. No. 8,354,509 B2, U.S. Pat. No. 8,008,449 B2, and U.S. Pat. No. 7,595,048 B2].

Anti-PD-1 antibodies may also be useful in chronic viral infection. Memory CD8+ T cells generated after an acute viral infection are highly functional and constitute an important component of protective immunity. In contrast, chronic infections are often characterized by varying degrees of functional impairment (exhaustion) of virus-specific T-cell responses, and this defect is a principal reason for the inability of the host to eliminate the persisting pathogen. Although functional effector T cells are initially generated during the early stages of infection, they gradually lose function during the course of a chronic infection. Barber et al. [*Nature* 439: 682-687 (2006)] showed that mice infected with a laboratory strain of LCMV developed chronic infection resulted in high levels of virus in the blood and other tissues. These mice initially developed a robust T cell response, but eventually succumbed to the infection upon T cell exhaustion. Barber et al. found that the decline in number and function of the effector T cells in chronically infected mice could be reversed by injecting an antibody that blocked the interaction between PD-1 and PD-L1.

The citation of any reference herein should not be construed as an admission that such reference is available as "prior art" to the instant application.

SUMMARY OF THE INVENTION

The present invention provides a canine fragment crystallizable region (cFc region) of an antibody in which the cFc has been genetically modified to augment, decrease, or eliminate one or more effector functions. In one aspect of the present invention, the genetically modified cFc decreases or eliminates one or more effector functions. In another aspect of the invention the genetically modified cFc augments one or more effector function.

In certain embodiments, the genetically modified cFc region is a genetically modified canine IgGB Fc region. In another such embodiment, the genetically modified cFc region is a genetically modified canine IgGC Fc region. In a particular embodiment the effector function is antibody-dependent cytotoxicity (ADCC) that is augmented, decreased, or eliminated. In another embodiment the effector function is complement-dependent cytotoxicity (CDC) that is augmented, decreased, or eliminated. In yet another embodiment, the cFc region has been genetically modified to augment, decrease, or eliminate both the ADCC and the CDC.

The present invention further provides canine frames and/or full length heavy chains that comprise the genetically modified cFc regions. Accordingly, the present invention provides full length heavy chains of antibodies in which the full length heavy chains comprise the genetically modified cFc regions of the present invention. Such full length heavy chains can also be combined with corresponding canine light (kappa or lambda) chains to form a complete antibody. In particular embodiments of this type, the resulting antibody binds to a particular canine antigen with specificity. In certain such embodiments the canine antigen is canine PD-1. In yet other embodiments the canine antigen is canine PD-L1. In still other embodiments, the canine antigen is the IL-4 receptor alpha chain. In yet other embodiments the canine antigen is canine thymic stromal lymphopoietin protein (cTSLP) [see, U.S. Pat. No. 7,718,772 B2, the contents of which are hereby incorporated by reference in their entireties.]

In certain embodiments, the genetically modified cFc region comprises the amino acid sequence of SEQ ID NO: 130 (or SEQ ID NO: 132) in which one to seven of the following amino acid residues are replaced by another amino acid residue at the indicated positions: P4, D31, N63, G64, T65, A93, or P95. The amino acid substituting for P4, D31, N63, G64, T65, A93, and/or P95 are individually selected from one of the other 19 standard naturally occurring amino acids, as listed in Table 1 below. The present invention further provides variants of the genetically modified cFc regions that comprise an amino acid sequence that is 90%, 95%, 98%, or 99% identical to the amino acid sequence of such genetically modified cFc regions and retain at least 50%, 75%, 90%, 95%, or more of the augmentation, decrease, or elimination of the ADCC and/or the CDC as the genetically modified cFc regions comprising the amino acid sequence of SEQ ID NO: 130 (or SEQ ID NO: 132) in which one or more of the following amino acid residues were replaced: i.e., at P4, D31, N63, G64, T65, A93, or P95.

In other embodiments two to five of the following amino acid residues are replaced by another amino acid residue at the indicated positions: P4, D31, N63, G64, T65, A93, or P95. In particular embodiments of this type, the genetically modified cFc region comprises the amino acid sequence of SEQ ID NO: 130 or SEQ ID NO: 132 with the following substitutions: P4A, D31A, N63A, A93G, and P95A. In related embodiments, the genetically modified cFc region comprises the amino acid sequence of SEQ ID NO: 130 or SEQ ID NO: 132 with the following substitutions: P4A, D31A, N63A, and P95A. In other embodiments, the genetically modified cFc region comprises the amino acid sequence of SEQ ID NO: 130 or SEQ ID NO: 132 with substitutions at D31 and N63. In particular embodiments of this type, the aspartic acid residue at position 31 is replaced with a glutamic acid residue, an asparagine residue, or an alanine residue, whereas the asparagine residue at position 63 is replaced with a glutamine residue, a histidine residue, or an alanine residue. In a more particular embodiment of this type, the genetically modified cFc region comprises the amino acid sequence of SEQ ID NO: 130 or SEQ ID NO: 132 with the following substitutions: D31A and N63A. In particular embodiments, the genetically modified cFc region is encoded by the nucleotide sequence of SEQ ID NO: 129 or SEQ ID NO: 131 comprising nucleotide changes that correspond to the amino acid sequences that they encode.

In another embodiments, the genetically modified cFc region comprises the amino acid sequence of SEQ ID NO: 130 or SEQ ID NO: 132 with the substitution at A93. In a particular embodiment of this type, the substitution is A93G. In a related embodiment the the substitution is A93S. As shown below in Example 4, the substitution of A93G leads to an enhancement in complement C1q binding, which is indicative of increasing CDC activity.

In related embodiments the genetically modified cFc region further comprises a hinge region that comprises the amino acid sequence of SEQ ID NO: 109. In other embodiments the genetically modified Fc region further comprises a hinge region that comprises the amino acid sequence of SEQ ID NO: 110. In still other embodiments the genetically modified Fc region further comprises a hinge region that comprises the amino acid sequence of SEQ ID NO: 111. In yet other embodiments the genetically modified Fc region further comprises a genetically modified hinge region that comprises the amino acid sequence of SEQ ID NO: 112.

In alternative embodiments, the present invention provides a canine IgGD Fc region with a genetically modified hinge region from a canine IgGD antibody, a hinge region from a canine IgGA antibody, a hinge region from a canine IgGB antibody, or a hinge region from a canine IgGC antibody. Moreover, the present invention provides full length heavy chains of antibodies in which the full length heavy chains comprise the canine IgGD Fc region of the present invention with a genetically modified hinge region from a canine IgGD antibody, a hinge region from a canine IgGA antibody, a hinge region from a canine IgGB antibody, or a hinge region from a canine IgGC antibody. Such full length heavy chains also can be combined with corresponding canine light (kappa or lambda) chains to form a complete antibody.

Accordingly, the present invention provides a canine IgGD Fc region that further comprises a genetically modified hinge region from a canine IgGD antibody. In particular embodiments of this type the canine IgGD Fc region and genetically modified hinge region comprise the amino acid sequence of SEQ ID NO: 6 or an amino acid sequence that is 90%, 95%, 98%, or 99% identical to the amino acid sequence of SEQ ID NO: 6, which comprises a proline residue at position 10 (P10). In a more particular embodiment the canine IgGD Fc region and genetically modified hinge region is encoded by the nucleotide sequence of SEQ ID NO: 5. In other embodiments, the canine IgGD Fc region further comprises a hinge region from a canine IgGA antibody. In particular embodiments of this type the canine IgGD Fc region and hinge region comprise the amino acid sequence of SEQ ID NO: 8 or an amino acid sequence that is 90%, 95%, 98%, or 99% identical to the amino acid sequence of SEQ ID NO: 8. In a more particular embodiment the canine IgGD Fc region and hinge region is encoded by the nucleotide sequence of SEQ ID NO: 7. In still other embodiments, the canine IgGD Fc region further comprises a hinge region from a canine IgGB antibody. In particular embodiments of this type the canine IgGD Fc region and hinge region comprise the amino acid sequence of SEQ ID NO: 10 or an amino acid sequence that is 90%, 95%, 98%, or 99% identical to the amino acid sequence of SEQ ID NO: 10. In a more particular embodiment the canine IgGD Fc region and hinge region is encoded by the nucleotide sequence of SEQ ID NO: 9. In yet other embodiments, the canine IgGD Fc region further comprises a hinge region from a canine IgGC antibody. In particular embodiments of this type the canine IgGD cFc region and hinge region comprise the amino acid sequence of SEQ ID NO: 12 or an amino acid sequence that is 90%, 95%, 98%, or 99% identical to the amino acid sequence of SEQ ID NO: 12. In a more particular embodiment the canine IgGD cFc region and hinge region is encoded by the nucleotide sequence of SEQ ID NO: 11. The present invention further provides caninized antibodies that comprise these canine IgGD Fc regions and hinge regions. In a particular embodiment the caninized antibody or antigen binding fragment thereof binds canine Programmed Death Receptor 1 (canine PD-1) with specificity.

The present invention therefore provides caninized anti-canine PD-1 antibodies with specificity and/or that have a high binding affinity for canine PD-1. In particular embodiments, the caninized anti-canine PD-1 antibodies also have the ability to block the binding of canine PD-1 to canine PD-L1. In specific embodiments the caninized anti-canine PD-1 antibodies have a high binding affinity to canine PD-1, as well as have the ability to also block the binding of canine PD-1 to canine PD-L2. The caninized antibodies or antigen binding fragments thereof that specifically bind canine PD-1 can comprise a canine IgG heavy chain of the present invention and a canine kappa or lambda light chain. In particular embodiments the caninized anti-canine PD-1 antibodies are caninized murine anti-canine PD-1 antibodies. The present invention also relates to use of such caninized antibodies in the treatment of disease such as cancer and/or those due to infections.

In particular embodiments the caninized anti-canine PD-1 antibody comprises a genetically modified cFc region of the present invention. In alternative embodiments the caninized anti-canine PD-1 antibody comprises the canine IgGD Fc region with a genetically modified hinge region from a canine IgGD antibody, a hinge region from a canine IgGA antibody, a hinge region from a canine IgGB antibody, or a hinge region from a canine IgGC antibody. The present invention further provides such caninized anti-canine PD-1 antibodies comprising the canine frames of the present invention in combination with CDRs obtained from mouse anti-canine PD-1 antibodies, i.e., three light chain CDRs: CDR light 1 (CDRL1), CDR light 2 (CDRL2), and CDR light 3 (CDRL3) and three heavy chain CDRs CDR heavy 1 (CDRH1), CDR heavy 2 (CDRH2) and CDR heavy 3 (CDRH3).

In particular embodiments, the caninized murine anti-canine PD-1 antibodies comprise the genetically modified cFc region of IgGB or IgGC of the present invention or alternatively, the canine IgGD Fc region, together with a genetically modified hinge region from a canine IgGD antibody, a hinge region from a canine IgGA antibody, a hinge region from a canine IgGB antibody, or a hinge region from a canine IgGC antibody in combination with CDRs obtained from mouse anti-canine PD-1 antibodies. Moreover, the present invention not only provides caninized mouse anti-canine PD-1 antibodies with specific CDRs as detailed herein, but further provides caninized mouse anti-canine PD-1 antibodies comprising conservatively modified variants of those CDRs as well as variants that comprise (e.g., share) the same canonical structure.

Accordingly in particular embodiments the caninized anti-canine PD-1 antibody further comprises complementary determining regions (CDRs) in which the CDRs have canonical structures of: H1-1, H2-1, and H3-6, respectively for CDR1, CDR2, and CDR3 of the heavy chain, i.e., CDR1 of the heavy chain has the canonical structure class 1, CDR2 of the heavy chain has the canonical structure class 1, and CDR3 of the heavy chain has the canonical structure class 6. In even more particular embodiments, the CDRs for the corresponding light chains have canonical structures of: L1-3, L2-1, and L3-1, respectively for CDR1, CDR2, and CDR3 of the light chain. In other embodiments the caninized anti-canine PD-1 antibody further comprises complementary determining regions (CDRs) in which the CDRs have canonical structures of: H1-1, H2-1, and H3-11, respectively for CDR1, CDR2, and CDR3 of the heavy chain. In even more particular embodiments of this type, the CDRs for the corresponding light chains have canonical structures of: L1-2A, L2-1, and L3-1, respectively for CDR1, CDR2, and CDR3 of the light chain. In still other embodiments the caninized anti-canine PD-1 antibody further comprises complementary determining regions (CDRs) in which the CDRs have canonical structures of: H1-1, H2-2A, and H3-11, respectively for CDR1, CDR2, and CDR3 of the heavy chain. In even more particular embodiments of this type, the CDRs for the corresponding light chains have canonical structures of: L1-2A, L2-1, and L3-1, respectively for CDR1, CDR2, and CDR3 of the light chain. In yet other embodiments the caninized anti-canine PD-1 antibody further comprises complementary determining regions (CDRs) in which the CDRs have canonical structures of: H1-1, H2-2A, and H3-13, respectively for CDR1, CDR2, and CDR3 of the heavy chain. In even more particular embodiments of this type, the CDRs for the corresponding light chains have canonical structures of: L1-4, L2-1, and L3-1, respectively for CDR1, CDR2, and CDR3 of the light chain.

In more particular embodiments, the caninized antibody of the present invention or antigen binding fragment thereof comprises one or more of the heavy chain complementary determining region 1 (VH CDR1) with an amino acid sequence of SEQ ID NO: 27, SEQ ID NO: 28, SEQ ID NO: 29, or SEQ ID NO: 30. In another embodiment, the heavy chain complementary determining region 2 (VH CDR2) comprises an amino acid sequence of SEQ ID NO: 31, SEQ ID NO: 32, SEQ ID NO: 33, SEQ ID NO: 34, or SEQ ID NO: 35. In still another embodiment the heavy chain complementary determining region 3 (VH CDR3) comprises an amino acid sequence of SEQ ID NO: 36, SEQ ID NO: 37, SEQ ID NO: 38, or SEQ ID NO: 146. In a particular embodiment of this type, the caninized antibody or antigen binding fragment comprises both a VH CDR1 comprising an amino acid sequence of SEQ ID NO: 27, SEQ ID NO: 28, SEQ ID NO: 29, or SEQ ID NO: 30 and a VH CDR2 comprising an amino acid sequence of SEQ ID NO: 31, SEQ ID NO: 32, SEQ ID NO: 33, SEQ ID NO: 34, or SEQ ID NO: 35. In another such embodiment, the caninized antibody or antigen binding fragment comprises both a VH CDR1 comprising an amino acid sequence of SEQ ID NO: 27, SEQ ID NO: 28, SEQ ID NO: 29, or SEQ ID NO: 30 and a VH CDR3 comprising an amino acid sequence of SEQ ID NO: 36, SEQ ID NO: 37, SEQ ID NO: 38, or SEQ ID NO: 146. In yet another such embodiment, the caninized antibody or antigen binding fragment comprises both a VH CDR2 comprising an amino acid sequence of SEQ ID NO: 31, SEQ ID NO: 32, SEQ ID NO: 33, SEQ ID NO: 34, or SEQ ID NO: 35 and a VH CDR3 comprising an amino acid sequence of SEQ ID NO: 36, SEQ ID NO: 37, SEQ ID NO: 38, or SEQ ID NO: 146. In still another such embodiment, the caninized antibody or antigen binding fragment comprises a VH CDR1 comprising an amino acid sequence of SEQ ID NO: 27, SEQ ID NO: 28, SEQ ID NO: 29, or SEQ ID NO: 30, a VH CDR2 comprising an amino acid sequence of SEQ ID NO: 31, SEQ ID NO: 32, SEQ ID NO: 33, SEQ ID NO: 34, or SEQ ID NO: 35, and a VH CDR3 comprising an amino acid sequence of SEQ ID NO: 36, SEQ ID NO: 37, SEQ ID NO: 38, or SEQ ID NO: 146.

In particular embodiments, the caninized antibody or antigen binding fragment also comprises a light chain complementary determining region 1 (VL CDR1) comprising an amino acid sequence of SEQ ID NO: 13, SEQ ID NO: 14, or SEQ ID NO: 15. In related embodiments the light chain complementary determining region 2 (VL CDR2) comprises an amino acid sequence of SEQ ID NO: 16, SEQ ID NO: 17, SEQ ID NO: 18, SEQ ID NO: 19, SEQ ID NO: 20, or SEQ ID NO: 21. In still another embodiment the light chain complementary determining region 3 (VL CDR3) comprises an amino acid sequence of SEQ ID NO: 22, SEQ ID NO: 23, SEQ ID NO: 24, SEQ ID NO: 25, or SEQ ID NO: 26. In a particular embodiment of this type, the caninized antibody or antigen binding fragment comprises both a VL CDR1 comprising an amino acid sequence of SEQ ID NO: 13, SEQ ID NO: 14, or SEQ ID NO: 15 and a VL CDR2 comprising an amino acid sequence of SEQ ID NO: 16, SEQ ID NO: 17, SEQ ID NO: 18, SEQ ID NO: 19, SEQ ID NO: 20, or SEQ ID NO: 21.

In another such embodiment, the caninized antibody or antigen binding fragment comprises both a VL CDR1 comprising an amino acid sequence of SEQ ID NO: 13, SEQ ID NO: 14, or SEQ ID NO: 15 and a VL CDR3 comprising an amino acid sequence of SEQ ID NO: 22, SEQ ID NO: 23, SEQ ID NO: 24, SEQ ID NO: 25, or SEQ ID NO: 26. In yet another such embodiment, the caninized antibody or antigen binding fragment comprises both a VL CDR2 comprising an amino acid sequence of SEQ ID NO: 16, SEQ ID NO: 17, SEQ ID NO: 18, SEQ ID NO: 19, SEQ ID NO: 20, or SEQ ID NO: 21 and a VL CDR3 comprising an amino acid sequence of SEQ ID NO: 22, SEQ ID NO: 23, SEQ ID NO: 24, SEQ ID NO: 25, or SEQ ID NO: 26. In still another such embodiment, the caninized antibody or antigen binding fragment comprises a VL CDR1 comprising an amino acid sequence of SEQ ID NO: 13, SEQ ID NO: 14, or SEQ ID NO: 15, a VL CDR2 comprising an amino acid sequence of SEQ ID NO: 16, SEQ ID NO: 17, SEQ ID NO: 18, SEQ ID NO: 19, SEQ ID NO: 20, or SEQ ID NO: 21, and a VL CDR3 comprising an amino acid sequence of SEQ ID NO: 22, SEQ ID NO: 23, SEQ ID NO: 24, SEQ ID NO: 25, or SEQ ID NO: 26.

The present invention further provides caninized antibodies that comprise the amino acid sequence of SEQ ID NO: 40 or that is 90%, 95%, 98%, or 99% identical to the amino acid sequence of SEQ ID NO: 40, SEQ ID NO: 42 or that is 90%, 95%, 98%, or 99% identical to the amino acid sequence of SEQ ID NO: 42, SEQ ID NO: 44 or that is 90%, 95%, 98%, or 99% identical to the amino acid sequence of SEQ ID NO: 44, SEQ ID NO: 46 or that is 90%, 95%, 98%, or 99% identical to the amino acid sequence of SEQ ID NO: 46, SEQ ID NO: 48 or that is 90%, 95%, 98%, or 99% identical to the amino acid sequence of SEQ ID NO: 48, SEQ ID NO: 50 or that is 90%, 95%, 98%, or 99% identical to the amino acid sequence of SEQ ID NO: 50, SEQ ID NO: 52 or that is 90%, 95%, 98%, or 99% identical to the amino acid sequence of SEQ ID NO: 52, SEQ ID NO: 54 or that is 90%, 95%, 98%, or 99% identical to the amino acid sequence of SEQ ID NO: 54, SEQ ID NO: 56 or that is 90%, 95%, 98%, or 99% identical to the amino acid sequence of SEQ ID NO: 56, SEQ ID NO: 58 or that is 90%, 95%, 98%, or 99% identical to the amino acid sequence of SEQ ID NO: 58, SEQ ID NO: 60 or that is 90%, 95%, 98%, or 99% identical to the amino acid sequence of SEQ ID NO: 60, SEQ ID NO: 62 or that is 90%, 95%, 98%, or 99% identical to the amino acid sequence of SEQ ID NO: 62, SEQ ID NO: 64 or that is 90%, 95%, 98%, or 99% identical to the amino acid sequence of SEQ ID NO: 64, or SEQ ID NO: 66 or that is 90%, 95%, 98%, or 99% identical to the amino acid sequence of SEQ ID NO: 66, or antigen binding fragments of these caninized antibodies.

In particular embodiments, the heavy chain of an antibody comprises the amino acid sequence of SEQ ID NO: 40, 52, 56, or 64 (or 90%, 95%, 98%, or 99% identical to SEQ ID NO: 40, 52, 56, or 64) that comprises (i) P, A, G, or S at position 239, (ii) A, G, or S at position 266, (iii) A, G, or S at position 298, (iv) G, P, or A at position 299, (v) T, A, G, or S at position 300, (vi) A, G, or S at position 328, and (vii) P, A, G, or S at position 330. In other embodiments, the heavy chain of an antibody comprises the amino acid sequence of SEQ ID NO: 42, 54, 58, or 66 (or 90%, 95%, 98%, or 99% identical to SEQ ID NO: 42, 54, 58, or 66) that comprises (i) P, A, G, or S at position 237, (ii) A, G, or S at position 264, (iii) A, G, or S at position 296, (iv) G, P, or A at position 297, (v) T, A, G, or S at position 298, (vi) A, G, or S at position 326, and (vii) P, A, G, or S at position 328. In yet other embodiments, the heavy chain of an antibody comprises the amino acid sequence of SEQ ID NO: 44, 50, or 60 (or 90%, 95%, 98%, or 99% identical to SEQ ID NO: 44, 50, or 60) that comprises (i) P, A, G, or S at position 244, (ii) A, G, or S at position 271, (iii) A, G, or S at position 303, (iv) G, P, or A at position 304, (v) T, A, G, or S at position 305, (vi) A, G, or S at position 333, and (vii) P, A, G, or S at position 335. In still other embodiments, the heavy chain of an antibody comprises the amino acid sequence of SEQ ID NO: 46 or 62 (or 90%, 95%, 98%, or 99% identical to SEQ ID NO: 46 or 62) that comprises (i) P, A, G, or S at position 242, (ii) A, G, or S at position 269, (iii) A, G, or S at position 301, (iv) G, P, or A at position 302, (v) T, A, G, or S at position 303, (vi) A, G, or S at position 331, and (vii) P, A, G, or S at position 333. In yet other embodiments, the heavy chain of an antibody comprises the amino acid sequence of SEQ ID NO: 48 (or 90%, 95%, 98%, or 99% identical to SEQ ID NO: 48) that comprises (i) P, A, G, or S at position 246, (ii) A, G, or S at position 273, (iii) A, G, or S at position 305, (iv) G, P, or A at position 306, (v) T, A, G, or S at position 307, (vi) A, G, or S at position 335, and (vii) P, A, G, or S at position 337.

In still other embodiments, the heavy chain of an antibody comprises the amino acid sequence of SEQ ID NO: 40, 52, 56, or 64 (or 90%, 95%, 98%, or 99% identical to SEQ ID NO: 40, 52, 56, or 64) that comprises (i) P, A, G, or S at position 239, (ii) A at position 266, (iii) A at position 298, (iv) G, P, or A at position 299, (v) T, A, G, or S at position 300, (vi) A, G, or S at position 328, and (vii) P, A, G, or S at position 330. In other embodiments, the heavy chain of an antibody comprises the amino acid sequence of SEQ ID NO: 42, 54, 58, or 66 (or 90%, 95%, 98%, or 99% identical to SEQ ID NO: 42, 54, 58, or 66) that comprises (i) P, A, G, or S at position 237, (ii) A at position 264, (iii) A at position 296, (iv) G, P, or A at position 297, (v) T, A, G, or S at position 298, (vi) A, G, or S at position 326, and (vii) P, A, G, or S at position 328. In yet other embodiments, the heavy chain of an antibody comprises the amino acid sequence of SEQ ID NO: 44, 50, or 60 (or 90%, 95%, 98%, or 99% identical to SEQ ID NO: 44, 50, or 60) that comprises (i) P, A, G, or S at position 244, (ii) A at position 271, (iii) A at position 303, (iv) G, P, or A at position 304, (v) T, A, G, or S at position 305, (vi) A, G, or S at position 333, and (vii) P, A, G, or S at position 335. In still other embodiments, the heavy chain of an antibody comprises the amino acid sequence of SEQ ID NO: 46 or 62 (or 90%, 95%, 98%, or 99% identical to SEQ ID NO: 46 or 62) that comprises (i) P, A, G, or S at position 242, (ii) A at position 269, (iii) A at position 301, (iv) G, P, or A at position 302, (v) T, A, G, or S at position 303, (vi) A, G, or S at position 331, and (vii) P, A, G, or S at position 333. In yet other embodiments, the heavy chain of an antibody comprises the amino acid sequence of SEQ ID NO: 48 (or 90%, 95%, 98%, or 99% identical to SEQ ID NO: 48) that comprises (i) P, A, G, or S at position 246, (ii) A at position 273, (iii) A at position 305, (iv) G, P, or A at position 306, (v) T, A, G, or S at position 307, (vi) A, G, or S at position 335, and (vii) P, A, G, or S at position 337.

In still other embodiments, the heavy chain of an antibody comprises the amino acid sequence of SEQ ID NO: 40, 52, 56, or 64 (or 90%, 95%, 98%, or 99% identical to SEQ ID NO: 40, 52, 56, or 64) that comprises (i) A at position 239, (ii) A at position 266, (iii) A at position 298, (iv) P at position 299, (v) A at position 300, (vi) G, at position 328, and (vii) A, at position 330. In other embodiments, the heavy chain of an antibody comprises the amino acid sequence of SEQ ID NO: 42, 54, 58, or 66 (or 90%, 95%, 98%, or 99% identical to SEQ ID NO: 42, 54, 58, or 66) that comprises (i) A at position 237, (ii) A at position 264, (iii) A at position 296, (iv) P at position 297, (v) A at position 298, (vi) G at position 326, and (vii) A at position 328. In yet other embodiments, the heavy chain of an antibody comprises the amino acid sequence of SEQ ID NO: 44, 50, or 60 (or 90%, 95%, 98%, or 99% identical to SEQ ID NO: 44, 50, or 60) that comprises (i) A at position 244, (ii) A at position 271, (iii) A at position 303, (iv) P at position 304, (v) A at position 305, (vi) G at position 333, and (vii) A at position 335. In still other embodiments, the heavy chain of an antibody comprises the amino acid sequence of SEQ ID NO: 46 or 62 (or 90%, 95%, 98%, or 99% identical to SEQ ID NO: 46 or 62) that comprises (i) A at position 242, (ii) A at position 269, (iii) A at position 301, (iv) P at position 302, (v) A at position 303, (vi) G at position 331, and (vii) A at position 333. In yet other embodiments, the heavy chain of an antibody comprises the amino acid sequence of SEQ ID NO: 48 (or 90%, 95%, 98%, or 99% identical to SEQ ID NO: 48) that comprises (i) A at position 246, (ii) A at position 273, (iii) A at position 305, (iv) P at position 306, (v) A at position 307, (vi) G at position 335, and (vii) A at position 337.

In yet other embodiments, the heavy chain of an antibody comprises the amino acid sequence of SEQ ID NO: 40, 52, 56, or 64 (or 90%, 95%, 98%, or 99% identical to SEQ ID NO: 40, 52, 56, or 64) that comprises (i) P at position 239, (ii) A, G, or S at position 266, (iii) A, G, or S at position 298, (iv) G at position 299, (v) T at position 300, (vi) A at position 328, and (vii) P at position 330. In other embodiments, the heavy chain of an antibody comprises the amino acid sequence of SEQ ID NO: 42, 54, 58, or 66 (or 90%, 95%, 98%, or 99% identical to SEQ ID NO: 42, 54, 58, or 66) that comprises (i) P at position 237, (ii) A, G, or S at position 264, (iii) A, G, or S at position 296, (iv) G at position 297, (v) T at position 298, (vi) A at position 326, and (vii) P at position 328. In yet other embodiments, the heavy chain of an antibody comprises the amino acid sequence of SEQ ID NO: 44, 50, or 60 (or 90%, 95%, 98%, or 99% identical to SEQ ID NO: 44, 50, or 60) that comprises (i) P at position 244, (ii) A, G, or S at position 271, (iii) A, G, or S at position 303, (iv) G at position 304, (v) T at position 305, (vi) A at position 333, and (vii) P at position 335. In still other embodiments, the heavy chain of an antibody comprises the amino acid sequence of SEQ ID NO: 46 or 62 (or 90%, 95%, 98%, or 99% identical to SEQ ID NO: 46 or 62) that comprises (i) P at position 242, (ii) A, G, or S at position 269, (iii) A, G, or S at position 301, (iv) G at position 302, (v) T at position 303, (vi) A at position 331, and (vii) P at position 333. In yet other embodiments, the heavy chain of an antibody comprises the amino acid sequence of SEQ ID NO: 48 (or 90%, 95%, 98%, or 99% identical to SEQ ID NO: 48) that comprises (i) P at position 246, (ii) A, G, or S at position 273, (iii) A, G, or S at position 305, (iv) G at position 306, (v) T at position 307, (vi) A at position 335, and (vii) P at position 337.

In still other embodiments, the heavy chain of an antibody comprises the amino acid sequence of SEQ ID NO: 40, 52, 56, or 64 (or 90%, 95%, 98%, or 99% identical to SEQ ID NO: 40, 52, 56, or 64) that comprises (i) P at position 239, (ii) A at position 266, (iii) A at position 298, (iv) G at position 299, (v) T at position 300, (vi) A at position 328, and (vii) P at position 330. In other embodiments, the heavy chain of an antibody comprises the amino acid sequence of SEQ ID NO: 42, 54, 58, or 66 (or 90%, 95%, 98%, or 99% identical to SEQ ID NO: 42, 54, 58, or 66) that comprises (i) P at position 237, (ii) A at position 264, (iii) A at position 296, (iv) G at position 297, (v) T at position 298, (vi) A at position 326, and (vii) P at position 328. In yet other embodiments, the heavy chain of an antibody comprises the amino acid sequence of SEQ ID NO: 44, 50, or 60 (or 90%, 95%, 98%, or 99% identical to SEQ ID NO: 44, 50, or 60) that comprises (i) P at position 244, (ii) A at position 271, (iii) A at position 303, (iv) G at position 304, (v) T at position 305, (vi) A at position 333, and (vii) P at position 335. In still other embodiments, the heavy chain of an antibody comprises the amino acid sequence of SEQ ID NO: 46 or 62 (or 90%, 95%, 98%, or 99% identical to SEQ ID NO: 46 or 62) that comprises (i) P at position 242, (ii) A at position 269, (iii) A at position 301, (iv) G at position 302, (v) T at position 303, (vi) A at position 331, and (vii) P at position 333. In yet other embodiments, the heavy chain of an antibody comprises the amino acid sequence of SEQ ID NO: 48 (or 90%, 95%, 98%, or 99% identical to SEQ ID NO: 48) that comprises (i) P at position 246, (ii) A at position 273, (iii) A at position 305, (iv) G at position 306, (v) T at position 307, (vi) A at position 335, and (vii) P at position 337.

In other embodiments, the heavy chain of an antibody comprises the amino acid sequence of SEQ ID NO: 40, 52, 56, or 64 (or 90%, 95%, 98%, or 99% identical to SEQ ID NO: 40, 52, 56, or 64) that comprises (i) P, A, G, or S at position 239, (ii) A, G, or S at position 266, (iii) A, G, or S at position 298, (iv) G at position 299, (v) T at position 300, (vi) A, G, or S at position 328, and (vii) P, A, G, or S at position 330. In other such embodiments, the heavy chain of an antibody comprises the amino acid sequence of SEQ ID NO: 42, 54, 58, or 66 (or 90%, 95%, 98%, or 99% identical to SEQ ID NO: 42, 54, 58, or 66) that comprises (i) P, A, G, or S at position 237, (ii) A, G, or S at position 264, (iii) A, G, or S at position 296, (iv) G at position 297, (v) T at position 298, (vi) A, G, or S at position 326, and (vii) P, A, G, or S at position 328. In yet other embodiments, the heavy chain of an antibody comprises the amino acid sequence of SEQ ID NO: 44, 50, or 60 (or 90%, 95%, 98%, or 99% identical to SEQ ID NO: 44, 50, or 60) that comprises (i) P, A, G, or S at position 244, (ii) A, G, or S at position 271, (iii) A, G, or S at position 303, (iv) G at position 304, (v) T at position 305, (vi) A, G, or S at position 333, and (vii) P, A, G, or S at position 335. In still other embodiments, the heavy chain of an antibody comprises the amino acid sequence of SEQ ID NO: 46 or 62 (or 90%, 95%, 98%, or 99% identical to SEQ ID NO: 46 or 62) that comprises (i) P, A, G, or S at position 242, (ii) A, G, or S at position 269, (iii) A, G, or S at position 301, (iv) G at position 302, (v) T at position 303, (vi) A, G, or S at position 331, and (vii) P, A, G, or S at position 333. In yet other embodiments, the heavy chain of an antibody comprises the amino acid sequence of SEQ ID NO: 48 (or 90%, 95%, 98%, or 99% identical to SEQ ID NO: 48) that comprises (i) P, A, G, or S at position 246, (ii) A, G, or S at position 273, (iii) A, G, or S at position 305, (iv) G at position 306, (v) T at position 307, (vi) A, G, or S at position 335, and (vii) P, A, G, or S at position 337.

In yet other embodiments, the heavy chain of an antibody comprises the amino acid sequence of SEQ ID NO: 40, 52, 56, or 64 (or 90%, 95%, 98%, or 99% identical to SEQ ID NO: 40, 52, 56, or 64) that comprises (i) P, A, G, or S at position 239, (ii) A at position 266, (iii) A at position 298, (iv) G at position 299, (v) T at position 300, (vi) A, G, or S at position 328, and (vii) P, A, G, or S at position 330. In other such embodiments, the heavy chain of an antibody comprises the amino acid sequence of SEQ ID NO: 42, 54, 58, or 66 (or 90%, 95%, 98%, or 99% identical to SEQ ID NO: 42, 54, 58, or 66) that comprises (i) P, A, G, or S at position 237, (ii) A at position 264, (iii) A at position 296, (iv) G at position 297, (v) T at position 298, (vi) A, G, or S at position 326, and (vii) P, A, G, or S at position 328. In yet other embodiments, the heavy chain of an antibody comprises the amino acid sequence of SEQ ID NO: 44, 50, or 60 (or 90%, 95%, 98%, or 99% identical to SEQ ID NO: 44, 50, or 60) that comprises (i) P, A, G, or S at position 244, (ii) A at position 271, (iii) A at position 303, (iv) G at position 304, (v) T at position 305, (vi) A, G, or S at position 333, and (vii) P, A, G, or S at position 335. In still other embodiments, the heavy chain of an antibody comprises the amino acid sequence of SEQ ID NO: 46 or 62 (or 90%, 95%, 98%, or 99% identical to SEQ ID NO: 46 or 62) that comprises (i) P, A, G, or S at position 242, (ii) A at position 269, (iii) A at position 301, (iv) G at position 302, (v) T at position 303, (vi) A, G, or S at position 331, and (vii) P, A, G, or S at position 333. In yet other embodiments, the heavy chain of an antibody comprises the amino acid sequence of SEQ ID NO: 48 (or 90%, 95%, 98%, or 99% identical to SEQ ID NO: 48) that comprises (i) P, A, G, or S at position 246, (ii) A at position 273, (iii) A at position 305, (iv) G at position 306, (v) T at position 307, (vi) A, G, or S at position 335, and (vii) P, A, G, or S at position 337.

In yet other embodiments, the heavy chain of an antibody comprises the amino acid sequence of SEQ ID NO: 40, 52, 56, or 64 (or 90%, 95%, 98%, or 99% identical to SEQ ID NO: 40, 52, 56, or 64) that comprises (i) A at position 239, (ii) A at position 266, (iii) A at position 298, (iv) G at position 299, (v) T at position 300, (vi) G at position 328, and (vii) A at position 330. In other such embodiments, the heavy chain of an antibody comprises the amino acid sequence of SEQ ID NO: 42, 54, 58, or 66 (or 90%, 95%, 98%, or 99% identical to SEQ ID NO: 42, 54, 58, or 66) that comprises (i) A at position 237, (ii) A at position 264, (iii) A at position 296, (iv) G at position 297, (v) T at position 298, (vi) G at position 326, and (vii) A at position 328. In yet other embodiments, the heavy chain of an antibody comprises the amino acid sequence of SEQ ID NO: 44, 50, or 60 (or 90%, 95%, 98%, or 99% identical to SEQ ID NO: 44, 50, or 60) that comprises (i) A at position 244, (ii) A at position 271, (iii) A at position 303, (iv) G at position 304, (v) T at position 305, (vi) G at position 333, and (vii) A at position 335. In still other embodiments, the heavy chain of an antibody comprises the amino acid sequence of SEQ ID NO: 46 or 62 (or 90%, 95%, 98%, or 99% identical to SEQ ID NO: 46 or 62) that comprises (i) A at position 242, (ii) A at position 269, (iii) A at position 301, (iv) G at position 302, (v) Tat position 303, (vi) G at position 331, and (vii) A at position 333. In yet other embodiments, the heavy chain of an antibody comprises the amino acid sequence of SEQ ID NO: 48 (or 90%, 95%, 98%, or 99% identical to SEQ ID NO: 48) that comprises (i) A at position 246, (ii) A at position 273, (iii) A at position 305, (iv) G at position 306, (v) T at position 307, (vi) G at position 335, and (vii) A at position 337.

In addition, the present invention provides caninized antibody or antigen binding fragment thereof that further comprise a canine light chain that comprises the amino acid sequence of SEQ ID NO: 72, SEQ ID NO: 78, SEQ ID NO: 84, SEQ ID NO: 90, SEQ ID NO: 96, SEQ ID NO: 102, or SEQ ID NO: 108.

Accordingly, the present invention further provides a caninized antibody or antigen binding fragment thereof that comprises a heavy chain comprising the amino acid sequence of SEQ ID NO: 68 and a light chain comprising the amino acid sequence of SEQ ID NO: 72. In a related embodiment, the caninized antibody or antigen binding fragment thereof comprises a heavy chain comprising the amino acid sequence of SEQ ID NO: 70 and a light chain comprising the amino acid sequence of SEQ ID NO: 72. In another embodiment, the caninized antibody or antigen binding fragment thereof comprises a heavy chain comprising the amino acid sequence of SEQ ID NO: 74 and a light chain comprising the amino acid sequence of SEQ ID NO: 78. In a related embodiment, the caninized antibody or antigen binding fragment thereof comprises a heavy chain comprising the amino acid sequence of SEQ ID NO: 76 and a light chain comprising the amino acid sequence of SEQ ID NO: 78. In yet another embodiment, the caninized antibody or antigen binding fragment thereof comprises a heavy chain comprising the amino acid sequence of SEQ ID NO: 80 and a light chain comprising the amino acid sequence of SEQ ID NO: 84. In a related embodiment, the caninized antibody or antigen binding fragment thereof comprises a heavy chain comprising the amino acid sequence of SEQ ID NO: 82 and a light chain comprising the amino acid sequence of SEQ ID NO: 84. In still another embodiment, the caninized antibody or antigen binding fragment thereof comprises a heavy chain comprising the amino acid sequence of SEQ ID NO: 86 and a light chain comprising the amino acid sequence of SEQ ID NO: 90. In a related embodiment, the caninized antibody or antigen binding fragment thereof comprises a heavy chain comprising the amino acid sequence of SEQ ID NO: 88 and a light chain comprising the amino acid sequence of SEQ ID NO: 90. In yet another embodiment, the caninized antibody or antigen binding fragment thereof comprises a heavy chain comprising the amino acid sequence of SEQ ID NO: 92 and a light chain comprising the amino acid sequence of SEQ ID NO: 96. In a related embodiment, the caninized antibody or antigen binding fragment thereof comprises a heavy chain comprising the amino acid sequence of SEQ ID NO: 94 and a light chain comprising the amino acid sequence of SEQ ID NO: 96. In still another embodiment, the caninized antibody or antigen binding fragment thereof comprises a heavy chain comprising the amino acid sequence of SEQ ID NO: 98 and a light chain comprising the amino acid sequence of SEQ ID NO: 102. In a related embodiment, the caninized antibody or antigen binding fragment thereof comprises a heavy chain comprising the amino acid sequence of SEQ ID NO: 100 and a light chain comprising the amino acid sequence of SEQ ID NO: 102. In yet another embodiment, the caninized antibody or antigen binding fragment thereof comprises a heavy chain comprising the amino acid sequence of SEQ ID NO: 104 and a light chain comprising the amino acid sequence of SEQ ID NO: 108. In a related embodiment, the caninized antibody or antigen binding fragment thereof comprises a heavy chain comprising the amino acid sequence of SEQ ID NO: 106 and a light chain comprising the amino acid sequence of SEQ ID NO: 108.

The present invention further provides a caninized antibody or antigen binding fragment thereof that comprises a heavy chain comprising the amino acid sequence of SEQ ID NO: 40 and a light chain comprising the amino acid sequence of SEQ ID NO: 72. In a related embodiment, the caninized antibody or antigen binding fragment thereof comprises a heavy chain comprising the amino acid sequence of SEQ ID NO: 42 and a light chain comprising the amino acid sequence of SEQ ID NO: 72. In another embodiment, the caninized antibody or antigen binding fragment thereof comprises a heavy chain comprising the amino acid sequence of SEQ ID NO: 44 and a light chain comprising the amino acid sequence of SEQ ID NO: 78. In a related embodiment, the caninized antibody or antigen binding fragment thereof comprises a heavy chain comprising the amino acid sequence of SEQ ID NO: 46 and a light chain comprising the amino acid sequence of SEQ ID NO: 78. In yet another embodiment, the caninized antibody or antigen binding fragment thereof comprises a heavy chain comprising the amino acid sequence of SEQ ID NO: 48 and a light chain comprising the amino acid sequence of SEQ ID NO:

84. In a related embodiment, the caninized antibody or antigen binding fragment thereof comprises a heavy chain comprising the amino acid sequence of SEQ ID NO: 50 and a light chain comprising the amino acid sequence of SEQ ID NO: 84. In still another embodiment, the caninized antibody or antigen binding fragment thereof comprises a heavy chain comprising the amino acid sequence of SEQ ID NO: 52 and a light chain comprising the amino acid sequence of SEQ ID NO: 90. In a related embodiment, the caninized antibody or antigen binding fragment thereof comprises a heavy chain comprising the amino acid sequence of SEQ ID NO: 54 and a light chain comprising the amino acid sequence of SEQ ID NO: 90. In yet another embodiment, the caninized antibody or antigen binding fragment thereof comprises a heavy chain comprising the amino acid sequence of SEQ ID NO: 56 and a light chain comprising the amino acid sequence of SEQ ID NO: 96. In a related embodiment, the caninized antibody or antigen binding fragment thereof comprises a heavy chain comprising the amino acid sequence of SEQ ID NO: 58 and a light chain comprising the amino acid sequence of SEQ ID NO: 96.

In still another embodiment, the caninized antibody or antigen binding fragment thereof comprises a heavy chain comprising the amino acid sequence of SEQ ID NO: 60 and a light chain comprising the amino acid sequence of SEQ ID NO: 102. In a related embodiment, the caninized antibody or antigen binding fragment thereof comprises a heavy chain comprising the amino acid sequence of SEQ ID NO: 62 and a light chain comprising the amino acid sequence of SEQ ID NO: 102. In yet another embodiment, the caninized antibody or antigen binding fragment thereof comprises a heavy chain comprising the amino acid sequence of SEQ ID NO: 64 and a light chain comprising the amino acid sequence of SEQ ID NO: 108. In a related embodiment, the caninized antibody or antigen binding fragment thereof comprises a heavy chain comprising the amino acid sequence of SEQ ID NO: 66 and a light chain comprising the amino acid sequence of SEQ ID NO: 108.

The present invention further provides nucleic acids that encode any of the amino acid sequences of the present invention including the CDRs, cFc regions, the cFc regions with the hinge regions, and the heavy chains, and the light chains of the caninized antibodies of the present invention. The present invention further provides expression vectors that comprise one or more of the nucleic acids of the present invention. The present invention further provides host cells that comprise one or more expression vectors of the present invention and methods for expressing the CDRs, and/or cFc regions, and/or the cFc regions with the hinge regions, and/or the heavy chains, and/or the light chains of the caninized antibodies of the present invention using such host cells. The present invention also provides host cells that have been genetically engineered to express the CDRs, and/or cFc regions, and/or the cFc regions with the hinge regions, and/or the heavy chains, and/or the light chains of the caninized antibodies of the present invention in the absence of such vectors. In particular embodiments, these nucleic acids, expression vectors, polypeptides, or host cells of the invention are useful in methods of making an antibody.

In particular embodiments, the antibody is a recombinant antibody or an antigen binding fragment thereof. In related embodiments, the variable heavy chain domain and variable light chain domain are connected by a flexible linker to form a single-chain antibody.

In particular embodiments, the antibody or antigen binding fragment is a Fab fragment. In other embodiments, the antibody or antigen binding fragment is a Fab' fragment. In other embodiments, the antibody or antigen binding fragment is a (Fab')$_2$ fragment. In still other embodiments, the antibody or antigen binding fragment is a diabody. In particular embodiments, the antibody or antigen binding fragment is a domain antibody. In particular embodiments, the antibody or antigen binding fragment is a camelized single domain antibody.

In particular embodiments, a caninized murine anti-canine PD-1 antibody or antigen binding fragment increases the immune response of the canine subject being treated.

In certain embodiments when bound to canine PD-1, the caninized antibody or antigen binding fragment thereof binds to at least one amino acid residue within one or more amino acid sequences of the following: SEQ ID NO: 138, SEQ ID NO: 139, SEQ ID NO: 140, SEQ ID NO: 141, of SEQ ID NO: 142, SEQ ID NO: 143, SEQ ID NO: 144, and/or SEQ ID NO: 145.

Furthermore, the present invention provides caninized antibodies to canine PD-1, that comprise variants of the CDRs of the present invention that have the corresponding canonical structures provided herein and/or that bind to the amino acid sequence of SEQ ID NO: 144. In particular embodiments of this type, the dissociation constant (Kd) for caninized antibody-canine PD-1 binding is $1 \times 10^{-5}$ to $1 \times 10^{-12}$M. In more particular embodiments the caninized antibodies to canine PD-1, comprise variants of the CDRs of the present invention that have the corresponding canonical structures provided herein and bind to the amino acid sequence of SEQ ID NO: 145. The present invention therefore includes caninized antibodies and antigen binding fragments thereof that bind canine PD-1 with specificity, that when they are bound to canine PD-1, the antibody binds to at least one amino acid residue within SEQ ID NO: 144. In particular embodiments of this type, the antibodies and antigen binding fragments thereof bind canine PD-1 and block the binding of canine PD-1 to canine Programmed Death Ligand 1 (PD-L1).

Accordingly, in particular embodiments when bound to canine PD-1, the caninized antibody (including the antibodies with one or more variant CDR, e.g., a variant including a conservatively modified variant and/or a variant that comprises a defined canonical structure class) binds to at least one amino acid residue within one or more amino acid sequences of the following: SEQ ID NO: 138, SEQ ID NO: 139, SEQ ID NO: 140, SEQ ID NO: 141, of SEQ ID NO: 142, SEQ ID NO: 143, and/or SEQ ID NO: 145. In even more particular embodiments when bound to canine PD-1, the caninized antibodies or antigen binding fragments thereof bind to one or more amino acid residues of the following arginine residues: $R_{62}$, $R_{69}$, $R_{72}$, $R_{75}$, and $R_{90}$ of SEQ ID NO: 114. In specific embodiments when bound to canine PD-1, the caninized antibodies or antigen binding fragments thereof bind to at least one amino acid residue within SEQ ID NO: 145. In more specific embodiments when bound to canine PD-1, the antibodies or antigen binding fragments thereof bind to one or more amino acid residues of the following arginine residues: $R_{62}$, $R_{69}$, $R_{72}$, and $R_{75}$ of SEQ ID NO: 114. In even more specific embodiments when bound to canine PD-1, the antibodies or antigen binding fragments thereof bind to $R_{75}$ of SEQ ID NO: 114.

The present invention further provides caninized antibodies or antigen binding fragments thereof that bind to canine PD-1 with a dissociation constant (Kd) that is lower (e.g., $1 \times 10^{-13}$M, or lower) than $1 \times 10^{-12}$M. In particular embodiments the caninized antibodies or antigen binding fragments thereof bind to canine PD-1 with a dissociation constant of $1 \times 10^{-5}$ M to $1 \times 10^{-12}$ M. In more particular embodiments the caninized antibodies or antigen binding fragments thereof bind to canine PD-1 with a dissociation constant of $1 \times 10^{-7}$ M to $1 \times 10^{-11}$ M. In still more particular embodiments the caninized antibodies or antigen binding fragments thereof bind to canine PD-1 with a dissociation constant of $1 \times 10^{-8}$ M to $1 \times 10^{-11}$ M. In yet more particular embodiments the caninized antibodies or antigen binding fragments thereof bind to canine PD-1 with a dissociation constant of $1 \times 10^{-8}$ M to $1 \times 10^{-10}$ M.

The present invention also provides caninized antibodies or antigen binding fragments thereof that bind to canine PD-1 with an on rate ($k_{on}$) that is greater than $1 \times 10^{7}$ M$^{-1}$ s$^{-1}$. In particular embodiments the caninized antibodies or antigen binding fragments thereof bind to canine PD-1 with an on rate of $1 \times 10^{2}$ M$^{-1}$ s$^{-1}$ to $1 \times 10^{7}$ M$^{-1}$ s$^{-1}$. In more particular embodiments the caninized antibodies or antigen binding fragments thereof bind to canine PD-1 with an on rate of $1 \times 10^{3}$ M$^{-1}$ s$^{-1}$ to $1 \times 10^{6}$ M$^{-1}$ s$^{-1}$. In still more particular embodiments the caninized antibodies or antigen binding fragments thereof bind to canine PD-1 with an on rate of $1 \times 10^{3}$ M$^{-1}$ s$^{-1}$ to $1 \times 10^{5}$ M$^{-1}$ s$^{-1}$. In yet more particular embodiments the caninized antibodies or antigen binding fragments thereof bind to canine PD-1 on rate of $1 \times 10^{4}$ M$^{-1}$ s$^{-1}$ to $1 \times 10^{5}$ M$^{-1}$ s$^{-1}$.

The present invention further provides caninized antibodies or antigen binding fragments thereof that bind to canine PD-1 with an off rate ($k_{off}$) slower than $1 \times 10^{-7}$ s$^{-1}$. In particular embodiments the caninized antibodies or antigen binding fragments thereof bind to canine PD-1 with an off rate of $1 \times 10^{-3}$ s$^{-1}$ to $1 \times 10^{-8}$ s$^{-1}$. In more particular embodiments the caninized antibodies or antigen binding fragments thereof bind to canine PD-1 with an off rate of $1 \times 10^{-4}$ s$^{-1}$ to $1 \times 10^{-7}$ s$^{-1}$. In still more particular embodiments the caninized antibodies or antigen binding fragments thereof bind to canine PD-1 with an off rate of $1 \times 10^{-5}$ s$^{-1}$ to $1 \times 10^{--7}$ s$^{-1}$.

In related embodiments, the caninized antibodies or antigen binding fragments thereof stimulate antigen-specific memory responses to a tumor or pathogen. In particular embodiments, the caninized antibodies or antigen binding fragments thereof stimulate an antibody response in vivo. In other particular embodiments, the caninized antibodies or antigen binding fragments thereof stimulate an immune response in an animal subject. In more specific embodiments the animal subject is a canine. In a related embodiment, the animal subject is a feline.

Accordingly, any of the caninized antibodies of the present invention can exhibit one, two, three, four, five, or all these properties, i.e., the aforesaid dissociation constants with canine PD-1, the aforesaid on rates for binding with canine PD-1, the aforesaid off rates for dissociating from from the caninized antibody-canine PD-1 binding complex, stimulating an antigen-specific memory responses to a tumor or pathogen, stimulating an antibody response in vivo, and/or stimulating an immune response in an animal subject.

In more particular embodiments the caninized antibodies and antigen binding fragments thereof of the present invention bind canine PD-1 and also block the binding of canine PD-1 to PD-L1. In even more particular embodiments the caninized antibodies and antigen binding fragments thereof of the present invention bind canine PD-1, block the binding of canine PD-1 to PD-L1, and also block the binding of canine PD-1 to PD-L2.

The present invention further provides nucleic acids that encode the caninized murine anti-canine PD-1 antibodies or portions thereof of the present invention. In related embodiments such antibodies or antigen binding fragments can be used for the preparation of a medicament to treat cancer in a canine subject. Alternatively, or in conjunction, the present invention provides for the use of any of the antibodies or antibody fragments of the present invention for diagnostic use. In yet additional embodiments, a kit is provided comprising any of the caninized antibodies or antigen binding fragments disclosed herein.

The present invention further includes pharmaceutical compositions comprising an anti-canine antigen antibody or binding fragment thereof (e.g., an anti-canine PD-1 antibody or antigen binding fragment thereof) together with a pharmaceutically acceptable carrier or diluent. The present invention also provides a method of increasing the activity of an immune cell, comprising administering to a subject (e.g., a canine) in need thereof a therapeutically effective amount of the pharmaceutical composition of the present invention. In certain embodiments the method is used for the treatment of cancer. In other embodiments, the method is used in the treatment of an infection or infectious disease. In still other embodiments, a caninized antibody of the present invention or antigen binding fragment thereof is used as a vaccine adjuvant. In yet another embodiment, a caninized anti-TSLP antibody is administered to a canine to treat atopic dermatitis.

These and other aspects of the present invention will be better appreciated by reference to the following Brief Description of the Drawings and the Detailed Description.

BRIEF DESCRIPTION OF THE DRAWINGS

FIGS. 5A and 5B show the binding of caninized mAbs and their variants (beginning at 1 μg/ml) to Fc$_\gamma$RI. Various mAbs were tested for their ability to bind to FcRI. Antibodies are designated as: can 2H9 ADCC (1062) VH4/VL3, can 2H9 ADCC mut 1 VH4/VL3, can 2H9 ADCC mut 2 VH4/VL3, can 2H9 IgGD VH4/VL3, can 2H9 VH4/VL3, and can 3B6 VH4/VL4 in FIG. 5A; and can 2H9 ADCC (1059) VH4/VL3, can 2H9 ADCC (1060) VH4/VL3, can 2H9 ADCC (1061) VH4/VL3, can 2H9 IgGB ADCC (1068) VH4/VL3, can 2H9 VH4/VL3, and can 3B6 VH4/VL4 in FIG. 5B.

DETAILED DESCRIPTION

Abbreviations

Figure 1:
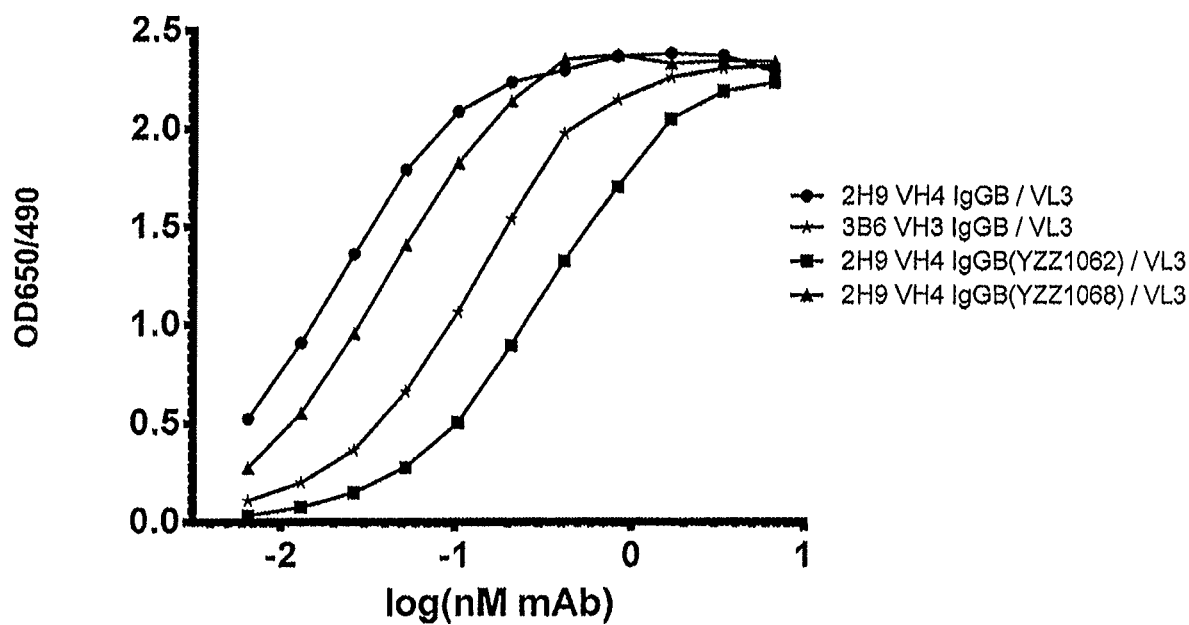
FIG. 1 shows the reactivity of caninized monoclonal antibodies (mAbs) against extracellular domain of canine PD-1, as a function of OD 650/490 versus the log mAb (nM). Various caninized mAbs were tested for their binding to extracellular domain of canine PD-1 by ELISA. The four mAbs tested were designated as: 2H9 VH4 IgGB/VL3, 3B6 VH3 IgGB/VL3, 2H9 VH4 IgGB (YZZ1062)/VL3, and 2H9 VH4 IgGB (YZZ1068)/VL3.
Figure 2:
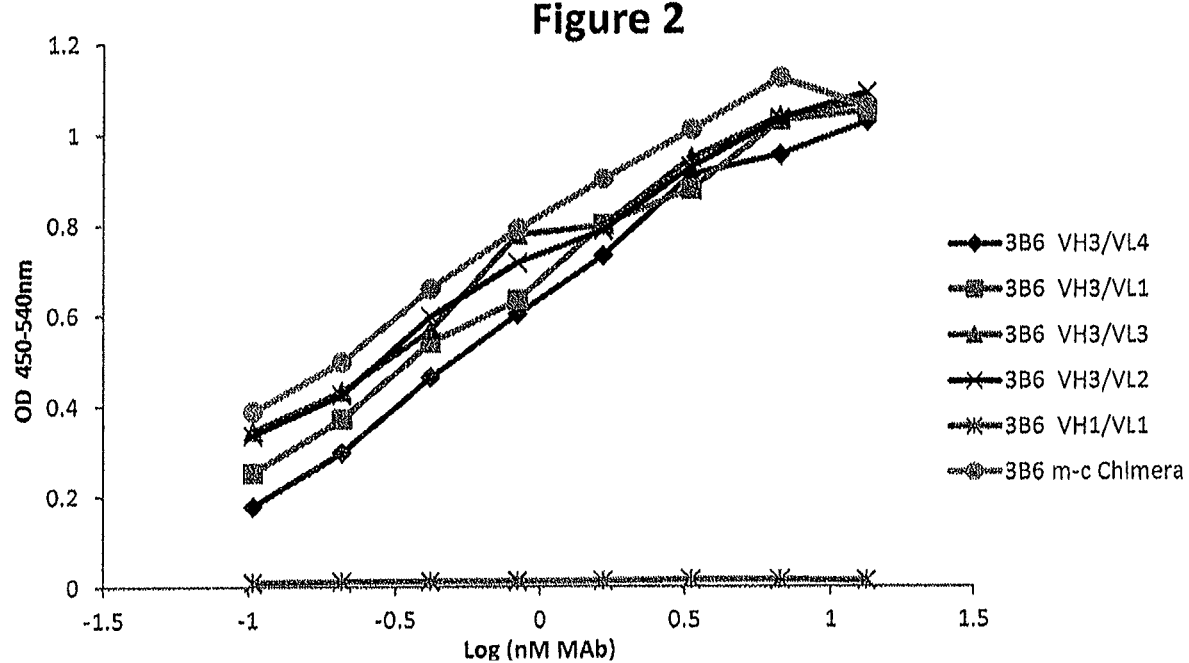
FIG. 2 shows the reactivity of caninized mAbs against cell surface-expressed canine PD-1. Various mouse mAbs were tested for their binding to canine PD-1 expressed on CHO cells by CELISA as a function of OD 450/540 versus the log mAb (nM). The six mAbs tested were designated as: 3B6 VH3/VL4, 3B6 VH3/VL1, 3B6 VH3/VL3, 3B6 VH3/VL2, 3B6 VH1/VL1, and 3B6 m-c Chimera.
Figure 3:
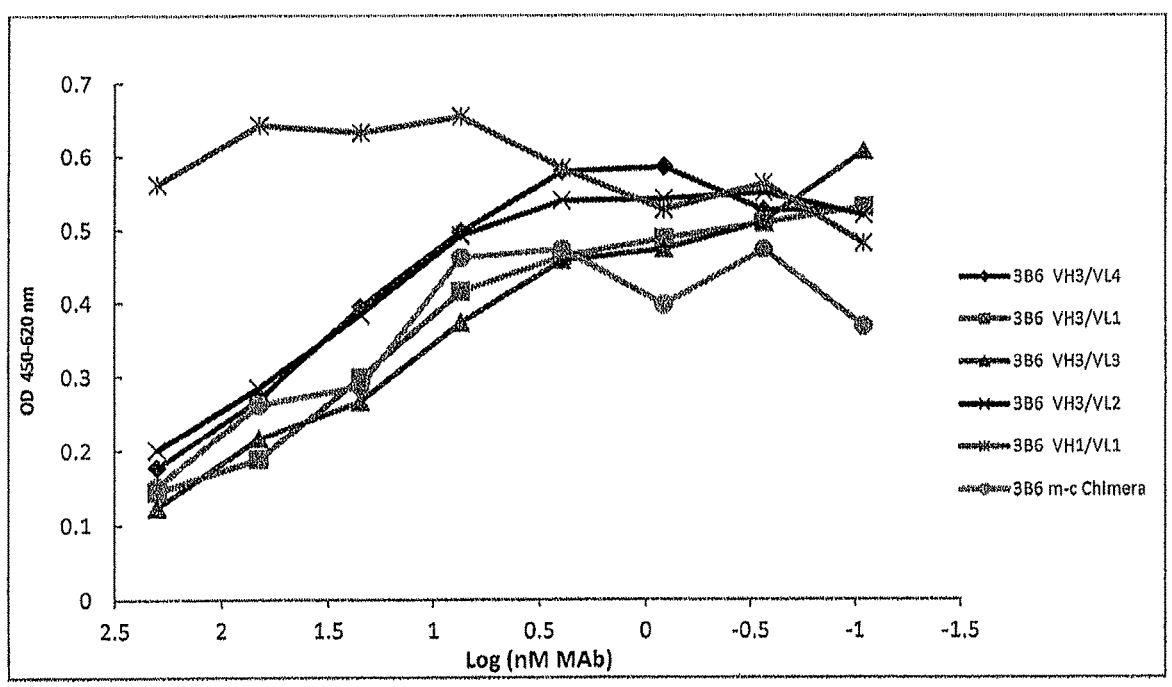
FIG. 3 shows ligand blockade with caninized mAbs against canine PD-1. Various caninized mAbs were tested for their ability to inhibit binding of PD-1 expressed on CHO cells to PD-L1 as a function of OD 450/540 versus the log mAb (nM). The six mAbs tested were designated as: 3B6 VH3/VL4, 3B6 VH3/VL1, 3B6 VH3/VL3, 3B6 VH3/VL2, 3B6 VH1/VL1, and 3B6 m-c Chimera.

Throughout the detailed description and examples of the invention the following abbreviations will be used:

ADCC Antibody-dependent cellular cytotoxicity
CDC Complement-dependent cyotoxicity
CDR Complementarity determining region in the immunoglobulin variable regions, defined for human antibodies using the Kabat numbering system
CHO Chinese hamster ovary
EC50 concentration resulting in 50% efficacy or binding
ELISA Enzyme-linked immunosorbant assay
FR Antibody framework region: the immunoglobulin variable regions excluding the CDR regions.
HRP Horseradish peroxidase
IFN interferon
IC50 concentration resulting in 50% inhibition
IgG Immunoglobulin G
Kabat An immunoglobulin alignment and numbering system for humam Antibodies pioneered by Elvin A. Kabat [*Sequences of Proteins of Immunological Interest,* 5th Ed. Public Health Service, National Institutes of Health, Bethesda, Md. (1991)]
mAb Monoclonal antibody (also Mab or MAb)
MES 2-(N-morpholino)ethanesulfonic acid
MOA Mechanism of action
NHS Normal human serum
PCR Polymerase chain reaction
PK Pharmacokinetics
SEB Staphylococcus Enterotoxin B
TT Tetanus toxoid
V region The segment of human IgG chains which is variable in sequence between different antibodies. It extends to Kabat residue 109 in the light chain and 113 in the heavy chain.
VH Immunoglobulin heavy chain variable region
VK Immunoglobulin kappa light chain variable region

Definitions

So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, including the appended claims, the singular forms of words such as "a," "an," and "the," include their corresponding plural references unless the context clearly dictates otherwise.

"Activation" as it applies to cells or to receptors refers to the activation or treatment of a cell or receptor with a ligand, unless indicated otherwise by the context or explicitly. "Ligand" encompasses natural and synthetic ligands, e.g., cytokines, cytokine variants, analogues, muteins, and binding compounds derived from antibodies. "Ligand" also encompasses small molecules, e.g., peptide mimetics of cytokines and peptide mimetics of antibodies. "Activation" can refer to cell activation as regulated by internal mechanisms as well as by external or environmental factors.

"Activity" of a molecule may describe or refer to the binding of the molecule to a ligand or to a receptor, to catalytic activity; to the ability to stimulate gene expression or cell signaling, differentiation, or maturation; to antigenic activity, to the modulation of activities of other molecules, and the like. "Activity" of a molecule may also refer to activity in modulating or maintaining cell-to-cell interactions, e.g., adhesion, or activity in maintaining a structure of a cell, e.g., cell membranes or cytoskeleton. "Activity" can also mean specific activity, e.g., [catalytic activity]/[mg protein], or [immunological activity]/[mg protein], concentration in a biological compartment, or the like. "Activity" may refer to modulation of components of the innate or the adaptive immune systems.

"Administration" and "treatment," as it applies to an animal, e.g., a canine experimental subject, cell, tissue, organ, or biological fluid, refers to contact of an exogenous pharmaceutical, therapeutic, diagnostic agent, or composition to the animal e.g., a canine subject, cell, tissue, organ, or biological fluid. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding compound, or by another cell.

The term "subject" includes any organism, preferably an animal, more preferably a mammal (e.g., canine, feline, or human) and most preferably a canine.

As used herein, the term "feline" refers to any member of the Felidae family. Members of this family include wild, zoo, and domestic members, such as any member of the subfamilies Felinae, e.g., cats, lions, tigers, pumas, jaguars, leopards, snow leopards, panthers, North American mountain lions, cheetahs, lynx, bobcats, caracals or any cross breeds thereof. Cats also include domestic cats, pure-bred and/or mongrel companion cats, show cats, laboratory cats, cloned cats, and wild or feral cats.

As used herein, a "substitution of an amino acid residue" with another amino acid residue in an amino acid sequence is equivalent to "replacing an amino acid residue" with another amino acid residue and denotes that a particular amino acid residue at a specific position in the amino acid sequence has been replaced by (or substituted for) by a different amino acid. For example, one such substitution (replacement) is denoted as P4A of an Fc region of an IgGB or IgGC amino acid sequence, in which case, the proline residue at amino acid position 4 of the amino acid sequence of the Fc region of an IgGB or the Fc region of an IgGC has been substituted for (replaced) by an alanine residue.

Accordingly, such amino acid substitutions can be particularly designed i.e., purposefully replacing an alanine with a serine at a specific position in the amino acid sequence by e.g., recombinant DNA technology. Alternatively, a particular amino acid residue or string of amino acid residues of an antibody can be replaced by one or more amino acid residues through more natural selection processes e.g., based on the ability of the antibody produced by a cell to bind to a given region on that antigen, e.g., one containing an epitope or a portion thereof, and/or for the antibody to comprise a particular CDR that retains the same canonical structure as the CDR it is replacing. Such substitutions/replacements can lead to "variant" CDRs and/or antibodies.

"Treat" or "treating" means to administer a therapeutic agent, such as a composition containing any of the antibodies or antigen binding fragments of the present invention, internally or externally to a canine subject or patient having one or more disease symptoms, or being suspected of having a disease, for which the agent has therapeutic activity.

Typically, the agent is administered in an amount effective to alleviate and/or ameliorate one or more disease symptom in the treated subject or population, whether by inducing the regression of or inhibiting the progression of such symptom(s) by any clinically measurable degree. The amount of a therapeutic agent that is effective to alleviate any particular disease symptom (also referred to as the "therapeutically effective amount") may vary according to factors such as the disease state, age, and weight of the subject (e.g., canine), and the ability of the pharmaceutical composition to elicit a desired response in the subject. Whether a disease symptom has been alleviated or ameliorated can be assessed by any clinical measurement typically used by veterinarians or other skilled healthcare providers to assess the severity or progression status of that symptom. While an embodiment of the present invention (e.g., a treatment method or article of manufacture) may not be effective in alleviating the target disease symptom(s) in every subject, it should alleviate the target disease symptom(s) in a statistically significant number of subjects as determined by any statistical test known in the art such as the Student's t-test, the chi$^2$-test, the U-test according to Mann and Whitney, the Kruskal-Wallis test (H-test), Jonckheere-Terpstra-test and the Wilcoxon-test.

"Treatment," as it applies to a human, veterinary (e.g., canine) or research subject, refers to therapeutic treatment, as well as research and diagnostic applications. "Treatment" as it applies to a human, veterinary (e.g., canine), or research subject, or cell, tissue, or organ, encompasses contact of the caninized antibodies or antigen binding fragments of the present invention to a canine or other animal subject, a cell, tissue, physiological compartment, or physiological fluid.

Canine PD-1 has been found to comprise the amino acid sequence of SEQ ID NO: 114 [U.S. provisional application No. 61/918,946, filed on Dec. 20, 2013, the contents of which are hereby incorporated herein in their entireties]. In a specific embodiment canine PD-1 is encoded by a nucleic acid that comprises the nucleotide sequence of SEQ ID NO: 113.

Canine PD-L1 has been found to comprise the amino acid sequence of SEQ ID NO: 120 [U.S. provisional application No. 61/918,946, filed on Dec. 20, 2013, supra]. In a specific embodiment canine PD-L1 is encoded by a nucleotide sequence comprising SEQ ID NO: 119.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the mammalian body (e.g., canine body) of cancerous cells, cells or tissues infected with pathogens, or invading pathogens.

Caninized Anti-Canine Antigen Antibodies

As used herein, the term "canine" includes all domestic dogs, Canis lupus familiaris or Canis familiaris, unless otherwise indicated.

As used herein, an antibody is said to bind specifically to a polypeptide comprising a given antigen sequence (in this case a portion of the amino acid sequence of a canine antigen, e.g., canine PD-1) if it binds to polypeptides comprising that portion of the amino acid sequence of the canine antigen, e.g., canine PD-1, but does not bind to other canine proteins lacking that portion of the sequence of the canine antigen, e.g., canine PD-1. For example, an antibody that specifically binds to a polypeptide comprising canine PD-1 may bind to a FLAG®-tagged form of canine PD-1, but will not bind to other FLAG®-tagged canine proteins with specificity. An antibody, or binding compound derived from the antigen-binding site of an antibody, binds to its canine antigen, or a variant or mutein thereof, "with specificity" when it has an affinity for that canine antigen or a variant or mutein thereof which is at least ten-times greater, more preferably at least 20-times greater, and even more preferably at least 100-times greater than its affinity for any other canine antigen tested.

As used herein, the term "antibody" refers to any form of antibody that exhibits the desired biological activity. Thus, it is used in the broadest sense and specifically covers, but is not limited to, monoclonal antibodies (including full length monoclonal antibodies), polyclonal antibodies, multispecific antibodies (e.g., bispecific antibodies), caninized antibodies, fully canine antibodies, chimeric antibodies and camelized single domain antibodies. "Parental antibodies" are antibodies obtained by exposure of an immune system to an antigen prior to modification of the antibodies for an intended use, such as caninization of an antibody for use as a canine therapeutic antibody.

As used herein, unless otherwise indicated, "antibody fragment" or "antigen binding fragment" refers to antigen binding fragments of antibodies, i.e. antibody fragments that retain the ability to bind specifically to the antigen bound by the full-length antibody, e.g. fragments that retain one or more CDR regions. Examples of antigen binding fragments include, but are not limited to, Fab, Fab', F(ab')$_2$, and Fv fragments; diabodies; linear antibodies; single-chain antibody molecules, e.g., sc-Fv; nanobodies and multispecific antibodies formed from antibody fragments.

A "Fab fragment" is comprised of one light chain and the $C_H1$ and variable regions of one heavy chain. The heavy chain of a Fab molecule cannot form a disulfide bond with another heavy chain molecule. A "Fab fragment" can be the product of papain cleavage of an antibody.

A "fragment crystallizable" ("Fc") region contains two heavy chain fragments (i.e., two identical polypeptides) comprising the $C_H2$ and $C_H3$ domains of an antibody. The two heavy chain fragments are held together by two or more disulfide bonds and by hydrophobic interactions of the $C_H3$ domains. In the present invention, the amino acid sequence for each of the four canine IgG Fc fragments is based on the identified boundary of CH1 and CH2 domains as determined by Tang et al. [*Vet. Immunol. Immunopathol.* 80: 259-270 (2001)].

A "Fab' fragment" contains one light chain and a portion or fragment of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a $F(ab')_2$ molecule.

A "$F(ab')_2$ fragment" contains two light chains and two heavy chains containing a portion of the constant region between the $C_H1$ and $C_H2$ domains, such that an interchain disulfide bond is formed between the two heavy chains. A $F(ab')_2$ fragment thus is composed of two Fab' fragments that are held together by a disulfide bond between the two heavy chains. An "$F(ab')_2$ fragment" can be the product of pepsin cleavage of an antibody.

The "Fv region" comprises the variable regions from both the heavy and light chains, but lacks the constant regions.

The term "single-chain Fv" or "scFv" antibody refers to antibody fragments comprising the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for antigen binding. [See, Pluckthun, THE PHARMACOLOGY OF MONOCLONAL ANTIBODIES, vol. 113 Rosenburg and Moore eds., Springer-Verlag, New York, pp. 269-315 (1994); WO 88/01649; and U.S. Pat. Nos. 4,946,778, 5,260,203.]

As used herein, the term "canonical structure" refers to the local conformation that can be adopted by each of the hypervariable regions of the heavy and light chain of an antibody within the framework that they reside. For each hypervariable region, there are a small number of canonical structures (generally denoted by simple integers such as 1 or 2 etc.), which can be predicted with great accuracy from the amino acid sequences of the corresponding hypervariable region (particularly within the context of the amino acid sequence of its framework, as provided below for the corresponding caninized murine anti-canine PD-1 variable domains). These canonical structures can be determinative regarding whether a modification of the amino acid sequence of a given CDR will result in the retention or loss of the ability to bind to its antigen binding partner [See, Chothia and Lesk, *Canonical Structures for the hypervariable regions of immunoglobulins, J. Mol. Biol.* 196:901-917 (1987); Chothia et al., *Conformation of immunoglobulin hypervaribale regions, Nature,* 34:877-883(1989); and Al-Lazikani et al., *Standard Conformations for the canonical structures of immunoglobulins, J. Mol. Biol.* 273:927-948 (1997)].

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

A "bivalent antibody" comprises two antigen binding sites. In some instances, the two binding sites have the same antigen specificities. However, bivalent antibodies may be bispecific (see below).

In certain embodiments, monoclonal antibodies herein also include camelized single domain antibodies. [See, e.g., Muyldermans et al., *Trends Biochem. Sci.* 26:230 (2001); Reichmann et al., *J. Immunol. Methods* 231:25 (1999); WO 94/04678; WO 94/25591; U.S. Pat. No. 6,005,079]. In one embodiment, the present invention provides single domain antibodies comprising two $V_H$ domains with modifications such that single domain antibodies are formed.

As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. [See, EP 0 404 097 B1; WO 93/11161; and Holliger et al., *Proc. Natl. Acad. Sci. USA* 90: 6444-6448 (1993)]. For a review of engineered antibody variants [generally see Holliger and Hudson *Nat. Biotechnol.* 23:1126-1136 (2005)].

Typically, an antibody or antigen binding fragment of the invention retains at least 10% of its canine PD-1 binding activity (when compared to the parental antibody) when that activity is expressed on a molar basis. Preferably, an antibody or antigen binding fragment of the invention retains at least 20%, 50%, 70%, 80%, 90%, 95% or 100% or more of the canine antigen, (e.g., PD-1) binding affinity as the parental antibody. It is also intended that a caninized antibody or antigen binding fragment of the invention can include conservative or non-conservative amino acid substitutions (referred to as "conservative variants" or "function conserved variants" of the antibody) that do not substantially alter its biologic activity.

"Isolated antibody" refers to the purification status and in such context means the molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

As used herein, a "chimeric antibody" is an antibody having the variable domain from a first antibody and the constant domain from a second antibody, where the first and second antibodies are from different species. [U.S. Pat. No. 4,816,567; and Morrison et al., *Proc. Natl. Acad. Sci. USA* 81: 6851-6855 (1984)]. Typically the variable domains are obtained from an antibody from an experimental animal (the "parental antibody"), such as a rodent, and the constant domain sequences are obtained from the animal subject antibodies, e.g., canine, so that the resulting chimeric antibody will be less likely to elicit an adverse immune response in a canine subject, than the parental (e.g., rodent) antibody.

As used herein, the term "caninized antibody" refers to forms of antibodies that contain sequences from both canine and non-canine (e.g., murine) antibodies. In general, the caninized antibody will comprise substantially all of at least one, and typically two, variable domains, in which all or substantially all of the hypervariable loops correspond to those of a non-canine immunoglobulin (e.g., comprising 6 murine anti-canine PD-1 CDRs as exemplified below), and all or substantially all of the canine frame.

The term "fully canine antibody" refers to an antibody that comprises canine immunoglobulin protein sequences only. A fully canine antibody may contain murine carbohydrate chains if produced in a mouse, in a mouse cell, or in a hybridoma derived from a mouse cell. Similarly, "mouse antibody" refers to an antibody that comprises mouse immunoglobulin sequences only. Alternatively, a fully canine antibody may contain rat carbohydrate chains if produced in a rat, in a rat cell, or in a hybridoma derived from a rat cell. Similarly, "rat antibody" refers to an antibody that comprises rat immunoglobulin sequences only.

The variable regions of each light/heavy chain pair form the antibody binding site. Thus, in general, an intact antibody has two binding sites. Except in bifunctional or bispecific antibodies, the two binding sites are, in general, the same.

Typically, the variable domains of both the heavy and light chains comprise three hypervariable regions, also called complementarity determining regions (CDRs), located within relatively conserved framework regions (FR). The CDRs are usually flanked by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain for human antibodies is, generally, in accordance with the definitions of *Sequences of Proteins of Immunological Interest*, Kabat, et al.; National Institutes of Health, Bethesda, Md.; 5$^{th}$ ed.; NIH Publ. No. 91-3242 (1991); Kabat, *Adv. Prot. Chem.* 32:1-75 (1978); Kabat, et al., *J. Biol. Chem.* 252:6609-6616 (1977); Chothia, et al., *J. Mol. Biol.* 196:901-917 (1987) or Chothia, et al., *Nature* 342:878-883 (1989)].

As used herein, the term "hypervariable region" refers to the amino acid residues of an antibody that are responsible for antigen-binding. The hypervariable region comprises amino acid residues from a "complementarity determining region" or "CDR" (i.e. CDRL1, CDRL2 and CDRL3 in the light chain variable domain and CDRH1, CDRH2 and CDRH3 in the heavy chain variable domain). [See Kabat et al. *Sequences of Proteins of Immunological Interest,* 5th Ed. Public Health Service, National Institutes of Health, Bethesda, Md. (1991), definining the CDR regions of a human antibody by sequence; see also Chothia and Lesk, *J. Mol. Biol.* 196: 901-917 (1987) defining the CDR regions of an antibody by structure]. As used herein, the term "framework" or "FR" residues refers to those variable domain residues other than the hypervariable region residues defined herein as CDR residues.

As used herein the term "canine frame" refers to the amino acid sequence of the heavy chain and light chain of a canine antibody other than the hypervariable region residues defined herein as CDR residues. In both chains, the amino acid sequences of the native canine CDRs are replaced with the corresponding foreign CDRs (e.g., those from a mouse antibody). Optionally the heavy and/or light chains of the canine antibody may contain some foreign non-CDR residues, e.g., so as to preserve the conformation of the foreign CDRs within the canine antibody, and/or to modify the Fc function, as exemplified below.

As used herein, an "anti-canine PD-1 antibody" refers to an antibody that was raised against canine PD-1 (in a mammal such as a mouse or rabbit) and that specifically binds to canine PD-1. An antibody that "specifically binds to canine PD-1," or an antibody that "specifically binds to a polypeptide comprising the amino acid sequence of SEQ ID NO: 114", is an antibody that exhibits preferential binding to canine PD-1 as compared to other antigens, e.g., binds canine PD-1 "with specificity". The binding does not require absolute binding specificity. An anti-canine PD-1 antibody is considered "specific" for canine PD-1 if its binding is determinative of the presence of canine PD-1 in a sample, or if it is capable of altering the activity of canine PD-1 without unduly interfering with the activity of other molecules in a canine sample, e.g., without producing undesired results such as false positives in a diagnostic context or side effects in a therapeutic context. The degree of specificity necessary for an anti-canine PD-1 antibody may depend on the intended use of the antibody, and at any rate is defined by its suitability for use for an intended purpose.

Accordingly the present invention provides caninized anti-canine PD-1 antibodies or antigen binding fragments thereof (including in isolated form) that bind canine PD-1 (e.g., with specificity) and uses of such antibodies or fragments thereof. In specific embodiments murine anti-canine PD-1 CDRs from murine anti-canine PD-1 antibodies are provided that have been shown to both bind canine PD-1 and to block the binding of canine PD-1 to at least one of its ligands, e.g., canine PD-L1. These CDRs can be inserted into a modified canine frame of the present invention to make a caninized murine anti-canine PD-1 antibody, as exemplified herein.

More specifically, a "caninized murine anti-PD-1 antibody" of the present invention refers to an antibody that comprises the three heavy chain CDRs and the three light chain CDRs from a murine anti-canine PD-1 antibody together with a canine frame or a modified canine frame. A modified canine frame comprises one or more amino acids changes as exemplified herein that further optimize the effectiveness of the caninized antibody, e.g., to augment, reduce, or eliminate antibody effector functions, to increase its binding to the canine antigen, e.g., canine PD-1, and/or increase its ability to block the binding of the canine antigen, e.g., canine PD-1, to its natural binding partner, (e.g., canine PD-L1 in the case where the antigen is canine PD-1).

"Homology" refers to sequence similarity between two polynucleotide sequences or between two polypeptide sequences when they are optimally aligned. When a position in both of the two compared sequences is occupied by the same base or amino acid monomer subunit, e.g., if a position in each of two DNA molecules is occupied by adenine, then the molecules are homologous at that position. The percent of homology is the number of homologous positions shared by the two sequences divided by the total number of positions compared×100. For example, if 6 of 10 of the positions in two sequences are matched or homologous when the sequences are optimally aligned then the two sequences are 60% homologous. Generally, the comparison is made when two sequences are aligned to give maximum percent homology.

"Isolated nucleic acid molecule" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or even up to twenty or more other proteins or portions or fragments thereof, or may include operably linked regulatory sequences that control expression of the coding region of the recited nucleic acid sequences, and/or may include vector sequences.

The phrase "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous.

Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that not all progeny will have precisely identical DNA content, due to deliberate or inadvertent mutations. Mutant progeny that have the same function or biological activity as screened for in the originally transformed cell are included. Where distinct designations are intended, it will be clear from the context.

As used herein, "germline sequence" refers to a sequence of unrearranged immunoglobulin DNA sequences. Any suitable source of unrearranged immunoglobulin sequences may be used. Human germline sequences may be obtained, for example, from JOINSOLVER® germline databases on the website for the National Institute of Arthritis and Musculoskeletal and Skin Diseases of the United States National Institutes of Health. Mouse germline sequences may be obtained, for example, as described in Giudicelli et al. [*Nucleic Acids Res.* 33:D256-D261 (2005)].

Properties of Caninized Antibodies

In canine, there are four IgG heavy chains referred to as A, B, C, and D. These heavy chains represent four different subclasses of dog IgG, which are referred to as IgGA, IgGB, IgGC and IgGD. The DNA and amino acid sequences of these four heavy chains were first identified by Tang et al. [*Vet. Immunol. Immunopathol.* 80: 259-270 (2001)]. The amino acid and DNA sequences for these heavy chains are also available from the GenBank data bases. For example, the amino acid sequence of IgGA heavy chain has accession number AAL35301.1, IgGB has accession number AAL35302.1, IgGC has accession number AAL35303.1, and IgGD has accession number (AAL35304.1). Canine antibodies also contain two types of light chains, kappa and lambda. The DNA and amino acid sequence of these light chains can be obtained from GenBank Databases. For example the kappa light chain amino acid sequence has accession number ABY 57289.1 and the lambda light chain has accession number ABY 55569.1. In the present invention, the amino acid sequence for each of the four canine IgG Fc fragments is based on the identified boundary of CH1 and CH2 domains as determined by Tang et al, supra.

The development of a therapeutic monoclonal antibody is a complex process that entails coordination of a complex set of activities to generate the desired antibody. These include optimization of the antibody specificity, affinity, functional activity, expression level in engineered cell lines, long-term stability, elimination or enhancement of effector functions and development of commercially viable manufacturing and purification methods. Considering the objectives of the present invention and aside from the capacity to activate cells of the immune systems, a caninized or canine monoclonal antibody against canine PD-1 optimally has three additional attributes:

1. lack of effector functions such as antibody-dependent cytotoxicity (ADCC) and complement-dependent cytotoxicity (CDC),
2. relatively long half-life in vivo; and
3. be readily purified on a large scale using industry standard technologies such as that based on protein A chromatography.

None of the naturally occurring canine IgG subclasses satisfy all these criteria. For example, IgGB can be purified using protein A, but has a high level of ADCC activity. IgGC also has considerable ADCC activity. On the other hand, IgGA binds weakly to protein A, but displays undesirable ADCC activity. Moreover, neither IgGC nor IgGD can be purified on protein A columns, although IgGD display no ADCC activity. Additionally IgGC has short serum half-life as it does not bind to the canine FcRn receptor. The present invention overcomes this difficulty by providing modified canine IgG antibodies specific to canine antigens, e.g., canine PD-1; such antibodies lack effector functions such as ADCC and CDC, display relatively long half-life, and can be easily of purified using industry standard protein A chromatography.

Heretofore, genetically modified canine IgGs that lacked both ADCC and CDC effector functions and in addition, could be purified by protein A chromatography had not been previously described. As disclosed herein, a single substitution at a position in canine IgG that is analogous to that of human and mouse IgG, such as N297A or D265A, does not completely eliminate both ADCC and CDC effector functions in the corresponding canine antibody. For example, while each of the substitutions N297 and D265 in human or murine antibodies results in abrogation of binding to $Fc_\gamma$ receptor and C1q, neither substitution alone completely abrogated the binding of canine antibodies to C1q. Instead, as further disclosed below, in order to eliminate both ADCC and CDC in canine antibodies of IgGB or IgGC sub-classes, it proved necessary to make a double substitution in the Fc of the canine antibody combining both an asparagine-to-alanine and an aspartic acid-to-alanine substitution. Moreover, completely unexpectedly, one substitution that had been shown to reduce effector functions in human antibodies actually resulted in an increase in binding of corresponding canine IgG to $Fc_\gamma R$ and C1q.

In order to generate variants of canine IgGB and IgGC that lack effector functions, modified canine IgGB or modified canine IgGC heavy chains can be generated. A total of seven amino acid residues which are present in both of these canine fragment crystallizable regions (cFcs) were identified for such possible substitution, These seven amino acid residues are: P4, D31, N63, G64, T65, A93, and P95 for both the amino acid sequence of SEQ ID NO: 130 for the Fc of canine IgGB; and the amino acid sequence of SEQ ID NO: 132 for the Fc of canine IgGC. Accordingly, the amino acid sequence of SEQ ID NO: 2 differs from that of SEQ ID NO: 130 by having the amino acid residues at positions: 4, 31, 63, 64, 65, 93, and 95, which are proline (P), aspartic acid (D), asparagine (N), glycine (G), threonine (T), alanine (A), and proline (P), respectively, in the amino acid sequence of SEQ ID NO: 130 as "X" (or "Xaa" in the three letter code) for all seven positions, signifying that these seven amino acid positions can be any of the twenty natural amino acids (see list in column 1 of Table 1 below). Similarly, the amino acid sequence of SEQ ID NO: 4 differs from that of SEQ ID NO: 132 by having the amino acid residues at positions 4, 31, 63, 64, 65, 93, and 95 are listed as "X" (or "Xaa" in the three letter code) for all seven positions, signifying that these seven amino acid positions can be any of the twenty natural amino acids. The amino acid sequence of SEQ ID NO: 2 is encoded by the nucleotide sequence of SEQ ID NO: 1, whereas the amino acid sequence of SEQ ID NO: 4 is encoded by the nucleotide sequence of SEQ ID NO: 3.

In one embodiment, the cFc comprises the amino acid sequence of SEQ ID NO: 130 with the following substitutions P4(A, G, or S), D31(A, G, or S) N63(A, G, or S), G64(A or P), T65(A, G, or S), A93(G or S), and P95(A, G, or S); in which P4 (A G, or S) signifies that the proline residue at position 4 is replaced by either an alanine, glycine, or serine residue, and similarly G64(P or A) signifies that the glycine residue at position 64 is replaced by either a proline or an alanine residue, etc.). In a particular embodiment, the cFc comprises the amino acid sequence of SEQ ID NO: 130 with the following substitutions: P4A, D31A, N63A, G64P, T65A, A93G, and P95A.

In a related embodiment, the cFc comprises the amino acid sequence of SEQ ID NO: 4, which contains 7 amino acids designated as Xaa, with the following amino acid residues: A4, A31, A63, G64, T65, G93, and A95, i.e., the amino acid sequence of SEQ ID NO: 132 with the following five (5) amino acid residue changes: P4A, D31A, N63A, A93G, and P95A and the remaining two amino acid residues of the seven, G64 and T65, being retained from the amino acid sequence of SEQ ID NO: 132.

The amino acid sequences of SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, and SEQ ID NO: 66 all contain "X" (or "Xaa" in the three letter code) at seven amino acid positions, signifying that these seven amino acid positions can be any of the twenty natural amino acids listed in column 1 of Table 1 below. Notably SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, and SEQ ID NO: 66 comprise either the amino acid sequence of SEQ ID NO: 2 or that of SEQ ID NO: 4 within their respective sequences. Specific examples of the amino acid residues at one or more of these seven positions of the amino acid sequences are delineated above and below, and are therefore included within the genus of the individual amino acid sequences of SEQ ID NO: 2, SEQ ID NO: 4, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, and SEQ ID NO: 66, as well as within the caninized antibodies that comprise these sequences.

Table 10 provided below, specifically correlates the seven amino acid positions that can be replaced, as disclosed herein, of the cIgGB Fc (SEQ ID NO: 130 and SEQ ID NO: 2) and the cIgGC Fc (SEQ ID NO: 132 and SEQ ID NO: 4) with that of the full length canine heavy chains that comprises these cFc amino acid sequences, i.e., SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, and SEQ ID NO: 66. Accordingly, the actual position in the full length sequence IgGB or IgGC can be readily coordinated with that of the cFc that it comprises through the use of Table 10 below.

In particular embodiments, the heavy chain of an antibody comprises the amino acid sequence of SEQ ID NO: 40, 52, 56, or 64 comprising (i) P, A, G, or S at position 239, (ii) D, A, G, or S at position 266, (iii) N, A, G, or S at position 298, (iv) G, P, or A at position 299, (v) T, A, G, or S at position 300, (vi) A, G, or S at position 328, and (vii) P, A, G, or S at position 330. In other embodiments, the heavy chain of an antibody comprises the amino acid sequence of SEQ ID NO: 42, 54, 58, or 66 comprising (i) P, A, G, or S at position 237, (ii) D, A, G, or S at position 264, (iii) N, A, G, or S at position 296, (iv) G, P, or A at position 297, (v) T, A, G, or S at position 298, (vi) A, G, or S at position 326, and (vii) P, A, G, or S at position 328. In yet other embodiments, the heavy chain of an antibody comprises the amino acid sequence of SEQ ID NO: 44, 50, or 60 comprising (i) P, A, G, or S at position 244, (ii) D, A, G, or S at position 271, (iii) N, A, G, or S at position 303, (iv) G, P, or A at position 304, (v) T, A, G, or S at position 305, (vi) A, G, or S at position 333, and (vii) P, A, G, or S at position 335. In still other embodiments, the heavy chain of an antibody comprises the amino acid sequence of SEQ ID NO: 46 or 62 comprising (i) P, A, G, or S at position 242, (ii) D, A, G, or S at position 269, (iii) N, A, G, or S at position 301, (iv) G, P, or A at position 302, (v) T, A, G, or S at position 303, (vi) A, G, or S at position 331, and (vii) P, A, G, or S at position 333. In yet other embodiments, the heavy chain of an antibody comprises the amino acid sequence of SEQ ID NO: 48 comprising (i) P, A, G, or S at position 246, (ii) D, A, G, or S at position 273, (iii) N, A, G, or S at position 305, (iv) G, P, or A at position 306, (v) T, A, G, or S at position 307, (vi) A, G, or S at position 335, and (vii) P, A, G, or S at position 337.

The present invention also provides modified canine IgGDs which comprise a hinge region from either IgGA, IgGB, or IgGC in place of its natural IgGD hinge region. Alternatively, the IgGD hinge region can be genetically modified by replacing a serine residue with a proline residue as shown in Table 5. Such modifications can lead to a canine IgGD lacking fab arm exchange. The modified canine IgGDs can be constructed using standard methods of recombinant DNA technology [e.g., Maniatis et al., *Molecular Cloning, A Laboratory Manual* (1982)]. In order to construct these variants, the nucleic acids encoding the amino acid sequence of canine IgGD can be modified so that it encodes the modified IgGDs. The modified nucleic acid sequences are then cloned into expression plasmids for protein expression. The nucleic acids encoding the canine IgGD Fcs with the substitute hinge region are exemplified by nucleotide sequences of SEQ ID NOs: 7, 9, and 11 which encode the amino acid sequences of SEQ ID NOs: 8, 10, and 12. A nucleic acid encoding a canine IgGD Fc with a modified IgGD hinge region comprises the nucleotide sequence of SEQ ID NO: 5 which encodes the amino acid sequence of SEQ ID NO: 6.

The present invention further provides full length canine heavy chains that can be matched with corresponding light chains to make a caninized antibody. Accordingly, the present invention further provides caninized murine anti-canine antigen antibodies (including isolated caninized murine anti-canine PD-1 antibodies) and methods of use of the antibodies or antigen binding fragments thereof in the treatment of disease e.g., the treatment of cancer in canines.

Moreover, the present invention provides caninized murine anti-canine PD-1 antibodies or antigen binding fragments that bind to canine PD-1 and block the binding of canine PD-1 to canine PD-L1. In certain embodiments the caninized murine anti-canine PD-1 antibodies comprise a modified canine IgGB Fc, modified canine IgGC Fc, or a modified canine IgGD lacking fab arm exchange as described herein.

The antibody or antigen binding fragment thereof that binds the canine antigen, e.g., canine PD-1, can comprise one, two, three, four, five, or six of the complementarity determining regions (CDRs) of the murine anti-canine antibody as described herein. The one, two, three, four, five, or six CDRs may be independently selected from the CDR sequences of those provided below. In a further embodiment, the antibody or antigen-binding fragment thereof that binds canine PD-1 comprises a canine antibody kappa light chain comprising a murine light chain CDR-1, CDR-2 and/or CDR-3 and a canine antibody heavy chain IgG comprising a murine heavy chain CDR-1, CDR-2 and/or CDR-3. Accordingly, the present invention further provides full length canine heavy chains then can be matched e.g., with the corresponding light chains to make a caninized antibody [see Table 2 below, in which the sequences of seven sets of CDRs of murine anti-canine PD-1, e.g., 1B5, 2G9, 2H9, 3B6, 4D12, 5G5, and 7C9 are provided].

In other embodiments, the invention provides antibodies or antigen binding fragments thereof that bind PD-1 with specificity and have canine antibody kappa light chains comprising one to six different CDRs comprising at least 80%, 85%, 90%, 95%, 98% or 99% sequence identity with the amino acid sequences of SEQ ID NOs: 13, 14, 15, 16, 17, 18, 19, 20, 21, 22, 23, 24, 25, and/or 26 and canine antibody heavy chain IgG comprising one to six different CDRs comprising at least 80%, 85%, 90%, 95%, 98% or 99% sequence identity with the amino acid sequences of SEQ ID NOs: 27, 28, 29, 30, 31, 32, 33, 34, 35, 36, 37, 38, and/or 146, while still exhibiting the desired binding and functional properties. In another embodiment the antibody or antigen binding fragment of the present invention comprises a canine frame comprising of a combination of IgG heavy chain sequence with a kappa light chain having one or more of the above-mentioned CDR amino acid sequences with 0, 1, 2, 3, 4, or 5 conservative or non-conservative amino acid substitutions, while still exhibiting the desired binding and functional properties.

Sequence identity refers to the degree to which the amino acids of two polypeptides are the same at equivalent positions when the two sequences are optimally aligned. As used herein one amino acid sequence is 100% "identical" to a second amino acid sequence when the amino acid residues of both sequences are identical. Accordingly, an amino acid sequence is 50% "identical" to a second amino acid sequence when 50% of the amino acid residues of the two amino acid sequences are identical. The sequence comparison is performed over a contiguous block of amino acid residues comprised by a given protein, e.g., a protein, or a portion of the polypeptide being compared. In a particular embodiment, selected deletions or insertions that could otherwise alter the correspondence between the two amino acid sequences are taken into account.

Sequence similarity includes identical residues and non-identical, biochemically related amino acids. Biochemically related amino acids that share similar properties and may be interchangeable are discussed "Conservatively modified variants" or "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity of the protein. Those of skill in this art recognize that, in general, single amino acid substitutions in non-essential regions of a polypeptide do not substantially alter biological activity [see, e.g., Watson et al., *Molecular Biology of the Gene*, The Benjamin/Cummings Pub. Co., p. 224 (4th Ed.; 1987)]. In addition, substitutions of structurally or functionally similar amino acids are less likely to disrupt biological activity. Exemplary conservative substitutions are set forth in Table I directly below.

TABLE 1

EXEMPLARY CONSERVATIVE AMINO ACID SUBSTITUTIONS

| Original residue | Conservative substitution |
| --- | --- |
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala; Gly |
| Ser (S) | Thr |
| Thr (T) | Ser |
| Trp (W) | Tyr; Phe |
| Tyr (Y) | Trp; Phe |
| Val (V) | Ile; Leu |

Function-conservative variants of the antibodies of the invention are also contemplated by the present invention. "Function-conservative variants," as used herein, refers to antibodies or fragments in which one or more amino acid residues have been changed without altering a desired property, such an antigen affinity and/or specificity. Such variants include, but are not limited to, replacement of an amino acid with one having similar properties, such as the conservative amino acid substitutions of Table I above.

Nucleic Acids,

The present invention further comprises the nucleic acids encoding the immunoglobulin chains of caninized murine anti-canine PD-1 antibodies and antigen binding fragments thereof disclosed herein (see Examples below).

Also included in the present invention are nucleic acids that encode immunoglobulin polypeptides comprising amino acid sequences that are at least about 70% identical, preferably at least about 80% identical, more preferably at least about 90% identical and most preferably at least about 95% identical (e.g., 95%, 96%, 97%, 98%, 99%, 100%) to the amino acid sequences of the CDRs and/or canine cFc's and/or antibodies provided herein when the comparison is performed by a BLAST algorithm wherein the parameters of the algorithm are selected to give the largest match between the respective sequences over the entire length of the respective reference sequences. The present invention further provides nucleic acids that encode immunoglobulin polypeptides comprising amino acid sequences that are at least about 70% similar, preferably at least about 80% similar, more preferably at least about 90% similar and most preferably at least about 95% similar (e.g., 95%, 96%, 97%, 98%, 99%, 100%) to any of the reference amino acid sequences when the comparison is performed with a BLAST algorithm, wherein the parameters of the algorithm are selected to give the largest match between the respective sequences over the entire length of the respective reference sequences.

As used herein, nucleotide and amino acid sequence percent identity can be determined using C, MacVector (MacVector, Inc. Cary, N.C. 27519), Vector NTI (Informax, Inc. Md.), Oxford Molecular Group PLC (1996) and the Clustal W algorithm with the alignment default parameters, and default parameters for identity. These commercially available programs can also be used to determine sequence similarity using the same or analogous default parameters. Alternatively, an Advanced Blast search under the default filter conditions can be used, e.g., using the GCG (Genetics Computer Group, Program Manual for the GCG Package, Version 7, Madison, Wis.) pileup program using the default parameters.

The following references relate to BLAST algorithms often used for sequence analysis: BLAST ALGORITHMS: Altschul, S. F., et al., *J. Mol. Biol.* 215:403-410 (1990); Gish, W., et al., *Nature Genet.* 3:266-272 (1993); Madden, T. L., et al., *Meth. Enzymol.* 266:131-141(1996); Altschul, S. F., et al., *Nucleic Acids Res.* 25:3389-3402 (1997); Zhang, J., et al., *Genome Res.* 7:649-656 (1997); Wootton, J. C., et al., *Comput. Chem.* 17:149-163 (1993); Hancock, J. M. et al., *Comput. Appl. Biosci.* 10:67-70 (1994); ALIGNMENT SCORING SYSTEMS: Dayhoff, M. O., et al., "A model of evolutionary change in proteins." in *Atlas of Protein Sequence and Structure*, vol. 5, suppl. 3. M. O. Dayhoff (ed.), pp. 345-352, (1978); Natl. Biomed. Res. Found., Washington, D.C.; Schwartz, R. M., et al., "Matrices for detecting distant relationships." in Atlas of Protein Sequence and Structure, vol. 5, suppl. 3." (1978), M. O. Dayhoff (ed.), pp. 353-358 (1978), *Natl. Biomed. Res. Found.*, Washington, D.C.; Altschul, S. F., *J. Mol. Biol.* 219:555-565 (1991); States, D. J., et al., *Methods* 3:66-70(1991); Henikoff, S., et al., *Proc. Natl. Acad. Sci. USA* 89:10915-10919 (1992); Altschul, S. F., et al., *J. Mol. Evol.* 36:290-300 (1993); ALIGNMENT STATISTICS: Karlin, S., et al., *Proc. Natl. Acad. Sci. USA* 87:2264-2268 (1990); Karlin, S., et al., *Proc. Natl. Acad. Sci. USA* 90:5873-5877 (1993); Dembo, A., et al., *Ann. Prob.* 22:2022-2039 (1994); and Altschul, S. F. "Evaluating the statistical significance of multiple distinct local alignments." in *Theoretical and Computational Methods in Genome Research* (S. Suhai, ed.), pp. 1-14, Plenum, New York (1997).

This present invention also provides expression vectors comprising the nucleic acids (including isolated nucleic acids) of the invention, wherein the nucleic acid is operably linked to control sequences that are recognized by a host cell when the host cell is transfected with the vector. Also provided are host cells comprising an expression vector of the present invention and methods for producing the antibody or antigen binding fragment thereof disclosed herein comprising culturing a host cell harboring an expression vector encoding the antibody or antigen binding fragment in culture medium, and isolating the antigen or antigen binding fragment thereof from the host cell or culture medium.

A caninized murine anti-canine PD-1 antibody for example, can be produced recombinantly by methods that are known in the field. Mammalian cell lines available as hosts for expression of the antibodies or fragments disclosed herein are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines. Mammalian host cells include human, mouse, rat, dog, monkey, pig, goat, bovine, horse, and hamster cells. Cell lines of particular preference are selected through determining which cell lines have high expression levels. Other cell lines that may be used are insect cell lines, such as Sf9 cells, amphibian cells, bacterial cells, plant cells and fungal cells. When recombinant expression vectors encoding the heavy chain or antigen-binding portion or fragment thereof, the light chain and/or antigen-binding fragment thereof are introduced into mammalian host cells, the antibodies are produced by culturing the host cells for a period of time sufficient to allow for expression of the antibody in the host cells or, more preferably, secretion of the antibody into the culture medium in which the host cells are grown.

Antibodies can be recovered from the culture medium using standard protein purification methods. Further, expression of antibodies of the invention (or other moieties therefrom) from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4.

In general, glycoproteins produced in a particular cell line or transgenic animal will have a glycosylation pattern that is characteristic for glycoproteins produced in the cell line or transgenic animal. Therefore, the particular glycosylation pattern of an antibody will depend on the particular cell line or transgenic animal used to produce the antibody. However, all antibodies encoded by the nucleic acid molecules provided herein, or comprising the amino acid sequences provided herein, comprise the instant invention, independent of the glycosylation pattern that the antibodies may have. Similarly, in particular embodiments, antibodies with a glycosylation pattern comprising only non-fucosylated N-glycans may be advantageous, because these antibodies have been shown to typically exhibit more potent efficacy than their fucosylated counterparts both in vitro and in vivo [See for example, Shinkawa et al., *J. Biol. Chem.* 278: 3466-3473 (2003); U.S. Pat. Nos. 6,946,292 and 7,214,775].

The present invention further includes antibody fragments of the caninized murine anti-canine PD-1 antibodies disclosed herein. The antibody fragments include $F(ab)_2$ fragments, which may be produced by enzymatic cleavage of an IgG by, for example, pepsin. Fab fragments may be produced by, for example, reduction of $F(ab)_2$ with dithiothreitol or mercaptoethylamine. A Fab fragment is a $V_L$-$C_L$ chain appended to a $V_H$-$C_{H1}$ chain by a disulfide bridge. A $F(ab)_2$ fragment is two Fab fragments which, in turn, are appended by two disulfide bridges. The Fab portion of an $F(ab)_2$ molecule includes a portion of the $F_c$ region between which disulfide bridges are located. An $F_V$ fragment is a $V_L$ or $V_H$ region.

In one embodiment, the antibody or antigen binding fragment comprises a heavy chain constant region, e.g., a canine constant region, such as IgGA, IgGB, IgGC and IgGD canine heavy chain constant region or a variant thereof. In another embodiment, the antibody or antigen binding fragment comprises a light chain constant region, e.g., a canine light chain constant region, such as lambda or kappa canine light chain region or variant thereof. By way of example, and not limitation the canine heavy chain constant region can be from IgGB and the canine light chain constant region can be from kappa.

Antibody Engineering

Caninized murine anti-canine PD-1 antibodies of the present invention can be engineered to include modifications in the canine frame of a parental (i.e., canine) monoclonal antibody, e.g. to improve the properties of the antibody, as detailed below.

The cross-blocking caninized antibodies and antigen-binding fragments thereof discussed herein can be identified based on their ability to cross-compete with any of IB5, 3B6, 4D12, 7C9, 2H9, 5G5, and/or 2G9 in standard binding assays (e.g., BIACore®, ELISA, as exemplified below, or flow cytometry). For example, standard ELISA assays can be used in which a recombinant canine PD-1 protein is immobilized on the plate, one of the antibodies is fluorescently labeled and the ability of non-labeled antibodies to compete off the binding of the labeled antibody is evaluated. Additionally or alternatively, BIAcore® analysis can be used to assess the ability of the antibodies to cross-compete. The ability of a test antibody to inhibit the binding of, for example, IB5, 3B6, 4D12, 7C9, 2H9, 5G5, and/or 2G9, to canine PD-1 demonstrates that the test antibody can compete with IB5, 3B6, 4D12, 7C9, 2H9, 5G5, and/or 2G9 for binding to canine PD-1 and thus, may, in some cases, bind to the same epitope on canine PD-1 as IB5, 3B6, 4D12, 7C9, 2H9, 5G5, and/or 2G9. As stated above, antibodies and fragments that bind to the same epitope as any of the anti-canine PD-1 antibodies or fragments of the present invention also form part of the present invention.

Pharmaceutical Compositions and Administration

To prepare pharmaceutical or sterile compositions of a caninized murine anti-canine PD-1 antibody or antigen binding fragment thereof it can be admixed with a pharmaceutically acceptable carrier or excipient. [See, e.g., *Remington's Pharmaceutical Sciences and U.S. Pharmacopeia: National Formulary*, Mack Publishing Company, Easton, Pa. (1984)].

Formulations of therapeutic and diagnostic agents may be prepared by mixing with acceptable carriers, excipients, or stabilizers in the form of, e.g., lyophilized powders, slurries, aqueous solutions or suspensions [see, e.g., Hardman, et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, N.Y.]. In one embodiment, anti-PD-1 antibodies of the present invention are diluted to an appropriate concentration in a sodium acetate solution pH 5-6, and NaCl or sucrose is added for tonicity. Additional agents, such as polysorbate 20 or polysorbate 80, may be added to enhance stability.

Toxicity and therapeutic efficacy of the antibody compositions, administered alone or in combination with another agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index ($LD_{50}/ED_{50}$). In particular aspects, antibodies exhibiting high therapeutic indices are desirable. The data obtained from these cell culture assays and animal studies can be used in formulating a range of dosage for use in canines. The dosage of such compounds lies preferably within a range of circulating concentrations that include the $ED_{50}$ with little or no toxicity. The dosage may vary within this range depending upon the dosage form employed and the route of administration.

The mode of administration can vary. Suitable routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial. In particular embodiments, the caninized murine anti-canine PD-1 antibody or antigen binding fragment thereof can be administered by an invasive route such as by injection. In further embodiments of the invention, a murine anti-canine PD-1 antibody or antigen binding fragment thereof, or pharmaceutical composition thereof, is administered intravenously, subcutaneously, intramuscularly, intraarterially, intratumorally, or by inhalation, aerosol delivery. Administration by non-invasive routes (e.g., orally; for example, in a pill, capsule or tablet) is also within the scope of the present invention.

The pharmaceutical compositions disclosed herein may also be administered by infusion. Examples of well-known implants and modules form administering pharmaceutical compositions include: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art.

Alternately, one may administer a caninized murine anti-canine PD-1 antibody in a local rather than systemic manner, for example, via injection of the antibody directly into an arthritic joint or pathogen-induced lesion characterized by immunopathology, often in a depot or sustained release formulation. Furthermore, one may administer the antibody in a targeted drug delivery system, for example, in a liposome coated with a tissue-specific antibody, targeting, for example, arthritic joint or pathogen-induced lesion characterized by immunopathology. The liposomes will be targeted to and taken up selectively by the afflicted tissue.

The administration regimen depends on several factors, including the serum or tissue turnover rate of the therapeutic antibody, the level of symptoms, the immunogenicity of the therapeutic antibody, and the accessibility of the target cells in the biological matrix. Preferably, the administration regimen delivers sufficient therapeutic antibody to effect improvement in the target disease state, while simultaneously minimizing undesired side effects. Accordingly, the amount of biologic delivered depends in part on the particular therapeutic antibody and the severity of the condition being treated. Guidance in selecting appropriate doses of therapeutic antibodies is available [see, e.g., Wawrzynczak *Antibody Therapy*, Bios Scientific Pub. Ltd, Oxfordshire, UK (1996); Kresina (ed.) *Monoclonal Antibodies, Cytokines and Arthritis*, Marcel Dekker, New York, N.Y. (1991); Bach (ed.) *Monoclonal Antibodies and Peptide Therapy in Autoimmune Diseases*, Marcel Dekker, New York, N.Y. (1993); Baert, et al. *New Engl. J. Med.* 348:601-608 (2003); Milgrom et al. *New Engl. J. Med.* 341:1966-1973 (1999); Slamon et al. *New Engl. J. Med.* 344:783-792 (2001); Beniaminovitz et al. *New Engl. J. Med.* 342:613-619 (2000); Ghosh et al. *New Engl. J. Med.* 348:24-32 (2003); Lipsky et al. *New Engl. J. Med.* 343:1594-1602 (2000)].

Determination of the appropriate dose is made by the veterinarian, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

Antibodies or antigen binding fragments thereof disclosed herein may be provided by continuous infusion, or by doses administered, e.g., daily, 1-7 times per week, weekly, biweekly, monthly, bimonthly, quarterly, semiannually, annually etc. Doses may be provided, e.g., intravenously, subcutaneously, topically, orally, nasally, rectally, intramuscular, intracerebrally, intraspinally, or by inhalation. A total weekly dose is generally at least 0.05 µg/kg body weight, more generally at least 0.2 µg/kg, 0.5 µg/kg, 1 µg/kg, 10 µg/kg, 100 µg/kg, 0.25 mg/kg, 1.0 mg/kg, 2.0 mg/kg, 5.0 mg/ml, 10 mg/kg, 25 mg/kg, 50 mg/kg or more [see, e.g., Yang, et al. *New Engl. J. Med.* 349:427-434 (2003); Herold, et al. *New Engl. J. Med.* 346:1692-1698 (2002); Liu, et al. *J. Neurol. Neurosurg. Psych.* 67:451-456 (1999); Portielji, et al. *Cancer Immunol. Immunother.* 52:133-144 (2003)]. Doses may also be provided to achieve a pre-determined target concentration of a caninized murine anti-canine PD-1 antibody in the subject's serum, such as 0.1, 0.3, 1, 3, 10, 30, 100, 300 µg/ml or more. In other embodiments, a caninized murine anti-canine PD-1 antibody of the present invention is administered subcutaneously or intravenously, on a weekly, biweekly, "every 4 weeks," monthly, bimonthly, or quarterly basis at 10, 20, 50, 80, 100, 200, 500, 1000 or 2500 mg/subject.

As used herein, "inhibit" or "treat" or "treatment" includes a postponement of development of the symptoms associated with a disorder and/or a reduction in the severity of the symptoms of such disorder. The terms further include ameliorating existing uncontrolled or unwanted symptoms, preventing additional symptoms, and ameliorating or preventing the underlying causes of such symptoms. Thus, the terms denote that a beneficial result has been conferred on a vertebrate subject with a disorder, disease or symptom, or with the potential to develop such a disorder, disease or symptom.

As used herein, the terms "therapeutically effective amount", "therapeutically effective dose" and "effective amount" refer to an amount of a caninized murine anti-canine PD-1 antibody or antigen binding fragment thereof of the present invention that, when administered alone or in combination with an additional therapeutic agent to a cell, tissue, or subject, is effective to cause a measurable improvement in one or more symptoms of a disease or condition or the progression of such disease or condition. A therapeutically effective dose further refers to that amount of the binding compound sufficient to result in at least partial amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. An effective amount of a therapeutic will result in an improvement of a diagnostic measure or parameter by at least 10%; usually by at least 20%; preferably at least about 30%; more preferably at least 40%, and most preferably by at least 50%. An effective amount can also result in an improvement in a subjective measure in cases where subjective measures are used to assess disease severity.

Other Combination Therapies

As previously described, a caninized murine anti-canine PD-1 antibody or antigen binding fragment thereof may be coadministered with one or other more therapeutic agents (such as a chemotherapeutic agent). The antibody may be linked to the agent (as an immunocomplex) or can be administered separately from the agent. In the latter case (separate administration), the antibody can be administered before, after or concurrently with the agent or can be co-administered with other known therapies.

Kits

Further provided are kits comprising one or more components that include, but are not limited to, an antibody or antigen binding fragment, as discussed herein, which specifically binds PD-1 (e.g., a caninized murine anti-canine PD-1 antibody or antigen binding fragment thereof) in association with one or more additional components including, but not limited to a pharmaceutically acceptable carrier and/or a chemotherapeutic agent, as discussed herein. The binding composition and/or the chemotherapeutic agent can be formulated as a pure composition or in combination with a pharmaceutically acceptable carrier, in a pharmaceutical composition.

In one embodiment, the kit includes a binding composition of the present invention (e.g., a caninized murine anti-canine PD-1 or a pharmaceutical composition thereof in one container (e.g., in a sterile glass or plastic vial) and a pharmaceutical composition thereof and/or a chemotherapeutic agent in another container (e.g., in a sterile glass or plastic vial).

If the kit includes a pharmaceutical composition for parenteral administration to a subject, the kit can also include a device for performing such administration. For example, the kit can include one or more hypodermic needles or other injection devices as discussed above. The kit can also include a package insert including information concerning the pharmaceutical compositions and dosage forms in the kit. Generally, such information aids pet owners and veterinarians in using the enclosed pharmaceutical compositions and dosage forms effectively and safely. For example, the following information regarding a combination of the invention may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references, manufacturer/distributor information and patent information.

As a matter of convenience, an antibody or specific binding agent disclosed herein can be provided in a kit, i.e., a packaged combination of reagents in predetermined amounts with instructions for performing the diagnostic or detection assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

EXAMPLES

Example 1

Canine PD-1 and PD-L1

Canine PD-1 and PD-L1:

U.S. provisional application No. 61/918,946, filed on Dec. 20, 2013, hereby incorporated by reference in its entireties, provides: the full length nucleotide sequence for canine PD-1 (cPD-1) of SEQ ID NO: 113 [SEQ ID NO: 133 includes the signal sequence]; the corresponding translated amino acid sequence of SEQ ID NO: 114 [SEQ ID NO: 134 includes the signal sequence]; the nucleotide sequence encoding the extra-cellular domain (ECD) of canine PD-1, SEQ ID NO: 115; the amino acid sequence of the ECD of canine PD-1, SEQ ID NO: 116; the nucleotide sequence of canine PD-1 ECD plus a GT linker and the Fc part of human IgG1 Fc gene, of SEQ ID NO: 117; and the amino acid sequence of the canine PD-1 ECD plus a GT linker and the Fc part of human IgG1 Fc gene, SEQ ID NO: 118 [SEQ ID NO: 137 includes the signal sequence].

U.S. provisional application No. 61/918,946 further provides: the full length nucleotide sequence for canine PD-L1 (cPD-L1) of SEQ ID NO: 119 [SEQ ID NO: 135 includes the signal sequence]; the corresponding translated amino acid sequence of SEQ ID NO: 120 [SEQ ID NO: 136 includes the signal sequence]; the nucleotide sequence encoding the extra-cellular domain (ECD) of canine PD-L1, SEQ ID NO: 121; the amino acid sequence of the ECD of canine PD-L1, SEQ ID NO: 122; the nucleotide sequence of canine PD-L1 ECD plus a GT linker and the Fc part of human IgG1 Fc gene, SEQ ID NO: 123; and the amino acid sequence of canine PD-L1 ECD plus a GT linker and the Fc part of human IgG1 Fc gene, SEQ ID NO: 124.

Example 2

Murine Anti-Canine PD-1 Antibodies

Generation of Anti-Canine PD1 Monoclonal Antibodies.

A total of three Balb/c mice were immunized multiple times (with 10 µg each time) over a 17 day period. The immunizing antigen was the canine PD-1 ECD-Fc fusion protein. Following immunization, serum was collected from each mouse and tested for reactivity with canine PD-1 ECD-HIS tagged protein. The spleen cells of the mouse with the highest serum anti-PD-1 ECD-HIS titer were fused to the myeloma P3X63 Ag8.653 cell line. Approximately 2 weeks following fusion, supernatant from putative hybridoma cells were tested by ELISA for their reactivity to the PD-1 ECD-HIS tagged protein. Hybridomas producing strong positive signals in the ELISA were subcloned by limiting dilution and tested again for reactivity to canine PD-1 ECD-HIS tagged protein.

Confirmation of Monoclonal Antibodies Reactivity Against Canine PD-1:

The reactivity of antibodies secreted by hybridomas to ECD of canine PD-1 was confirmed by ELISA. Hybridoma cells were cultured using CELLine bioreactors (Integrabiosciences) for 10-30 days. Cells were initially maintained in DMEM supplemented with 4 mM L-glutamine and 10% Ultra Low IgG fetal bovine serum (FBS) from Gibco. Hybridoma cells were seeded in CELLine bioreactor cell chambers at a cell density of approximately $2 \times 10^6$ cells/mL in 15 mL of the same medium with the FBS concentration increased to 20%. The outer chamber was filled with 1 L of nutrient medium (DMEM with 4 mM L-glutamine and 2% standard FBS). Hybridoma cells in the cell chamber were expanded to approximately $2.5 \times 10^7$ cells/mL over 3-7 days. Then, 10 mL of cell suspension was harvested from the cell chamber and replaced with fresh media to allow for re-expansion of cells and subsequent harvests. This procedure was repeated as necessary to obtain adequate amounts of mAb from each hybridoma clone. Harvested cell suspensions were centrifuged and the supernatants were filtered through 0.2 micron filter membranes. For antibody purification, each clone's supernatant was purified using a Protein G Sepharose 4 Fast flow 5 mL column (GE Healthcare) by gravity flow. After washing with Tris-EDTA (TE) buffer pH 8.0, bound antibodies were eluted using 0.1 M glycine buffer, pH 2.7, followed by pH neutralization using 1 M Tris, pH 8.0. Antibodies were concentrated and buffer exchanged into phosphate-buffered saline (PBS) using Centriprep® YM-10,10 kDa NMWL centrifugal filter units (Millipore). Antibody concentrations were quantified using spectrophotometry.

Purified anti-canine PD-1 mAbs were tested for reactivity with the HIS-tagged ECD domain of canine PD-1 by ELISA as follows: HIS-tagged canine PD-1 ECD protein is diluted to 10 µg/mL in coating buffer (Carbonate/Bicarbonate pH 9.0) and dispensed at 100 µl/well in 96-well flat bottomed ELISA plates (NUNC). The plates are incubated at 4° C. overnight. The plates are then washed three times with phosphate buffered saline containing 0.05% Tween® 20 (PBST). Next, 200 µl of blocking buffer (5% skim milk in PBST) is added to each well and the plates are incubated at 37° C. for 60 minutes. The plates are then washed three times with PBST. Next, 100 µl of test mAbs diluted in blocking buffer is added to the first wells of the appropriate columns. Test mAbs are then diluted two-fold to the appropriate plate position. Following incubation of the plates at 37° C. for 60 minutes, the plates are washed three times with PBST. Next, 100 µl per well of a 1:2,000 dilution of a horseradish peroxidase conjugated goat anti-mouse IgG (KPL) is added to the plates, which are then incubated at 37° C. for 60 minutes. Then the plates are washed three times with PBST, and 100 µl/well of 3,3',5,5' tetramethyl benzidine, (TMB) substrate (from KPL) is added to the plates. The color reaction is allowed to develop for 5-20 minutes at 37° C. prior to measuring absorbance at 650 nm.

CHO Cells Expressing Canine PD-1 Protein.

The full length canine PD-1 gene was cloned into plasmid p96793. In this plasmid the expression of the PD-1 protein is driven by an hCMV promoter. CHO DXB11 cells (dhfr−) were maintained in MEM-alpha (Gibco) supplemented with 10% fetal bovine serum. Transfection of CHO cells with plasmid p96793 was carried out in 75 cm² flasks containing approximately $6 \times 10^6$ cells by liposome-mediated gene delivery using Lipofectamine (Invitrogen). After 48 hours, cells were passaged into MEM-alpha medium without nucleosides, supplemented with 10% FBS and 400 µg/mL hygromycin B (selective medium). Limited-dilution cloning was performed on the pool of dhfr+, hygromycin resistant cells. Clones were assessed for expression of canine PD-1 by immunofluorescence assay. Briefly, cell monolayers were fixed in 96 well plates with 80% acetone. Fixed and dried cell monolayers were then incubated for 1 hour with a polyclonal goat anti-human PD-1 antibody (R&D Systems). Plates were washed with PBS, then incubated for 1 hour with a fluorescein-labeled rabbit anti-goat IgG antibody (KPL). Plates were washed with PBS. Clones exhibiting fluorescence were expanded and cell stocks were established.

Reactivity of Mouse mAbs Against Canine PD-1 Proteins Expressed on CHO Cells:

The reactivity of mouse anti-canine PD-1 mAbs with canine PD-1 on CHO cells was determined by a cell-based assay using CHO cells that express PD-1. Briefly, the CHO cells expressing canine PD-1 were cultured to 80-100% confluency in 50 µl media (DMEM/HAM's F12, 10% FBS). Next, 50 µl of media containing various concentrations of purified mAbs were added for 1 hour at 37° C. Following three washes with PBS-Tween, 100 µl of goat anti-mouse horse raddish peroxidase (HRP) diluted 1:1000 in culture media was added for one hour at 37° C. After three additional washes with PBS-Tween, bound mAbs were visualized with a peroxidase substrate (TMB). The absorbance increase due to peroxidase activity at 450 nm was measured in a microplate reader.

Characterization of Mouse Anti-Canine PD-1 Antibodies:

As detailed above, as well as in U.S. provisional application No. 61/918,946, filed on Dec. 20, 2013, hereby incorporated by reference in its entireties, the mouse anti-canine PD-1 antibodies were characterized by a number of parameters including: their reactivity with the ECD of canine PD-1 by ELISA, their reactivity with PD-1 expressed on the surface of CHO cells, their ability to block the binding of PD-1 with it PD-L1, and their ability to bind to PBMC cells from healthy dogs and dogs with cancer. The amino acid sequences of the CDRs of the seven mouse anti-canine PD-1 antibodies selected (denoted as IB5, 2G9, 2H9, 3B6, 4D12, 5G5, and 7C9, respectively) had substantial homology as demonstrated in Table 2 below.

TABLE 2

AMINO ACID SEQUENCES OF THE CDRs

| | Sequence | SEQ ID NO. |
|---|---|---|
| VL CDR1 | | |
| 1B5 | Lys Ser Ser Gln Ser Leu Leu Asn Ser Val Asn Gln Lys Asn Tyr Leu Ala | 13 |
| 2G9 | Arg Ser Ser Gln Asn Ile Val His Ser Asn Gly Asn Thr Tyr Leu Glu | 14 |
| 2H9 | His Ala Ser Gln Asn Ile Asn Val Trp Leu Ser | 15 |
| 3B6 | Lys Ser Ser Gln Ser Leu Leu Asn Ser Val Asn Gln Lys Asn Tyr Leu Ala | 13 |
| 4D12 | Lys Ser Ser Gln Ser Leu Leu Asn Ser Val Asn Gln Lys Asn Tyr Leu Ala | 13 |
| 5G5 | His Ala Ser Gln Asn Ile Asn Val Trp Leu Ser | 15 |
| 7C9 | Lys Ser Ser Gln Ser Leu Leu Asn Ser Val Asn Gln Lys Asn Tyr Leu Ala | 13 |
| VL CDR2 | | |
| 1B5 | Phe Ala Ser Thr Arg Val Ser | 16 |
| 2G9 | Lys Val Ser Asn Arg Phe Ser | 17 |
| 2H9 | Lys Ala Ser His Leu His Thr | 18 |
| 3B6 | Phe Ala Ser Ala Arg Val Ser | 19 |
| 4D12 | Phe Ala Ser Thr Arg Ile Ser | 20 |
| 5G5 | Lys Ala Ser Asn Leu His Thr | 21 |
| 7C9 | Phe Ala Ser Thr Arg Val Ser | 16 |
| VL CDR3 | | |
| 1B5 | Gln Gln Tyr Phe Ser Thr Pro Leu Thr | 22 |
| 2G9 | Phe Gln Gly Ser His Val Pro Tyr Thr | 23 |
| 2H9 | Gln Gln Gly Gln Ser Trp Pro Leu Thr | 24 |
| 3B6 | Gln Gln Tyr Phe Ser Thr Pro Leu Thr | 25 |
| 4D12 | Gln Gln Tyr Phe Ser Thr Pro Leu Thr | 25 |
| 5G5 | Gln Gln Gly Gln Ser Tyr Pro Leu Thr | 26 |
| 7C9 | Gln Gln Tyr Phe Ser Thr Pro Leu Thr | 22 |
| VH CDR1 | | |
| 1B5 | Gly Tyr Thr Phe Thr Thr Tyr Gly Met Ser | 27 |
| 2G9 | Gly Tyr Thr Phe Thr Arg Tyr Asn Met His | 28 |
| 2H9 | Gly Phe Asn Ile Lys Asn Thr Tyr Met His | 29 |
| 3B6 | Gly Tyr Thr Phe Thr Thr Tyr Gly Met Ser | 27 |
| 4D12 | Gly Tyr Thr Phe Thr Thr Tyr Gly Met Ser | 27 |
| 5G5 | Gly Phe Asn Ile Lys Asn Thr Tyr Met His | 29 |
| 7C9 | Gly Phe Ser Leu Thr Ser Tyr Gly Val His | 30 |
| VH CDR2 | | |
| 1B5 | Trp Ile Asn Ile Tyr Ser Gly Ile Pro Thr Tyr Ala Asp Asp Phe Lys Gly | 31 |
| 2G9 | Thr Ile Tyr Pro Gly Tyr Gly Asp Thr Ser Tyr Asn Gln Lys Phe Lys Gly | 32 |
| 2H9 | Arg Ile Ala Pro Ala Asn Val Asp Thr Lys Tyr Ala Pro Lys Phe Gln Gly | 33 |
| 3B6 | Trp Ile Asn Ile Tyr Ser Gly Ile Pro Thr Tyr Ala Asp Asp Phe Lys Gly | 31 |
| 4D12 | Trp Ile Asn Ile Tyr Ser Gly Met Pro Thr Tyr Ala Asp Asp Phe Lys Gly | 34 |

TABLE 2 -continued

AMINO ACID SEQUENCES OF THE CDRs

| | | | | | | | | | | | | | | | SEQ ID NO. |
|---|---|---|---|---|---|---|---|---|---|---|---|---|---|---|---|
| 5G5 | Arg | Ile | Asp | Pro | Ala | Asn | Val | Asn | Thr | Lys | Tyr | Ala | Pro | Lys Phe Gln Gly | 35 |
| 7C9 | Trp | Ile | Asn | Ile | Tyr | Ser | Gly | Ile | Pro | Thr | Tyr | Ala | Asp | Asp Phe Lys Gly | 31 |

VHCDR3

| | | | | | | | | | | | | SEQ ID NO. |
|---|---|---|---|---|---|---|---|---|---|---|---|---|
| 1B5 | Phe | Asp | Gly | Pro | Asp | Tyr | | | | | | 36 |
| 2G9 | Glu | Phe | Ala | Asp | Asp | Tyr | Pro | Ile | Pro | Pro | Phe Asp Tyr | 37 |
| 2H9 | Ile | Tyr | Tyr | Asp | Tyr | Asp | Gly | Asp | Ile | Asp | Val | 38 |
| 3B6 | Phe | Asp | Gly | Pro | Asp | Tyr | | | | | | 36 |
| 4D12 | Phe | Asp | Gly | Pro | Asp | Tyr | | | | | | 36 |
| 5G5 | Ile | Phe | Tyr | Asp | Tyr | Asp | Gly | Asp | Ile | Asp | Val | 146 |
| 7C9 | Phe | Asp | Gly | Pro | Asp | Tyr | | | | | | 36 |

Canonical Structures (Classes) for VH Chain CDRs

| | |
|---|---|
| mAbs: 4D12, 3B6, 7C9, and 1B5: | CDR: H1-1; CDR2: H2-1; CDR3: H3-6 |
| mAb: 5G5: | CDR: H1-1; CDR2: H2-1; CDR3: H3-11 |
| mAb: 2H9 | CDR: H1-1; CDR2: H2-2A; CDR3: H3-11 |
| mAb: 2G9 | CDR: H1-1; CDR2: H2-2A; CDR3: H3-13 |

Canonical Structures (Classes) for VL Chain CDRs

| | |
|---|---|
| mAbs: 4D12, 3B6, 7C9, 1B5: | CDRL: L1-3; CDR2: L2-1; CDR3: L3-1 |
| mAb: 5G5: | CDR: L1-2A; CDR2: L2-1; CDR3:L3-1 |
| mAb: 2H9 | CDR: L1-2A; CDR2: L2-1; CDR3:L3-1 |
| mAb: 2G9 | CDR: L1-4; CDR2: L2-1; CDR3:L3-1 |

Example 3

Caninization and Characterization of Caninized Antibodies

In order to produce caninized antibodies it was necessary to identify the DNA sequence encoding the heavy and light chains of canine IgG. The nucleotide and amino acid sequences of the canine heavy chain can be obtained from the NCBI gene and protein databases. There are four known IgG subclasses of canine IgG: IgGA, IgGB, IgGC, and IgGD and two types of light chains: kappa and lambda. Table 7 lists the amino acid and nucleotide SEQ ID NOs of the unmodified canine Fc fragments.

Without being bound by any specific approach, the process of producing variants of anti-PD-1 monoclonal antibodies with various contents of canine and mouse sequences involved the general following scheme:
 i) Determine the nucleotide sequence of VH and VL chains of mouse mAbs;
 ii) Identify the H and L chain CDRs of mouse mAbs;
 iii) Identify a suitable H and L chain of canine IgG;
 iv) Determine the nucleotide sequence of canine IgG H and L chains;
 v) Replace the nucleotide sequence encoding endogenous canine H and L chain CDRs with nucleotide sequences encoding the respective mouse CDRs. Also, optionally replace some canine framework residues with selected residues from the mouse framework regions;
 vi) Synthesize the nucleotide from step (v) and insert it into a suitable expression plasmid; Transfect plasmids into appropriate cells, e.g., HEK 293 cells;
 vii) Purify the expressed antibody from HEK 293 supernatent; and
 viii) Test purified antibody for binding to canine PD-1.

A set of experiments was conducted following the above steps which resulted in a set of variant caninized antibodies with various contents of canine and mouse sequences.

Reactivity of Caninized mAbs against canine PD-1 proteins expressed on CHO cells:

The reactivity of caninized anti-canine PD-1 mAbs with canine PD-1 on CHO cells was determined by a cell-based assay using CHO cells that express canine PD-1. Briefly, the CHO cells expressing canine PD-1 were cultured to 80-100% confluency in 50 µl media (DMEM/HAM's F12, 10% FBS). Next, 50 µl of media containing various concentrations of purified mAbs were added for 1 hour at 37° C. Following three washes with PBS-Tween, 100 µl of goat anti-dog horse raddish peroxidase (HRP)-labelled antibody diluted 1:1000 in culture media was added for one hour at 37° C. After three additional washes with PBS-Tween, bound mAbs were visualized with a peroxidase substrate (TMB). The absorbance increase due to peroxidase activity at 450 nm was measured in a microplate reader.

Binding Studies of Mouse Anti-Canine PD-1 mAbs and Caninized Mouse Anti-Canine PD-1 mAbs with Canine PD-1

Approximately 70 resonance units (RU) of the canine PD-1 antigen was immobilized directly by amine coupling. Affinity measuments were made via label-free surface plasmon resonance based technology (e.g., Biacore® T200) with an association time of 300 seconds, a dissociation time of 1200 seconds, and at concentrations of 50, 100, 200 (×2) 400, and 800 nanomolar (nM). A fitting model of 1:1 binding was used. The antigen (canine PD-1) was immobilized on the sensor chip through amine coupling and the four antibodies as indicated in Table 14 below, were used as analytes that flowed through the antigen surface. The results demonstrated that the binding affinities of the anti-canine PD-1 antibodies of the present invention for the canine PD-1 antigen were strong, having nanomolar and even subnanomolar dissociation constants (Kd). Moreover, the mouse anti-canine PD-1 monoclonal antibody and the corresponding caninized mouse anti-canine PD-1 monoclonal antibody from the same clone yielded strikingly similar Kd values (see Table 14 below).

TABLE 14

Binding Constant Determinations

| Antibody | $k_{on}$ ($k^1$) $M^{-1}s^{-1}$ | $k_{off}$ ($k^{-1}$) $s^{-1}$ | Kd M | Chi$^2$ (RU$^2$) | Rmax (RU) |
|---|---|---|---|---|---|
| Murine 2H9 | $2.3 \times 10^4$ | $\leq 5 \times 10^{-6\#}$ | $\leq 2.0 \times 10^{-10\#}$ | 0.19 | 25.6 |
| Caninized 2H9 | $1.0 \times 10^4$ | $5.9 \times 10^{-6}$ | $5.9 \times 10^{-10}$ | 0.10 | 27.7 |
| Murine 3B6 | $1.8 \times 10^4$ | $3.4 \times 10^{-5}$ | $2.0 \times 10^{-9}$ | 0.13 | 48.7 |
| Caninized 3B6 | $1.6 \times 10^4$ | $4.7 \times 10^{-5}$ | $2.9 \times 10^{-9}$ | 0.07 | 49.9 |

The off-rate was so slow that it was below the detection limit of the instrument used.

Ligand Blockade by Caninized Anti-Canine PD1 mAbs:

For caninized antibodies which react with canine PD-1 (cPD-1), a cell-based ELISA (CELISA) assay was used which is based on the CHO cell line expressing canine PD-1. Briefly, cPD-1 CHO cells were placed in 96-well plates at $4 \times 10^4$ cells per well and the cells were incubated at 37° C. for 18-24 hours till they are 95-100% confluent. The cell culture media was aspirated off, the plates were washed 3× with PBS plus 0.05% Tween® 20 and 1× CHO media. 3-fold serial dilutions of caninized anti-cPD1 mAbs were made in CHO media, starting at 30 µg/mL, and 50 µL/well of each antibody dilution was added down the plate. The plates were then incubated at 37° C., 5% CO$_2$ for 30 min, with shaking. Human PD-L1-Fc was added to 4 µg/ml in CHO media, 50 µL/well without removing or washing the incbuated anti-PD1 mAbs, then incubated at 37° C., 5% CO$_2$ for 45 min, with shaking. The plates were washed with 6× with PBS plus 0.05% Tween® 20. 100 µl/well of anti-human Fc-HRP (Calbiochem) (1:2500) in CHO media was added and incubated at 37° C./5% CO$_2$ for 30-60 min. (anti-human Fc-HRP does not bind canine Fc.) The plates were washed with 5× PBS plus 0.05% Tween® 20. 100 µl/well TMB microwell substrate was added and then incubated at room temp for 10 minutes. The reaction was stopped with 100 µl/well 1.5 M phosphoric acid. Measure A450-A620 on the ELISA reader.

Figure 4:
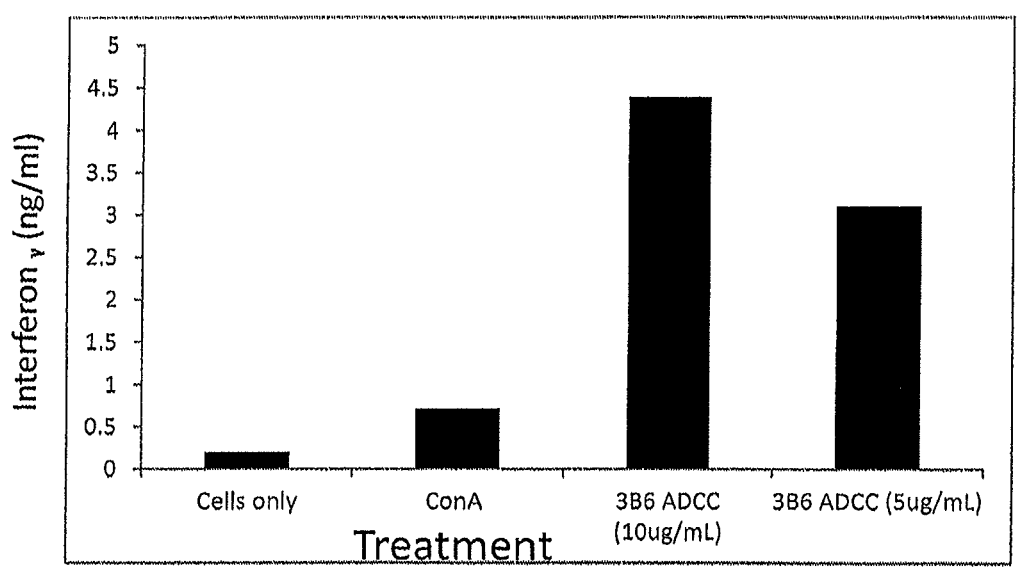
FIG. 4 shows the cytokine secretion induced by caninized mAbs against canine PD-1. Various caninized mAbs and their variants were tested for their ability to induce cytokine secretion from PBMC from healthy dogs.

Cytokine Release from Dog PBMC:

PBMC were prepared from EDTA blood samples obtained from healthy dogs and dogs with cancer, using Ficoll separation. Cells were washed 3 times, and resuspended in complete tissue culture medium at a concentration of $2.5 \times 10^5$ cells per well in triplicate wells in 96-well plates. Cells were activated with concanavalin A at 1 µg/ml. Test antibodies were added at various concentrations and the cultures were incubated for 96 hours. Controls included cells incubated with conA and no antibody, or conA and irrelevant isotype-matched antibodies. After 96 hours in culture, supernatants were collected and assayed for IFN-$_\gamma$ release, using a commercial canine IFN-$_\gamma$ ELISA kit (R & D Systems) [see, FIG. 4].

Example 4

Genetically Modified Canine IgGs

In order to generate variants of canine IgG that lack effector functions, a number of mutant canine IgGB heavy chains were generated. These variants may include one of the following single or combined substitutions in the Fc portion of the heavy chain amino acid sequence: P4A, D31A, N63A, G64P, T65A, A93G, and P95A. Variant heavy chains (i.e., containing such amino acid substitutions) were cloned into expression plasmids and transfected into HEK 293 cells along with a plasmid containing the gene encoding a light chain. Intact antibodies expressed and purified from HEK 293 cells were evaluated for binding to Fc$_\gamma$RI and C1q to assess their potential for mediation of immune effector functions. Table 3 lists examples of the plasmids encoding the genetically modified caninized heavy chains, the caninized heavy chains; and the genetic modifications in these heavy chains. The variant heavy chains were used for assessment of effector function in the genetically modified mAbs. All of the heavy chains comprised the CDRs from the 2H9 murine anti-canine PD-1 antibody.

TABLE 3

| Plasmid | Heavy chain | Modification | AA position in native Fc |
|---|---|---|---|
| YZZ1057/Mut-1 | can2H9VH4 | D31 to A | D31 |
| YZZ1058/Mut-2 | can2H9VH4 | N63 to A | N63 |
| YZZ1062 | can2H9VH4 | D31 to A + N63 to A | D31 and N63 |
| YZZ1059 | can2H9VH4 | P4 to A | P4 |
| YZZ1060 | can2H9VH4 | A93 to G | A93 |
| YZZ1061 | can2H9VH4 | P95 to A | P95 |
| YZZ1068 | can2H9VH4 | D31 to A, N63 to A, P4 to A, A93 to G, and P95 to A | D31, N63, P4, A93, P95 |

Fc$_\gamma$RI Binding:

Binding to FcR$_\gamma$I is a measure of the ability of an antibody to mediate ADCC. In order to assess this property for the caninized antibodies an assay to measure binding of caninized antibodies to Fc$_\gamma$RI was conducted as follows: Coat 96-well plates with 100 µl per well of 2.5 µg/mL PD-1 HIS. Incubate at 2-7° C. overnight. Equilibrate the plates to room temp for 15 minutes. Wash plates 3× with phosphate buffered saline containing 0.05% Tween® 20 (PBST) and then block the wells using 200 µL/well of 5% NFDM (Non Fat Dried Milk). Incubate for 60 minutes at 36-38° C. Wash 3× with PBST. Make 2-fold dilution of antibodies starting at 1 µg/mL in 5% NFDM. Add 100 µL/well of diluted antibodies. Incubate for 60 minutes at 36-38° C. Wash 6× with PBST. Add 100 µL/well of recombinant human CD64 protein (R&D systems) diluted to 1 µg/mL. Incubate for 60 minutes at 36-38° C. Wash 6× with PBST. Add 100 µL/well biotinylated-anti-CD64 antibody (R&D systems) diluted to 1:3000. Incubate for 60 minutes at 36-38° C. Wash 6× with PBST. Add 100 µL/well Streptavidin-HRP antibody (R&D systems) diluted to 1:7500. Incubate for 60 minutes at 36-38° C. Wash 6× with PBST. Add 100 µL/well TMB substrate. Incubate for 10 minutes at 15-30° C. Read plates using ELISA plate reader at 450-540 nm.

Figure 5B:
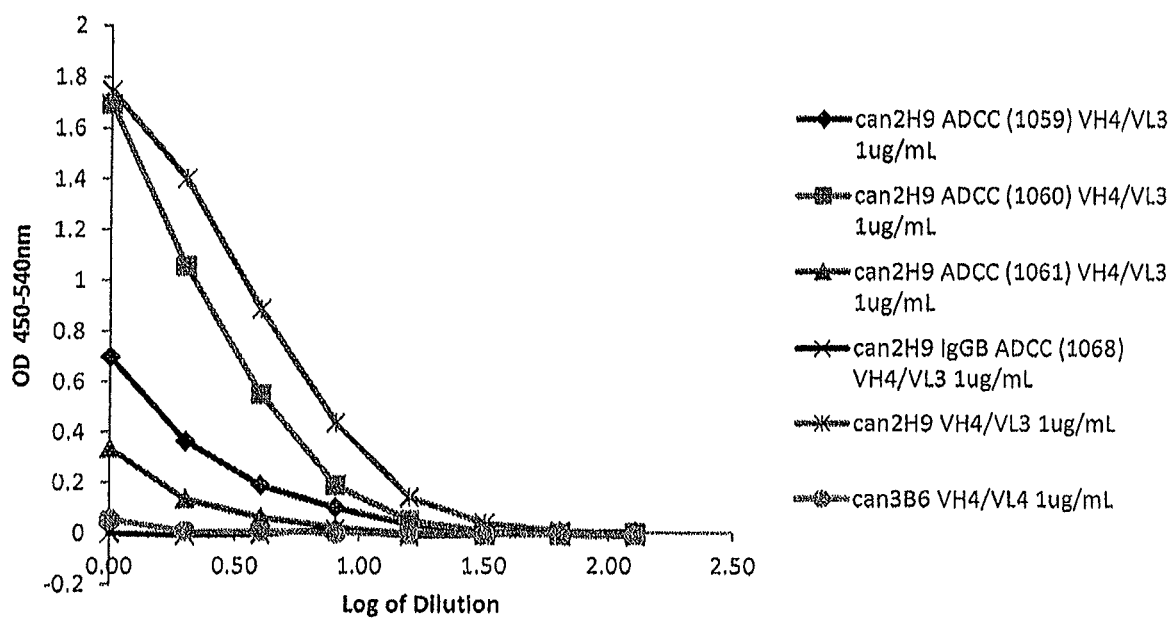

Results: FIG. 5A shows that caninized mAb designated can2H9 ADCC mut-1 VH4/VL3 which has the genetic modification of D31A or the mAb designated can2H9 ADCC mut-2 VH4/VL3 which has the genetic modification of N63A display a near complete reduction in binding to Fc$_\gamma$RI. On the other hand, the mab designated can2H9 ADCC (1062) VH4/VL3 which contains the combined D31A plus N63A genetic modifications lacks detectable binding to Fc$_\gamma$RI. In FIG. 5A, can2H9 IgGD VH4/VL3 is a caninized antibody which contains the Fc from canine IgGD and can3B6 VH4/VL4 IgGB is a caninized antibody that does not bind to the coating antigen (PD-1 HIS), and caninized mAb designated can2H9 VH4/VL3 is an antibody that contains un-modified IgGB Fc. FIG. 5B shows that the caninized mAb designated can2H9 ADCC(1059) VH4/VL3 which contains the genetic modification of P4A and the mAb designated can2H9 ADCC (1061) VH4/VL3 which contain the genetic modification of P95A display considerable reduction in binding to Fc$_\gamma$RI, whereas the mAb designated can2H9 ADCC(1060) VH4/VL3 which contains the genetic modification of A93G displays a slight reduction in binding to Fc$_\gamma$RI. On the other hand, the mAb designated can 2H9 IgGB ADCC (1068) VH4/VL3 which contains five genetic modifications (D31A, N63A, P4A, A93G, P95A) is completely lacking in binding to Fc$_\gamma$RI.

C1q Binding:

Binding to the first component of complement, C1q, is a measure of the ability of an antibody to mediate CDC. In order to assess this property for the caninized antibodies an assay to measure binding of caninized antibodies to C1q was conducted as follows: Coat 96-well plates with 2.5 µg/mL PD-1 HIS. Incubate at 2-7° C. overnight. Equilibrate to room temperature for 15 minutes. Wash with PBST 3×. Block with 200 µL/well with 5% BSA. Incubate for 60 minutes at 36-38° C. Wash with PBST 3×. Make a 2-fold dilution of antibodies starting at 1 µg/mL in 5% BSA. Add 100 µL/well diluted antibodies. Incubate for 60 minutes at 36-38° C. Wash with PBST 6×. Add 100 µL/well C1q protein diluted to 4 µg/mL. Incubate for 60 minutes at 36-38° C. Wash with PBST 6×. Add 100 µL/well Goat-Anti-C1q antibody diluted to 1:3000. Incubate for 60 minutes at 36-38° C. Wash with PBST 6×. Add 100 µL/well of donkey-anti-Goat-HRP antibody diluted 1:10000. Incubate for 60 minutes at 36-38° C. Wash with PBST 6×. Add 100 µL/well TMB substrate. Incubate for 10 minutes at 15-30° C. Read on ELISA plate reader at 450-540 nm.

Figure 6A:
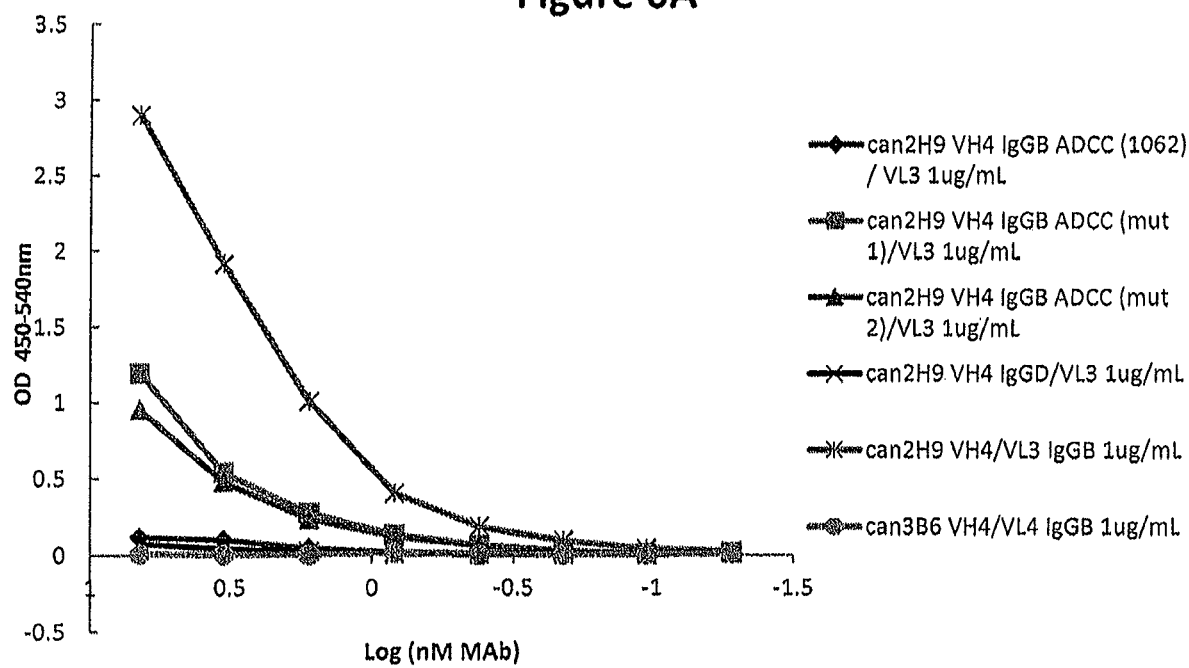
FIGS. 6A and 6B show the binding of caninized mAbs and their variants (beginning at 1 μg/ml) to C1Q. Various mAbs were tested for their ability to bind to C1Q. Antibodies are designated as: can 2H9 VH4 IgGB ADCC (1062)/VL3, can 2H9 VH4 IgGB ADCC (mut 1)/VL3, can 2H9 VH4 IgGB ADCC (mut 2)/VL3, can 2H9 VH4 IgGD/VL3, can 2H9 VH4/VL3, and can 3B6 VH4/VL4 IgGB in FIG. 6A; and can 2H9 VH4 IgGB ADCC (1059)/VL3, can 2H9 VH4 IgGB ADCC (1060)/VL3, can 2H9 VH4 IgGB ADCC (1061)/VL3, can 2H9 VH4 IgGB ADCC (1068)/VL3, can 2H9 VH4/VL3 IgGB, and can 3B6 VH4/VL4 IgGB in FIG. 6B.

Results: FIG. 6A shows that the caninized mAb designated can2H9VH4 IgGB ADCC (mut-1)/VL3, which has the genetic modification of D31A or the mAb designated can2H9 VH4 IgGB ADCC (mut-2)/VL3 which has the genetic modification N63A display considerable reduction in binding to C1q. On the other hand, the mAb designated can2H9 VH4 IgGB ADCC (1062)/VL3 which contains the combined D31A plus N63A genetic modifications lacks detectable binding to C1q.

Figure 6B:
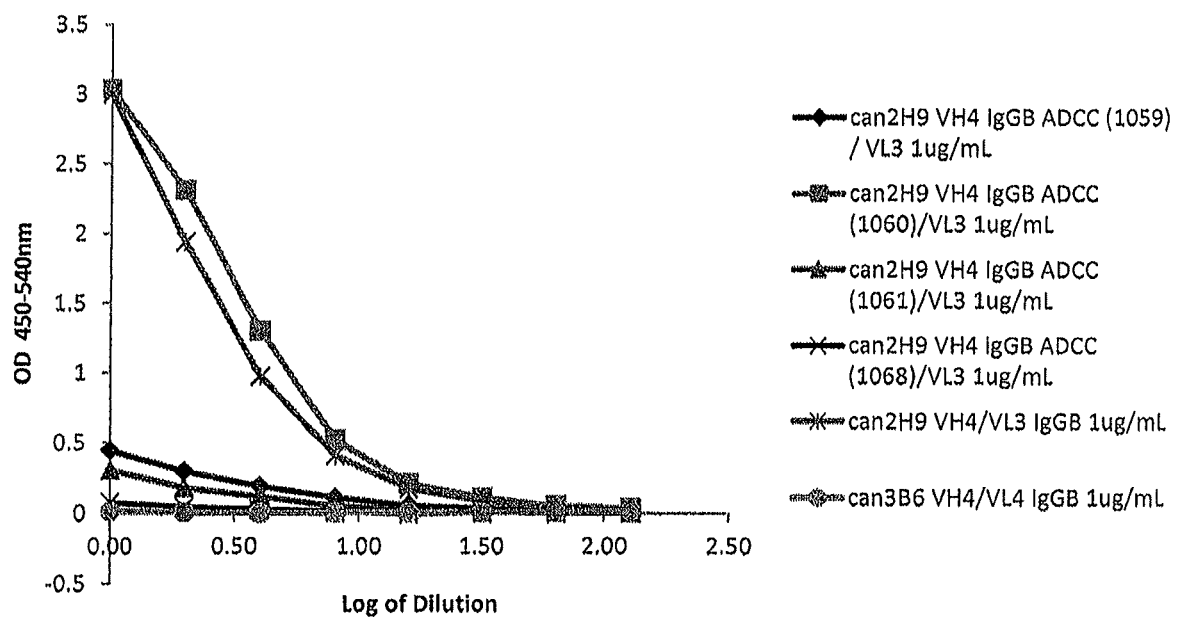
Figure 7A:
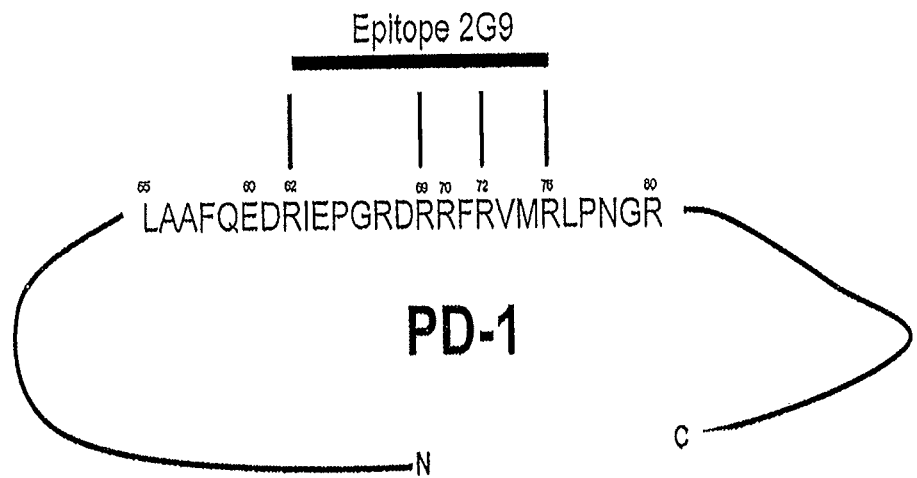
FIG. 7A shows the characterization of the interface between canine PD-1 and the caninized antibody 2G9. The amino acid positions are with respect to the PD-1 amino acid sequence without the signal sequence, i.e., SEQ ID NO: 114. The determination was performed by chemical cross-linking, High-Mass MALDI mass spectrometry and nLC-Orbitrap mass spectrometry.
Figure 7B:
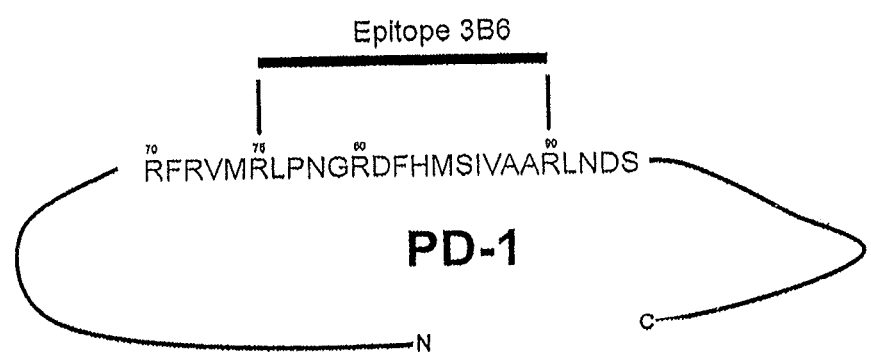
FIG. 7B shows the characterization of the interface between canine PD-1 and the caninized antibody 3B6. The amino acid positions are with respect to the PD-1 amino acid sequence without the signal sequence, i.e., SEQ ID NO: 114. The determination was performed by chemical cross-linking, High-Mass MALDI mass spectrometry and nLC-Orbitrap mass spectrometry.

In FIG. 6A, can2H9 VH4 IgGD/VL3 is a caninized antibody which contains the Fc from canine IgGD and can3B6 VH4/VL4 IgGB is a caninized antibody that does not bind to the coating antigen (PD-1 HIS), and caninized mAb designated can2H9 VH4/VL3 IgGB is an antibody that contains un-mutated IgGB Fc. FIG. 6B shows that the caninized mAb designated can2H9 VH4 IgGB ADCC (1059)/VL3 which contains the substitution P4A and the mAb designated can2H9 VH4 IgGB ADCC (1061)/VL3 which contains the substitution P95A display considerable reduction in binding to C1q, whereas the mAb designated can2H9 VH4 IgGB ADCC(1060)/VL3 which contains the substitution A93G display an enhancement in binding to C1q. On the other hand, the mAb designated can2H9 VH4 IgGB ADCC (1068)/VL3 which contains five substitutions (D31A, N63A, P4A, A93G, P95A), is completely lacking in binding to C1q. In FIG. 6B, the mAb designated can3B6 VH4/VL4 IgGB is a caninized antibody that does not bind to the coating antigen (PD-1 HIS), and caninized mAb designated can2H9 VH4/VL3 IgGB is an antibody that contains un-mutated IgGB Fc.

TABLE 4

MODIFIED cFc or NATIVE cFc WITH HINGE SEQUENCES

| # | N. | A. | Modified Fcs |
|---|---|---|---|
| 1* | ✓ |   | Modified Fc -cIgGB |
| 2* |   | ✓ | Modified Fc -cIgGB |
| 3* | ✓ |   | Modified Fc -cIgGC |
| 4* |   | ✓ | Modified Fc -cIgGC |
| 5# | ✓ |   | cIgGD Fc with S of cIgGD hinge to P |
| 6# |   | ✓ | cIgGD Fc with S of cIgGD hinge to P |
| 7 | ✓ |   | cIgGD Fc with A hinge |
| 8 |   | ✓ | cIgGD Fc with A hinge |
| 9 | ✓ |   | cIgGD Fc with B hinge |
| 10 |   | ✓ | cIgGD Fc with B hinge |
| 11 | ✓ |   | cIgGD Fc with C hinge |
| 12 |   | ✓ | cIgGD Fc with C hinge |

*The substitutions are at P4, D31, N63, G64, T65, A93, and P95 of amino acid sequences SEQ ID NOs: 2 and 4; or at the nucleotides that encode those amino acids for nucleotide sequences SEQ ID NOs: 1 and 3.
Single amino acid substitution as shown in Table 5 below in hinge region of IgGD.

TABLE 5

HINGE REGION SEQUENCES

| # | A.A. | Hinge | Sequence |
|---|---|---|---|
| 109 | ✓ | IgGA | FNECRCTDTPPCPVPEP |
| 110 | ✓ | IgGB | PKRENGRVPRPPDCPKCPAPEM |
| 111 | ✓ | IgGC | AKECECKCNCNNCPCPGCGL |
| 112 | ✓ | IgGD# | PKESTCKCIPPCPVPES |

Single amino acid substitution of a serine to a proline as in bold and underlined.

TABLE 6

CANINE PD-1/PD-L1 SEQUENCES

| # | N. | A. | PD-1 | Description | # | N. | A. | PD-L1 | Description |
|---|---|---|---|---|---|---|---|---|---|
| 113 | ✓ |   | ✓ | Full Length | 119 | ✓ |   | ✓ | Full Length |
| 114 |   | ✓ | ✓ | Full Length | 120 |   | ✓ | ✓ | Full Length |
| 115 | ✓ |   | ✓ | ECD | 121 | ✓ |   | ✓ | ECD |
| 116 |   | ✓ | ✓ | ECD | 122 |   | ✓ | ✓ | ECD |
| 117 | ✓ |   | ✓ | cECD-hIgG1 | 123 | ✓ |   | ✓ | cECD-hIgG1 |
| 118 |   | ✓ | ✓ | cECD-hIgG1 | 124 |   | ✓ | ✓ | cECD-hIgG1 |
| 133 | ✓ |   | ✓ | +signal seq. | 135 | ✓ |   | ✓ | +signal seq. |
| 134 |   | ✓ | ✓ | +signal seq. | 136 |   | ✓ | ✓ | +signal seq. |
| 137 |   | ✓ | ✓ | +signal seq. |   |   |   |   |   |

TABLE 7

NATIVE cFc SEQUENCES

| # | N. | A. | |
|---|---|---|---|
| 125 | ✓ | | Fc-cIgGA |
| 126 | | ✓ | Fc-cIgGA |
| 127 | ✓ | | Fc-cIgGD |
| 128 | | ✓ | Fc-cIgGD |
| 129 | ✓ | | Fc-cIgGB |
| 130 | | ✓ | Fc-cIgGB |
| 131 | ✓ | | Fc-cIgGC |
| 132 | | ✓ | Fc-cIgGC |

TABLE 8

CDR AMINO ACID SEQUENCES

| # | A.A. | CDR |
|---|---|---|
| 13 | ✓ | VL CDR1 1B5, 3B6, 4D12, 7C9 |
| 14 | ✓ | VL CDR1 2G9 |
| 15 | ✓ | VL CDR1 2H9, 5G5 |
| 16 | ✓ | VL CDR2 1B5, 7C9 |
| 17 | ✓ | VL CDR2 2G9 |
| 18 | ✓ | VL CDR2 2H9 |
| 19 | ✓ | VL CDR2 3B6 |
| 20 | ✓ | VL CDR2 4D12 |
| 21 | ✓ | VL CDR2 5G5 |
| 22 | ✓ | VL CDR3 1B5, 7C9 |
| 23 | ✓ | VL CDR3 2G9 |
| 24 | ✓ | VL CDR3 2H9 |
| 25 | ✓ | VL CDR3 4D12 |
| 26 | ✓ | VL CDR3 5G5 |
| 27 | ✓ | VH CDR1 1B5, 3B6, 4D12 |
| 28 | ✓ | VH CDR1 2G9 |
| 29 | ✓ | VH CDR1 2H9, 5G5 |
| 30 | ✓ | VH CDR1 7C9 |
| 31 | ✓ | VH CDR2 1B5, 3B6, 7C9 |
| 32 | ✓ | VH CDR2 2G9 |
| 33 | ✓ | VH CDR2 2H9 |
| 34 | ✓ | VH CDR2 4D12 |
| 35 | ✓ | VH CDR2 5G5 |
| 36 | ✓ | VH CDR3 1B5, 3B6, 4D12, 7C9 |
| 37 | ✓ | VH CDR3 2G9 |
| 38 | ✓ | VH CDR3 2H9 |
| 146 | ✓ | VH CDR3 5G5 |

TABLE 9

INDIVIDUAL SUBSTITUTED CANINIZED HEAVY CHAINS

| # | N. | A. | |
|---|---|---|---|
| 39 | ✓ | | 3B6- VH3-CH1-hinge-FC -cIgGB Fc |
| 40 | | ✓ | 3B6- VH3-CH1-hinge-FC -cIgGB Fc |
| 41 | ✓ | | 3B6- VH3-CH1-hinge-FC -cIgGC Fc |
| 42 | | ✓ | 3B6- VH3-CH1-hinge-FC -cIgGC Fc |
| 43 | ✓ | | 2H9- VH4-CH1-hinge-FC -cIgGB Fc |
| 44 | | ✓ | 2H9- VH4-CH1-hinge-FC -cIgGB Fc |
| 45 | ✓ | | 2H9- VH4-CH1-hinge-FC -cIgGC Fc |
| 46 | | ✓ | 2H9- VH4-CH1-hinge-FC -cIgGC Fc |
| 47 | ✓ | | 2G9- VH6-CH1-hinge-FC -cIgGB Fc |
| 48 | | ✓ | 2G9- VH6-CH1-hinge-FC -cIgGB Fc |
| 49 | ✓ | | 2G9- VH6-CH1-hinge-FC -cIgGC Fc |
| 50 | | ✓ | 2G9- VH6-CH1-hinge-FC -cIgGC Fc |
| 51 | ✓ | | 7C9- VH3-CH1-hinge-FC -cIgGB Fc |
| 52 | | ✓ | 7C9- VH3-CH1-hinge-FC -cIgGB Fc |
| 53 | ✓ | | 7C9- VH3-CH1-hinge-FC -cIgGC Fc |
| 54 | | ✓ | 7C9- VH3-CH1-hinge-FC -cIgGC Fc |
| 55 | ✓ | | 1B5- VH3-CH1-hinge-FC -cIgGB Fc |
| 56 | | ✓ | 1B5- VH3-CH1-hinge-FC -cIgGB Fc |
| 57 | ✓ | | 1B5- VH3-CH1-hinge-FC -cIgGC Fc |
| 58 | | ✓ | 1B5- VH3-CH1-hinge-FC -cIgGC Fc |
| 59 | ✓ | | 5G5- VH3-CH1-hinge-FC -cIgGB Fc |
| 60 | | ✓ | 5G5- VH3-CH1-hinge-FC -cIgGB Fc |

TABLE 9-continued

INDIVIDUAL SUBSTITUTED CANINIZED HEAVY CHAINS

| # | N. | A. | |
|---|---|---|---|
| 61 | ✓ | | 5G5- VH3-CH1-hinge-FC -cIgGC Fc |
| 62 | | ✓ | 5G5- VH3-CH1-hinge-FC -cIgGC Fc |
| 63 | ✓ | | 4D12- VH3-CH1-hinge-FC -cIgGB Fc |
| 64 | | ✓ | 4D12- VH3-CH1-hinge-FC -cIgGB Fc |
| 65 | ✓ | | 4D12- VH3-CH1-hinge-FC -cIgGC Fc |
| 66 | | ✓ | 4D12- VH3-CH1-hinge-FC -cIgGC Fc |

The potential specific substitutions are at P4, D31, N63, G64, T65, A93, and P95

TABLE 10

CORRELATION OF AMINO ACID RESIDUE POSITIONS OF NATIVE AND SUBSTITUTED cFc WITH THAT OF THE CORRESPONDING SUBSTITUTED CANINE HEAVY CHAINS[#]

| 130/132 | P4 | D31 | N63 | G64 | T65 | A93 | P95 |
|---|---|---|---|---|---|---|---|
| 2/4 | 4 | 31 | 63 | 64 | 65 | 93 | 95 |
| 40 | 239 | 266 | 298 | 299 | 300 | 328 | 330 |
| 42 | 237 | 264 | 296 | 297 | 298 | 326 | 328 |
| 44 | 244 | 271 | 303 | 304 | 305 | 333 | 335 |
| 46 | 242 | 269 | 301 | 302 | 303 | 331 | 333 |
| 48 | 246 | 273 | 305 | 306 | 307 | 335 | 337 |
| 50 | 244 | 271 | 303 | 304 | 305 | 333 | 335 |
| 52 | 239 | 266 | 298 | 299 | 300 | 328 | 330 |
| 54 | 237 | 264 | 296 | 297 | 298 | 326 | 328 |
| 56 | 239 | 266 | 298 | 299 | 300 | 328 | 330 |
| 58 | 237 | 264 | 296 | 297 | 298 | 326 | 328 |
| 60 | 244 | 271 | 303 | 304 | 305 | 333 | 335 |
| 62 | 242 | 269 | 301 | 302 | 303 | 331 | 333 |
| 64 | 239 | 266 | 298 | 299 | 300 | 328 | 330 |
| 66 | 237 | 264 | 296 | 297 | 298 | 326 | 328 |

[#]First Column lists SEQ ID NOs.; remaining columns list corresponding amino acid positions. For the two native amino acid sequences (SEQ ID NOs. 130 and 132), the one letter code for the natural amino acid residues are also provided.

TABLE 11

INDIVIDUAL UNSUBSTITUTED CANINIZED HEAVY AND LIGHT CHAINS

| # | N. | A. | |
|---|---|---|---|
| 67 | ✓ | | 3B6- VH3-CH1-hinge-FC -cIgGA Fc |
| 68 | | ✓ | 3B6- VH3-CH1-hinge-FC -cIgGA Fc |
| 69 | ✓ | | 3B6- VH3-CH1-hinge-FC -cIgGD Fc |
| 70 | | ✓ | 3B6- VH3-CH1-hinge-FC -cIgGD Fc |
| 71 | ✓ | | 3B6- VL3-CL-Kappa |
| 72 | | ✓ | 3B6- VL3-CL-Kappa |
| 73 | ✓ | | 2H9- VH4-CH1-hinge-FC -cIgGA Fc |
| 74 | | ✓ | 2H9- VH4-CH1-hinge-FC -cIgGA Fc |
| 75 | ✓ | | 2H9-VH4-CH1-hinge-FC-cIgGD Fc |
| 76 | | ✓ | 2H9-VH4-CH1-hinge-FC -cIgGD Fc |
| 77 | ✓ | | 2H9-VL3-CL-Kappa |
| 78 | | ✓ | 2H9-VL3-CL-Kappa |
| 79 | ✓ | | 2G9- VH6-CH1-hinge-FC -cIgGA Fc |
| 80 | | ✓ | 2G9- VH6-CH1-hinge-FC -cIgGA Fc |
| 81 | ✓ | | 2G9- VH6-CH1-hinge-FC -cIgGD Fc |
| 82 | | ✓ | 2G9- VH6-CH1-hinge-FC -cIgGD Fc |
| 83 | ✓ | | 2G9-VL3-CL-Kappa |
| 84 | | ✓ | 2G9-VL3-CL-Kappa |
| 85 | ✓ | | 7C9- VH3-CH1-hinge-FC -cIgGA Fc |
| 86 | | ✓ | 7C9- VH3-CH1-hinge-FC -cIgGA Fc |
| 87 | ✓ | | 7C9- VH3-CH1-hinge-FC -cIgGD Fc |
| 88 | | ✓ | 7C9- VH3-CH1-hinge-FC -cIgGD Fc |
| 89 | ✓ | | 7C9- VL3- CL-Kappa |
| 90 | | ✓ | 7C9- VL3- CL- Kappa |
| 91 | ✓ | | 1B5- VH3-CH1- hinge-FC-cIgGA Fc |
| 92 | | ✓ | 1B5- VH3-CH1- hinge-FC-cIgGA Fc |
| 93 | ✓ | | 1B5- VH3-CH1- hinge-FC-cIgGD Fc |
| 94 | | ✓ | 1B5- VH3-CH1- hinge-FC -cIgGD Fc |
| 95 | ✓ | | 1B5- VL3- CL-Kappa |

TABLE 11-continued

INDIVIDUAL UNSUBSTITUTED CANINIZED
HEAVY AND LIGHT CHAINS

| # | N. | A. | |
|---|---|---|---|
| 96 | | ✓ | 1B5- VL3- CL-Kappa |
| 97 | ✓ | | 5G5- VH3-CH1- hinge-FC-cIgGA Fc |
| 98 | | ✓ | 5G5- VH3-CH1- hinge-FC-cIgGA Fc |
| 99 | ✓ | | 5G5-VH3-CH1- hinge-FC-cIgGD Fc |
| 100 | | ✓ | 5G5-VH3-CH1- hinge-FC-cIgGD Fc |
| 101 | ✓ | | 5G5- VL3-CL-Kappa |
| 102 | | ✓ | 5G5- VL3-CL-Kappa |
| 103 | ✓ | | 4D12-VH3-CH1- hinge-FC-cIgGA Fc |
| 104 | | ✓ | 4D12-VH3-CH1- hinge-FC-cIgGA Fc |
| 105 | ✓ | | 4D12-VH3-CH1- hinge-FC-cIgGD Fc |
| 106 | | ✓ | 4D12-VH3-CH1- hinge-FC-cIgGD Fc |
| 107 | ✓ | | 4D12- VL3-CL-Kappa |
| 108 | | ✓ | 4D12- VL3-CL-Kappa |

Example 5

Epitope Mapping of Anti-Canine PD-1 Antibodies

Introduction

The interaction of antibodies with their cognate protein antigens is mediated through the binding of specific amino acids (paratopes) of the antibodies with specific amino acids (epitopes) of target antigens. An epitope is an antigenic determinant that causes a specific reaction by an immunoglobulin. It consists of a group of amino acids on the surface of the antigen.

A protein of interest may contain several epitopes that are recognized by different antibodies. The epitopes recognized by antibodies are classified as linear or conformational epitopes. Linear epitopes are formed by a stretch of continuous sequence of amino acids in a protein, while conformational epitopes are composed of amino acids that are discontinuous (e.g, far apart) in the primary amino acid sequence, but are brought together upon three-dimensional protein folding.

Epitope mapping refers to the process of identifying the amino acid sequences (i.e., epitopes) that are recognized by antibodies on their target antigens. Identification of epitopes recognized by monoclonal antibodies (mAbs) on target antigens has important applications. For example, it can aid in the development of new therapeutics, diagnostics, and vaccines. Epitope mapping can also aid in the selection of optimized therapeutic mAbs and help elucidate their mechanisms of action. Epitope information can also elucidate unique cancer epitopes and define the protective or pathogenic effects of vaccines.

Epitope mapping can be carried out using polyclonal or monoclonal antibodies and several methods are employed for epitope identification depending on the suspected nature of the epitope (i.e., linear versus conformational). Mapping linear epitopes is more straightforward and relatively easy to perform. For this purpose, commercial services for linear epitope mapping often employ peptide scanning. In this case, an overlapping set of short peptide sequences of the target protein are chemically synthesized and tested for their ability to bind antibodies of interest. The strategy is rapid, high-throughput, and relatively inexpensive to perform. On the other hand, mapping of discontinuous epitope is more technically challenging and requires more specialized techniques such as x-ray co-crystallography of a monoclonal antibody together with its target protein, Hydrogen-Deuterium (H/D) exchange, and/or Mass Spectroscopy coupled with enzymatic digestion.

Mapping of PD-1 Epitopes Using a ProImmune® MicroArray:

In order to identify the amino acids that form the epitopes for anti-PD1 mAbs, a total of 28 peptides that are 15 amino acids long and overlapping by 10 amino acids were chemically synthesized. This library of overlapping peptides was designed to cover the full length canine PD-1 protein. The determination of peptide-antibody binding was performed by attachment of antibody samples to the ProArray Ultra® peptide microarray, followed by incubation with a fluorescent-labelled secondary antibody. All peptides are synthesized separately, and then bound to the ProArray Ultra® slide surface alongside ProImmune® murine IgG controls. This optimized process ensures that peptides are presented on the array in such a manner as to closely mimic the properties of the corresponding protein region, circumventing the inherent physiochemical variation of the free peptides themselves and making a compatible, combined peptide and protein array platform. The test analytes (peptides) are dispensed onto the ProArray Ultra® slide in discrete spots and appropriate gal-files enable exact alignment of the resulting array features back to the analyte deposited. ProArray Ultra® slides were blocked using a validated blocking buffer to reduce non-specific binding of the mAbs. They were then incubated with the mAb samples, followed by incubation with a specific fluorescent-labelled secondary antibody. After several washing steps, the ProArray Ultra® arrays were dried and scanned using a high-resolution fluorescence microarray scanning system. After scanning the fluorescent labelled ProArray Ultra® slides, the scanner recorded an image which was evaluated using image analysis software—enabling interpretation and quantification of the levels of fluorescent intensities associated with each fluorescent spot on the scanned microarray slide. The results of this experiment indicated some of the canine PD-1 peptides were recognized by some of the mAbs evaluated. The identity of the mAbs and the amino acid sequence recognized by these mAbs are listed in Table 12. This study indicates that mAb 2H9 recognizes an epitope located in the extracellular domain of canine PD-1 comprised of the amino acid sequence represented by SEQ ID NO: 138 and that mAb 1A1 recognizes an epitope comprising the amino acid sequence represented by SEQ ID NO: 138 and the overlapping amino acid sequence represented by the amino acid sequence represented by SEQ ID NO: 139.

Mapping of PD-1 Epitopes Using Mass Spectroscopy:

In order to identify potentially discontinuous epitopes recognized by anti-canine PD-1 a method based on chemical crosslinking and mass spectrometry detection was used (CovalX® Instrument Incorporated). The application of this technology to epitope mapping of canine PD-1 resulted in identification of at least portions of epitopes recognized by the indicated mAbs which are listed in Table 13. As can be seen from Table 13, mAb 3B6 recognizes at least a portion of an epitope located in the extracellular domain of canine PD-1 within the amino acid sequence represented by SEQ ID NO: 140 and that mAb 2G9 recognizes at least a portion of an epitope within the amino acid sequence represented by SEQ ID NO: 141. On the other hand, mAb 1E4 and mAb 1B5 recognize at least a portion of an epitope within the amino acid sequence represented by SEQ ID NO: 142 and acid sequence represented by SEQ ID NO: 143, respectively.

As depicted in FIG. 9A a determination performed by chemical cross-linking, High-Mass MALDI mass spectrometry and nLC-Orbitrap mass spectrometry shows that the epitope on canine PD-1 recognized by caninized antibody 2G9 comprises $R_{62}$, $R_{69}$, $R_{72}$, and $R_{75}$ of SEQ ID NO: 114.

The analogous determination for the epitope on canine PD-1 recognized by caninized antibody 3B6 comprises $R_{75}$ and $R_{90}$ of SEQ ID NO: 114. Accordingly, $R_{75}$ appears to be a particularly important amino acid residue in one or more epitopes of canine PD-1. Interestingly, after performing these analyses, the amino acid sequence for the CDRs of 1A1 were found to be identical to that of 2G9. The consistency between the region on PD-1 that 2G9 binds with that found for 1A1, which were obtained by these two very different methodologies, indicates that this region contains amino acid residues comprised by a PD-1 epitope that is recognized by the anti-caninine PD-1 antibodies (see, Tables 12 and 13 below).

Moreover, the region of the amino acid sequence of PD-1 that is recognized by the blocking antibodies of the present invention tested is within the extracellular domain of canine PD-1. The region recognized is comprised by the following peptide (see, Tables 12 and 13 below).

NQTDKLAAFQEDRIEPGRDRRFRVM*
RLPNGRDFHMSIVAARLNDS (SEQ ID NO:144)

Within this peptide, is a shorter peptide that is in bold. This shorter peptide was recognized with the ProImmune® MicroArray (see, Table 12).

DRIEPGRDRRFRVM*RLPNGR (SEQ ID NO:145)

Notably, $R_{62}$, $R_{69}$, $R_{72}$, and $R_{75}$ of SEQ ID NO: 114 are all comprised by both the longer peptide (SEQ ID NO: 144) and the shorter peptide (SEQ ID NO: 145), whereas $R_{90}$ of SEQ ID NO: 114 is in the longer peptide. These five arginine residues appear to be important amino acid residues in one or more epitopes of canine PD-1. As indicated in the Tables 6-8, the starred methionine residue (*) has also been reported as being a threonine residue.

TABLE 12

PD-1 EPITOPES RECOGNIZED BY ANTI-CANINE PD-1 MAABS USING PROIMMUNE ® MICROARRAY

| ANTIBODY | ANTIGEN PEPTIDE | SEQ ID NO: |
|---|---|---|
| 2H9 | GRDRRFRVM*RLPNGR | 138 |
| 1A1# | DRIEPGRDRRFRVM*R | 139 |
| 1A1 | GRDRRFRVM*RLPNGR | 138 |

*This methionine residue has also been reported as being a threonine residue.
The CDRs of 1A1 are identical to those of 2G9.

TABLE 13

PD-1 EPITOPES RECOGNIZED BY ANTI-CANINE PD-1 MAABS USING MASS SPECTROMETRY

| ANTIBODY | PEPTIDE ANTIGEN | SEQ ID NO: |
|---|---|---|
| 3B6 | RFRVM*RLPNGRDFHMSIVAARLNDS | 140 |
| 2G9 | LAAFQEDRIEPGRDRRFRVM*RLPNGR | 141 |
| 1E4# | EDRIEPGRDRRFRVM*RLPNGRDFHMSIVAAR | 142 |
| 1B5 | NQTDKLAAFQEDRIEPGRDRRFRVM*RLPNGR | 143 |

*This methionine residue has also been reported as being a threonine residue.
The CDRs of 1E4 are most closely related to those or 2G9.

All references cited herein are incorporated by reference to the same extent as if each individual publication, database entry (e.g., Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g., Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

We claim:

1. A canine fragment crystallizable region (cFc region) that comprises the amino acid sequence of SEQ ID NO: 132 that has been modified to comprise the substituted amino acid residues selected from the group consisting of (i) P4A, (ii) D31A, (iii) A93G, (iv) P95A, and (v) P4A, D31A, N63A, A93G and P95A.

2. A caninized antibody that comprises the cFc region of claim 1.

3. The caninized antibody of claim 2 wherein the caninized antibody binds canine Programmed Death Receptor 1 (canine PD-1) with specificity.

4. The caninized antibody of claim 3, wherein the cFc region further comprises a hinge region that comprises an amino acid sequence selected from the group consisting of SEQ ID NO: 109, SEQ ID NO: 110, SEQ ID NO: 111, and SEQ ID NO: 112.

5. The caninized antibody of claim 3 that further comprises a heavy chain complementary determining region 1 (VH CDR1) that comprises the amino acid sequence of SEQ ID NO: 28; a heavy chain complementary determining region 2 (VH CDR2) that comprises the amino acid sequence of SEQ ID NO: 32; and a heavy chain complementary determining region 3 (VH CDR3) that comprises the amino acid sequence of SEQ ID NO: 37; and further comprises a light chain complementary determining region 1 (VL CDR1) that comprises the amino acid sequence of SEQ ID NO: 14; a light chain complementary determining region 2 (VL CDR2) that comprises the amino acid sequence of SEQ ID NO: 17; and a light chain complementary determining region 3 (VL CDR3) that comprises the amino acid sequence of SEQ ID NO: 23.

6. A pharmaceutical composition comprising the antibody of claim 5, and a pharmaceutically acceptable carrier or diluent.

7. A canine fragment crystallizable region (cFc region) that comprises the amino acid sequence of SEQ ID NO: 132 that has been modified to comprise the substituted amino acids residues of D31A and N63A.

8. A caninized antibody that comprises the cFc region of claim 7.

9. The caninized antibody of claim 8 that further comprises a heavy chain complementary determining region 1 (VH CDR1) that comprises the amino acid sequence of SEQ ID NO: 27; a heavy chain complementary determining region 2 (VH CDR2) that comprises the amino acid sequence of SEQ ID NO: 31; a heavy chain complementary determining region 3 (VH CDR3) that comprises the amino acid sequence of SEQ ID NO: 36; a light chain complementary determining region 1 (VL CDR1) that comprises the amino acid sequence of SEQ ID NO: 13; a light chain complementary determining region 2 (VL CDR2) that comprises the amino acid sequence of SEQ ID NO: 19; and a light chain complementary determining region 3 (VL CDR3) that comprises the amino acid sequence of SEQ ID NO: 25; wherein the caninized antibody binds canine Programmed Death Receptor 1 (canine PD-1) with specificity.

10. A pharmaceutical composition comprising the antibody of claim 9, and a pharmaceutically acceptable carrier or diluent.

11. The caninized antibody of claim 8 that further comprises a heavy chain complementary determining region 1 (VH CDR1) that comprises the amino acid sequence of SEQ ID NO: 29; a heavy chain complementary determining region 2 (VH CDR2) that comprises the amino acid sequence of SEQ ID NO: 33; a heavy chain complementary determining region 3 (VH CDR3) that comprises the amino acid sequence of SEQ ID NO: 38; a light chain complementary determining region 1 (VL CDR1) that comprises the amino acid sequence of SEQ ID NO: 15; a light chain complementary determining region 2 (VL CDR2) that comprises the amino acid sequence of SEQ ID NO: 18; and a light chain complementary determining region 3 (VL CDR3) that comprises the amino acid sequence of SEQ ID NO: 24; wherein the caninized antibody binds canine Programmed Death Receptor 1 (canine PD-1) with specificity.

12. A pharmaceutical composition comprising the antibody of claim 11, and a pharmaceutically acceptable carrier or diluent.

13. The caninized antibody of claim 8, comprising a heavy chain that comprises the amino acid sequence of SEQ ID NO: 42; wherein there is a proline residue at amino acid position 237, an alanine residue at amino acid position 264, an alanine residue at amino acid position 296, a glycine residue at amino acid position 297, a threonine residue at amino acid position 298, an alanine residue at amino acid position 326, and a proline residue at amino acid position 328; wherein said caninized antibody further comprises a canine light chain that comprises the amino acid sequence SEQ ID NO: 72, wherein the caninized antibody binds canine Programmed Death Receptor 1 (canine PD-1) with specificity.

14. A pharmaceutical composition comprising the antibody of claim 13, and a pharmaceutically acceptable carrier or diluent.

15. A caninized antibody comprising a heavy chain that comprises the amino acid sequence of SEQ ID NO: 46; wherein there is a proline residue at amino acid position 242, an alanine residue at amino acid position 269, an alanine residue at amino acid position 301, a glycine residue at amino acid position 302, a threonine residue at amino acid position 303, an alanine residue at amino acid position 331, and a proline residue at amino acid position 333; wherein said caninized antibody further comprises a canine light chain that comprises the amino acid sequence SEQ ID NO: 78, wherein the caninized antibody binds canine Programmed Death Receptor 1 (canine PD-1) with specificity.

16. A pharmaceutical composition comprising the antibody of claim 15, and a pharmaceutically acceptable carrier or diluent.

* * * * *

SEQUENCE LISTING

```
<160> NUMBER OF SEQ ID NOS: 146

<210> SEQ ID NO 1
<211> LENGTH: 690
<212> TYPE: DNA
<213> ORGANISM: Artificial Sequence
<220> FEATURE:
<223> OTHER INFORMATION: modified canine sequence
<220> FEATURE:
<221> NAME/KEY: misc_feature
<222> LOCATION: (10)..(12)
<223> OTHER INFORMATION: n is a, c, g, or t
<220> FEATURE:
<221> NAME/KEY: misc_feature
<222> LOCATION: (91)..(93)
<223> OTHER INFORMATION: n is a, c, g, or t
<220> FEATURE:
```

```
<221> NAME/KEY: misc_feature
<222> LOCATION: (187)..(195)
<223> OTHER INFORMATION: n is a, c, g, or t
<220> FEATURE:
<221> NAME/KEY: misc_feature
<222> LOCATION: (277)..(279)
<223> OTHER INFORMATION: n is a, c, g, or t
<220> FEATURE:
<221> NAME/KEY: misc_feature
<222> LOCATION: (283)..(285)
<223> OTHER INFORMATION: n is a, c, g, or t

<400> SEQUENCE: 1
ctgggcggcn nnagcgtgtt tattttccg ccgaaaccga agatacccct gctgattgcg      60
cgcaccccgg aagtgacctg cgtggtggtg nnnctggatc cggaagatcc ggaagtgcag    120
attagctggt ttgtggatgg caaacagatg cagaccgcga aacccagcc gcgcgaagaa     180 cagtttnnnn nnnnntatcg cgtggtgagc gtgctgccga ttggccatca ggattggctg    240
aaaggcaaac agtttacctg caaagtgaac aacaaannnc tgnnnagccc gattgaacgc    300
accattagca aagcgcgcgg ccaggcgcat cagccgagcg tgtatgtgct gccgccgagc    360
cgcgaagaac tgagcaaaaa caccgtgagc ctgacctgcc tgattaaaga tttttttccg    420
ccggatattg atgtggaatg gcagagcaac ggccagcagg aaccggaaag caaatatcgc    480
accaccccgc cgcagctgga tgaagatggc agctattttc tgtatagcaa actgagcgtg    540
gataaaagcc gctggcagcg cggcgatacc tttatttgcg cggtgatgca tgaagcgctg    600
cataaccatt atacccagga aagcctgagc catagcccgg gcaaacataa ccattatacc    660
caggaaagcc tgagccatag cccgggcaaa                                     690

<210> SEQ ID NO 2
<211> LENGTH: 215
<212> TYPE: PRT
<213> ORGANISM: Artificial Sequence
<220> FEATURE:
<223> OTHER INFORMATION: modified canine sequence
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (63)..(65)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid
<220> FEATURE:
<221> NAME/KEY: misc_feature
<222> LOCATION: (95)..(95)
<223> OTHER INFORMATION: Xaa can be any naturally occurring amino acid

<400> SEQUENCE: 2

Leu Gly Gly Xaa Ser Val Phe Ile Phe Pro Pro Lys Pro Lys Asp Thr
1               5                   10                  15

Leu Leu Ile Ala Arg Thr Pro Glu Val Thr Cys Val Val Val Xaa Leu
            20                  25                  30

Asp Pro Glu Asp Pro Glu Val Gln Ile Ser Trp Phe Val Asp Gly Lys
        35                  40                  45

Gln Met Gln Thr Ala Lys Thr Gln Pro Arg Glu Glu Gln Phe Xaa Xaa
    50                  55                  60
```

Xaa Tyr Arg Val Val Ser Val Leu Pro Ile Gly His Gln Asp Trp Leu
 65                  70                  75                  80

Lys Gly Lys Gln Phe Thr Cys Lys Val Asn Asn Lys Xaa Leu Xaa Ser
                 85                  90                  95

Pro Ile Glu Arg Thr Ile Ser Lys Ala Arg Gly Gln Ala His Gln Pro
            100                 105                 110

Ser Val Tyr Val Leu Pro Pro Ser Arg Glu Glu Leu Ser Lys Asn Thr
        115                 120                 125

Val Ser Leu Thr Cys Leu Ile Lys Asp Phe Phe Pro Pro Asp Ile Asp
130                 135                 140

Val Glu Trp Gln Ser Asn Gly Gln Gln Glu Pro Glu Ser Lys Tyr Arg
145                 150                 155                 160

Thr Thr Pro Pro Gln Leu Asp Glu Asp Gly Ser Tyr Phe Leu Tyr Ser
                165                 170                 175

Lys Leu Ser Val Asp Lys Ser Arg Trp Gln Arg Gly Asp Thr Phe Ile
            180                 185                 190

Cys Ala Val Met His Glu Ala Leu His Asn His Tyr Thr Gln Glu Ser
        195                 200                 205

Leu Ser His Ser Pro Gly Lys
    210                 215

<210> SEQ ID NO 3
<211> LENGTH: 690
<212> TYPE: DNA
<213> ORGANISM: Artificial Sequence
<220> FEATURE:
<223> OTHER INFORMATION: modified canine sequence
<220> FEATURE:
<221> NAME/KEY: misc_feature
<222> LOCATION: (10)..(12)
<223> OTHER INFORMATION: n is a, c, g, or t
<220> FEATURE:
<221> NAME/KEY: misc_feature
<222> LOCATION: (91)..(93)
<223> OTHER INFORMATION: n is a, c, g, or t
<220> FEATURE:
<221> NAME/KEY: misc_feature
<222> LOCATION: (187)..(195)
<223> OTHER INFORMATION: n is a, c, g, or t
<220> FEATURE:
<221> NAME/KEY: misc_feature
<222> LOCATION: (277)..(279)
<223> OTHER INFORMATION: n is a, c, g, or t
<220> FEATURE:
<221> NAME/KEY: misc_feature
<222> LOCATION: (283)..(285)
<223> OTHER INFORMATION: n is a, c, g, or t

<400> SEQUENCE: 3
ctgggcggcn nnagcgtgtt tattttccg ccgaaaccga agatattct ggtgaccgcg      60 cgcaccccga ccgtgacctg cgtggtggtg nnnctggatc cggaaaaccc ggaagtgcag    120
attagctggt ttgtggatag caaacaggtg cagaccgcga cacccagcc gcgcgaagaa    180 cagagcnnnn nnnnntatcg cgtggtgagc gtgctgccga ttggccatca ggattggctg    240
agcggcaaac agtttaaatg caaagtgaac aacaaannnc tgnnnagccc gattgaagaa    300
attattagca aaccccgggg ccaggcgcat cagccgaacg tgtatgtgct gccgccgagc    360
cgcgatgaaa tgagcaaaaa caccgtgacc ctgacctgcc tggtgaaaga tttttttccg    420
ccggaaattg atgtggaatg gcagagcaac ggccagcagg aaccggaaag caaatatcgc    480
atgaccccgc cgcagctgga tgaagatggc agctattttc tgtatagcaa actgagcgtg    540

```
gataaaagcc gctggcagcg cggcgatacc tttatttgcg cggtgatgca tgaagcgctg      600
cataaccatt atacccagat tagcctgagc catagcccgg gcaaacataa ccattatacc      660
cagattagcc tgagccatag cccgggcaaa                                       690
```

```
<210> SEQ ID NO 4
<211> LENGTH: 215
<212> TYPE: PRT
<213> ORGANISM: Artificial Sequence
<220> FEATURE:
<223> OTHER INFORMATION: modified canine sequence
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (63)..(65)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid
<220> FEATURE:
<221> NAME/KEY: misc_feature
<222> LOCATION: (95)..(95)
<223> OTHER INFORMATION: Xaa can be any naturally occurring amino acid

<400> SEQUENCE: 4

Leu Gly Gly Xaa Ser Val Phe Ile Phe Pro Pro Lys Pro Lys Asp Ile
1               5                   10                  15

Leu Val Thr Ala Arg Thr Pro Thr Val Thr Cys Val Val Val Xaa Leu
            20                  25                  30

Asp Pro Glu Asn Pro Glu Val Gln Ile Ser Trp Phe Val Asp Ser Lys
        35                  40                  45

Gln Val Gln Thr Ala Asn Thr Gln Pro Arg Glu Glu Gln Ser Xaa Xaa
    50                  55                  60

Xaa Tyr Arg Val Val Ser Val Leu Pro Ile Gly His Gln Asp Trp Leu
65                  70                  75                  80

Ser Gly Lys Gln Phe Lys Cys Lys Val Asn Asn Lys Xaa Leu Xaa Ser
                85                  90                  95

Pro Ile Glu Glu Ile Ile Ser Lys Thr Pro Gly Gln Ala His Gln Pro
            100                 105                 110

Asn Val Tyr Val Leu Pro Pro Ser Arg Asp Glu Met Ser Lys Asn Thr
        115                 120                 125

Val Thr Leu Thr Cys Leu Val Lys Asp Phe Phe Pro Pro Glu Ile Asp
    130                 135                 140

Val Glu Trp Gln Ser Asn Gly Gln Gln Glu Pro Glu Ser Lys Tyr Arg
145                 150                 155                 160

Met Thr Pro Pro Gln Leu Asp Glu Asp Gly Ser Tyr Phe Leu Tyr Ser
                165                 170                 175

Lys Leu Ser Val Asp Lys Ser Arg Trp Gln Arg Gly Asp Thr Phe Ile
            180                 185                 190

Cys Ala Val Met His Glu Ala Leu His Asn His Tyr Thr Gln Ile Ser
        195                 200                 205

Leu Ser His Ser Pro Gly Lys
    210                 215
```

```
<210> SEQ ID NO 5
<211> LENGTH: 699
<212> TYPE: DNA
<213> ORGANISM: Artificial Sequence
<220> FEATURE:
<223> OTHER INFORMATION: modified canine sequence

<400> SEQUENCE: 5
ccgaaagaaa gcacctgcaa atgcattccg ccgtgcccgg tgccggaaag cctgggcggc      60
ccgagcgtgt ttattttcc gccgaaaccg aaagatattc tgcgcattac ccgcaccccg     120
gaaattacct gcgtggtgct ggatctgggc cgcgaagatc cggaagtgca gattagctgg     180
tttgtggatg gcaaagaagt gcataccgcg aaaacccagc cgcgcgaaca gcagtttaac     240
agcacctatc gcgtggtgag cgtgctgccg attgaacatc aggattggct gaccggcaaa     300
gaatttaaat gccgcgtgaa ccatattggc ctgccgagcc cgattgaacg caccattagc     360
aaagcgcgcg gccaggcgca tcagccgagc gtgtatgtgc tgccgccgag cccgaaagaa     420
ctgagcagca gcgataccgt gaccctgacc tgcctgatta agattttttt ccgccggaa     480
attgatgtgg aatggcagag caacggccag ccggaaccgg aaagcaaata tcataccacc     540
gcgccgcagc tggatgaaga tggcagctat tttctgtata gcaaactgag cgtggataaa     600
agccgctggc agcagggcga tacctttacc tgcgcggtga tgcatgaagc gctgcagaac     660
cattataccg atctgagcct gagccatagc ccgggcaaa                             699

<210> SEQ ID NO 6
<211> LENGTH: 233
<212> TYPE: PRT
<213> ORGANISM: Artificial Sequence
<220> FEATURE:
<223> OTHER INFORMATION: modified canine sequence

<400> SEQUENCE: 6

Pro Lys Glu Ser Thr Cys Lys Cys Ile Pro Pro Cys Pro Val Pro Glu
1               5                   10                  15

Ser Leu Gly Gly Pro Ser Val Phe Ile Phe Pro Pro Lys Pro Lys Asp
            20                  25                  30

Ile Leu Arg Ile Thr Arg Thr Pro Glu Ile Thr Cys Val Val Leu Asp
        35                  40                  45

Leu Gly Arg Glu Asp Pro Glu Val Gln Ile Ser Trp Phe Val Asp Gly
    50                  55                  60

Lys Glu Val His Thr Ala Lys Thr Gln Pro Arg Glu Gln Gln Phe Asn
65                  70                  75                  80

Ser Thr Tyr Arg Val Val Ser Val Leu Pro Ile Glu His Gln Asp Trp
                85                  90                  95

Leu Thr Gly Lys Glu Phe Lys Cys Arg Val Asn His Ile Gly Leu Pro
            100                 105                 110

Ser Pro Ile Glu Arg Thr Ile Ser Lys Ala Arg Gly Gln Ala His Gln
        115                 120                 125

Pro Ser Val Tyr Val Leu Pro Pro Ser Pro Lys Glu Leu Ser Ser Ser
    130                 135                 140

Asp Thr Val Thr Leu Thr Cys Leu Ile Lys Asp Phe Phe Pro Pro Glu
145                 150                 155                 160

Ile Asp Val Glu Trp Gln Ser Asn Gly Gln Pro Glu Pro Glu Ser Lys
                165                 170                 175

Tyr His Thr Thr Ala Pro Gln Leu Asp Glu Asp Gly Ser Tyr Phe Leu
            180                 185                 190
```

Tyr Ser Lys Leu Ser Val Asp Lys Ser Arg Trp Gln Gln Gly Asp Thr
    195                 200                 205

Phe Thr Cys Ala Val Met His Glu Ala Leu Gln Asn His Tyr Thr Asp
    210                 215                 220

Leu Ser Leu Ser His Ser Pro Gly Lys
225                 230

<210> SEQ ID NO 7
<211> LENGTH: 699
<212> TYPE: DNA
<213> ORGANISM: Artificial Sequence
<220> FEATURE:
<223> OTHER INFORMATION: modified canine sequence

<400> SEQUENCE: 7
tttaacgaat gccgctgcac cgataccccg ccgtgcccgg tgccggaacc gctgggcggc        60
ccgagcgtgt ttatttttcc gccgaaaccg aaagatattc tgcgcattac ccgcacccg       120 gaaattacct gcgtggtgct ggatctgggc cgcgaagatc cggaagtgca gattagctgg      180
tttgtggatg gcaaagaagt gcataccgcg aaaacccagc cgcgcgaaca gcagtttaac      240
agcacctatc gcgtggtgag cgtgctgccg attgaacatc aggattggct gaccggcaaa      300
gaatttaaat gccgcgtgaa ccatattggc ctgccgagcc cgattgaacg caccattagc      360
aaagcgcgcg gccaggcgca tcagccgagc gtgtatgtgc tgccgccgag cccgaaagaa      420
ctgagcagca gcgataccgt gaccctgacc tgcctgatta agatttttt ccgccggaa      480 attgatgtgg aatggcagag caacggccag ccggaaccgg aaagcaaata tcataccacc      540
gcgccgcagc tggatgaaga tggcagctat tttctgtata gcaaactgag cgtggataaa      600
agccgctggc agcagggcga taccttacc tgcgcggtga tgcatgaagc gctgcagaac      660
cattataccg atctgagcct gagccatagc ccgggcaaa                             699

<210> SEQ ID NO 8
<211> LENGTH: 233
<212> TYPE: PRT
<213> ORGANISM: Artificial Sequence
<220> FEATURE:
<223> OTHER INFORMATION: modified canine sequence

<400> SEQUENCE: 8

Phe Asn Glu Cys Arg Cys Thr Asp Thr Pro Pro Cys Pro Val Pro Glu
1               5                   10                  15

Pro Leu Gly Gly Pro Ser Val Phe Ile Phe Pro Pro Lys Pro Lys Asp
            20                  25                  30

Ile Leu Arg Ile Thr Arg Thr Pro Glu Ile Thr Cys Val Val Leu Asp
        35                  40                  45

Leu Gly Arg Glu Asp Pro Glu Val Gln Ile Ser Trp Phe Val Asp Gly
    50                  55                  60

Lys Glu Val His Thr Ala Lys Thr Gln Pro Arg Glu Gln Gln Phe Asn
65                  70                  75                  80

Ser Thr Tyr Arg Val Val Ser Val Leu Pro Ile Glu His Gln Asp Trp
                85                  90                  95

Leu Thr Gly Lys Glu Phe Lys Cys Arg Val Asn His Ile Gly Leu Pro
            100                 105                 110

Ser Pro Ile Glu Arg Thr Ile Ser Lys Ala Arg Gly Gln Ala His Gln
        115                 120                 125

Pro Ser Val Tyr Val Leu Pro Pro Ser Pro Lys Glu Leu Ser Ser Ser
    130                 135                 140

Asp Thr Val Thr Leu Thr Cys Leu Ile Lys Asp Phe Phe Pro Glu
145                 150                 155                 160

Ile Asp Val Glu Trp Gln Ser Asn Gly Gln Pro Glu Pro Glu Ser Lys
                165                 170                 175

Tyr His Thr Thr Ala Pro Gln Leu Asp Glu Asp Gly Ser Tyr Phe Leu
            180                 185                 190

Tyr Ser Lys Leu Ser Val Asp Lys Ser Arg Trp Gln Gln Gly Asp Thr
        195                 200                 205

Phe Thr Cys Ala Val Met His Glu Ala Leu Gln Asn His Tyr Thr Asp
    210                 215                 220

Leu Ser Leu Ser His Ser Pro Gly Lys
225                 230

<210> SEQ ID NO 9
<211> LENGTH: 714
<212> TYPE: DNA
<213> ORGANISM: Artificial Sequence
<220> FEATURE:
<223> OTHER INFORMATION: modified canine sequence

<400> SEQUENCE: 9
ccgaaacgcg aaaacggccg cgtgccgcgc cgccggatt gcccgaaatg cccggcgccg      60
gaaatgctgg gcggcccgag cgtgtttatt tttccgccga aaccgaaaga tattctgcgc    120
attacccgca ccccggaaat tacctgcgtg gtgctggatc tgggccgcga agatccggaa    180
gtgcagatta gctggtttgt ggatggcaaa gaagtgcata ccgcgaaaac ccagccgcgc    240
gaacagcagt ttaacagcac ctatcgcgtg gtgagcgtgc tgccgattga acatcaggat    300
tggctgaccg gcaaagaatt taaatgccgc gtgaaccata ttggcctgcc gagcccgatt    360
gaacgcacca ttagcaaagc gcgcggccag gcgcatcagc cgagcgtgta tgtgctgccg    420
ccgagcccga agaactgag cagcagcgat accgtgaccc tgacctgcct gattaaagat    480
ttttttccgc cggaaattga tgtggaatgg cagagcaacg gccagccgga accggaaagc    540
aaatatcata ccaccgcgcc gcagctggat gaagatggca gctatttct gtatagcaaa    600 ctgagcgtgg ataaaagccg ctggcagcag ggcgataccttaccctgcgc ggtgatgcat    660 gaagcgctgc agaaccatta taccgatctg agcctgagcc atagcccggg caaa          714

<210> SEQ ID NO 10
<211> LENGTH: 238
<212> TYPE: PRT
<213> ORGANISM: Artificial Sequence
<220> FEATURE:
<223> OTHER INFORMATION: modified canine sequence

<400> SEQUENCE: 10

Pro Lys Arg Glu Asn Gly Arg Val Pro Arg Pro Pro Asp Cys Pro Lys
1               5                   10                  15

Cys Pro Ala Pro Glu Met Leu Gly Gly Pro Ser Val Phe Ile Phe Pro
            20                  25                  30

Pro Lys Pro Lys Asp Ile Leu Arg Ile Thr Arg Thr Pro Glu Ile Thr
        35                  40                  45

Cys Val Val Leu Asp Leu Gly Arg Glu Asp Pro Glu Val Gln Ile Ser
    50                  55                  60

Trp Phe Val Asp Gly Lys Glu Val His Thr Ala Lys Thr Gln Pro Arg
65                  70                  75                  80

Glu Gln Gln Phe Asn Ser Thr Tyr Arg Val Val Ser Val Leu Pro Ile

```
                85                  90                  95
Glu His Gln Asp Trp Leu Thr Gly Lys Glu Phe Lys Cys Arg Val Asn
            100                 105                 110

His Ile Gly Leu Pro Ser Pro Ile Glu Arg Thr Ile Ser Lys Ala Arg
        115                 120                 125

Gly Gln Ala His Gln Pro Ser Val Tyr Val Leu Pro Pro Ser Pro Lys
    130                 135                 140

Glu Leu Ser Ser Ser Asp Thr Val Thr Leu Thr Cys Leu Ile Lys Asp
145                 150                 155                 160

Phe Phe Pro Pro Glu Ile Asp Val Glu Trp Gln Ser Asn Gly Gln Pro
                165                 170                 175

Glu Pro Glu Ser Lys Tyr His Thr Thr Ala Pro Gln Leu Asp Glu Asp
            180                 185                 190

Gly Ser Tyr Phe Leu Tyr Ser Lys Leu Ser Val Asp Lys Ser Arg Trp
        195                 200                 205

Gln Gln Gly Asp Thr Phe Thr Cys Ala Val Met His Glu Ala Leu Gln
    210                 215                 220

Asn His Tyr Thr Asp Leu Ser Leu Ser His Ser Pro Gly Lys
225                 230                 235

<210> SEQ ID NO 11
<211> LENGTH: 708
<212> TYPE: DNA
<213> ORGANISM: Artificial Sequence
<220> FEATURE:
<223> OTHER INFORMATION: modified canine sequence

<400> SEQUENCE: 11
gccaaggagt gcgagtgcaa gtgcaactgc aacaactgcc cctgccccgg ctgcggcctg      60
ctgggcggcc ccagcgtgtt catcttcccc cccaagccca aggacatcct gagaatcacc     120
agaacccccg agatcacctg cgtggtgctg gacctgggca gagaggaccc cgaggtgcag     180
atcagctggt tcgtggacgg caaggaggtg cacaccgcca gacccagcc cagagagcag     240
cagttcaaca gcacctacag agtggtgagc gtgctgccca tcgagcacca ggactggctg     300
accggcaagg agttcaagtg cagagtgaac cacatcggcc tgcccagccc catcgagaga     360
accatcagca aggccagagg ccaggcccac cagcccagcg tgtacgtgct gcccccagc      420
cccaaggagc tgagcagcag cgacaccgtg accctgacct gcctgatcaa ggacttcttc     480
cccccgaga tcgacgtgga gtggcagagc aacggccagc ccgagcccga gagcaagtac     540
cacaccaccg cccccagct ggacgaggac ggcagctact tcctgtacag caagctgagc     600
gtggacaaga gcagatggca gcagggcgac accttcacct gcgccgtgat gcacgaggcc     660
ctgcagaacc actacaccga cctgagcctg agccacagcc ccggcaag              708

<210> SEQ ID NO 12
<211> LENGTH: 236
<212> TYPE: PRT
<213> ORGANISM: Artificial Sequence
<220> FEATURE:
<223> OTHER INFORMATION: modified canine sequence

<400> SEQUENCE: 12

Ala Lys Glu Cys Glu Cys Lys Cys Asn Cys Asn Asn Cys Pro Cys Pro
1               5                   10                  15

Gly Cys Gly Leu Leu Gly Gly Pro Ser Val Phe Ile Phe Pro Pro Lys
            20                  25                  30
```

-continued

```
Pro Lys Asp Ile Leu Arg Ile Thr Arg Thr Pro Glu Ile Thr Cys Val
         35                  40                  45
Val Leu Asp Leu Gly Arg Glu Asp Pro Glu Val Gln Ile Ser Trp Phe
 50                  55                  60
Val Asp Gly Lys Glu Val His Thr Ala Lys Thr Gln Pro Arg Glu Gln
 65                  70                  75                  80
Gln Phe Asn Ser Thr Tyr Arg Val Val Ser Val Leu Pro Ile Glu His
                 85                  90                  95
Gln Asp Trp Leu Thr Gly Lys Glu Phe Lys Cys Arg Val Asn His Ile
            100                 105                 110
Gly Leu Pro Ser Pro Ile Glu Arg Thr Ile Ser Lys Ala Arg Gly Gln
        115                 120                 125
Ala His Gln Pro Ser Val Tyr Val Leu Pro Pro Ser Pro Lys Glu Leu
    130                 135                 140
Ser Ser Ser Asp Thr Val Thr Leu Thr Cys Leu Ile Lys Asp Phe Phe
145                 150                 155                 160
Pro Pro Glu Ile Asp Val Glu Trp Gln Ser Asn Gly Gln Pro Glu Pro
                165                 170                 175
Glu Ser Lys Tyr His Thr Thr Ala Pro Gln Leu Asp Glu Asp Gly Ser
            180                 185                 190
Tyr Phe Leu Tyr Ser Lys Leu Ser Val Asp Lys Ser Arg Trp Gln Gln
        195                 200                 205
Gly Asp Thr Phe Thr Cys Ala Val Met His Glu Ala Leu Gln Asn His
    210                 215                 220
Tyr Thr Asp Leu Ser Leu Ser His Ser Pro Gly Lys
225                 230                 235

<210> SEQ ID NO 13
<211> LENGTH: 17
<212> TYPE: PRT
<213> ORGANISM: Mus musculus

<400> SEQUENCE: 13

Lys Ser Ser Gln Ser Leu Leu Asn Ser Val Asn Gln Lys Asn Tyr Leu
1               5                   10                  15
Ala

<210> SEQ ID NO 14
<211> LENGTH: 16
<212> TYPE: PRT
<213> ORGANISM: Mus musculus

<400> SEQUENCE: 14

Arg Ser Ser Gln Asn Ile Val His Ser Asn Gly Asn Thr Tyr Leu Glu
1               5                   10                  15

<210> SEQ ID NO 15
<211> LENGTH: 11
<212> TYPE: PRT
<213> ORGANISM: Mus musculus

<400> SEQUENCE: 15

His Ala Ser Gln Asn Ile Asn Val Trp Leu Ser
1               5                   10

<210> SEQ ID NO 16
<211> LENGTH: 7
<212> TYPE: PRT
<213> ORGANISM: Mus musculus
```

<400> SEQUENCE: 16

Phe Ala Ser Thr Arg Val Ser
1               5

<210> SEQ ID NO 17
<211> LENGTH: 7
<212> TYPE: PRT
<213> ORGANISM: Mus musculus

<400> SEQUENCE: 17

Lys Val Ser Asn Arg Phe Ser
1               5

<210> SEQ ID NO 18
<211> LENGTH: 7
<212> TYPE: PRT
<213> ORGANISM: Mus musculus

<400> SEQUENCE: 18

Lys Ala Ser His Leu His Thr
1               5

<210> SEQ ID NO 19
<211> LENGTH: 7
<212> TYPE: PRT
<213> ORGANISM: Mus musculus

<400> SEQUENCE: 19

Phe Ala Ser Ala Arg Val Ser
1               5

<210> SEQ ID NO 20
<211> LENGTH: 7
<212> TYPE: PRT
<213> ORGANISM: Mus musculus

<400> SEQUENCE: 20

Phe Ala Ser Thr Arg Ile Ser
1               5

<210> SEQ ID NO 21
<211> LENGTH: 7
<212> TYPE: PRT
<213> ORGANISM: Mus musculus

<400> SEQUENCE: 21

Lys Ala Ser Asn Leu His Thr
1               5

<210> SEQ ID NO 22
<211> LENGTH: 9
<212> TYPE: PRT
<213> ORGANISM: Mus musculus

<400> SEQUENCE: 22

Gln Gln Tyr Phe Ser Thr Pro Leu Thr
1               5

<210> SEQ ID NO 23
<211> LENGTH: 9
<212> TYPE: PRT
<213> ORGANISM: Mus musculus

<400> SEQUENCE: 23

```
Phe Gln Gly Ser His Val Pro Tyr Thr
1               5
```

<210> SEQ ID NO 24
<211> LENGTH: 9
<212> TYPE: PRT
<213> ORGANISM: Mus musculus

<400> SEQUENCE: 24

```
Gln Gln Gly Gln Ser Trp Pro Leu Thr
1               5
```

<210> SEQ ID NO 25
<211> LENGTH: 9
<212> TYPE: PRT
<213> ORGANISM: Mus musculus

<400> SEQUENCE: 25

```
Gln Gln Tyr Phe Ser Thr Pro Leu Thr
1               5
```

<210> SEQ ID NO 26
<211> LENGTH: 9
<212> TYPE: PRT
<213> ORGANISM: Mus musculus

<400> SEQUENCE: 26

```
Gln Gln Gly Gln Ser Tyr Pro Leu Thr
1               5
```

<210> SEQ ID NO 27
<211> LENGTH: 10
<212> TYPE: PRT
<213> ORGANISM: Mus musculus

<400> SEQUENCE: 27

```
Gly Tyr Thr Phe Thr Thr Tyr Gly Met Ser
1               5                   10
```

<210> SEQ ID NO 28
<211> LENGTH: 10
<212> TYPE: PRT
<213> ORGANISM: Mus musculus

<400> SEQUENCE: 28

```
Gly Tyr Thr Phe Thr Arg Tyr Asn Met His
1               5                   10
```

<210> SEQ ID NO 29
<211> LENGTH: 10
<212> TYPE: PRT
<213> ORGANISM: Mus musculus

<400> SEQUENCE: 29

```
Gly Phe Asn Ile Lys Asn Thr Tyr Met His
1               5                   10
```

<210> SEQ ID NO 30
<211> LENGTH: 10
<212> TYPE: PRT
<213> ORGANISM: Mus musculus

<400> SEQUENCE: 30

```
Gly Phe Ser Leu Thr Ser Tyr Gly Val His
```

-continued

```
<210> SEQ ID NO 31
<211> LENGTH: 17
<212> TYPE: PRT
<213> ORGANISM: Mus musculus

<400> SEQUENCE: 31

Trp Ile Asn Ile Tyr Ser Gly Ile Pro Thr Tyr Ala Asp Asp Phe Lys
1               5                   10                  15

Gly

<210> SEQ ID NO 32
<211> LENGTH: 17
<212> TYPE: PRT
<213> ORGANISM: Mus musculus

<400> SEQUENCE: 32

Thr Ile Tyr Pro Gly Tyr Gly Asp Thr Ser Tyr Asn Gln Lys Phe Lys
1               5                   10                  15

Gly

<210> SEQ ID NO 33
<211> LENGTH: 17
<212> TYPE: PRT
<213> ORGANISM: Mus musculus

<400> SEQUENCE: 33

Arg Ile Ala Pro Ala Asn Val Asp Thr Lys Tyr Ala Pro Lys Phe Gln
1               5                   10                  15

Gly

<210> SEQ ID NO 34
<211> LENGTH: 17
<212> TYPE: PRT
<213> ORGANISM: Mus musculus

<400> SEQUENCE: 34

Trp Ile Asn Ile Tyr Ser Gly Met Pro Thr Tyr Ala Asp Asp Phe Lys
1               5                   10                  15

Gly

<210> SEQ ID NO 35
<211> LENGTH: 17
<212> TYPE: PRT
<213> ORGANISM: Mus musculus

<400> SEQUENCE: 35

Arg Ile Asp Pro Ala Asn Val Asn Thr Lys Tyr Ala Pro Lys Phe Gln
1               5                   10                  15

Gly

<210> SEQ ID NO 36
<211> LENGTH: 6
<212> TYPE: PRT
<213> ORGANISM: Mus musculus

<400> SEQUENCE: 36

Phe Asp Gly Pro Asp Tyr
1               5
```

```
<210> SEQ ID NO 37
<211> LENGTH: 13
<212> TYPE: PRT
<213> ORGANISM: Mus musculus

<400> SEQUENCE: 37

Glu Phe Ala Asp Asp Tyr Pro Ile Pro Pro Phe Asp Tyr
1               5                   10

<210> SEQ ID NO 38
<211> LENGTH: 11
<212> TYPE: PRT
<213> ORGANISM: Mus musculus

<400> SEQUENCE: 38

Ile Tyr Tyr Asp Tyr Asp Gly Asp Ile Asp Val
1               5                   10

<210> SEQ ID NO 39
<211> LENGTH: 1350
<212> TYPE: DNA
<213> ORGANISM: Artificial Sequence
<220> FEATURE:
<223> OTHER INFORMATION: caninized mouse antibody
<220> FEATURE:
<221> NAME/KEY: misc_feature
<222> LOCATION: (715)..(717)
<223> OTHER INFORMATION: n is a, c, g, or t
<220> FEATURE:
<221> NAME/KEY: misc_feature
<222> LOCATION: (796)..(798)
<223> OTHER INFORMATION: n is a, c, g, or t
<220> FEATURE:
<221> NAME/KEY: misc_feature
<222> LOCATION: (892)..(900)
<223> OTHER INFORMATION: n is a, c, g, or t
<220> FEATURE:
<221> NAME/KEY: misc_feature
<222> LOCATION: (982)..(984)
<223> OTHER INFORMATION: n is a, c, g, or t
<220> FEATURE:
<221> NAME/KEY: misc_feature
<222> LOCATION: (988)..(990)
<223> OTHER INFORMATION: n is a, c, g, or t

<400> SEQUENCE: 39
gaggtgcagc tggtgcagag cggcggcgac ctggtgaagc ccggcggcag cgtgagactg      60
agctgcgtgg ccagcggcta caccttcacc acctacggca tgagctgggt gagacaggcc     120
cccggcaagg gcctgcagtg gatgggctgg atcaacatct acagcggcat ccccacctac     180
gccgacgact tcaagggcag attcaccttc agcctggaca ccgccaagaa caccgcctac     240
ctgcagctga acagcctgag agccgaggac accgccgtgt actactgcac cagattcgac     300
ggccccgact actggggcca gggcaccctg gtgaccgtga gcagcgccag caccaccgcc     360
cccagcgtgt tccccctggc cccagctgc ggcagcacca gcggcagcac cgtggccctg     420
gcctgcctgg tgagcggcta cttccccgag ccgtgaccg tgagctggaa cagcggcagc     480
ctgaccagcg gcgtgcacac cttccccagc gtgctgcaga gcagcggcct gtacagcctg     540
agcagcatgg tgaccgtgcc cagcagcaga tggcccagcg agaccttcac ctgcaacgtg     600
gcccaccccg ccagcaagac caaggtggac aagcccgtgc caagagaga gaacggcaga     660 gtgcccagac cccccgactg ccccaagtgc cccgccccg agatgctggg cggcnnnagc     720
gtgttcatct cccccccaa gcccaaggac accctgctga tcgccagaac ccccgaggtg     780
acctgcgtgg tggtgnnnct ggaccccgag gaccccgagg tgcagatcag ctggttcgtg     840
```

```
gacggcaagc agatgcagac cgccaagacc cagcccagag aggagcagtt cnnnnnnnnn    900
tacagagtgg tgagcgtgct gcccatcggc caccaggact ggctgaaggg caagcagttc    960
acctgcaagg tgaacaacaa gnnnctgnnn agccccatcg agagaaccat cagcaaggcc   1020
agaggccagg cccaccagcc cagcgtgtac gtgctgcccc ccagcagaga ggagctgagc   1080
aagaacaccg tgagcctgac ctgcctgatc aaggacttct ccccccccga catcgacgtg   1140
gagtggcaga gcaacggcca gcaggagccc gagagcaagt acagaaccac cccccccag    1200 ctggacgagg acggcagcta cttcctgtac agcaagctga gcgtggacaa gagcagatgg   1260
cagagaggcg acaccttcat ctgcgccgtg atgcacgagg ccctgcacaa ccactacacc   1320
caggagagcc tgagccacag ccccggcaag                                    1350
```

```
<210> SEQ ID NO 40
<211> LENGTH: 450
<212> TYPE: PRT
<213> ORGANISM: Artificial Sequence
<220> FEATURE:
<223> OTHER INFORMATION: caninized mouse antibody
<220> FEATURE:
<221> NAME/KEY: misc_feature
<222> LOCATION: (239)..(239)
<223> OTHER INFORMATION: Xaa can be any naturally occurring amino acid
<220> FEATURE:
<221> NAME/KEY: misc_feature
<222> LOCATION: (266)..(266)
<223> OTHER INFORMATION: Xaa can be any naturally occurring amino acid
<220> FEATURE:
<221> NAME/KEY: misc_feature
<222> LOCATION: (298)..(300)
<223> OTHER INFORMATION: Xaa can be any naturally occurring amino acid
<220> FEATURE:
<221> NAME/KEY: misc_feature
<222> LOCATION: (328)..(328)
<223> OTHER INFORMATION: Xaa can be any naturally occurring amino acid
<220> FEATURE:
<221> NAME/KEY: misc_feature
<222> LOCATION: (330)..(330)
<223> OTHER INFORMATION: Xaa can be any naturally occurring amino acid

<400> SEQUENCE: 40

Glu Val Gln Leu Val Gln Ser Gly Gly Asp Leu Val Lys Pro Gly Gly
1               5                   10                  15

Ser Val Arg Leu Ser Cys Val Ala Ser Gly Tyr Thr Phe Thr Thr Tyr
            20                  25                  30

Gly Met Ser Trp Val Arg Gln Ala Pro Gly Lys Gly Leu Gln Trp Met
        35                  40                  45

Gly Trp Ile Asn Ile Tyr Ser Gly Ile Pro Thr Tyr Ala Asp Asp Phe
    50                  55                  60

Lys Gly Arg Phe Thr Phe Ser Leu Asp Thr Ala Lys Asn Thr Ala Tyr
65                  70                  75                  80

Leu Gln Leu Asn Ser Leu Arg Ala Glu Asp Thr Ala Val Tyr Tyr Cys
                85                  90                  95

Thr Arg Phe Asp Gly Pro Asp Tyr Trp Gly Gln Gly Thr Leu Val Thr
            100                 105                 110

Val Ser Ser Ala Ser Thr Thr Ala Pro Ser Val Phe Pro Leu Ala Pro
        115                 120                 125

Ser Cys Gly Ser Thr Ser Gly Ser Thr Val Ala Leu Ala Cys Leu Val
    130                 135                 140

Ser Gly Tyr Phe Pro Glu Pro Val Thr Val Ser Trp Asn Ser Gly Ser
145                 150                 155                 160

Leu Thr Ser Gly Val His Thr Phe Pro Ser Val Leu Gln Ser Ser Gly
```

```
                        165                 170                 175

Leu Tyr Ser Leu Ser Ser Met Val Thr Val Pro Ser Ser Arg Trp Pro
                180                 185                 190

Ser Glu Thr Phe Thr Cys Asn Val Ala His Pro Ala Ser Lys Thr Lys
            195                 200                 205

Val Asp Lys Pro Val Pro Lys Arg Glu Asn Gly Arg Val Pro Arg Pro
        210                 215                 220

Pro Asp Cys Pro Lys Cys Pro Ala Pro Glu Met Leu Gly Gly Xaa Ser
225                 230                 235                 240

Val Phe Ile Phe Pro Pro Lys Pro Lys Asp Thr Leu Leu Ile Ala Arg
                245                 250                 255

Thr Pro Glu Val Thr Cys Val Val Val Xaa Leu Asp Pro Glu Asp Pro
                260                 265                 270

Glu Val Gln Ile Ser Trp Phe Val Asp Gly Lys Gln Met Gln Thr Ala
            275                 280                 285

Lys Thr Gln Pro Arg Glu Glu Gln Phe Xaa Xaa Xaa Tyr Arg Val Val
        290                 295                 300

Ser Val Leu Pro Ile Gly His Gln Asp Trp Leu Lys Gly Lys Gln Phe
305                 310                 315                 320

Thr Cys Lys Val Asn Asn Lys Xaa Leu Xaa Ser Pro Ile Glu Arg Thr
                325                 330                 335

Ile Ser Lys Ala Arg Gly Gln Ala His Gln Pro Ser Val Tyr Val Leu
                340                 345                 350

Pro Pro Ser Arg Glu Glu Leu Ser Lys Asn Thr Val Ser Leu Thr Cys
            355                 360                 365

Leu Ile Lys Asp Phe Phe Pro Pro Asp Ile Asp Val Glu Trp Gln Ser
        370                 375                 380

Asn Gly Gln Gln Glu Pro Glu Ser Lys Tyr Arg Thr Thr Pro Pro Gln
385                 390                 395                 400

Leu Asp Glu Asp Gly Ser Tyr Phe Leu Tyr Ser Lys Leu Ser Val Asp
                405                 410                 415

Lys Ser Arg Trp Gln Arg Gly Asp Thr Phe Ile Cys Ala Val Met His
                420                 425                 430

Glu Ala Leu His Asn His Tyr Thr Gln Glu Ser Leu Ser His Ser Pro
            435                 440                 445

Gly Lys
    450

<210> SEQ ID NO 41
<211> LENGTH: 1344
<212> TYPE: DNA
<213> ORGANISM: Artificial Sequence
<220> FEATURE:
<223> OTHER INFORMATION: caninized mouse antibody
<220> FEATURE:
<221> NAME/KEY: misc_feature
<222> LOCATION: (709)..(711)
<223> OTHER INFORMATION: n is a, c, g, or t
<220> FEATURE:
<221> NAME/KEY: misc_feature
<222> LOCATION: (790)..(792)
<223> OTHER INFORMATION: n is a, c, g, or t
<220> FEATURE:
<221> NAME/KEY: misc_feature
<222> LOCATION: (886)..(894)
<223> OTHER INFORMATION: n is a, c, g, or t
<220> FEATURE:
<221> NAME/KEY: misc_feature
<222> LOCATION: (976)..(978)
<223> OTHER INFORMATION: n is a, c, g, or t
```

<220> FEATURE:
<221> NAME/KEY: misc_feature
<222> LOCATION: (982)..(984)
<223> OTHER INFORMATION: n is a, c, g, or t

<400> SEQUENCE: 41

```
gaggtgcagc tggtgcagag cggcggcgac ctggtgaagc ccggcggcag cgtgagactg      60
agctgcgtgg ccagcggcta caccttcacc acctacggca tgagctgggt gagacaggcc     120
cccggcaagg gcctgcagtg gatgggctgg atcaacatct acagcggcat ccccacctac     180
gccgacgact tcaagggcag attcaccttc agcctggaca ccgccaagaa caccgcctac     240
ctgcagctga acagcctgag agccgaggac accgccgtgt actactgcac cagattcgac     300
ggccccgact actggggcca gggcaccctg gtgaccgtga gcagcgccag caccaccgcc     360
cccagcgtgt tccccctggc ccccagctgc ggcagccaga gcggcagcac cgtggccctg     420
gcctgcctgg tgagcggcta catccccgag cccgtgaccg tgagctggaa cagcgtgagc     480
ctgaccagcg gcgtgcacac cttccccagc gtgctgcaga gcagcggcct gtacagcctg     540
agcagcatgg tgaccgtgcc cagcagcaga tggcccagcg agaccttcac ctgcaacgtg     600
gcccaccccg ccaccaacac caaggtggac aagcccgtgg ccaaggagtg cgagtgcaag     660
tgcaactgca caactgccc ctgccccggc tgcggcctgc tgggcggcnn nagcgtgttc     720
atcttccccc ccaagcccaa ggacatcctg gtgaccgcca gacccccac cgtgacctgc     780
gtggtggtgn nnctggaccc cgagaacccc gaggtgcaga tcagctggtt cgtggacagc     840
aagcaggtgc agaccgccaa cacccagccc agagaggagc agagcnnnnn nnnntacaga     900
gtggtgagcg tgctgcccat cggccaccag gactggctga gcggcaagca gttcaagtgc     960
aaggtgaaca acaagnnnct gnnnagcccc atcgaggaga tcatcagcaa gaccccgcc    1020
caggcccacc agcccaacgt gtacgtgctg ccccccagca gagacgagat gagcaagaac    1080
accgtgaccc tgacctgcct ggtgaaggac ttcttccccc cgagatcga cgtggagtgg    1140
cagagcaacg gccagcagga gcccgagagc aagtacagaa tgacccccc ccagctggac    1200
gaggacggca gctacttcct gtacagcaag ctgagcgtgg acaagagcag atggcagaga    1260
ggcgacacct tcatctgcgc cgtgatgcac gaggccctgc acaaccacta cacccagatc    1320
agcctgagcc acagccccgg caag                                          1344
```

<210> SEQ ID NO 42
<211> LENGTH: 448
<212> TYPE: PRT
<213> ORGANISM: Artificial Sequence
<220> FEATURE:
<223> OTHER INFORMATION: caninized mouse antibody
<220> FEATURE:
<221> NAME/KEY: misc_feature
<222> LOCATION: (237)..(237)
<223> OTHER INFORMATION: Xaa can be any naturally occurring amino acid
<220> FEATURE:
<221> NAME/KEY: misc_feature
<222> LOCATION: (264)..(264)
<223> OTHER INFORMATION: Xaa can be any naturally occurring amino acid
<220> FEATURE:
<221> NAME/KEY: misc_feature
<222> LOCATION: (296)..(298)
<223> OTHER INFORMATION: Xaa can be any naturally occurring amino acid
<220> FEATURE:
<221> NAME/KEY: misc_feature
<222> LOCATION: (326)..(326)
<223> OTHER INFORMATION: Xaa can be any naturally occurring amino acid
<220> FEATURE:
<221> NAME/KEY: misc_feature
<222> LOCATION: (328)..(328)

<223> OTHER INFORMATION: Xaa can be any naturally occurring amino acid

<400> SEQUENCE: 42

```
Glu Val Gln Leu Val Gln Ser Gly Gly Asp Leu Val Lys Pro Gly Gly
 1               5                  10                  15

Ser Val Arg Leu Ser Cys Val Ala Ser Gly Tyr Thr Phe Thr Thr Tyr
            20                  25                  30

Gly Met Ser Trp Val Arg Gln Ala Pro Gly Lys Gly Leu Gln Trp Met
        35                  40                  45

Gly Trp Ile Asn Ile Tyr Ser Gly Ile Pro Thr Tyr Ala Asp Asp Phe
    50                  55                  60

Lys Gly Arg Phe Thr Phe Ser Leu Asp Thr Ala Lys Asn Thr Ala Tyr
65                  70                  75                  80

Leu Gln Leu Asn Ser Leu Arg Ala Glu Asp Thr Ala Val Tyr Tyr Cys
                85                  90                  95

Thr Arg Phe Asp Gly Pro Asp Tyr Trp Gly Gln Gly Thr Leu Val Thr
            100                 105                 110

Val Ser Ser Ala Ser Thr Thr Ala Pro Ser Val Phe Pro Leu Ala Pro
        115                 120                 125

Ser Cys Gly Ser Gln Ser Gly Ser Thr Val Ala Leu Ala Cys Leu Val
    130                 135                 140

Ser Gly Tyr Ile Pro Glu Pro Val Thr Val Ser Trp Asn Ser Val Ser
145                 150                 155                 160

Leu Thr Ser Gly Val His Thr Phe Pro Ser Val Leu Gln Ser Ser Gly
                165                 170                 175

Leu Tyr Ser Leu Ser Ser Met Val Thr Val Pro Ser Ser Arg Trp Pro
            180                 185                 190

Ser Glu Thr Phe Thr Cys Asn Val Ala His Pro Ala Thr Asn Thr Lys
        195                 200                 205

Val Asp Lys Pro Val Ala Lys Glu Cys Glu Cys Lys Cys Asn Cys Asn
    210                 215                 220

Asn Cys Pro Cys Pro Gly Cys Gly Leu Leu Gly Gly Xaa Ser Val Phe
225                 230                 235                 240

Ile Phe Pro Pro Lys Pro Lys Asp Ile Leu Val Thr Ala Arg Thr Pro
                245                 250                 255

Thr Val Thr Cys Val Val Val Xaa Leu Asp Pro Glu Asn Pro Glu Val
            260                 265                 270

Gln Ile Ser Trp Phe Val Asp Ser Lys Gln Val Gln Thr Ala Asn Thr
        275                 280                 285

Gln Pro Arg Glu Glu Gln Ser Xaa Xaa Xaa Tyr Arg Val Val Ser Val
    290                 295                 300

Leu Pro Ile Gly His Gln Asp Trp Leu Ser Gly Lys Gln Phe Lys Cys
305                 310                 315                 320

Lys Val Asn Asn Lys Xaa Leu Xaa Ser Pro Ile Glu Glu Ile Ile Ser
                325                 330                 335

Lys Thr Pro Gly Gln Ala His Gln Pro Asn Val Tyr Val Leu Pro Pro
            340                 345                 350

Ser Arg Asp Glu Met Ser Lys Asn Thr Val Thr Leu Thr Cys Leu Val
        355                 360                 365

Lys Asp Phe Phe Pro Glu Ile Asp Val Glu Trp Gln Ser Asn Gly
    370                 375                 380

Gln Gln Glu Pro Glu Ser Lys Tyr Arg Met Thr Pro Pro Gln Leu Asp
385                 390                 395                 400
```

-continued

```
Glu Asp Gly Ser Tyr Phe Leu Tyr Ser Lys Leu Ser Val Asp Lys Ser
            405                 410                 415

Arg Trp Gln Arg Gly Asp Thr Phe Ile Cys Ala Val Met His Glu Ala
        420                 425                 430

Leu His Asn His Tyr Thr Gln Ile Ser Leu Ser His Ser Pro Gly Lys
    435                 440                 445

<210> SEQ ID NO 43
<211> LENGTH: 1365
<212> TYPE: DNA
<213> ORGANISM: Artificial Sequence
<220> FEATURE:
<223> OTHER INFORMATION: caninized mouse antibody
<220> FEATURE:
<221> NAME/KEY: misc_feature
<222> LOCATION: (730)..(732)
<223> OTHER INFORMATION: n is a, c, g, or t
<220> FEATURE:
<221> NAME/KEY: misc_feature
<222> LOCATION: (811)..(813)
<223> OTHER INFORMATION: n is a, c, g, or t
<220> FEATURE:
<221> NAME/KEY: misc_feature
<222> LOCATION: (907)..(915)
<223> OTHER INFORMATION: n is a, c, g, or t
<220> FEATURE:
<221> NAME/KEY: misc_feature
<222> LOCATION: (997)..(999)
<223> OTHER INFORMATION: n is a, c, g, or t
<220> FEATURE:
<221> NAME/KEY: misc_feature
<222> LOCATION: (1003)..(1005)
<223> OTHER INFORMATION: n is a, c, g, or t

<400> SEQUENCE: 43
gaggtgcagc tggtgcagag cggcggcgac ctggtgaagc ccggcggcag cgtgagactg      60
agctgcgtgg ccagcggctt caacatcaag aacacctaca tgcactgggt gagacaggcc     120
cccggcaagg gcctgcagtg gatcggcaga atcgccccg ccaacgtgga caccaagtac     180 gccccaagt tccagggcaa ggccaccatc agcgccgaca ccgccaagaa caccgcctac     240
atgcagctga acagcctgag agccgaggac accgccgtgt actactgcgt gctgatctac     300
tacgactacg acgcgacat cgacgtgtgg ggccagggca ccctggtgac cgtgagcagc     360
gccagcacca ccgccccccag cgtgttcccc ctggccccca gctgcggcag caccagcggc     420
agcaccgtgg ccctggcctg cctggtgagc ggctacttcc ccgagcccgt gaccgtgagc     480
tggaacagcg gcagcctgac cagcggcgtg cacaccttcc ccagcgtgct gcagagcagc     540
ggcctgtaca gcctgagcag catggtgacc gtgcccagca gcagatggcc cagcgagacc     600
ttcacctgca acgtggccca ccccgccagc aagaccaagg tggacaagcc cgtgcccaag     660
agagagaacg gcagagtgcc cagacccccc gactgcccca gtgccccgc ccccgagatg     720 ctgggcggcn nnagcgtgtt catcttcccc cccaagccca aggacaccct gctgatcgcc     780
agaacccccg aggtgacctg cgtggtggtg nnnctggacc ccgaggaccc cgaggtgcag     840
atcagctggt tcgtggacgg caagcagatg cagaccgcca agacccagcc cagagaggag     900
cagttcnnnn nnnntacag agtggtgagc gtgctgccca tcggccacca ggactggctg     960
aagggcaagc agttcacctg caaggtgaac aacaagnnnc tgnnnagccc catcgagaga    1020
accatcagca aggccagagg ccaggcccac cagcccagcg tgtacgtgct gcccccagc    1080 agagaggagc tgagcaagaa caccgtgagc ctgacctgcc tgatcaagga cttcttcccc    1140
cccgacatcg acgtggagtg gcagagcaac ggccagcagg agcccgagag caagtacaga    1200
```

```
accaccccccc cccagctgga cgaggacggc agctacttcc tgtacagcaa gctgagcgtg    1260
gacaagagca gatggcagag aggcgacacc ttcatctgcg ccgtgatgca cgaggccctg    1320
cacaaccact acacccagga gagcctgagc acagccccg gcaag                     1365
```

<210> SEQ ID NO 44
<211> LENGTH: 455
<212> TYPE: PRT
<213> ORGANISM: Artificial Sequence
<220> FEATURE:
<223> OTHER INFORMATION: caninized mouse antibody
<220> FEATURE:
<221> NAME/KEY: misc_feature
<222> LOCATION: (244)..(244)
<223> OTHER INFORMATION: Xaa can be any naturally occurring amino acid
<220> FEATURE:
<221> NAME/KEY: misc_feature
<222> LOCATION: (271)..(271)
<223> OTHER INFORMATION: Xaa can be any naturally occurring amino acid
<220> FEATURE:
<221> NAME/KEY: misc_feature
<222> LOCATION: (303)..(305)
<223> OTHER INFORMATION: Xaa can be any naturally occurring amino acid
<220> FEATURE:
<221> NAME/KEY: misc_feature
<222> LOCATION: (333)..(333)
<223> OTHER INFORMATION: Xaa can be any naturally occurring amino acid
<220> FEATURE:
<221> NAME/KEY: misc_feature
<222> LOCATION: (335)..(335)
<223> OTHER INFORMATION: Xaa can be any naturally occurring amino acid

<400> SEQUENCE: 44

```
Glu Val Gln Leu Val Gln Ser Gly Gly Asp Leu Val Lys Pro Gly Gly
1               5                   10                  15

Ser Val Arg Leu Ser Cys Val Ala Ser Gly Phe Asn Ile Lys Asn Thr
            20                  25                  30

Tyr Met His Trp Val Arg Gln Ala Pro Gly Lys Gly Leu Gln Trp Ile
        35                  40                  45

Gly Arg Ile Ala Pro Ala Asn Val Asp Thr Lys Tyr Ala Pro Lys Phe
    50                  55                  60

Gln Gly Lys Ala Thr Ile Ser Ala Asp Thr Ala Lys Asn Thr Ala Tyr
65                  70                  75                  80

Met Gln Leu Asn Ser Leu Arg Ala Glu Asp Thr Ala Val Tyr Tyr Cys
                85                  90                  95

Val Leu Ile Tyr Tyr Asp Tyr Asp Gly Asp Ile Asp Val Trp Gly Gln
            100                 105                 110

Gly Thr Leu Val Thr Val Ser Ser Ala Ser Thr Thr Ala Pro Ser Val
        115                 120                 125

Phe Pro Leu Ala Pro Ser Cys Gly Ser Thr Ser Gly Ser Thr Val Ala
    130                 135                 140

Leu Ala Cys Leu Val Ser Gly Tyr Phe Pro Glu Pro Val Thr Val Ser
145                 150                 155                 160

Trp Asn Ser Gly Ser Leu Thr Ser Gly Val His Thr Phe Pro Ser Val
                165                 170                 175

Leu Gln Ser Ser Gly Leu Tyr Ser Leu Ser Ser Met Val Thr Val Pro
            180                 185                 190

Ser Ser Arg Trp Pro Ser Glu Thr Phe Thr Cys Asn Val Ala His Pro
        195                 200                 205

Ala Ser Lys Thr Lys Val Asp Lys Pro Val Pro Lys Arg Glu Asn Gly
    210                 215                 220

Arg Val Pro Arg Pro Pro Asp Cys Pro Lys Cys Pro Ala Pro Glu Met
```

```
                225                 230                 235                 240
Leu Gly Gly Xaa Ser Val Phe Ile Phe Pro Pro Lys Pro Lys Asp Thr
                245                 250                 255
Leu Leu Ile Ala Arg Thr Pro Glu Val Thr Cys Val Val Xaa Leu
            260                 265                 270
Asp Pro Glu Asp Pro Glu Val Gln Ile Ser Trp Phe Val Asp Gly Lys
            275                 280                 285
Gln Met Gln Thr Ala Lys Thr Gln Pro Arg Glu Glu Gln Phe Xaa Xaa
        290                 295                 300
Xaa Tyr Arg Val Val Ser Val Leu Pro Ile Gly His Gln Asp Trp Leu
305                 310                 315                 320
Lys Gly Lys Gln Phe Thr Cys Lys Val Asn Asn Lys Xaa Leu Xaa Ser
                325                 330                 335
Pro Ile Glu Arg Thr Ile Ser Lys Ala Arg Gly Gln Ala His Gln Pro
                340                 345                 350
Ser Val Tyr Val Leu Pro Pro Ser Arg Glu Glu Leu Ser Lys Asn Thr
            355                 360                 365
Val Ser Leu Thr Cys Leu Ile Lys Asp Phe Phe Pro Pro Asp Ile Asp
        370                 375                 380
Val Glu Trp Gln Ser Asn Gly Gln Gln Glu Pro Glu Ser Lys Tyr Arg
385                 390                 395                 400
Thr Thr Pro Pro Gln Leu Asp Glu Asp Gly Ser Tyr Phe Leu Tyr Ser
                405                 410                 415
Lys Leu Ser Val Asp Lys Ser Arg Trp Gln Arg Gly Asp Thr Phe Ile
                420                 425                 430
Cys Ala Val Met His Glu Ala Leu His Asn His Tyr Thr Gln Glu Ser
                435                 440                 445
Leu Ser His Ser Pro Gly Lys
            450                 455

<210> SEQ ID NO 45
<211> LENGTH: 1359
<212> TYPE: DNA
<213> ORGANISM: Artificial Sequence
<220> FEATURE:
<223> OTHER INFORMATION: caniinized mouse antibody
<220> FEATURE:
<221> NAME/KEY: misc_feature
<222> LOCATION: (724)..(726)
<223> OTHER INFORMATION: n is a, c, g, or t
<220> FEATURE:
<221> NAME/KEY: misc_feature
<222> LOCATION: (805)..(807)
<223> OTHER INFORMATION: n is a, c, g, or t
<220> FEATURE:
<221> NAME/KEY: misc_feature
<222> LOCATION: (901)..(909)
<223> OTHER INFORMATION: n is a, c, g, or t
<220> FEATURE:
<221> NAME/KEY: misc_feature
<222> LOCATION: (991)..(993)
<223> OTHER INFORMATION: n is a, c, g, or t
<220> FEATURE:
<221> NAME/KEY: misc_feature
<222> LOCATION: (997)..(999)
<223> OTHER INFORMATION: n is a, c, g, or t

<400> SEQUENCE: 45
gaggtgcagc tggtgcagag cggcggcgac ctggtgaagc ccggcggcag cgtgagactg      60
agctgcgtgg ccagcggctt caacatcaag aacacctaca tgcactgggt gagacaggcc     120
cccggcaagg gcctgcagtg gatcggcaga atcgcccccg ccaacgtgga caccaagtac    180
```

```
gcccccaagt tccagggcaa ggccaccatc agcgccgaca ccgccaagaa caccgcctac    240
atgcagctga acagcctgag agccgaggac accgccgtgt actactgcgt gctgatctac    300
tacgactacg acggcgacat cgacgtgtgg ggccagggca ccctggtgac cgtgagcagc    360
gccagcacca ccgcccccag cgtgttcccc ctggccccca gctgcggcag ccagagcggc    420
agcaccgtgg ccctggcctg cctggtgagc ggctacatcc ccgagcccgt gaccgtgagc    480
tggaacagcg tgagcctgac cagcggcgtg cacaccttcc ccagcgtgct gcagagcagc    540
ggcctgtaca gcctgagcag catggtgacc gtgcccagca gcagatggcc cagcgagacc    600
ttcacctgca acgtggccca ccccgccacc aacaccaagg tggacaagcc cgtggccaag    660
gagtgcgagt gcaagtgcaa ctgcaacaac tgccctgcc ccggctgcgg cctgctgggc    720
ggcnnnagcg tgttcatctt ccccccccaag cccaaggaca tcctggtgac cgccagaacc    780
cccaccgtga cctgcgtggt ggtgnnnctg daccccgaga accccgaggt gcagatcagc    840
tggttcgtgg acagcaagca ggtgcagacc gccaacaccc agcccagaga ggagcagagc    900
nnnnnnnnnt acagagtggt gagcgtgctg cccatcggcc accaggactg gctgagcggc    960
aagcagttca gtgcaaggt gaacaacaag nnnctgnnna gccccatcga ggagatcatc   1020
agcaagaccc ccggccaggc ccaccagccc aacgtgtacg tgctgccccc cagcagagac   1080
gagatgagca gaacaccgt gaccctgacc tgcctggtga aggacttctt ccccccccgag   1140 atcgacgtgg agtggcagag caacggccag caggagcccg agcaagta cagaatgacc   1200 ccccccccagc tggacgagga cggcagctac ttcctgtaca gcaagctgag cgtggacaag   1260
agcagatggc agagaggcga caccttcatc tgcgccgtga tgcacgaggc cctgcacaac   1320
cactacaccc cagatcagcct gagccacagc cccggcaag                         1359
```

<210> SEQ ID NO 46
<211> LENGTH: 453
<212> TYPE: PRT
<213> ORGANISM: Artificial Sequence
<220> FEATURE:
<223> OTHER INFORMATION: caninized mouse antibody
<220> FEATURE:
<221> NAME/KEY: misc_feature
<222> LOCATION: (242)..(242)
<223> OTHER INFORMATION: Xaa can be any naturally occurring amino acid
<220> FEATURE:
<221> NAME/KEY: misc_feature
<222> LOCATION: (269)..(269)
<223> OTHER INFORMATION: Xaa can be any naturally occurring amino acid
<220> FEATURE:
<221> NAME/KEY: misc_feature
<222> LOCATION: (301)..(303)
<223> OTHER INFORMATION: Xaa can be any naturally occurring amino acid
<220> FEATURE:
<221> NAME/KEY: misc_feature
<222> LOCATION: (331)..(331)
<223> OTHER INFORMATION: Xaa can be any naturally occurring amino acid
<220> FEATURE:
<221> NAME/KEY: misc_feature
<222> LOCATION: (333)..(333)
<223> OTHER INFORMATION: Xaa can be any naturally occurring amino acid

<400> SEQUENCE: 46

```
Glu Val Gln Leu Val Gln Ser Gly Gly Asp Leu Val Lys Pro Gly Gly
1               5                   10                  15

Ser Val Arg Leu Ser Cys Val Ala Ser Gly Phe Asn Ile Lys Asn Thr
            20                  25                  30

Tyr Met His Trp Val Arg Gln Ala Pro Gly Lys Gly Leu Gln Trp Ile
        35                  40                  45
```

```
Gly Arg Ile Ala Pro Ala Asn Val Asp Thr Lys Tyr Ala Pro Lys Phe
    50                  55                  60

Gln Gly Lys Ala Thr Ile Ser Ala Asp Thr Ala Lys Asn Thr Ala Tyr
65                  70                  75                  80

Met Gln Leu Asn Ser Leu Arg Ala Glu Asp Thr Ala Val Tyr Tyr Cys
                85                  90                  95

Val Leu Ile Tyr Tyr Asp Tyr Asp Gly Asp Ile Asp Val Trp Gly Gln
            100                 105                 110

Gly Thr Leu Val Thr Val Ser Ser Ala Ser Thr Thr Ala Pro Ser Val
        115                 120                 125

Phe Pro Leu Ala Pro Ser Cys Gly Ser Gln Ser Gly Ser Thr Val Ala
    130                 135                 140

Leu Ala Cys Leu Val Ser Gly Tyr Ile Pro Glu Pro Val Thr Val Ser
145                 150                 155                 160

Trp Asn Ser Val Ser Leu Thr Ser Gly Val His Thr Phe Pro Ser Val
                165                 170                 175

Leu Gln Ser Ser Gly Leu Tyr Ser Leu Ser Ser Met Val Thr Val Pro
            180                 185                 190

Ser Ser Arg Trp Pro Ser Glu Thr Phe Thr Cys Asn Val Ala His Pro
        195                 200                 205

Ala Thr Asn Thr Lys Val Asp Lys Pro Val Ala Lys Glu Cys Glu Cys
    210                 215                 220

Lys Cys Asn Cys Asn Asn Cys Pro Cys Pro Gly Cys Gly Leu Leu Gly
225                 230                 235                 240

Gly Xaa Ser Val Phe Ile Phe Pro Pro Lys Pro Lys Asp Ile Leu Val
                245                 250                 255

Thr Ala Arg Thr Pro Thr Val Thr Cys Val Val Val Xaa Leu Asp Pro
            260                 265                 270

Glu Asn Pro Glu Val Gln Ile Ser Trp Phe Val Asp Ser Lys Gln Val
        275                 280                 285

Gln Thr Ala Asn Thr Gln Pro Arg Glu Glu Gln Ser Xaa Xaa Xaa Tyr
    290                 295                 300

Arg Val Val Ser Val Leu Pro Ile Gly His Gln Asp Trp Leu Ser Gly
305                 310                 315                 320

Lys Gln Phe Lys Cys Lys Val Asn Asn Lys Xaa Leu Xaa Ser Pro Ile
                325                 330                 335

Glu Glu Ile Ile Ser Lys Thr Pro Gly Gln Ala His Gln Pro Asn Val
            340                 345                 350

Tyr Val Leu Pro Pro Ser Arg Asp Glu Met Ser Lys Asn Thr Val Thr
        355                 360                 365

Leu Thr Cys Leu Val Lys Asp Phe Phe Pro Pro Glu Ile Asp Val Glu
    370                 375                 380

Trp Gln Ser Asn Gly Gln Gln Glu Pro Glu Ser Lys Tyr Arg Met Thr
385                 390                 395                 400

Pro Pro Gln Leu Asp Glu Asp Gly Ser Tyr Phe Leu Tyr Ser Lys Leu
                405                 410                 415

Ser Val Asp Lys Ser Arg Trp Gln Arg Gly Asp Thr Phe Ile Cys Ala
            420                 425                 430

Val Met His Glu Ala Leu His Asn His Tyr Thr Gln Ile Ser Leu Ser
        435                 440                 445

His Ser Pro Gly Lys
    450
```

```
<210> SEQ ID NO 47
<211> LENGTH: 1371
<212> TYPE: DNA
<213> ORGANISM: Artificial Sequence
<220> FEATURE:
<223> OTHER INFORMATION: caninized mouse antibody
<220> FEATURE:
<221> NAME/KEY: misc_feature
<222> LOCATION: (736)..(738)
<223> OTHER INFORMATION: n is a, c, g, or t
<220> FEATURE:
<221> NAME/KEY: misc_feature
<222> LOCATION: (817)..(819)
<223> OTHER INFORMATION: n is a, c, g, or t
<220> FEATURE:
<221> NAME/KEY: misc_feature
<222> LOCATION: (913)..(921)
<223> OTHER INFORMATION: n is a, c, g, or t
<220> FEATURE:
<221> NAME/KEY: misc_feature
<222> LOCATION: (1003)..(1005)
<223> OTHER INFORMATION: n is a, c, g, or t
<220> FEATURE:
<221> NAME/KEY: misc_feature
<222> LOCATION: (1009)..(1011)
<223> OTHER INFORMATION: n is a, c, g, or t

<400> SEQUENCE: 47
```

| | | | | | |
|---|---|---|---|---|---|
| gaggtgcagc | tggtgcagag | cggcggcgac | ctggtgaagc | ccggcggcag | cgtgagactg | 60 |
| agctgcgtgg | ccagcggcta | caccttcacc | agatacaaca | tgcactgggt | gagacaggcc | 120 |
| cccggcaagg | gcctgcagtg | gatcggcacc | atctaccccg | gctacggcga | caccagctac | 180 |
| aaccagaagt | tcaagggcaa | ggccaccctg | agcgtggaca | cgccaagaa | caccgcctac | 240 |
| atgcagctga | acagcctgag | agccgaggac | accgccgtgt | acttctgcag | cagagagttc | 300 |
| gccgacgact | accccatccc | cccttcgac | tactggggcc | agggcaccct | ggtgaccgtg | 360 |
| agcagcgcca | gcaccaccgc | ccccagcgtg | ttccccctgg | cccccagctg | cggcagcacc | 420 |
| agcggcagca | ccgtggccct | ggcctgcctg | gtgagcggct | acttccccga | gcccgtgacc | 480 |
| gtgagctgga | acagcggcag | cctgaccagc | ggcgtgcaca | ccttccccag | cgtgctgcag | 540 |
| agcagcggcc | tgtacagcct | gagcagcatg | gtgaccgtgc | ccagcagcag | atggcccagc | 600 |
| gagaccttca | cctgcaacgt | ggcccacccc | gccagcaaga | ccaaggtgga | caagcccgtg | 660 |
| cccaagagag | agaacggcag | agtgcccaga | ccccccgact | gccccaagtg | ccccgccccc | 720 |
| gagatgctgg | gcggcnnnag | cgtgttcatc | ttccccccca | gcccaagga | caccctgctg | 780 |
| atcgccagaa | cccccgaggt | gacctgcgtg | gtggtgnnnc | tggaccccga | ggaccccgag | 840 |
| gtgcagatca | gctggttcgt | ggacggcaag | cagatgcaga | ccgccaagac | ccagcccaga | 900 |
| gaggagcagt | tcnnnnnnnn | ntacagagtg | gtgagcgtgc | tgcccatcgg | ccaccaggac | 960 |
| tggctgaagg | gcaagcagtt | cacctgcaag | gtgaacaaca | agnnnctgnn | nagccccatc | 1020 |
| gagagaacca | tcagcaaggc | cagaggccag | gcccaccagc | ccagcgtgta | cgtgctgccc | 1080 |
| cccagcagag | aggagctgag | caagaacacc | gtgagcctga | cctgcctgat | caaggacttc | 1140 |
| ttcccccccg | acatcgacgt | ggagtggcag | agcaacggcc | agcaggagcc | cgagagcaag | 1200 |
| tacagaacca | cccccccca | gctggacgag | gacggcagct | acttcctgta | cagcaagctg | 1260 |
| agcgtggaca | agagcagatg | gcagagaggc | gacaccttca | tctgcgccgt | gatgcacgag | 1320 |
| gccctgcaca | accactacac | ccaggagagc | ctgagccaca | gcccggcaa | g | 1371 |

```
<210> SEQ ID NO 48
<211> LENGTH: 457
```

```
<212> TYPE: PRT
<213> ORGANISM: Artificial Sequence
<220> FEATURE:
<223> OTHER INFORMATION: caninized mouse antibody
<220> FEATURE:
<221> NAME/KEY: misc_feature
<222> LOCATION: (246)..(246)
<223> OTHER INFORMATION: Xaa can be any naturally occurring amino acid
<220> FEATURE:
<221> NAME/KEY: misc_feature
<222> LOCATION: (273)..(273)
<223> OTHER INFORMATION: Xaa can be any naturally occurring amino acid
<220> FEATURE:
<221> NAME/KEY: misc_feature
<222> LOCATION: (305)..(307)
<223> OTHER INFORMATION: Xaa can be any naturally occurring amino acid
<220> FEATURE:
<221> NAME/KEY: misc_feature
<222> LOCATION: (335)..(335)
<223> OTHER INFORMATION: Xaa can be any naturally occurring amino acid
<220> FEATURE:
<221> NAME/KEY: misc_feature
<222> LOCATION: (337)..(337)
<223> OTHER INFORMATION: Xaa can be any naturally occurring amino acid

<400> SEQUENCE: 48

Glu Val Gln Leu Val Gln Ser Gly Gly Asp Leu Val Lys Pro Gly Gly
 1               5                  10                  15

Ser Val Arg Leu Ser Cys Val Ala Ser Gly Tyr Thr Phe Thr Arg Tyr
            20                  25                  30

Asn Met His Trp Val Arg Gln Ala Pro Gly Lys Gly Leu Gln Trp Ile
        35                  40                  45

Gly Thr Ile Tyr Pro Gly Tyr Gly Asp Thr Ser Tyr Asn Gln Lys Phe
    50                  55                  60

Lys Gly Lys Ala Thr Leu Ser Val Asp Ile Ala Lys Asn Thr Ala Tyr
65                  70                  75                  80

Met Gln Leu Asn Ser Leu Arg Ala Glu Asp Thr Ala Val Tyr Phe Cys
                85                  90                  95

Ser Arg Glu Phe Ala Asp Asp Tyr Pro Ile Pro Pro Phe Asp Tyr Trp
            100                 105                 110

Gly Gln Gly Thr Leu Val Thr Val Ser Ser Ala Ser Thr Thr Ala Pro
        115                 120                 125

Ser Val Phe Pro Leu Ala Pro Ser Cys Gly Ser Thr Ser Gly Ser Thr
    130                 135                 140

Val Ala Leu Ala Cys Leu Val Ser Gly Tyr Phe Pro Glu Pro Val Thr
145                 150                 155                 160

Val Ser Trp Asn Ser Gly Ser Leu Thr Ser Gly Val His Thr Phe Pro
                165                 170                 175

Ser Val Leu Gln Ser Ser Gly Leu Tyr Ser Leu Ser Ser Met Val Thr
            180                 185                 190

Val Pro Ser Ser Arg Trp Pro Ser Glu Thr Phe Thr Cys Asn Val Ala
        195                 200                 205

His Pro Ala Ser Lys Thr Lys Val Asp Lys Pro Val Pro Lys Arg Glu
    210                 215                 220

Asn Gly Arg Val Pro Arg Pro Pro Asp Cys Pro Lys Cys Pro Ala Pro
225                 230                 235                 240

Glu Met Leu Gly Gly Xaa Ser Val Phe Ile Phe Pro Pro Lys Pro Lys
                245                 250                 255

Asp Thr Leu Leu Ile Ala Arg Thr Pro Glu Val Thr Cys Val Val Val
            260                 265                 270

Xaa Leu Asp Pro Glu Asp Pro Glu Val Gln Ile Ser Trp Phe Val Asp
```

```
                275                 280                 285
Gly Lys Gln Met Gln Thr Ala Lys Thr Gln Pro Arg Glu Glu Gln Phe
    290                 295                 300
Xaa Xaa Xaa Tyr Arg Val Val Ser Val Leu Pro Ile Gly His Gln Asp
305                 310                 315                 320
Trp Leu Lys Gly Lys Gln Phe Thr Cys Lys Val Asn Asn Lys Xaa Leu
                325                 330                 335
Xaa Ser Pro Ile Glu Arg Thr Ile Ser Lys Ala Arg Gly Gln Ala His
                340                 345                 350
Gln Pro Ser Val Tyr Val Leu Pro Pro Ser Arg Glu Glu Leu Ser Lys
                355                 360                 365
Asn Thr Val Ser Leu Thr Cys Leu Ile Lys Asp Phe Phe Pro Pro Asp
370                 375                 380
Ile Asp Val Glu Trp Gln Ser Asn Gly Gln Gln Glu Pro Glu Ser Lys
385                 390                 395                 400
Tyr Arg Thr Thr Pro Pro Gln Leu Asp Glu Asp Gly Ser Tyr Phe Leu
                405                 410                 415
Tyr Ser Lys Leu Ser Val Asp Lys Ser Arg Trp Gln Arg Gly Asp Thr
                420                 425                 430
Phe Ile Cys Ala Val Met His Glu Ala Leu His Asn His Tyr Thr Gln
                435                 440                 445
Glu Ser Leu Ser His Ser Pro Gly Lys
    450                 455

<210> SEQ ID NO 49
<211> LENGTH: 1365
<212> TYPE: DNA
<213> ORGANISM: Artificial Sequence
<220> FEATURE:
<223> OTHER INFORMATION: caninized mouse antibody
<220> FEATURE:
<221> NAME/KEY: misc_feature
<222> LOCATION: (730)..(732)
<223> OTHER INFORMATION: n is a, c, g, or t
<220> FEATURE:
<221> NAME/KEY: misc_feature
<222> LOCATION: (811)..(813)
<223> OTHER INFORMATION: n is a, c, g, or t
<220> FEATURE:
<221> NAME/KEY: misc_feature
<222> LOCATION: (907)..(915)
<223> OTHER INFORMATION: n is a, c, g, or t
<220> FEATURE:
<221> NAME/KEY: misc_feature
<222> LOCATION: (997)..(999)
<223> OTHER INFORMATION: n is a, c, g, or t
<220> FEATURE:
<221> NAME/KEY: misc_feature
<222> LOCATION: (1003)..(1005)
<223> OTHER INFORMATION: n is a, c, g, or t

<400> SEQUENCE: 49
gaggtgcagc tggtgcagag cggcggcgac ctggtgaagc ccggcggcag cgtgagactg     60
agctgcgtgg ccagcggcta caccttcacc agatacaaca tgcactgggt gagacaggcc    120
cccggcaagg gcctgcagtg gatcggcacc atctacccccg gctacggcga caccagctac    180
aaccagaagt tcaagggcaa ggccaccctg agcgtggaca tcgccaagaa caccgcctac    240
atgcagctga acagcctgag agccgaggac accgccgtgt acttctgcag cagagagttc    300
gccgacgact accccatccc ccccttcgac tactggggcc agggcacccct ggtgaccgtg    360 agcagcgcca gcaccaccgc ccccagcgtg ttccccctgg cccccagctg cggcagccag    420
```

```
agcggcagca ccgtggccct ggcctgcctg gtgagcggct acatccccga gcccgtgacc      480
gtgagctgga acagcgtgag cctgaccagc ggcgtgcaca ccttccccag cgtgctgcag      540
agcagcggcc tgtacagcct gagcagcatg gtgaccgtgc ccagcagcag atggcccagc      600
gagaccttca cctgcaacgt ggcccacccc gccaccaaca ccaaggtgga caagcccgtg      660
gccaaggagt gcgagtgcaa gtgcaactgc aacaactgcc cctgccccgg ctgcggcctg      720
ctgggcggcn nnagcgtgtt catcttcccc cccaagccca aggacatcct ggtgaccgcc      780
agaaccccca ccgtgacctg cgtggtggtg nnnctggacc ccgagaaccc cgaggtgcag      840
atcagctggt tcgtggacag caagcaggtg cagaccgcca cacccagcc cagagaggag       900 cagagcnnnn nnnnntacag agtggtgagc gtgctgccca tcggccacca ggactggctg      960
agcggcaagc agttcaagtg caaggtgaac aacaagnnnc tgnnnagccc catcgaggag      1020
atcatcagca agaccccccgg ccaggcccac cagcccaacg tgtacgtgct gcccccccagc   1080 agagacgaga tgagcaagaa caccgtgacc ctgacctgcc tggtgaagga cttcttcccc    1140
cccgagatcg acgtggagtg gcagagcaac ggccagcagg agcccgagag caagtacaga    1200
atgacccccc cccagctgga cgaggacggc agctacttcc tgtacagcaa gctgagcgtg    1260
gacaagagca gatggcagag aggcgacacc ttcatctgcg ccgtgatgca cgaggccctg   1320
cacaaccact acacccagat cagcctgagc cacagccccg gcaag                    1365
```

<210> SEQ ID NO 50
<211> LENGTH: 455
<212> TYPE: PRT
<213> ORGANISM: Artificial Sequence
<220> FEATURE:
<223> OTHER INFORMATION: caninized mouse antibody
<220> FEATURE:
<221> NAME/KEY: misc_feature
<222> LOCATION: (244)..(244)
<223> OTHER INFORMATION: Xaa can be any naturally occurring amino acid
<220> FEATURE:
<221> NAME/KEY: misc_feature
<222> LOCATION: (271)..(271)
<223> OTHER INFORMATION: Xaa can be any naturally occurring amino acid
<220> FEATURE:
<221> NAME/KEY: misc_feature
<222> LOCATION: (303)..(305)
<223> OTHER INFORMATION: Xaa can be any naturally occurring amino acid
<220> FEATURE:
<221> NAME/KEY: misc_feature
<222> LOCATION: (333)..(333)
<223> OTHER INFORMATION: Xaa can be any naturally occurring amino acid
<220> FEATURE:
<221> NAME/KEY: misc_feature
<222> LOCATION: (335)..(335)
<223> OTHER INFORMATION: Xaa can be any naturally occurring amino acid

<400> SEQUENCE: 50

Glu Val Gln Leu Val Gln Ser Gly Gly Asp Leu Val Lys Pro Gly Gly
1               5                   10                  15

Ser Val Arg Leu Ser Cys Val Ala Ser Gly Tyr Thr Phe Thr Arg Tyr
            20                  25                  30

Asn Met His Trp Val Arg Gln Ala Pro Gly Lys Gly Leu Gln Trp Ile
        35                  40                  45

Gly Thr Ile Tyr Pro Gly Tyr Gly Asp Thr Ser Tyr Asn Gln Lys Phe
    50                  55                  60

Lys Gly Lys Ala Thr Leu Ser Val Asp Ile Ala Lys Asn Thr Ala Tyr
65                  70                  75                  80

Met Gln Leu Asn Ser Leu Arg Ala Glu Asp Thr Ala Val Tyr Phe Cys
                85                  90                  95

Ser Arg Glu Phe Ala Asp Asp Tyr Pro Ile Pro Pro Phe Asp Tyr Trp
            100                 105                 110

Gly Gln Gly Thr Leu Val Thr Val Ser Ser Ala Ser Thr Ala Pro
        115                 120                 125

Ser Val Phe Pro Leu Ala Pro Ser Cys Gly Ser Gln Ser Gly Ser Thr
    130                 135                 140

Val Ala Leu Ala Cys Leu Val Ser Gly Tyr Ile Pro Glu Pro Val Thr
145                 150                 155                 160

Val Ser Trp Asn Ser Val Ser Leu Thr Ser Gly Val His Thr Phe Pro
                165                 170                 175

Ser Val Leu Gln Ser Ser Gly Leu Tyr Ser Leu Ser Ser Met Val Thr
            180                 185                 190

Val Pro Ser Ser Arg Trp Pro Ser Glu Thr Phe Thr Cys Asn Val Ala
        195                 200                 205

His Pro Ala Thr Asn Thr Lys Val Asp Lys Pro Val Ala Lys Glu Cys
    210                 215                 220

Glu Cys Lys Cys Asn Cys Asn Asn Cys Pro Cys Pro Gly Cys Gly Leu
225                 230                 235                 240

Leu Gly Gly Xaa Ser Val Phe Ile Phe Pro Pro Lys Pro Lys Asp Ile
                245                 250                 255

Leu Val Thr Ala Arg Thr Pro Thr Val Thr Cys Val Val Val Xaa Leu
            260                 265                 270

Asp Pro Glu Asn Pro Glu Val Gln Ile Ser Trp Phe Val Asp Ser Lys
        275                 280                 285

Gln Val Gln Thr Ala Asn Thr Gln Pro Arg Glu Glu Gln Ser Xaa Xaa
    290                 295                 300

Xaa Tyr Arg Val Val Ser Val Leu Pro Ile Gly His Gln Asp Trp Leu
305                 310                 315                 320

Ser Gly Lys Gln Phe Lys Cys Lys Val Asn Asn Lys Xaa Leu Xaa Ser
                325                 330                 335

Pro Ile Glu Glu Ile Ile Ser Lys Thr Pro Gly Gln Ala His Gln Pro
            340                 345                 350

Asn Val Tyr Val Leu Pro Pro Ser Arg Asp Glu Met Ser Lys Asn Thr
        355                 360                 365

Val Thr Leu Thr Cys Leu Val Lys Asp Phe Phe Pro Pro Glu Ile Asp
    370                 375                 380

Val Glu Trp Gln Ser Asn Gly Gln Gln Glu Pro Glu Ser Lys Tyr Arg
385                 390                 395                 400

Met Thr Pro Pro Gln Leu Asp Glu Asp Gly Ser Tyr Phe Leu Tyr Ser
                405                 410                 415

Lys Leu Ser Val Asp Lys Ser Arg Trp Gln Arg Gly Asp Thr Phe Ile
            420                 425                 430

Cys Ala Val Met His Glu Ala Leu His Asn His Tyr Thr Gln Ile Ser
        435                 440                 445

Leu Ser His Ser Pro Gly Lys
    450                 455

<210> SEQ ID NO 51
<211> LENGTH: 1350
<212> TYPE: DNA
<213> ORGANISM: Artificial Sequence
<220> FEATURE:
<223> OTHER INFORMATION: caninized mouse antibody
<220> FEATURE:
<221> NAME/KEY: misc_feature
<222> LOCATION: (715)..(717)
<223> OTHER INFORMATION: n is a, c, g, or t
<220> FEATURE:
<221> NAME/KEY: misc_feature
<222> LOCATION: (796)..(798)
<223> OTHER INFORMATION: n is a, c, g, or t
<220> FEATURE:
<221> NAME/KEY: misc_feature
<222> LOCATION: (892)..(900)
<223> OTHER INFORMATION: n is a, c, g, or t
<220> FEATURE:
<221> NAME/KEY: misc_feature
<222> LOCATION: (982)..(984)
<223> OTHER INFORMATION: n is a, c, g, or t
<220> FEATURE:
<221> NAME/KEY: misc_feature
<222> LOCATION: (988)..(990)
<223> OTHER INFORMATION: n is a, c, g, or t

<400> SEQUENCE: 51

```
gaggtgcagc tggtgcagag cggcccaggc ctggtgaagc ccagccagag cctgagcctg      60
acctgcgtgg tgagcggctt cagcctgacc agctacggcg tgcactgggt gagacaggcc     120
cccggcaagg gcctgcagtg gatgggctgg atcaacatct acagcggcat ccccacctac     180
gccgacgact tcaagggcag attcaccttc agcctggaca ccgccaagaa caccgcctac     240
ctgcagctga gcagcctgag agccgaggac accgccgtgt actactgcgc cagattcgac     300
ggccccgact actggggcca gggcaccctg gtgaccgtga gcagccag caccaccgcc     360
cccagcgtgt tcccctggc ccccagctgc ggcagcacca gcggcagcac cgtggccctg     420
gcctgcctgg tgagcggcta cttccccgag cccgtgaccg tgagctggaa cagcggcagc     480
ctgaccagcg gcgtgcacac cttccccagc gtgctgcaga gcagcggcct gtacagcctg     540
agcagcatgg tgaccgtgcc agcagcaga tggcccagcg agaccttcac ctgcaacgtg     600
gcccaccccg ccagcaagac caaggtggac aagcccgtgc caagagaga gaacggcaga     660
gtgcccagac cccccgactg ccccaagtgc ccgcccccg agatgctggg cggcnnnagc     720
gtgttcatct ccccccca gcccaaggac accctgctga tcgccagaac ccccgaggtg     780
acctgcgtgg tggtgnnnct ggaccccgag accccgagg tgcagatcag ctggttcgtg     840
gacggcaagc agatgcagac cgccaagacc cagcccgag aggagcagtt cnnnnnnnnn     900
tacagagtgg tgagcgtgct gcccatcggc accaggact ggctgaaggg caagcagttc     960
acctgcaagg tgaacaacaa gnnnctgnnn agccccatcg agaaccat cagcaaggcc    1020
agaggccagg cccaccagcc cagcgtgtac gtgctgcccc cagcagaga ggagctgagc    1080
aagaacaccg tgagcctgac ctgcctgatc aaggacttct ccccccga catcgacgtg    1140
gagtggcaga gcaacggcca gcaggagccc gagagcaagt acagaaccac ccccccccag    1200
ctggacgagg acggcagcta cttcctgtac agcaagctga gcgtggacaa gagcagatgg    1260
cagagaggcg acaccttcat ctgcgccgtg atgcacgagg ccctgcacaa ccactacacc    1320
caggagagcc tgagccacag ccccggcaag                                     1350
```

<210> SEQ ID NO 52
<211> LENGTH: 450
<212> TYPE: PRT
<213> ORGANISM: Artificial Sequence
<220> FEATURE:
<223> OTHER INFORMATION: caninized mouse antibody
<220> FEATURE:
<221> NAME/KEY: misc_feature
<222> LOCATION: (239)..(239)
<223> OTHER INFORMATION: Xaa can be any naturally occurring amino acid
<220> FEATURE:

```
<221> NAME/KEY: misc_feature
<222> LOCATION: (266)..(266)
<223> OTHER INFORMATION: Xaa can be any naturally occurring amino acid
<220> FEATURE:
<221> NAME/KEY: misc_feature
<222> LOCATION: (298)..(300)
<223> OTHER INFORMATION: Xaa can be any naturally occurring amino acid
<220> FEATURE:
<221> NAME/KEY: misc_feature
<222> LOCATION: (328)..(328)
<223> OTHER INFORMATION: Xaa can be any naturally occurring amino acid
<220> FEATURE:
<221> NAME/KEY: misc_feature
<222> LOCATION: (330)..(330)
<223> OTHER INFORMATION: Xaa can be any naturally occurring amino acid

<400> SEQUENCE: 52
```

| | | | | | | | | | | | | | | |
|---|---|---|---|---|---|---|---|---|---|---|---|---|---|---|
| Glu | Val | Gln | Leu | Val | Gln | Ser | Gly | Pro | Gly | Leu | Val | Lys | Pro | Ser | Gln |
| 1 | | | | 5 | | | | | 10 | | | | | 15 | |
| Ser | Leu | Ser | Leu | Thr | Cys | Val | Val | Ser | Gly | Phe | Ser | Leu | Thr | Ser | Tyr |
| | | | 20 | | | | | 25 | | | | | 30 | | |
| Gly | Val | His | Trp | Val | Arg | Gln | Ala | Pro | Gly | Lys | Gly | Leu | Gln | Trp | Met |
| | | 35 | | | | | 40 | | | | | 45 | | | |
| Gly | Trp | Ile | Asn | Ile | Tyr | Ser | Gly | Ile | Pro | Thr | Tyr | Ala | Asp | Asp | Phe |
| | 50 | | | | | 55 | | | | | 60 | | | | |
| Lys | Gly | Arg | Phe | Thr | Phe | Ser | Leu | Asp | Thr | Ala | Lys | Asn | Thr | Ala | Tyr |
| 65 | | | | | 70 | | | | | 75 | | | | | 80 |
| Leu | Gln | Leu | Ser | Ser | Leu | Arg | Ala | Glu | Asp | Thr | Ala | Val | Tyr | Tyr | Cys |
| | | | | 85 | | | | | 90 | | | | | 95 | |
| Ala | Arg | Phe | Asp | Gly | Pro | Asp | Tyr | Trp | Gly | Gln | Gly | Thr | Leu | Val | Thr |
| | | | 100 | | | | | 105 | | | | | 110 | | |
| Val | Ser | Ser | Ala | Ser | Thr | Thr | Ala | Pro | Ser | Val | Phe | Pro | Leu | Ala | Pro |
| | | 115 | | | | | 120 | | | | | 125 | | | |
| Ser | Cys | Gly | Ser | Thr | Ser | Gly | Ser | Thr | Val | Ala | Leu | Ala | Cys | Leu | Val |
| 130 | | | | | 135 | | | | | 140 | | | | | |
| Ser | Gly | Tyr | Phe | Pro | Glu | Pro | Val | Thr | Val | Ser | Trp | Asn | Ser | Gly | Ser |
| 145 | | | | | 150 | | | | | 155 | | | | | 160 |
| Leu | Thr | Ser | Gly | Val | His | Thr | Phe | Pro | Ser | Val | Leu | Gln | Ser | Ser | Gly |
| | | | | 165 | | | | | 170 | | | | | 175 | |
| Leu | Tyr | Ser | Leu | Ser | Ser | Met | Val | Thr | Val | Pro | Ser | Ser | Arg | Trp | Pro |
| | | | 180 | | | | | 185 | | | | | 190 | | |
| Ser | Glu | Thr | Phe | Thr | Cys | Asn | Val | Ala | His | Pro | Ala | Ser | Lys | Thr | Lys |
| | | | 195 | | | | | 200 | | | | | 205 | | |
| Val | Asp | Lys | Pro | Val | Pro | Lys | Arg | Glu | Asn | Gly | Arg | Val | Pro | Arg | Pro |
| 210 | | | | | 215 | | | | | 220 | | | | | |
| Pro | Asp | Cys | Pro | Lys | Cys | Pro | Ala | Pro | Glu | Met | Leu | Gly | Gly | Xaa | Ser |
| 225 | | | | | 230 | | | | | 235 | | | | | 240 |
| Val | Phe | Ile | Phe | Pro | Pro | Lys | Pro | Lys | Asp | Thr | Leu | Leu | Ile | Ala | Arg |
| | | | | 245 | | | | | 250 | | | | | 255 | |
| Thr | Pro | Glu | Val | Thr | Cys | Val | Val | Val | Xaa | Leu | Asp | Pro | Glu | Asp | Pro |
| | | | 260 | | | | | 265 | | | | | 270 | | |
| Glu | Val | Gln | Ile | Ser | Trp | Phe | Val | Asp | Gly | Lys | Gln | Met | Gln | Thr | Ala |
| | | | | 275 | | | | | 280 | | | | | 285 | |
| Lys | Thr | Gln | Pro | Arg | Glu | Glu | Gln | Phe | Xaa | Xaa | Xaa | Tyr | Arg | Val | Val |
| | | | 290 | | | | | 295 | | | | | 300 | | |
| Ser | Val | Leu | Pro | Ile | Gly | His | Gln | Asp | Trp | Leu | Lys | Gly | Lys | Gln | Phe |
| 305 | | | | | 310 | | | | | 315 | | | | | 320 |
| Thr | Cys | Lys | Val | Asn | Asn | Lys | Xaa | Leu | Xaa | Ser | Pro | Ile | Glu | Arg | Thr |

```
            325                 330                 335
Ile Ser Lys Ala Arg Gly Gln Ala His Gln Pro Ser Val Tyr Val Leu
        340                 345                 350

Pro Pro Ser Arg Glu Glu Leu Ser Lys Asn Thr Val Ser Leu Thr Cys
        355                 360                 365

Leu Ile Lys Asp Phe Phe Pro Pro Asp Ile Asp Val Glu Trp Gln Ser
370                 375                 380

Asn Gly Gln Gln Glu Pro Glu Ser Lys Tyr Arg Thr Thr Pro Pro Gln
385                 390                 395                 400

Leu Asp Glu Asp Gly Ser Tyr Phe Leu Tyr Ser Lys Leu Ser Val Asp
                405                 410                 415

Lys Ser Arg Trp Gln Arg Gly Asp Thr Phe Ile Cys Ala Val Met His
            420                 425                 430

Glu Ala Leu His Asn His Tyr Thr Gln Glu Ser Leu Ser His Ser Pro
            435                 440                 445

Gly Lys
    450

<210> SEQ ID NO 53
<211> LENGTH: 1344
<212> TYPE: DNA
<213> ORGANISM: Artificial Sequence
<220> FEATURE:
<223> OTHER INFORMATION: caninized mouse antibody
<220> FEATURE:
<221> NAME/KEY: misc_feature
<222> LOCATION: (709)..(711)
<223> OTHER INFORMATION: n is a, c, g, or t
<220> FEATURE:
<221> NAME/KEY: misc_feature
<222> LOCATION: (790)..(792)
<223> OTHER INFORMATION: n is a, c, g, or t
<220> FEATURE:
<221> NAME/KEY: misc_feature
<222> LOCATION: (886)..(894)
<223> OTHER INFORMATION: n is a, c, g, or t
<220> FEATURE:
<221> NAME/KEY: misc_feature
<222> LOCATION: (976)..(978)
<223> OTHER INFORMATION: n is a, c, g, or t
<220> FEATURE:
<221> NAME/KEY: misc_feature
<222> LOCATION: (982)..(984)
<223> OTHER INFORMATION: n is a, c, g, or t

<400> SEQUENCE: 53
gaggtgcagc tggtgcagag cggccccggc ctggtgaagc ccagccagag cctgagcctg     60
acctgcgtgg tgagcggctt cagcctgacc agctacggcg tgcactgggt gagacaggcc    120
cccggcaagg gcctgcagtg gatgggctgg atcaacatct acagcggcat ccccacctac    180
gccgacgact tcaagggcag attcaccttc agcctggaca ccgccaagaa caccgcctac    240
ctgcagctga gcagcctgag agccgaggac accgccgtgt actactgcgc cagattcgac    300
ggccccgact actggggcca gggcaccctg gtgaccgtga gcgccgccag caccaccgcc    360
cccagcgtgt tcccccctggc cccagctgc ggcagccaga gcggcagcac cgtggccctg    420
gcctgcctgg tgagcggcta catccccgag ccgtgaccg tgagctggaa cagcgtgagc    480
ctgaccagcg gcgtgcacac cttccccagc gtgctgcaga gcagcggcct gtacagcctg    540
agcagcatgg tgaccgtgcc cagcagcaga tggcccagcg agaccttcac ctgcaacgtg    600
gcccaccccg ccaccaacac caaggtggac aagcccgtgg ccaaggagtg cgagtgcaag    660
tgcaactgca acaactgccc ctgccccggc tgcggcctgc tgggcggcnn nagcgtgttc    720
```

```
atcttccccc ccaagcccaa ggacatcctg gtgaccgcca gaaccccac cgtgacctgc    780 gtggtggtgn nnctggaccc cgagaacccc gaggtgcaga tcagctggtt cgtggacagc    840
aagcaggtgc agaccgccaa cacccagccc agagaggagc agagcnnnnn nnnntacaga    900
gtggtgagcg tgctgcccat cggccaccag gactggctga gcggcaagca gttcaagtgc    960
aaggtgaaca acaagnnnct gnnnagcccc atcgaggaga tcatcagcaa gaccccggc    1020 caggcccacc agcccaacgt gtacgtgctg cccccagca gagacgagat gagcaagaac    1080
accgtgaccc tgacctgcct ggtgaaggac ttcttccccc ccgagatcga cgtggagtgg    1140
cagagcaacg gccagcagga gcccgagagc aagtacagaa tgaccccccc ccagctggac    1200
gaggacggca gctacttcct gtacagcaag ctgagcgtgg acaagagcag atggcagaga    1260
ggcgacacct tcatctgcgc cgtgatgcac gaggccctgc acaaccacta cacccagatc    1320
agcctgagcc acagccccgg caag                                           1344
```

<210> SEQ ID NO 54
<211> LENGTH: 448
<212> TYPE: PRT
<213> ORGANISM: Artificial Sequence
<220> FEATURE:
<223> OTHER INFORMATION: caninized mouse antibody
<220> FEATURE:
<221> NAME/KEY: misc_feature
<222> LOCATION: (237)..(237)
<223> OTHER INFORMATION: Xaa can be any naturally occurring amino acid
<220> FEATURE:
<221> NAME/KEY: misc_feature
<222> LOCATION: (264)..(264)
<223> OTHER INFORMATION: Xaa can be any naturally occurring amino acid
<220> FEATURE:
<221> NAME/KEY: misc_feature
<222> LOCATION: (296)..(298)
<223> OTHER INFORMATION: Xaa can be any naturally occurring amino acid
<220> FEATURE:
<221> NAME/KEY: misc_feature
<222> LOCATION: (326)..(326)
<223> OTHER INFORMATION: Xaa can be any naturally occurring amino acid
<220> FEATURE:
<221> NAME/KEY: misc_feature
<222> LOCATION: (328)..(328)
<223> OTHER INFORMATION: Xaa can be any naturally occurring amino acid

<400> SEQUENCE: 54

Glu Val Gln Leu Val Gln Ser Gly Pro Gly Leu Val Lys Pro Ser Gln
1               5                   10                  15

Ser Leu Ser Leu Thr Cys Val Val Ser Gly Phe Ser Leu Thr Ser Tyr
            20                  25                  30

Gly Val His Trp Val Arg Gln Ala Pro Gly Lys Gly Leu Gln Trp Met
        35                  40                  45

Gly Trp Ile Asn Ile Tyr Ser Gly Ile Pro Thr Tyr Ala Asp Asp Phe
    50                  55                  60

Lys Gly Arg Phe Thr Phe Ser Leu Asp Thr Ala Lys Asn Thr Ala Tyr
65                  70                  75                  80

Leu Gln Leu Ser Ser Leu Arg Ala Glu Asp Thr Ala Val Tyr Tyr Cys
                85                  90                  95

Ala Arg Phe Asp Gly Pro Asp Tyr Trp Gly Gln Gly Thr Leu Val Thr
            100                 105                 110

Val Ser Ser Ala Ser Thr Thr Ala Pro Ser Val Phe Pro Leu Ala Pro
        115                 120                 125

Ser Cys Gly Ser Gln Ser Gly Ser Thr Val Ala Leu Ala Cys Leu Val
    130                 135                 140

Ser Gly Tyr Ile Pro Glu Pro Val Thr Val Ser Trp Asn Ser Val Ser
145                 150                 155                 160

Leu Thr Ser Gly Val His Thr Phe Pro Ser Val Leu Gln Ser Ser Gly
            165                 170                 175

Leu Tyr Ser Leu Ser Ser Met Val Thr Val Pro Ser Ser Arg Trp Pro
            180                 185                 190

Ser Glu Thr Phe Thr Cys Asn Val Ala His Pro Ala Thr Asn Thr Lys
            195                 200                 205

Val Asp Lys Pro Val Ala Lys Glu Cys Glu Cys Lys Cys Asn Cys Asn
210                 215                 220

Asn Cys Pro Cys Pro Gly Cys Gly Leu Leu Gly Gly Xaa Ser Val Phe
225                 230                 235                 240

Ile Phe Pro Pro Lys Pro Lys Asp Ile Leu Val Thr Ala Arg Thr Pro
            245                 250                 255

Thr Val Thr Cys Val Val Val Xaa Leu Asp Pro Glu Asn Pro Glu Val
            260                 265                 270

Gln Ile Ser Trp Phe Val Asp Ser Lys Gln Val Gln Thr Ala Asn Thr
            275                 280                 285

Gln Pro Arg Glu Glu Gln Ser Xaa Xaa Xaa Tyr Arg Val Val Ser Val
290                 295                 300

Leu Pro Ile Gly His Gln Asp Trp Leu Ser Gly Lys Gln Phe Lys Cys
305                 310                 315                 320

Lys Val Asn Asn Lys Xaa Leu Xaa Ser Pro Ile Glu Ile Ile Ser
            325                 330                 335

Lys Thr Pro Gly Gln Ala His Gln Pro Asn Val Tyr Val Leu Pro Pro
            340                 345                 350

Ser Arg Asp Glu Met Ser Lys Asn Thr Val Thr Leu Thr Cys Leu Val
            355                 360                 365

Lys Asp Phe Phe Pro Pro Glu Ile Asp Val Glu Trp Gln Ser Asn Gly
370                 375                 380

Gln Gln Glu Pro Glu Ser Lys Tyr Arg Met Thr Pro Pro Gln Leu Asp
385                 390                 395                 400

Glu Asp Gly Ser Tyr Phe Leu Tyr Ser Lys Leu Ser Val Asp Lys Ser
            405                 410                 415

Arg Trp Gln Arg Gly Asp Thr Phe Ile Cys Ala Val Met His Glu Ala
            420                 425                 430

Leu His Asn His Tyr Thr Gln Ile Ser Leu Ser His Ser Pro Gly Lys
            435                 440                 445

<210> SEQ ID NO 55
<211> LENGTH: 1350
<212> TYPE: DNA
<213> ORGANISM: Artificial Sequence
<220> FEATURE:
<223> OTHER INFORMATION: caninized mouse antidody
<220> FEATURE:
<221> NAME/KEY: misc_feature
<222> LOCATION: (715)..(717)
<223> OTHER INFORMATION: n is a, c, g, or t
<220> FEATURE:
<221> NAME/KEY: misc_feature
<222> LOCATION: (796)..(798)
<223> OTHER INFORMATION: n is a, c, g, or t
<220> FEATURE:
<221> NAME/KEY: misc_feature
<222> LOCATION: (892)..(900)
<223> OTHER INFORMATION: n is a, c, g, or t
<220> FEATURE:
<221> NAME/KEY: misc_feature

```
<222> LOCATION: (982)..(984)
<223> OTHER INFORMATION: n is a, c, g, or t
<220> FEATURE:
<221> NAME/KEY: misc_feature
<222> LOCATION: (988)..(990)
<223> OTHER INFORMATION: n is a, c, g, or t

<400> SEQUENCE: 55
gaggtgcagc tggtgcagag cggcgccgag gtgaagaagc ccggcgccag cgtgaaggtg      60
agctgcaagg ccagcggcta caccttcacc acctacggca tgagctgggt gagacaggcc     120
cccggcaagg gcctgcagtg gatgggctgg atcaacatct acagcggcat ccccacctac     180
gccgacgact tcaagggcag attcgccctg agcctggaca ccagcaccag caccgcctac     240
atggagctga acagcctgag agccgaggac accgccgtgt actactgcgc cagattcgac     300
ggccccgact actggggcca gggcacccty gtgaccgtga gcagccagc accaccgcc       360 cccagcgtgt tccccctggc cccagctgc ggcagcacca gcggcagcac cgtggccctg      420
gcctgcctgg tgagcggcta cttccccgag ccgtgaccg tgagctggaa cagcggcagc      480
ctgaccagcg gcgtgcacac cttccccagc gtgctgcaga gcagcggcct gtacagcctg     540
agcagcatgt tgaccgtgcc cagcagcaga tggcccagcg agaccttcac ctgcaacgtg     600
gcccaccccg ccagcaagac caaggtggac aagcccgtgc caagagaga gaacggcaga     660 gtgcccagac ccccgactg ccccaagtgc ccgcccccg agatgctggg cggcnnnagc      720
gtgttcatct tccccccaa gcccaaggac accctgctga tcgccagaac ccccgaggtg      780
acctgcgtgg tggtgnnnct ggaccccgag gaccccgagg tgcagatcag ctggttcgtg     840
gacggcaagc agatgcagac cgccaagacc cagcccgag aggagcagtt cnnnnnnnnn     900
tacagagtgg tgagcgtgct gcccatcggc caccaggact ggctgaaggg caagcagttc     960
acctgcaagg tgaacaacaa gnnnctgnnn agcccatcg agagaaccat cagcaaggcc     1020
agaggccagg cccaccagcc cagcgtgtac gtgctgcccc cagcagaga ggagctgagc     1080 aagaacaccg tgagcctgac ctgcctgatc aaggacttct ccccccga catcgacgtg      1140 gagtggcaga gcaacggcca gcaggagccc gagagcaagt acagaaccac cccccccag    1200 ctggacgagg acggcagcta cttcctgtac agcaagctga gcgtggacaa gagcagatgg    1260
cagagaggcg acaccttcat ctgcgccgtg atgcacgagg ccctgcacaa ccactacacc    1320
caggagagcc tgagccacag ccccggcaag                                     1350
```

<210> SEQ ID NO 56  
<211> LENGTH: 450  
<212> TYPE: PRT  
<213> ORGANISM: Artificial Sequence  
<220> FEATURE:  
<223> OTHER INFORMATION: caninized mouse antibody  
<220> FEATURE:  
<221> NAME/KEY: misc_feature  
<222> LOCATION: (239)..(239)  
<223> OTHER INFORMATION: Xaa can be any naturally occurring amino acid  
<220> FEATURE:  
<221> NAME/KEY: misc_feature  
<222> LOCATION: (266)..(266)  
<223> OTHER INFORMATION: Xaa can be any naturally occurring amino acid  
<220> FEATURE:  
<221> NAME/KEY: misc_feature  
<222> LOCATION: (298)..(300)  
<223> OTHER INFORMATION: Xaa can be any naturally occurring amino acid  
<220> FEATURE:  
<221> NAME/KEY: misc_feature  
<222> LOCATION: (328)..(328)  
<223> OTHER INFORMATION: Xaa can be any naturally occurring amino acid  
<220> FEATURE:

<221> NAME/KEY: misc_feature
<222> LOCATION: (330)..(330)
<223> OTHER INFORMATION: Xaa can be any naturally occurring amino acid

<400> SEQUENCE: 56

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Gly Met Ser Trp Val Arg Gln Ala Pro Gly Lys Gly Leu Gln Trp Met
        35                  40                  45

Gly Trp Ile Asn Ile Tyr Ser Gly Ile Pro Thr Tyr Ala Asp Asp Phe
    50                  55                  60

Lys Gly Arg Phe Ala Leu Ser Leu Asp Thr Ser Thr Ser Thr Ala Tyr
65                  70                  75                  80

Met Glu Leu Asn Ser Leu Arg Ala Glu Asp Thr Ala Val Tyr Tyr Cys
                85                  90                  95

Ala Arg Phe Asp Gly Pro Asp Tyr Trp Gly Gln Gly Thr Leu Val Thr
            100                 105                 110

Val Ser Ser Ala Ser Thr Thr Ala Pro Ser Val Phe Pro Leu Ala Pro
        115                 120                 125

Ser Cys Gly Ser Thr Ser Gly Ser Thr Val Ala Leu Ala Cys Leu Val
    130                 135                 140

Ser Gly Tyr Phe Pro Glu Pro Val Thr Val Ser Trp Asn Ser Gly Ser
145                 150                 155                 160

Leu Thr Ser Gly Val His Thr Phe Pro Ser Val Leu Gln Ser Ser Gly
                165                 170                 175

Leu Tyr Ser Leu Ser Ser Met Val Thr Val Pro Ser Ser Arg Trp Pro
            180                 185                 190

Ser Glu Thr Phe Thr Cys Asn Val Ala His Pro Ala Ser Lys Thr Lys
        195                 200                 205

Val Asp Lys Pro Val Pro Lys Arg Glu Asn Gly Arg Val Pro Arg Pro
    210                 215                 220

Pro Asp Cys Pro Lys Cys Pro Ala Pro Glu Met Leu Gly Gly Xaa Ser
225                 230                 235                 240

Val Phe Ile Phe Pro Pro Lys Pro Lys Asp Thr Leu Leu Ile Ala Arg
                245                 250                 255

Thr Pro Glu Val Thr Cys Val Val Val Xaa Leu Asp Pro Glu Asp Pro
            260                 265                 270

Glu Val Gln Ile Ser Trp Phe Val Asp Gly Lys Gln Met Gln Thr Ala
        275                 280                 285

Lys Thr Gln Pro Arg Glu Glu Gln Phe Xaa Xaa Xaa Tyr Arg Val Val
    290                 295                 300

Ser Val Leu Pro Ile Gly His Gln Asp Trp Leu Lys Gly Lys Gln Phe
305                 310                 315                 320

Thr Cys Lys Val Asn Asn Lys Xaa Leu Xaa Ser Pro Ile Glu Arg Thr
                325                 330                 335

Ile Ser Lys Ala Arg Gly Gln Ala His Gln Pro Ser Val Tyr Val Leu
            340                 345                 350

Pro Pro Ser Arg Glu Glu Leu Ser Lys Asn Thr Val Ser Leu Thr Cys
        355                 360                 365

Leu Ile Lys Asp Phe Phe Pro Pro Asp Ile Asp Val Glu Trp Gln Ser
    370                 375                 380

Asn Gly Gln Gln Glu Pro Glu Ser Lys Tyr Arg Thr Thr Pro Pro Gln
```

```
                385                 390                 395                 400
Leu Asp Glu Asp Gly Ser Tyr Phe Leu Tyr Ser Lys Leu Ser Val Asp
                    405                 410                 415

Lys Ser Arg Trp Gln Arg Gly Asp Thr Phe Ile Cys Ala Val Met His
                420                 425                 430

Glu Ala Leu His Asn His Tyr Thr Gln Glu Ser Leu Ser His Ser Pro
            435                 440                 445

Gly Lys
    450

<210> SEQ ID NO 57
<211> LENGTH: 1344
<212> TYPE: DNA
<213> ORGANISM: Artificial Sequence
<220> FEATURE:
<223> OTHER INFORMATION: caninized mouse antibody
<220> FEATURE:
<221> NAME/KEY: misc_feature
<222> LOCATION: (709)..(711)
<223> OTHER INFORMATION: n is a, c, g, or t
<220> FEATURE:
<221> NAME/KEY: misc_feature
<222> LOCATION: (790)..(792)
<223> OTHER INFORMATION: n is a, c, g, or t
<220> FEATURE:
<221> NAME/KEY: misc_feature
<222> LOCATION: (886)..(894)
<223> OTHER INFORMATION: n is a, c, g, or t
<220> FEATURE:
<221> NAME/KEY: misc_feature
<222> LOCATION: (976)..(978)
<223> OTHER INFORMATION: n is a, c, g, or t
<220> FEATURE:
<221> NAME/KEY: misc_feature
<222> LOCATION: (982)..(984)
<223> OTHER INFORMATION: n is a, c, g, or t

<400> SEQUENCE: 57
gaggtgcagc tggtgcagag cggcgccgag gtgaagaagc ccggcgccag cgtgaaggtg      60
agctgcaagg ccagcggcta caccttcacc acctacggca tgagctgggt gagacaggcc     120
cccggcaagg gcctgcagtg gatgggctgg atcaacacct acagcggcat ccccacctac     180
gccgacgact tcaagggcag attcgccctg agcctggaca ccagcaccag caccgcctac     240
atggagctga acagcctgag agccgaggac accgccgtgt actactgcgc cagattcgac     300
ggccccgact actggggcca gggcaccctg gtgaccgtga gcagcgccag caccaccgcc     360
cccagcgtgt tccccctggc ccccagctgc ggcagccaga gcggcagcac cgtggccctg     420
gcctgcctgg tgagcggcta catccccgag cccgtgaccg tgagctggaa cagcgtgagc     480
ctgaccagcg gcgtgcacac cttccccagc gtgctgcaga gcagcggcct gtacagcctg     540
agcagcatgg tgaccgtgcc cagcagcaga tgggccagcg agaccttcac ctgcaacgtg     600
gcccaccccg ccaccaacac caaggtggac aagcccgtgg ccaaggagtg cgagtgcaag     660
tgcaactgca caactgccc ctgccccggc tgcggcctgc tgggcggcnn nagcgtgttc     720
atcttccccc ccaagcccaa ggacatcctg gtgaccgcca aaccccac cgtgacctgc     780 gtggtggtgn nnctggaccc cgagaacccc gaggtgcaga tcagctggtt cgtggacagc     840
aagcaggtgc agaccgccaa cacccagccc agagaggagc agagcnnnnn nnnntacaga     900
gtggtgagcg tgctgcccat cggccaccag gactggctga gcggcaagca gttcaagtgc     960
aaggtgaaca acaagnnnct gnnnagcccc atcgaggaga tcatcagcaa gaccccggc    1020 caggcccacc agcccaacgt gtacgtgctg cccccagca gagacgagat gagcaagaac    1080
```

```
accgtgaccc tgacctgcct ggtgaaggac ttcttccccc ccgagatcga cgtggagtgg    1140
cagagcaacg gccagcagga gcccgagagc aagtacagaa tgaccccccc ccagctggac    1200
gaggacggca gctacttcct gtacagcaag ctgagcgtgg acaagagcag atggcagaga    1260
ggcgacacct tcatctgcgc cgtgatgcac gaggccctgc acaaccacta cacccagatc    1320
agcctgagcc acagccccgg caag                                           1344
```

<210> SEQ ID NO 58
<211> LENGTH: 448
<212> TYPE: PRT
<213> ORGANISM: Artificial Sequence
<220> FEATURE:
<223> OTHER INFORMATION: caninized mouse antibody
<220> FEATURE:
<221> NAME/KEY: misc_feature
<222> LOCATION: (237)..(237)
<223> OTHER INFORMATION: Xaa can be any naturally occurring amino acid
<220> FEATURE:
<221> NAME/KEY: misc_feature
<222> LOCATION: (264)..(264)
<223> OTHER INFORMATION: Xaa can be any naturally occurring amino acid
<220> FEATURE:
<221> NAME/KEY: misc_feature
<222> LOCATION: (296)..(298)
<223> OTHER INFORMATION: Xaa can be any naturally occurring amino acid
<220> FEATURE:
<221> NAME/KEY: misc_feature
<222> LOCATION: (326)..(326)
<223> OTHER INFORMATION: Xaa can be any naturally occurring amino acid
<220> FEATURE:
<221> NAME/KEY: misc_feature
<222> LOCATION: (328)..(328)
<223> OTHER INFORMATION: Xaa can be any naturally occurring amino acid

<400> SEQUENCE: 58

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Gly Met Ser Trp Val Arg Gln Ala Pro Gly Lys Gly Leu Gln Trp Met
        35                  40                  45

Gly Trp Ile Asn Ile Tyr Ser Gly Ile Pro Thr Tyr Ala Asp Asp Phe
    50                  55                  60

Lys Gly Arg Phe Ala Leu Ser Leu Asp Thr Ser Thr Ser Thr Ala Tyr
65                  70                  75                  80

Met Glu Leu Asn Ser Leu Arg Ala Glu Asp Thr Ala Val Tyr Tyr Cys
                85                  90                  95

Ala Arg Phe Asp Gly Pro Asp Tyr Trp Gly Gln Gly Thr Leu Val Thr
            100                 105                 110

Val Ser Ser Ala Ser Thr Thr Ala Pro Ser Val Phe Pro Leu Ala Pro
        115                 120                 125

Ser Cys Gly Ser Gln Ser Gly Ser Thr Val Ala Leu Ala Cys Leu Val
    130                 135                 140

Ser Gly Tyr Ile Pro Glu Pro Val Thr Val Ser Trp Asn Ser Val Ser
145                 150                 155                 160

Leu Thr Ser Gly Val His Thr Phe Pro Ser Val Leu Gln Ser Ser Gly
                165                 170                 175

Leu Tyr Ser Leu Ser Ser Met Val Thr Val Pro Ser Ser Arg Trp Pro
            180                 185                 190

Ser Glu Thr Phe Thr Cys Asn Val Ala His Pro Ala Thr Asn Thr Lys
        195                 200                 205

Val Asp Lys Pro Val Ala Lys Glu Cys Glu Cys Lys Cys Asn Cys Asn
    210                 215                 220

Asn Cys Pro Cys Pro Gly Cys Gly Leu Leu Gly Xaa Ser Val Phe
225                 230                 235                 240

Ile Phe Pro Pro Lys Pro Lys Asp Ile Leu Val Thr Ala Arg Thr Pro
                245                 250                 255

Thr Val Thr Cys Val Val Val Xaa Leu Asp Pro Glu Asn Pro Glu Val
                260                 265                 270

Gln Ile Ser Trp Phe Val Asp Ser Lys Gln Val Gln Thr Ala Asn Thr
            275                 280                 285

Gln Pro Arg Glu Glu Gln Ser Xaa Xaa Xaa Tyr Arg Val Val Ser Val
        290                 295                 300

Leu Pro Ile Gly His Gln Asp Trp Leu Ser Gly Lys Gln Phe Lys Cys
305                 310                 315                 320

Lys Val Asn Asn Lys Xaa Leu Xaa Ser Pro Ile Glu Glu Ile Ile Ser
                325                 330                 335

Lys Thr Pro Gly Gln Ala His Gln Pro Asn Val Tyr Val Leu Pro Pro
                340                 345                 350

Ser Arg Asp Glu Met Ser Lys Asn Thr Val Thr Leu Thr Cys Leu Val
            355                 360                 365

Lys Asp Phe Phe Pro Pro Glu Ile Asp Val Glu Trp Gln Ser Asn Gly
        370                 375                 380

Gln Gln Glu Pro Glu Ser Lys Tyr Arg Met Thr Pro Pro Gln Leu Asp
385                 390                 395                 400

Glu Asp Gly Ser Tyr Phe Leu Tyr Ser Lys Leu Ser Val Asp Lys Ser
                405                 410                 415

Arg Trp Gln Arg Gly Asp Thr Phe Ile Cys Ala Val Met His Glu Ala
            420                 425                 430

Leu His Asn His Tyr Thr Gln Ile Ser Leu Ser His Ser Pro Gly Lys
        435                 440                 445

<210> SEQ ID NO 59
<211> LENGTH: 1365
<212> TYPE: DNA
<213> ORGANISM: Artificial Sequence
<220> FEATURE:
<223> OTHER INFORMATION: caninized mouse antibody
<220> FEATURE:
<221> NAME/KEY: misc_feature
<222> LOCATION: (730)..(732)
<223> OTHER INFORMATION: n is a, c, g, or t
<220> FEATURE:
<221> NAME/KEY: misc_feature
<222> LOCATION: (811)..(813)
<223> OTHER INFORMATION: n is a, c, g, or t
<220> FEATURE:
<221> NAME/KEY: misc_feature
<222> LOCATION: (907)..(915)
<223> OTHER INFORMATION: n is a, c, g, or t
<220> FEATURE:
<221> NAME/KEY: misc_feature
<222> LOCATION: (997)..(999)
<223> OTHER INFORMATION: n is a, c, g, or t
<220> FEATURE:
<221> NAME/KEY: misc_feature
<222> LOCATION: (1003)..(1005)
<223> OTHER INFORMATION: n is a, c, g, or t

<400> SEQUENCE: 59
gaggtgcagc tggtgcagag cgtggccgag ctggtgaagc ccggcgccag cgtgaaggtg     60
agctgcaccg tgagcggctt caacatcaag aacacctaca tgcactgggt gagacaggcc    120

```
cccggcaagg gcctgcagtg gatcggcaga atcgaccccg ccaacgtgaa caccaagtac      180
gcccccaagt tccagggcag agccaccatc accgccgaca ccagcaccaa caccgcctac      240
atgcagctga gcagcctgag agccgaggac accgccgtgt actactgcgc cagaatctac      300
tacgactacg acgcgacat cgacgtgtgg ggccagggca ccctggtgac cgtgagcagc       360
gccagcacca ccgcccccag cgtgttcccc ctggccccca gctgcggcag caccagcggc      420
agcaccgtgg ccctggcctg cctggtgagc ggctacttcc ccgagcccgt gaccgtgagc      480
tggaacagcg gcagcctgac cagcggcgtg cacaccttcc ccagcgtgct gcagagcagc      540
ggcctgtaca gcctgagcag catggtgacc gtgcccagca gcagatggcc cagcgagacc      600
ttcacctgca acgtggccca ccccgccagc aagaccaagg tggacaagcc cgtgcccaag      660
agagagaacg gcagagtgcc cagaccccc gactgcccca gtgccccgc ccccgagatg        720
ctgggcggcn nnagcgtgtt catcttcccc cccaagccca aggacaccct gctgatcgcc      780
agaaccccg aggtgacctg cgtggtggtg nnnctggacc ccgaggaccc cgaggtgcag       840
atcagctggt tcgtggacgg caagcagatg cagaccgcca agacccagcc cagagaggag      900
cagttcnnnn nnnnntacag agtggtgagc gtgctgccca tcggccacca ggactggctg      960
aagggcaagc agttcacctg caaggtgaac aacaagnnnc tgnnnagccc catcgagaga      1020
accatcagca aggccagagg ccaggcccac cagcccagcg tgtacgtgct gcccccagc       1080
agagaggagc tgagcaagaa caccgtgagc ctgacctgcc tgatcaagga cttcttcccc      1140
cccgacatcg acgtggagtg gcagagcaac ggccagcagg agcccgagag caagtacaga      1200
accaccccc cccagctgga cgaggacggc agctacttcc tgtacagcaa gctgagcgtg       1260
gacaagagca gatggcagag aggcgacacc ttcatctgcg ccgtgatgca cgaggccctg      1320
cacaaccact acacccagga gagcctgagc cacagccccg gcaag                      1365
```

<210> SEQ ID NO 60
<211> LENGTH: 455
<212> TYPE: PRT
<213> ORGANISM: Artificial Sequence
<220> FEATURE:
<223> OTHER INFORMATION: caninized mouse antibody
<220> FEATURE:
<221> NAME/KEY: misc_feature
<222> LOCATION: (244)..(244)
<223> OTHER INFORMATION: Xaa can be any naturally occurring amino acid
<220> FEATURE:
<221> NAME/KEY: misc_feature
<222> LOCATION: (271)..(271)
<223> OTHER INFORMATION: Xaa can be any naturally occurring amino acid
<220> FEATURE:
<221> NAME/KEY: misc_feature
<222> LOCATION: (303)..(305)
<223> OTHER INFORMATION: Xaa can be any naturally occurring amino acid
<220> FEATURE:
<221> NAME/KEY: misc_feature
<222> LOCATION: (333)..(333)
<223> OTHER INFORMATION: Xaa can be any naturally occurring amino acid
<220> FEATURE:
<221> NAME/KEY: misc_feature
<222> LOCATION: (335)..(335)
<223> OTHER INFORMATION: Xaa can be any naturally occurring amino acid

<400> SEQUENCE: 60

Glu Val Gln Leu Val Gln Ser Val Ala Glu Leu Val Lys Pro Gly Ala
1               5                   10                  15

Ser Val Lys Val Ser Cys Thr Val Ser Gly Phe Asn Ile Lys Asn Thr
            20                  25                  30

```
Tyr Met His Trp Val Arg Gln Ala Pro Gly Lys Gly Leu Gln Trp Ile
         35                  40                  45
Gly Arg Ile Asp Pro Ala Asn Val Asn Thr Lys Tyr Ala Pro Lys Phe
 50                  55                  60
Gln Gly Arg Ala Thr Ile Thr Ala Asp Thr Ser Thr Asn Thr Ala Tyr
 65                  70                  75                  80
Met Gln Leu Ser Ser Leu Arg Ala Glu Asp Thr Ala Val Tyr Tyr Cys
                 85                  90                  95
Ala Arg Ile Tyr Tyr Asp Tyr Asp Gly Asp Ile Asp Val Trp Gly Gln
             100                 105                 110
Gly Thr Leu Val Thr Val Ser Ser Ala Ser Thr Thr Ala Pro Ser Val
             115                 120                 125
Phe Pro Leu Ala Pro Ser Cys Gly Ser Thr Ser Gly Ser Thr Val Ala
130                 135                 140
Leu Ala Cys Leu Val Ser Gly Tyr Phe Pro Glu Pro Val Thr Val Ser
145                 150                 155                 160
Trp Asn Ser Gly Ser Leu Thr Ser Gly Val His Thr Phe Pro Ser Val
                165                 170                 175
Leu Gln Ser Ser Gly Leu Tyr Ser Leu Ser Ser Met Val Thr Val Pro
            180                 185                 190
Ser Ser Arg Trp Pro Ser Glu Thr Phe Thr Cys Asn Val Ala His Pro
            195                 200                 205
Ala Ser Lys Thr Lys Val Asp Lys Pro Val Pro Lys Arg Glu Asn Gly
            210                 215                 220
Arg Val Pro Arg Pro Pro Asp Cys Pro Lys Cys Pro Ala Pro Glu Met
225                 230                 235                 240
Leu Gly Gly Xaa Ser Val Phe Ile Phe Pro Pro Lys Pro Lys Asp Thr
                245                 250                 255
Leu Leu Ile Ala Arg Thr Pro Glu Val Thr Cys Val Val Xaa Leu
            260                 265                 270
Asp Pro Glu Asp Pro Glu Val Gln Ile Ser Trp Phe Val Asp Gly Lys
            275                 280                 285
Gln Met Gln Thr Ala Lys Thr Gln Pro Arg Glu Glu Gln Phe Xaa Xaa
            290                 295                 300
Xaa Tyr Arg Val Val Ser Val Leu Pro Ile Gly His Gln Asp Trp Leu
305                 310                 315                 320
Lys Gly Lys Gln Phe Thr Cys Lys Val Asn Asn Lys Xaa Leu Xaa Ser
                325                 330                 335
Pro Ile Glu Arg Thr Ile Ser Lys Ala Arg Gly Gln Ala His Gln Pro
            340                 345                 350
Ser Val Tyr Val Leu Pro Pro Ser Arg Glu Glu Leu Ser Lys Asn Thr
            355                 360                 365
Val Ser Leu Thr Cys Leu Ile Lys Asp Phe Phe Pro Pro Asp Ile Asp
370                 375                 380
Val Glu Trp Gln Ser Asn Gly Gln Gln Glu Pro Glu Ser Lys Tyr Arg
385                 390                 395                 400
Thr Thr Pro Pro Gln Leu Asp Glu Asp Gly Ser Tyr Phe Leu Tyr Ser
                405                 410                 415
Lys Leu Ser Val Asp Lys Ser Arg Trp Gln Arg Gly Asp Thr Phe Ile
            420                 425                 430
Cys Ala Val Met His Glu Ala Leu His Asn His Tyr Thr Gln Glu Ser
            435                 440                 445
Leu Ser His Ser Pro Gly Lys
```

<210> SEQ ID NO 61
<211> LENGTH: 1359
<212> TYPE: DNA
<213> ORGANISM: Artificial Sequence
<220> FEATURE:
<223> OTHER INFORMATION: caninized mouse antibody
<220> FEATURE:
<221> NAME/KEY: misc_feature
<222> LOCATION: (724)..(726)
<223> OTHER INFORMATION: n is a, c, g, or t
<220> FEATURE:
<221> NAME/KEY: misc_feature
<222> LOCATION: (805)..(807)
<223> OTHER INFORMATION: n is a, c, g, or t
<220> FEATURE:
<221> NAME/KEY: misc_feature
<222> LOCATION: (901)..(909)
<223> OTHER INFORMATION: n is a, c, g, or t
<220> FEATURE:
<221> NAME/KEY: misc_feature
<222> LOCATION: (991)..(993)
<223> OTHER INFORMATION: n is a, c, g, or t
<220> FEATURE:
<221> NAME/KEY: misc_feature
<222> LOCATION: (997)..(999)
<223> OTHER INFORMATION: n is a, c, g, or t

<400> SEQUENCE: 61

```
gaggtgcagc tggtgcagag cgtggccgag ctggtgaagc ccggcgccag cgtgaaggtg      60
agctgcaccg tgagcggctt caacatcaag aacacctaca tgcactgggt gagacaggcc     120
cccggcaagg gcctgcagtg gatcggcaga atcgaccccg ccaacgtgaa caccaagtac     180
gcccccaagt tccagggcag agccaccatc accgccgaca ccagcaccaa caccgcctac     240
atgcagctga gcagcctgag agccgaggac accgccgtgt actactgcgc cagaatctac     300
tacgactacg acggcgacat cgacgtgtgg ggccagggca ccctggtgac cgtgagcagc     360
gccagcacca ccgcccccag cgtgttcccc ctggccccca gctgcggcag caccagcggc     420
agcaccgtgg ccctggcctg cctggtgagc ggctacttcc ccgagcccgt gaccgtgagc     480
tggaacagcg gcagcctgac cagcggcgtg cacaccttcc ccagcgtgct gcagagcagc     540
ggcctgtaca gcctgagcag catggtgacc gtgcccagca gcagatggcc cagcgagacc     600
ttcacctgca acgtggccca ccccgccagc aagaccaagg tggacaagcc cgtgcccaag     660
gagtgcgagt gcaagtgcaa ctgcaacaac tgcccctgcc ccggctgcgg cctgctgggc     720
ggcnnnagcg tgttcatctt cccccccaag cccaaggaca tcctggtgac cgccagaacc     780
cccaccgtga cctgcgtggt ggtgnnnctg gaccccgaga accccgaggt gcagatcagc     840
tggttcgtgg acagcaagca ggtgcagacc gccaacaccc agcccagaga ggagcagagc     900
nnnnnnnnnt acagagtggt gagcgtgctg cccatcggcc accaggactg gctgagcggc     960
aagcagttca gtgcaaggt gaacaacaag nnnctgnnna gccccatcga ggagatcatc    1020
agcaagaccc ccgccaggc ccaccagccc aacgtgtacg tgctgccccc cagcagagac    1080
gagatgagca agaacaccgt gaccctgacc tgcctggtga aggacttctt cccccccgag    1140
atcgacgtgg agtggcagag caacggccag caggagcccg agcaagta cagaatgacc    1200
cccccccagc tggacgagga cggcagctac ttcctgtaca gcaagctgag cgtggacaag    1260
agcagatggc agagaggcga caccttcatc tgcgccgtga tgcacgaggc cctgcacaac    1320
cactacaccc agatcagcct gagccacagc ccggcaag                           1359
```

```
<210> SEQ ID NO 62
<211> LENGTH: 453
<212> TYPE: PRT
<213> ORGANISM: Artificial Sequence
<220> FEATURE:
<223> OTHER INFORMATION: caninized mouse antibody
<220> FEATURE:
<221> NAME/KEY: misc_feature
<222> LOCATION: (242)..(242)
<223> OTHER INFORMATION: Xaa can be any naturally occurring amino acid
<220> FEATURE:
<221> NAME/KEY: misc_feature
<222> LOCATION: (269)..(269)
<223> OTHER INFORMATION: Xaa can be any naturally occurring amino acid
<220> FEATURE:
<221> NAME/KEY: misc_feature
<222> LOCATION: (301)..(303)
<223> OTHER INFORMATION: Xaa can be any naturally occurring amino acid
<220> FEATURE:
<221> NAME/KEY: misc_feature
<222> LOCATION: (331)..(331)
<223> OTHER INFORMATION: Xaa can be any naturally occurring amino acid
<220> FEATURE:
<221> NAME/KEY: misc_feature
<222> LOCATION: (333)..(333)
<223> OTHER INFORMATION: Xaa can be any naturally occurring amino acid

<400> SEQUENCE: 62

Glu Val Gln Leu Val Gln Ser Val Ala Glu Leu Val Lys Pro Gly Ala
1               5                   10                  15

Ser Val Lys Val Ser Cys Thr Val Ser Gly Phe Asn Ile Lys Asn Thr
            20                  25                  30

Tyr Met His Trp Val Arg Gln Ala Pro Gly Lys Gly Leu Gln Trp Ile
        35                  40                  45

Gly Arg Ile Asp Pro Ala Asn Val Asn Thr Lys Tyr Ala Pro Lys Phe
    50                  55                  60

Gln Gly Arg Ala Thr Ile Thr Ala Asp Thr Ser Thr Asn Thr Ala Tyr
65                  70                  75                  80

Met Gln Leu Ser Ser Leu Arg Ala Glu Asp Thr Ala Val Tyr Tyr Cys
                85                  90                  95

Ala Arg Ile Tyr Tyr Asp Tyr Asp Gly Asp Ile Asp Val Trp Gly Gln
            100                 105                 110

Gly Thr Leu Val Thr Val Ser Ser Ala Ser Thr Thr Ala Pro Ser Val
        115                 120                 125

Phe Pro Leu Ala Pro Ser Cys Gly Ser Thr Ser Gly Ser Thr Val Ala
    130                 135                 140

Leu Ala Cys Leu Val Ser Gly Tyr Phe Pro Glu Pro Val Thr Val Ser
145                 150                 155                 160

Trp Asn Ser Gly Ser Leu Thr Ser Gly Val His Thr Phe Pro Ser Val
                165                 170                 175

Leu Gln Ser Ser Gly Leu Tyr Ser Leu Ser Ser Met Val Thr Val Pro
            180                 185                 190

Ser Ser Arg Trp Pro Ser Glu Thr Phe Thr Cys Asn Val Ala His Pro
        195                 200                 205

Ala Ser Lys Thr Lys Val Asp Lys Pro Val Ala Lys Glu Cys Glu Cys
    210                 215                 220

Lys Cys Asn Cys Asn Asn Cys Pro Cys Pro Gly Cys Gly Leu Leu Gly
225                 230                 235                 240

Gly Xaa Ser Val Phe Ile Phe Pro Pro Lys Pro Lys Asp Ile Leu Val
                245                 250                 255

Thr Ala Arg Thr Pro Thr Val Thr Cys Val Val Val Xaa Leu Asp Pro
            260                 265                 270
```

```
Glu Asn Pro Glu Val Gln Ile Ser Trp Phe Val Asp Ser Lys Gln Val
        275                 280                 285

Gln Thr Ala Asn Thr Gln Pro Arg Glu Glu Gln Ser Xaa Xaa Xaa Tyr
        290                 295                 300

Arg Val Val Ser Val Leu Pro Ile Gly His Gln Asp Trp Leu Ser Gly
305                 310                 315                 320

Lys Gln Phe Lys Cys Lys Val Asn Asn Lys Xaa Leu Xaa Ser Pro Ile
                325                 330                 335

Glu Glu Ile Ile Ser Lys Thr Pro Gly Gln Ala His Gln Pro Asn Val
        340                 345                 350

Tyr Val Leu Pro Pro Ser Arg Asp Glu Met Ser Lys Asn Thr Val Thr
        355                 360                 365

Leu Thr Cys Leu Val Lys Asp Phe Phe Pro Pro Glu Ile Asp Val Glu
        370                 375                 380

Trp Gln Ser Asn Gly Gln Gln Glu Pro Glu Ser Lys Tyr Arg Met Thr
385                 390                 395                 400

Pro Pro Gln Leu Asp Glu Asp Gly Ser Tyr Phe Leu Tyr Ser Lys Leu
                405                 410                 415

Ser Val Asp Lys Ser Arg Trp Gln Arg Gly Asp Thr Phe Ile Cys Ala
                420                 425                 430

Val Met His Glu Ala Leu His Asn His Tyr Thr Gln Ile Ser Leu Ser
        435                 440                 445

His Ser Pro Gly Lys
        450

<210> SEQ ID NO 63
<211> LENGTH: 1350
<212> TYPE: DNA
<213> ORGANISM: Artificial Sequence
<220> FEATURE:
<223> OTHER INFORMATION: caninized mouse antibody
<220> FEATURE:
<221> NAME/KEY: misc_feature
<222> LOCATION: (715)..(717)
<223> OTHER INFORMATION: n is a, c, g, or t
<220> FEATURE:
<221> NAME/KEY: misc_feature
<222> LOCATION: (796)..(798)
<223> OTHER INFORMATION: n is a, c, g, or t
<220> FEATURE:
<221> NAME/KEY: misc_feature
<222> LOCATION: (892)..(900)
<223> OTHER INFORMATION: n is a, c, g, or t
<220> FEATURE:
<221> NAME/KEY: misc_feature
<222> LOCATION: (982)..(984)
<223> OTHER INFORMATION: n is a, c, g, or t
<220> FEATURE:
<221> NAME/KEY: misc_feature
<222> LOCATION: (988)..(990)
<223> OTHER INFORMATION: n is a, c, g, or t

<400> SEQUENCE: 63
gaggtgcagc tggtgcagag cggcgccgag gtgaagaagc ccggcgccag cgtgaaggtg      60
agctgcaagg ccagcggcta caccttcacc acctacggca tgagctgggt gagacaggcc     120
cccggcaagg gcctgcagtg gatgggctgg atcaacatct acagcggcat gcccacctac     180
gccgacgact tcaagggcag attcgccctg agcctggaca ccagcaccag caccgcctac     240
atggagctga acagcctgag agccgaggac accgccgtgt actactgcac cagattcgac     300
ggccccgact actgggggcca ggcaccctg gtgaccgtga gcagcgccag caccaccgcc     360
```

```
cccagcgtgt tcccccctggc ccccagctgc ggcagcacca gcggcagcac cgtggccctg    420
gcctgcctgg tgagcggcta cttccccgag cccgtgaccg tgagctggaa cagcggcagc    480
ctgaccagcg gcgtgcacac cttccccagc gtgctgcaga gcagcggcct gtacagcctg    540
agcagcatgg tgaccgtgcc cagcagcaga tggcccagcg agaccttcac ctgcaacgtg    600
gcccaccccg ccagcaagac caaggtggac aagcccgtgc caagagaga gaacggcaga    660 gtgcccagac ccccgactg cccaagtgc cccgccccg agatgctggg cggcnnnagc     720
gtgttcatct tccccccaa gcccaaggac accctgctga tcgccagaac ccccgaggtg    780
acctgcgtgg tggtgnnnct ggaccccgag gaccccgagg tgcagatcag ctggttcgtg    840
gacggcaagc agatgcagac cgccaagacc cagcccagag aggagcagtt cnnnnnnnnn    900
tacagagtgg tgagcgtgct gcccatcggc caccaggact ggctgaaggg caagcagttc    960
acctgcaagg tgaacaacaa gnnnctgnnn agccccatcg agagaaccat cagcaaggcc    1020
agaggccagg cccaccagcc cagcgtgtac gtgctgcccc ccagcagaga ggagctgagc    1080
aagaacaccg tgagcctgac ctgcctgatc aaggacttct tccccccga catcgacgtg    1140 gagtggcaga gcaacggcca gcaggagccc gagagcaagt acagaaccac ccccccccag    1200
ctggacgagg acggcagcta cttcctgtac agcaagctga gcgtggacaa gagcagatgg    1260
cagagaggcg acaccttcat ctgcgccgtg atgcacgagg ccctgcacaa ccactacacc    1320
caggagagcc tgagccacag ccccggcaag                                    1350
```

```
<210> SEQ ID NO 64
<211> LENGTH: 450
<212> TYPE: PRT
<213> ORGANISM: Artificial Sequence
<220> FEATURE:
<223> OTHER INFORMATION: caninized mouse antibody
<220> FEATURE:
<221> NAME/KEY: misc_feature
<222> LOCATION: (239)..(239)
<223> OTHER INFORMATION: Xaa can be any naturally occurring amino acid
<220> FEATURE:
<221> NAME/KEY: misc_feature
<222> LOCATION: (266)..(266)
<223> OTHER INFORMATION: Xaa can be any naturally occurring amino acid
<220> FEATURE:
<221> NAME/KEY: misc_feature
<222> LOCATION: (298)..(300)
<223> OTHER INFORMATION: Xaa can be any naturally occurring amino acid
<220> FEATURE:
<221> NAME/KEY: misc_feature
<222> LOCATION: (328)..(328)
<223> OTHER INFORMATION: Xaa can be any naturally occurring amino acid
<220> FEATURE:
<221> NAME/KEY: misc_feature
<222> LOCATION: (330)..(330)
<223> OTHER INFORMATION: Xaa can be any naturally occurring amino acid

<400> SEQUENCE: 64

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Gly Met Ser Trp Val Arg Gln Ala Pro Gly Lys Gly Leu Gln Trp Met
        35                  40                  45

Gly Trp Ile Asn Ile Tyr Ser Gly Met Pro Thr Tyr Ala Asp Asp Phe
    50                  55                  60

Lys Gly Arg Phe Ala Leu Ser Leu Asp Thr Ser Thr Ser Thr Ala Tyr
65                  70                  75                  80
```

Met Glu Leu Asn Ser Leu Arg Ala Glu Asp Thr Ala Val Tyr Tyr Cys
            85                  90                  95

Thr Arg Phe Asp Gly Pro Asp Tyr Trp Gly Gln Gly Thr Leu Val Thr
        100                 105                 110

Val Ser Ser Ala Ser Thr Thr Ala Pro Ser Val Phe Pro Leu Ala Pro
        115                 120                 125

Ser Cys Gly Ser Thr Gly Ser Thr Val Ala Leu Ala Cys Leu Val
130                 135                 140

Ser Gly Tyr Phe Pro Glu Pro Val Thr Val Ser Trp Asn Ser Gly Ser
145                 150                 155                 160

Leu Thr Ser Gly Val His Thr Phe Pro Ser Val Leu Gln Ser Ser Gly
                165                 170                 175

Leu Tyr Ser Leu Ser Ser Met Val Thr Val Pro Ser Ser Arg Trp Pro
                180                 185                 190

Ser Glu Thr Phe Thr Cys Asn Val Ala His Pro Ala Ser Lys Thr Lys
                195                 200                 205

Val Asp Lys Pro Val Pro Lys Arg Glu Asn Gly Arg Val Pro Arg Pro
210                 215                 220

Pro Asp Cys Pro Lys Cys Pro Ala Pro Glu Met Leu Gly Gly Xaa Ser
225                 230                 235                 240

Val Phe Ile Phe Pro Pro Lys Pro Lys Asp Thr Leu Leu Ile Ala Arg
                245                 250                 255

Thr Pro Glu Val Thr Cys Val Val Xaa Leu Asp Pro Glu Asp Pro
                260                 265                 270

Glu Val Gln Ile Ser Trp Phe Val Asp Gly Lys Gln Met Gln Thr Ala
                275                 280                 285

Lys Thr Gln Pro Arg Glu Glu Gln Phe Xaa Xaa Xaa Tyr Arg Val Val
290                 295                 300

Ser Val Leu Pro Ile Gly His Gln Asp Trp Leu Lys Gly Lys Gln Phe
305                 310                 315                 320

Thr Cys Lys Val Asn Asn Lys Xaa Leu Xaa Ser Pro Ile Glu Arg Thr
                325                 330                 335

Ile Ser Lys Ala Arg Gly Gln Ala His Gln Pro Ser Val Tyr Val Leu
                340                 345                 350

Pro Pro Ser Arg Glu Glu Leu Ser Lys Asn Thr Val Ser Leu Thr Cys
                355                 360                 365

Leu Ile Lys Asp Phe Phe Pro Pro Asp Ile Asp Val Glu Trp Gln Ser
                370                 375                 380

Asn Gly Gln Gln Glu Pro Glu Ser Lys Tyr Arg Thr Thr Pro Pro Gln
385                 390                 395                 400

Leu Asp Glu Asp Gly Ser Tyr Phe Leu Tyr Ser Lys Leu Ser Val Asp
                405                 410                 415

Lys Ser Arg Trp Gln Arg Gly Asp Thr Phe Ile Cys Ala Val Met His
                420                 425                 430

Glu Ala Leu His Asn His Tyr Thr Gln Glu Ser Leu Ser His Ser Pro
                435                 440                 445

Gly Lys
    450

<210> SEQ ID NO 65
<211> LENGTH: 1344
<212> TYPE: DNA
<213> ORGANISM: Artificial Sequence
<220> FEATURE:
<223> OTHER INFORMATION: caninized mouse antibody
<220> FEATURE:
<221> NAME/KEY: misc_feature
<222> LOCATION: (709)..(711)
<223> OTHER INFORMATION: n is a, c, g, or t
<220> FEATURE:
<221> NAME/KEY: misc_feature
<222> LOCATION: (790)..(792)
<223> OTHER INFORMATION: n is a, c, g, or t
<220> FEATURE:
<221> NAME/KEY: misc_feature
<222> LOCATION: (886)..(894)
<223> OTHER INFORMATION: n is a, c, g, or t
<220> FEATURE:
<221> NAME/KEY: misc_feature
<222> LOCATION: (976)..(978)
<223> OTHER INFORMATION: n is a, c, g, or t
<220> FEATURE:
<221> NAME/KEY: misc_feature
<222> LOCATION: (982)..(984)
<223> OTHER INFORMATION: n is a, c, g, or t

<400> SEQUENCE: 65

```
gaggtgcagc tggtgcagag cggcgccgag gtgaagaagc ccggcgccag cgtgaaggtg    60
agctgcaagg ccagcggcta caccttcacc acctacggca tgagctgggt gagacaggcc   120
cccggcaagg gcctgcagtg gatgggctgg atcaacatct acagcggcat gcccacctac   180
gccgacgact tcaagggcag attcgccctg agcctggaca ccagcaccag caccgcctac   240
atggagctga acagcctgag agccgaggac accgccgtgt actactgcac cagattcgac   300
ggccccgact actggggcca gggcaccctg gtgaccgtga gcagcgccag caccaccgcc   360
cccagcgtgt tccccctggc ccccagctgc ggcagcacca cggcagcac cgtggccctg   420
gcctgcctgg tgagcggcta cttccccgag cccgtgaccg tgagctggaa cagcggcagc   480
ctgaccagcg gcgtgcacac cttccccagc gtgctgcaga gcagcggcct gtacagcctg   540
agcagcatgg tgaccgtgcc cagcagcaga tgggcccagcg agaccttcac ctgcaacgtg   600
gcccaccccg ccagcaagac caaggtggac aagcccgtgg ccaaggagtg cgagtgcaag   660
tgcaactgca caactgccc ctgccccggc tgcggcctgc tgggcggcnn nagcgtgttc   720
atcttccccc ccaagcccaa ggacatcctg gtgaccgcca gaaccccac cgtgacctgc   780
gtggtggtgn nnctggaccc cgagaacccc gaggtgcaga tcagctggtt cgtggacagc   840
aagcaggtgc agaccgccaa cacccagccc agagaggagc agagcnnnnn nnnntacaga   900
gtggtgagcg tgctgcccat cggccaccag gactggctga gcggcaagca gttcaagtgc   960
aaggtgaaca acaagnnnct gnnnagcccc atcgaggaga tcatcagcaa gaccccggc  1020
caggcccacc agcccaacgt gtacgtgctg cccccccagca gagacgagat gagcaagaac  1080
accgtgaccc tgacctgcct ggtgaaggac ttcttccccc ccgagatcga cgtggagtgg  1140
cagagcaacg gccagcagga gcccgagagc aagtacagaa tgacccccc ccagctggac  1200
gaggacggca gctacttcct gtacagcaag ctgagcgtgg acaagagcag atggcagaga  1260
ggcgacacct tcatctgcgc cgtgatgcac gaggccctgc acaaccacta cacccagatc  1320
agcctgagcc acagccccgg caag                                         1344
```

<210> SEQ ID NO 66
<211> LENGTH: 448
<212> TYPE: PRT
<213> ORGANISM: Artificial Sequence
<220> FEATURE:
<223> OTHER INFORMATION: caninized mouse antibody
<220> FEATURE:
<221> NAME/KEY: misc_feature
<222> LOCATION: (237)..(237)

-continued

<223> OTHER INFORMATION: Xaa can be any naturally occurring amino acid
<220> FEATURE:
<221> NAME/KEY: misc_feature
<222> LOCATION: (264)..(264)
<223> OTHER INFORMATION: Xaa can be any naturally occurring amino acid
<220> FEATURE:
<221> NAME/KEY: misc_feature
<222> LOCATION: (296)..(298)
<223> OTHER INFORMATION: Xaa can be any naturally occurring amino acid
<220> FEATURE:
<221> NAME/KEY: misc_feature
<222> LOCATION: (326)..(326)
<223> OTHER INFORMATION: Xaa can be any naturally occurring amino acid
<220> FEATURE:
<221> NAME/KEY: misc_feature
<222> LOCATION: (328)..(328)
<223> OTHER INFORMATION: Xaa can be any naturally occurring amino acid

<400> SEQUENCE: 66

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Gly Met Ser Trp Val Arg Gln Ala Pro Gly Lys Gly Leu Gln Trp Met
        35                  40                  45

Gly Trp Ile Asn Ile Tyr Ser Gly Met Pro Thr Tyr Ala Asp Asp Phe
    50                  55                  60

Lys Gly Arg Phe Ala Leu Ser Leu Asp Thr Ser Thr Ser Thr Ala Tyr
65                  70                  75                  80

Met Glu Leu Asn Ser Leu Arg Ala Glu Asp Thr Ala Val Tyr Tyr Cys
                85                  90                  95

Thr Arg Phe Asp Gly Pro Asp Tyr Trp Gly Gln Gly Thr Leu Val Thr
            100                 105                 110

Val Ser Ser Ala Ser Thr Thr Ala Pro Ser Val Phe Pro Leu Ala Pro
        115                 120                 125

Ser Cys Gly Ser Thr Ser Gly Ser Thr Val Ala Leu Ala Cys Leu Val
    130                 135                 140

Ser Gly Tyr Phe Pro Glu Pro Val Thr Val Ser Trp Asn Ser Gly Ser
145                 150                 155                 160

Leu Thr Ser Gly Val His Thr Phe Pro Ser Val Leu Gln Ser Ser Gly
                165                 170                 175

Leu Tyr Ser Leu Ser Ser Met Val Thr Val Pro Ser Ser Arg Trp Pro
            180                 185                 190

Ser Glu Thr Phe Thr Cys Asn Val Ala His Pro Ala Ser Lys Thr Lys
        195                 200                 205

Val Asp Lys Pro Val Ala Lys Glu Cys Glu Cys Lys Cys Asn Cys Asn
    210                 215                 220

Asn Cys Pro Cys Pro Gly Cys Gly Leu Leu Gly Gly Xaa Ser Val Phe
225                 230                 235                 240

Ile Phe Pro Pro Lys Pro Lys Asp Ile Leu Val Thr Ala Arg Thr Pro
                245                 250                 255

Thr Val Thr Cys Val Val Val Xaa Leu Asp Pro Glu Asn Pro Glu Val
            260                 265                 270

Gln Ile Ser Trp Phe Val Asp Ser Lys Gln Val Gln Thr Ala Asn Thr
        275                 280                 285

Gln Pro Arg Glu Glu Gln Ser Xaa Xaa Xaa Tyr Arg Val Val Ser Val
    290                 295                 300

Leu Pro Ile Gly His Gln Asp Trp Leu Ser Gly Lys Gln Phe Lys Cys
305                 310                 315                 320

Lys Val Asn Asn Lys Xaa Leu Xaa Ser Pro Ile Glu Glu Ile Ser
            325                 330                 335

Lys Thr Pro Gly Gln Ala His Gln Pro Asn Val Tyr Val Leu Pro Pro
        340                 345                 350

Ser Arg Asp Glu Met Ser Lys Asn Thr Val Thr Leu Thr Cys Leu Val
        355                 360                 365

Lys Asp Phe Phe Pro Pro Glu Ile Asp Val Glu Trp Gln Ser Asn Gly
    370                 375                 380

Gln Gln Glu Pro Glu Ser Lys Tyr Arg Met Thr Pro Pro Gln Leu Asp
385                 390                 395                 400

Glu Asp Gly Ser Tyr Phe Leu Tyr Ser Lys Leu Ser Val Asp Lys Ser
                405                 410                 415

Arg Trp Gln Arg Gly Asp Thr Phe Ile Cys Ala Val Met His Glu Ala
            420                 425                 430

Leu His Asn His Tyr Thr Gln Ile Ser Leu Ser His Ser Pro Gly Lys
            435                 440                 445

<210> SEQ ID NO 67
<211> LENGTH: 1338
<212> TYPE: DNA
<213> ORGANISM: Artificial Sequence
<220> FEATURE:
<223> OTHER INFORMATION: caninized mouse antibody

<400> SEQUENCE: 67

```
gaggtgcagc tggtgcagag cggcggcgac ctggtgaagc ccggcggcag cgtgagactg      60
agctgcgtgg ccagcggcta caccttcacc acctacggca tgagctgggt gagacaggcc     120
cccggcaagg gcctgcagtg gatgggctgg atcaacatct acagcggcat ccccacctac     180
gccgacgact tcaagggcag attcaccttc agcctggaca ccgccaagaa caccgcctac     240
ctgcagctga acagcctgag agccgaggac accgccgtgt actactgcac cagattcgac     300
ggccccgact actggggcca gggcaccctg gtgaccgtga gcgccagc accaccgcc      360 cccagcgtgt tccccctggc ccccagctgc ggcagcacca gcggcagcac cgtggccctg     420
gcctgcctgg tgagcggcta cttccccgag cccgtgaccg tgagctggaa cagcggcagc     480
ctgaccagcg gcgtgcacac cttccccagc gtgctgcaga gcagcggcct gcacagcctg     540
agcagcatgg tgaccgtgcc cagcagcaga tggcccagcg agaccttcac ctgcaacgtg     600
gtgcaccccg ccagcaacac caaggtggac aagcccgtgt tcaacgagtg cagatgcacc     660
gacacccccc cctgccccgt gcccgagccc ctgggcggcc ccagcgtgct gatcttcccc     720
cccaagccca aggacatcct gagaatcacc agaaccccccg aggtgacctg cgtggtgctg     780
gacctgggca gagaggaccc cgaggtgcag atcagctggt tcgtggacgg caaggaggtg     840
cacaccgcca gacccagag cagagagcag cagttcaacg gcacctacag agtggtgagc     900
gtgctgccca tcgagcacca ggactggctg accggcaagg agttcaagtg cagagtgaac     960
cacatcgacc tgcccagccc catcgagaga accatcagca aggccagagg cagagcccac    1020
aagcccagcg tgtacgtgct gccccccagc cccaaggagc tgagcagcag cgacaccgtg    1080
agcatcacct gcctgatcaa ggacttctac cccccgaca tcgacgtgga gtggcagagc    1140
aacggccagc aggagcccga gagaaagcac agaatgaccc cccccagct ggacgaggac    1200 ggcagctact cctgtacag caagctgagc gtggacaaga gcagatggca gagggcgac    1260 ccccttcacct gcgccgtgat gcacgagacc ctgcagaacc actacaccga cctgagcctg    1320
```
agccacagcc ccggcaag                                                        1338

<210> SEQ ID NO 68
<211> LENGTH: 446
<212> TYPE: PRT
<213> ORGANISM: Artificial Sequence
<220> FEATURE:
<223> OTHER INFORMATION: caninized mouse antibody

<400> SEQUENCE: 68

```
Glu Val Gln Leu Val Gln Ser Gly Gly Asp Leu Val Lys Pro Gly Gly
1               5                   10                  15

Ser Val Arg Leu Ser Cys Val Ala Ser Gly Tyr Thr Phe Thr Thr Tyr
            20                  25                  30

Gly Met Ser Trp Val Arg Gln Ala Pro Gly Lys Gly Leu Gln Trp Met
        35                  40                  45

Gly Trp Ile Asn Ile Tyr Ser Gly Ile Pro Thr Tyr Ala Asp Asp Phe
    50                  55                  60

Lys Gly Arg Phe Thr Phe Ser Leu Asp Thr Ala Lys Asn Thr Ala Tyr
65                  70                  75                  80

Leu Gln Leu Asn Ser Leu Arg Ala Glu Asp Thr Ala Val Tyr Tyr Cys
                85                  90                  95

Thr Arg Phe Asp Gly Pro Asp Tyr Trp Gly Gln Gly Thr Leu Val Thr
            100                 105                 110

Val Ser Ser Ala Ser Thr Thr Ala Pro Ser Val Phe Pro Leu Ala Pro
        115                 120                 125

Ser Cys Gly Ser Thr Ser Gly Ser Thr Val Ala Leu Ala Cys Leu Val
    130                 135                 140

Ser Gly Tyr Phe Pro Glu Pro Val Thr Val Ser Trp Asn Ser Gly Ser
145                 150                 155                 160

Leu Thr Ser Gly Val His Thr Phe Pro Ser Val Leu Gln Ser Ser Gly
                165                 170                 175

Leu His Ser Leu Ser Ser Met Val Thr Val Pro Ser Ser Arg Trp Pro
            180                 185                 190

Ser Glu Thr Phe Thr Cys Asn Val Val His Pro Ala Ser Asn Thr Lys
        195                 200                 205

Val Asp Lys Pro Val Phe Asn Glu Cys Arg Cys Thr Asp Thr Pro Pro
    210                 215                 220

Cys Pro Val Pro Glu Pro Leu Gly Gly Pro Ser Val Leu Ile Phe Pro
225                 230                 235                 240

Pro Lys Pro Lys Asp Ile Leu Arg Ile Thr Arg Thr Pro Glu Val Thr
                245                 250                 255

Cys Val Val Leu Asp Leu Gly Arg Glu Asp Pro Glu Val Gln Ile Ser
            260                 265                 270

Trp Phe Val Asp Gly Lys Glu Val His Thr Ala Lys Thr Gln Ser Arg
        275                 280                 285

Glu Gln Gln Phe Asn Gly Thr Tyr Arg Val Val Ser Val Leu Pro Ile
    290                 295                 300

Glu His Gln Asp Trp Leu Thr Gly Lys Glu Phe Lys Cys Arg Val Asn
305                 310                 315                 320

His Ile Asp Leu Pro Ser Pro Ile Glu Arg Thr Ile Ser Lys Ala Arg
                325                 330                 335

Gly Arg Ala His Lys Pro Ser Val Tyr Val Leu Pro Pro Ser Pro Lys
            340                 345                 350

Glu Leu Ser Ser Ser Asp Thr Val Ser Ile Thr Cys Leu Ile Lys Asp
```

```
                355                 360                 365
Phe Tyr Pro Pro Asp Ile Asp Val Glu Trp Gln Ser Asn Gly Gln Gln
    370                 375                 380

Glu Pro Glu Arg Lys His Arg Met Thr Pro Pro Gln Leu Asp Glu Asp
385                 390                 395                 400

Gly Ser Tyr Phe Leu Tyr Ser Lys Leu Ser Val Asp Lys Ser Arg Trp
                405                 410                 415

Gln Gln Gly Asp Pro Phe Thr Cys Ala Val Met His Glu Thr Leu Gln
            420                 425                 430

Asn His Tyr Thr Asp Leu Ser Leu Ser His Ser Pro Gly Lys
            435                 440                 445

<210> SEQ ID NO 69
<211> LENGTH: 1338
<212> TYPE: DNA
<213> ORGANISM: Artificial Sequence
<220> FEATURE:
<223> OTHER INFORMATION: caninized mouse antibody

<400> SEQUENCE: 69
```

| | | | | | |
|---|---|---|---|---|---|
| gaggtgcagc | tggtgcagag | cggcggcgac | ctggtgaagc | cggcggcag | cgtgagactg | 60 |
| agctgcgtgg | ccagcggcta | caccttcacc | acctacggca | tgagctgggt | gagacaggcc | 120 |
| cccggcaagg | gcctgcagtg | gatgggctgg | atcaacacct | acagcggcat | ccccacctac | 180 |
| gccgacgact | tcaagggcag | attcaccttc | agcctggaca | ccgccaagaa | caccgcctac | 240 |
| ctgcagctga | acagcctgag | agccgaggac | accgccgtgt | actactgcac | cagattcgac | 300 |
| ggccccgact | actggggcca | gggcaccctg | gtgaccgtga | gcgccag | caccaccgcc | 360 |
| cccagcgtgt | tccccctggc | ccccagctgc | ggcagcacca | gcggcagcac | cgtggccctg | 420 |
| gcctgcctgg | tgagcggcta | cttccccgag | cccgtgaccg | tgagctggaa | cagcggcagc | 480 |
| ctgaccagcg | gcgtgcacac | cttccccagc | gtgctgcaga | gcagcggcct | gtacagcctg | 540 |
| agcagcaccg | tgaccgtgcc | cagcagcaga | tggcccagcg | agaccttcac | ctgcaacgtg | 600 |
| gtgcaccccg | ccagcaacac | caaggtggac | aagcccgtgc | caaggagag | cacctgcaag | 660 |
| tgcatcagcc | cctgccccgt | gcccgagagc | ctgggcggcc | ccagcgtgtt | catcttcccc | 720 |
| cccaagccca | aggacatcct | gagaatcacc | agaacccccg | agatcacctg | cgtggtgctg | 780 |
| gacctgggca | gagaggaccc | cgaggtgcag | atcagctggt | tcgtggacgg | caaggaggtg | 840 |
| cacaccgcca | agaccagcc | cagagagcag | cagttcaaca | gcacctacag | agtggtgagc | 900 |
| gtgctgccca | tcgagcacca | ggactggctg | accggcaagg | agttcaagtg | cagagtgaac | 960 |
| cacatcggcc | tgcccagccc | catcgagaga | accatcagca | aggccagagg | ccaggcccac | 1020 |
| cagcccagcg | tgtacgtgct | gccccccagc | cccaaggagc | tgagcagcag | cgacaccgtg | 1080 |
| accctgacct | gcctgatcaa | ggacttcttc | cccccggaga | tcgacgtgga | gtggcagagc | 1140 |
| aacggccagc | ccgagcccga | gagcaagtac | cacaccaccg | cccccagct | ggacgaggac | 1200 |
| ggcagctact | tcctgtacag | caagctgagc | gtggacaaga | gcagatggca | gcagggcgac | 1260 |
| accttcacct | gcgccgtgat | gcacgaggcc | ctgcagaacc | actacaccga | cctgagcctg | 1320 |
| agccacagcc | ccggcaag | | | | | 1338 |

```
<210> SEQ ID NO 70
<211> LENGTH: 446
<212> TYPE: PRT
<213> ORGANISM: Artificial Sequence
<220> FEATURE:
```

<223> OTHER INFORMATION: caninized mouse antibody

<400> SEQUENCE: 70

| | | | | | | | | | | | | | | |
|---|---|---|---|---|---|---|---|---|---|---|---|---|---|---|
| Glu | Val | Gln | Leu | Val | Gln | Ser | Gly | Gly | Asp | Leu | Val | Lys | Pro | Gly |
| 1 | | | | 5 | | | | | 10 | | | | | 15 |
| Ser | Val | Arg | Leu | Ser | Cys | Val | Ala | Ser | Gly | Tyr | Thr | Phe | Thr | Tyr |
| | | | 20 | | | | | 25 | | | | | 30 | |
| Gly | Met | Ser | Trp | Val | Arg | Gln | Ala | Pro | Gly | Lys | Gly | Leu | Gln | Trp | Met |
| | | 35 | | | | | 40 | | | | | 45 | | | |
| Gly | Trp | Ile | Asn | Ile | Tyr | Ser | Gly | Ile | Pro | Thr | Tyr | Ala | Asp | Asp | Phe |
| | 50 | | | | | 55 | | | | | 60 | | | | |
| Lys | Gly | Arg | Phe | Thr | Phe | Ser | Leu | Asp | Thr | Ala | Lys | Asn | Thr | Ala | Tyr |
| 65 | | | | | 70 | | | | | 75 | | | | | 80 |
| Leu | Gln | Leu | Asn | Ser | Leu | Arg | Ala | Glu | Asp | Thr | Ala | Val | Tyr | Tyr | Cys |
| | | | | 85 | | | | | 90 | | | | | 95 | |
| Thr | Arg | Phe | Asp | Gly | Pro | Asp | Tyr | Trp | Gly | Gln | Gly | Thr | Leu | Val | Thr |
| | | | 100 | | | | | 105 | | | | | 110 | | |
| Val | Ser | Ser | Ala | Ser | Thr | Thr | Ala | Pro | Ser | Val | Phe | Pro | Leu | Ala | Pro |
| | | 115 | | | | | 120 | | | | | 125 | | | |
| Ser | Cys | Gly | Ser | Thr | Ser | Gly | Ser | Thr | Val | Ala | Leu | Ala | Cys | Leu | Val |
| | 130 | | | | | 135 | | | | | 140 | | | | |
| Ser | Gly | Tyr | Phe | Pro | Glu | Pro | Val | Thr | Val | Ser | Trp | Asn | Ser | Gly | Ser |
| 145 | | | | | 150 | | | | | 155 | | | | | 160 |
| Leu | Thr | Ser | Gly | Val | His | Thr | Phe | Pro | Ser | Val | Leu | Gln | Ser | Ser | Gly |
| | | | | 165 | | | | | 170 | | | | | 175 | |
| Leu | Tyr | Ser | Leu | Ser | Ser | Thr | Val | Thr | Val | Pro | Ser | Ser | Arg | Trp | Pro |
| | | | 180 | | | | | 185 | | | | | 190 | | |
| Ser | Glu | Thr | Phe | Thr | Cys | Asn | Val | Val | His | Pro | Ala | Ser | Asn | Thr | Lys |
| | | 195 | | | | | 200 | | | | | 205 | | | |
| Val | Asp | Lys | Pro | Val | Pro | Lys | Glu | Ser | Thr | Cys | Lys | Cys | Ile | Ser | Pro |
| | 210 | | | | | 215 | | | | | 220 | | | | |
| Cys | Pro | Val | Pro | Glu | Ser | Leu | Gly | Gly | Pro | Ser | Val | Phe | Ile | Phe | Pro |
| 225 | | | | | 230 | | | | | 235 | | | | | 240 |
| Pro | Lys | Pro | Lys | Asp | Ile | Leu | Arg | Ile | Thr | Arg | Thr | Pro | Glu | Ile | Thr |
| | | | | 245 | | | | | 250 | | | | | 255 | |
| Cys | Val | Val | Leu | Asp | Leu | Gly | Arg | Glu | Asp | Pro | Glu | Val | Gln | Ile | Ser |
| | | | 260 | | | | | 265 | | | | | 270 | | |
| Trp | Phe | Val | Asp | Gly | Lys | Glu | Val | His | Thr | Ala | Lys | Thr | Gln | Pro | Arg |
| | | 275 | | | | | 280 | | | | | 285 | | | |
| Glu | Gln | Gln | Phe | Asn | Ser | Thr | Tyr | Arg | Val | Val | Ser | Val | Leu | Pro | Ile |
| | 290 | | | | | 295 | | | | | 300 | | | | |
| Glu | His | Gln | Asp | Trp | Leu | Thr | Gly | Lys | Glu | Phe | Lys | Cys | Arg | Val | Asn |
| 305 | | | | | 310 | | | | | 315 | | | | | 320 |
| His | Ile | Gly | Leu | Pro | Ser | Pro | Ile | Glu | Arg | Thr | Ile | Ser | Lys | Ala | Arg |
| | | | | 325 | | | | | 330 | | | | | 335 | |
| Gly | Gln | Ala | His | Gln | Pro | Ser | Val | Tyr | Val | Leu | Pro | Pro | Ser | Pro | Lys |
| | | | 340 | | | | | 345 | | | | | 350 | | |
| Glu | Leu | Ser | Ser | Ser | Asp | Thr | Val | Thr | Leu | Thr | Cys | Leu | Ile | Lys | Asp |
| | | 355 | | | | | 360 | | | | | 365 | | | |
| Phe | Phe | Pro | Pro | Glu | Ile | Asp | Val | Glu | Trp | Gln | Ser | Asn | Gly | Gln | Pro |
| | 370 | | | | | 375 | | | | | 380 | | | | |
| Glu | Pro | Glu | Ser | Lys | Tyr | His | Thr | Thr | Ala | Pro | Gln | Leu | Asp | Glu | Asp |
| 385 | | | | | 390 | | | | | 395 | | | | | 400 |

```
Gly Ser Tyr Phe Leu Tyr Ser Lys Leu Ser Val Asp Lys Ser Arg Trp
            405                 410                 415

Gln Gln Gly Asp Thr Phe Thr Cys Ala Val Met His Glu Ala Leu Gln
        420                 425                 430

Asn His Tyr Thr Asp Leu Ser Leu Ser His Ser Pro Gly Lys
        435                 440                 445

<210> SEQ ID NO 71
<211> LENGTH: 672
<212> TYPE: DNA
<213> ORGANISM: Artificial Sequence
<220> FEATURE:
<223> OTHER INFORMATION: caninized mouse antibody

<400> SEQUENCE: 71
gacatcgtga tgacccagac cccctgagc ctgagcgtga gccccggcga gcccgccagc       60
atgagctgca agagcagcca gagcctgctg aacagcgtga accagaagaa ctacctggcc     120
tggtacagac agaagcccgg ccagagcccc caggtgctgg tgtacttcgc cagcgccaga     180
gtgagcggcg tgcccgacag attcatcggc agcggcagcg gcaccgactt caccctgaga     240
atcagcagag tggaggccga cgacctgggc gtgtactact gccagcagta cttcagcacc     300
cccctgacct tcggccaggg caccaagctg gagctgaaga aaacgacgc ccagcccgcc       360 gtgtacctgt tccagcccag ccccgaccag ctgcacaccg gcagcgccag cgtggtgtgc     420
ctgctgaaca gcttctaccc caaggacatc aacgtgaagt ggaaggtgga cggcgtgatc     480
caggacaccg gcatccagga gagcgtgacc gagcaggaca gcaaggacag cacctacagc     540
ctgagcagca ccctgaccat gagcagcacc gagtacctga gccacgagct gtacagctgc     600
gagatcaccc acaagagcct gcccagcacc ctgatcaaga gcttccagag aagcgagtgc     660
cagagagtgg ac                                                        672

<210> SEQ ID NO 72
<211> LENGTH: 224
<212> TYPE: PRT
<213> ORGANISM: Artificial Sequence
<220> FEATURE:
<223> OTHER INFORMATION: caninized mouse antibody

<400> SEQUENCE: 72

Asp Ile Val Met Thr Gln Thr Pro Leu Ser Leu Ser Val Ser Pro Gly
1               5                   10                  15

Glu Pro Ala Ser Met Ser Cys Lys Ser Ser Gln Ser Leu Leu Asn Ser
            20                  25                  30

Val Asn Gln Lys Asn Tyr Leu Ala Trp Tyr Arg Gln Lys Pro Gly Gln
        35                  40                  45

Ser Pro Gln Val Leu Val Tyr Phe Ala Ser Ala Arg Val Ser Gly Val
    50                  55                  60

Pro Asp Arg Phe Ile Gly Ser Gly Ser Gly Thr Asp Phe Thr Leu Arg
65                  70                  75                  80

Ile Ser Arg Val Glu Ala Asp Asp Leu Gly Val Tyr Tyr Cys Gln Gln
                85                  90                  95

Tyr Phe Ser Thr Pro Leu Thr Phe Gly Gln Gly Thr Lys Leu Glu Leu
            100                 105                 110

Lys Arg Asn Asp Ala Gln Pro Ala Val Tyr Leu Phe Gln Pro Ser Pro
        115                 120                 125

Asp Gln Leu His Thr Gly Ser Ala Ser Val Val Cys Leu Leu Asn Ser
    130                 135                 140
```

```
Phe Tyr Pro Lys Asp Ile Asn Val Lys Trp Lys Val Asp Gly Val Ile
145                 150                 155                 160

Gln Asp Thr Gly Ile Gln Glu Ser Val Thr Glu Gln Asp Ser Lys Asp
            165                 170                 175

Ser Thr Tyr Ser Leu Ser Ser Thr Leu Thr Met Ser Ser Thr Glu Tyr
        180                 185                 190

Leu Ser His Glu Leu Tyr Ser Cys Glu Ile Thr His Lys Ser Leu Pro
        195                 200                 205

Ser Thr Leu Ile Lys Ser Phe Gln Arg Ser Glu Cys Gln Arg Val Asp
    210                 215                 220
```

<210> SEQ ID NO 73
<211> LENGTH: 1353
<212> TYPE: DNA
<213> ORGANISM: Artificial Sequence
<220> FEATURE:
<223> OTHER INFORMATION: caninized mouse antibody

<400> SEQUENCE: 73

```
gaggtgcagc tggtgcagag cggcggcgac ctggtgaagc ccggcggcag cgtgagactg      60
agctgcgtgg ccagcggctt caacatcaag aacacctaca tgcactgggt gagacaggcc     120
cccggcaagg gcctgcagtg gatcggcaga atcgcccccg ccaacgtgga caccaagtac     180
gcccccaagt tccagggcaa ggccaccatc agcgccgaca ccgccaagaa caccgcctac     240
atgcagctga acagcctgag agccgaggac accgccgtgt actactgcgt gctgatctac     300
tacgactacg acgcgacat cgacgtgtgg ggccagggca ccctggtgac cgtgagcagc     360
gccagcacca ccgcccccag cgtgttcccc ctggccccca gctgcggcag caccagcggc     420
agcaccgtgg ccctggcctg cctggtgagc ggctacttcc ccgagcccgt gaccgtgagc     480
tggaacagcg gcagcctgac cagcggcgtg cacaccttcc ccagcgtgct gcagagcagc     540
ggcctgcaca gcctgagcag catggtgacc gtgcccagca gcagatggcc cagcgagacc     600
ttcacctgca acgtggtgca ccccgccagc aacaccaagg tggacaagcc cgtgttcaac     660
gagtgcagat gcaccgacac ccccccctgc cccgtgcccg agcccctggg cggccccagc     720
gtgctgatct ccccccccaa gcccaaggac atcctgagaa tcaccagaac ccccgaggtg     780
acctgcgtgg tgctggacct gggcagagag gaccccgagg tgcagatcag ctggttcgtg     840
gacggcaagg aggtgcacac cgccaagacc cagagcagag agcagcagtt caacggcacc     900
tacagagtgg tgagcgtgct gcccatcgag caccaggact ggctgaccgg caaggagttc     960
aagtgcagag tgaaccacat cgacctgccc agccccatcg agagaaccat cagcaaggcc    1020
agaggcagag cccacaagcc cagcgtgtac gtgctgcccc cagccccaa ggagctgagc    1080
agcagcgaca ccgtgagcat cacctgcctg atcaaggact ctacccccc cgacatcgac    1140
gtggagtggc agagcaacgg ccagcaggag cccgagagaa gcacagaat gacccccccc    1200
cagctggacg aggacggcag ctacttcctg tacagcaagc tgagcgtgga caagagcaga    1260
tggcagcagg gcgacccctt cacctgcgcc gtgatgcacg agaccctgca gaaccactac    1320
accgacctga gcctgagcca gcccccggc aag                                   1353
```

<210> SEQ ID NO 74
<211> LENGTH: 451
<212> TYPE: PRT
<213> ORGANISM: Artificial Sequence
<220> FEATURE:
<223> OTHER INFORMATION: caninized mouse antibody

<400> SEQUENCE: 74

```
Glu Val Gln Leu Val Gln Ser Gly Gly Asp Leu Val Lys Pro Gly Gly
  1               5                  10                  15

Ser Val Arg Leu Ser Cys Val Ala Ser Gly Phe Asn Ile Lys Asn Thr
             20                  25                  30

Tyr Met His Trp Val Arg Gln Ala Pro Gly Lys Gly Leu Gln Trp Ile
         35                  40                  45

Gly Arg Ile Ala Pro Ala Asn Val Asp Thr Lys Tyr Ala Pro Lys Phe
     50                  55                  60

Gln Gly Lys Ala Thr Ile Ser Ala Asp Thr Ala Lys Asn Thr Ala Tyr
 65                  70                  75                  80

Met Gln Leu Asn Ser Leu Arg Ala Glu Asp Thr Ala Val Tyr Tyr Cys
                 85                  90                  95

Val Leu Ile Tyr Tyr Asp Tyr Asp Gly Asp Ile Asp Val Trp Gly Gln
            100                 105                 110

Gly Thr Leu Val Thr Val Ser Ser Ala Ser Thr Thr Ala Pro Ser Val
        115                 120                 125

Phe Pro Leu Ala Pro Ser Cys Gly Ser Thr Ser Gly Ser Thr Val Ala
    130                 135                 140

Leu Ala Cys Leu Val Ser Gly Tyr Phe Pro Glu Pro Val Thr Val Ser
145                 150                 155                 160

Trp Asn Ser Gly Ser Leu Thr Ser Gly Val His Thr Phe Pro Ser Val
                165                 170                 175

Leu Gln Ser Ser Gly Leu His Ser Leu Ser Ser Met Val Thr Val Pro
            180                 185                 190

Ser Ser Arg Trp Pro Ser Glu Thr Phe Thr Cys Asn Val Val His Pro
        195                 200                 205

Ala Ser Asn Thr Lys Val Asp Lys Pro Val Phe Asn Glu Cys Arg Cys
    210                 215                 220

Thr Asp Thr Pro Pro Cys Pro Val Pro Glu Pro Leu Gly Gly Pro Ser
225                 230                 235                 240

Val Leu Ile Phe Pro Pro Lys Pro Lys Asp Ile Leu Arg Ile Thr Arg
                245                 250                 255

Thr Pro Glu Val Thr Cys Val Val Leu Asp Leu Gly Arg Glu Asp Pro
            260                 265                 270

Glu Val Gln Ile Ser Trp Phe Val Asp Gly Lys Glu Val His Thr Ala
        275                 280                 285

Lys Thr Gln Ser Arg Glu Gln Gln Phe Asn Gly Thr Tyr Arg Val Val
    290                 295                 300

Ser Val Leu Pro Ile Glu His Gln Asp Trp Leu Thr Gly Lys Glu Phe
305                 310                 315                 320

Lys Cys Arg Val Asn His Ile Asp Leu Pro Ser Pro Ile Glu Arg Thr
                325                 330                 335

Ile Ser Lys Ala Arg Gly Arg Ala His Lys Pro Ser Val Tyr Val Leu
            340                 345                 350

Pro Pro Ser Pro Lys Glu Leu Ser Ser Ser Asp Thr Val Ser Ile Thr
        355                 360                 365

Cys Leu Ile Lys Asp Phe Tyr Pro Pro Asp Ile Asp Val Glu Trp Gln
    370                 375                 380

Ser Asn Gly Gln Gln Glu Pro Glu Arg Lys His Arg Met Thr Pro Pro
385                 390                 395                 400

Gln Leu Asp Glu Asp Gly Ser Tyr Phe Leu Tyr Ser Lys Leu Ser Val
```

```
            405                 410                 415
Asp Lys Ser Arg Trp Gln Gln Gly Asp Pro Phe Thr Cys Ala Val Met
        420                 425                 430

His Glu Thr Leu Gln Asn His Tyr Thr Asp Leu Ser Leu Ser His Ser
            435                 440                 445

Pro Gly Lys
    450

<210> SEQ ID NO 75
<211> LENGTH: 1353
<212> TYPE: DNA
<213> ORGANISM: Artificial Sequence
<220> FEATURE:
<223> OTHER INFORMATION: caninized mouse antibody

<400> SEQUENCE: 75
gaggtgcagc tggtgcagag cggcggcgac ctggtgaagc ccggcggcag cgtgagactg      60
agctgcgtgg ccagcggctt caacatcaag aacacctaca tgcactgggt gagacaggcc     120
cccggcaagg gcctgcagtg gatcggcaga atcgcccccg ccaacgtgga caccaagtac     180
gcccccaagt tccagggcaa ggccaccatc agcgccgaca ccgccaagaa caccgcctac     240
atgcagctga acagcctgag agccgaggac accgccgtgt actactgcgt gctgatctac     300
tacgactacg acggcgacat cgacgtgtgg ggccagggca ccctggtgac cgtgagcagc     360
gccagcacca ccgcccccag cgtgttcccc ctggccccca gctgcggcag caccagcggc     420
agcaccgtgg ccctggcctg cctggtgagc ggctacttcc ccgagcccgt gaccgtgagc     480
tggaacagcg gcagcctgac cagcggcgtg cacaccttcc cagcgtgct gcagagcagc      540 ggcctgtaca gcctgagcag caccgtgacc gtgcccagca gcagatggcc cagcgagacc     600
ttcacctgca acgtggtgca ccccgccagc aacaccaagg tggacaagcc cgtgcccaag     660
gagagcacct gcaagtgcat cagcccctgc cccgtgcccg agagcctggg cggccccagc     720
gtgttcatct tccccccccaa gcccaaggac atcctgagaa tcaccagaac ccccgagatc     780
acctgcgtgg tgctggacct gggcagagag gaccccgagg tgcagatcag ctggttcgtg     840
gacggcaagg aggtgcacac cgccaagacc cagcccagag agcagcagtt caacagcacc     900
tacagagtgg tgagcgtgct gcccatcgag caccaggact ggctgaccgg caaggagttc     960
aagtgcagag tgaaccacat cggcctgccc agccccatcg agaaccatca gcaaggcc      1020 agaggccagg cccaccagcc cagcgtgtac gtgctgcccc ccagccccaa ggagctgagc     1080
agcagcgaca ccgtgaccct gacctgcctg atcaaggact tcttccccccc cgagatcgac     1140 gtggagtggc agagcaacgg ccagcccgag cccgagagca gtaccacac caccgccccc      1200 cagctggacg aggacggcag ctacttcctg tacagcaagc tgagcgtgga caagagcaga     1260
tggcagcagg gcgacacctt cacctgcgcc gtgatgcacg aggccctgca gaaccactac     1320
accgacctga gcctgagcca cagccccggc aag                                 1353

<210> SEQ ID NO 76
<211> LENGTH: 451
<212> TYPE: PRT
<213> ORGANISM: Artificial Sequence
<220> FEATURE:
<223> OTHER INFORMATION: caninized mouse antibody

<400> SEQUENCE: 76

Glu Val Gln Leu Val Gln Ser Gly Gly Asp Leu Val Lys Pro Gly Gly
1               5                   10                  15
```

-continued

```
Ser Val Arg Leu Ser Cys Val Ala Ser Gly Phe Asn Ile Lys Asn Thr
         20                  25                  30
Tyr Met His Trp Val Arg Gln Ala Pro Gly Lys Gly Leu Gln Trp Ile
         35                  40                  45
Gly Arg Ile Ala Pro Ala Asn Val Asp Thr Lys Tyr Ala Pro Lys Phe
 50                  55                  60
Gln Gly Lys Ala Thr Ile Ser Ala Asp Thr Ala Lys Asn Thr Ala Tyr
 65                  70                  75                  80
Met Gln Leu Asn Ser Leu Arg Ala Glu Asp Thr Ala Val Tyr Tyr Cys
                 85                  90                  95
Val Leu Ile Tyr Tyr Asp Tyr Asp Gly Ile Asp Val Trp Gly Gln
                100                 105                 110
Gly Thr Leu Val Thr Val Ser Ser Ala Ser Thr Thr Ala Pro Ser Val
             115                 120                 125
Phe Pro Leu Ala Pro Ser Cys Gly Ser Thr Ser Gly Ser Thr Val Ala
 130                 135                 140
Leu Ala Cys Leu Val Ser Gly Tyr Phe Pro Glu Pro Val Thr Val Ser
145                 150                 155                 160
Trp Asn Ser Gly Ser Leu Thr Ser Gly Val His Thr Phe Pro Ser Val
                 165                 170                 175
Leu Gln Ser Ser Gly Leu Tyr Ser Leu Ser Ser Thr Val Thr Val Pro
             180                 185                 190
Ser Ser Arg Trp Pro Ser Glu Thr Phe Thr Cys Asn Val Val His Pro
         195                 200                 205
Ala Ser Asn Thr Lys Val Asp Lys Pro Val Pro Lys Glu Ser Thr Cys
 210                 215                 220
Lys Cys Ile Ser Pro Cys Pro Val Pro Glu Ser Leu Gly Gly Pro Ser
225                 230                 235                 240
Val Phe Ile Phe Pro Pro Lys Pro Lys Asp Ile Leu Arg Ile Thr Arg
                 245                 250                 255
Thr Pro Glu Ile Thr Cys Val Val Leu Asp Leu Gly Arg Glu Asp Pro
             260                 265                 270
Glu Val Gln Ile Ser Trp Phe Val Asp Gly Lys Glu Val His Thr Ala
         275                 280                 285
Lys Thr Gln Pro Arg Glu Gln Gln Phe Asn Ser Thr Tyr Arg Val Val
 290                 295                 300
Ser Val Leu Pro Ile Glu His Gln Asp Trp Leu Thr Gly Lys Glu Phe
305                 310                 315                 320
Lys Cys Arg Val Asn His Ile Gly Leu Pro Ser Pro Ile Glu Arg Thr
                 325                 330                 335
Ile Ser Lys Ala Arg Gly Gln Ala His Gln Pro Ser Val Tyr Val Leu
             340                 345                 350
Pro Pro Ser Pro Lys Glu Leu Ser Ser Ser Asp Thr Val Thr Leu Thr
         355                 360                 365
Cys Leu Ile Lys Asp Phe Phe Pro Pro Glu Ile Asp Val Glu Trp Gln
 370                 375                 380
Ser Asn Gly Gln Pro Glu Pro Glu Ser Lys Tyr His Thr Thr Ala Pro
385                 390                 395                 400
Gln Leu Asp Glu Asp Gly Ser Tyr Phe Leu Tyr Ser Lys Leu Ser Val
                 405                 410                 415
Asp Lys Ser Arg Trp Gln Gln Gly Asp Thr Phe Thr Cys Ala Val Met
             420                 425                 430
```

His Glu Ala Leu Gln Asn His Tyr Thr Asp Leu Ser Leu Ser His Ser
    435                 440                 445

Pro Gly Lys
    450

<210> SEQ ID NO 77
<211> LENGTH: 654
<212> TYPE: DNA
<213> ORGANISM: Artificial Sequence
<220> FEATURE:
<223> OTHER INFORMATION: caninized mouse antibody

<400> SEQUENCE: 77

```
gacatcgtga tgacccagac cccctgagc ctgagcgtga gcctgggcga gcccgccagc      60
atcagctgcc acgccagcca gaacatcaac gtgtggctga gctggtacag acagaagccc     120
ggccagatcc cccagctgct gatctacaag gccagccacc tgcacaccgg cgtgcccgac     180
agattcagcg gcagcggcag cggcaccgac ttcaccctga gaatcagcag agtggaggcc     240
gacgacgccg gcgtgtacta ctgccagcag ggccagagct ggcccctgac cttcggccag     300
ggcaccaagg tggagatcaa gagaaacgac gcccagcccg ccgtgtacct gttccagccc     360
agccccgacc agctgcacac cggcagcgcc agcgtggtgt gcctgctgaa cagcttctac     420
cccaaggaca tcaacgtgaa gtggaaggtg gacggcgtga tccaggacac cggcatccag     480
gagagcgtga ccgagcagga cagcaaggac agcacctaca gcctgagcag caccctgacc     540
atgagcagca ccgagtacct gagccacgag ctgtacagct gcgagatcac ccacaagagc     600
ctgcccagca ccctgatcaa gagcttccag agaagcgagt gccagagagt ggac            654
```

<210> SEQ ID NO 78
<211> LENGTH: 218
<212> TYPE: PRT
<213> ORGANISM: Artificial Sequence
<220> FEATURE:
<223> OTHER INFORMATION: caninized mouse antibody

<400> SEQUENCE: 78

Asp Ile Val Met Thr Gln Thr Pro Leu Ser Leu Ser Val Ser Leu Gly
1               5                   10                  15

Glu Pro Ala Ser Ile Ser Cys His Ala Ser Gln Asn Ile Asn Val Trp
            20                  25                  30

Leu Ser Trp Tyr Arg Gln Lys Pro Gly Gln Ile Pro Gln Leu Leu Ile
        35                  40                  45

Tyr Lys Ala Ser His Leu His Thr Gly Val Pro Asp Arg Phe Ser Gly
    50                  55                  60

Ser Gly Ser Gly Thr Asp Phe Thr Leu Arg Ile Ser Arg Val Glu Ala
65                  70                  75                  80

Asp Asp Ala Gly Val Tyr Tyr Cys Gln Gln Gly Gln Ser Trp Pro Leu
                85                  90                  95

Thr Phe Gly Gln Gly Thr Lys Val Glu Ile Lys Arg Asn Asp Ala Gln
            100                 105                 110

Pro Ala Val Tyr Leu Phe Gln Pro Ser Pro Asp Gln Leu His Thr Gly
        115                 120                 125

Ser Ala Ser Val Val Cys Leu Leu Asn Ser Phe Tyr Pro Lys Asp Ile
    130                 135                 140

Asn Val Lys Trp Lys Val Asp Gly Val Ile Gln Asp Thr Gly Ile Gln
145                 150                 155                 160

Glu Ser Val Thr Glu Gln Asp Ser Lys Asp Ser Thr Tyr Ser Leu Ser

```
                165                 170                 175
Ser Thr Leu Thr Met Ser Ser Thr Glu Tyr Leu Ser His Glu Leu Tyr
        180                 185                 190

Ser Cys Glu Ile Thr His Lys Ser Leu Pro Ser Thr Leu Ile Lys Ser
        195                 200                 205

Phe Gln Arg Ser Glu Cys Gln Arg Val Asp
    210                 215
```

<210> SEQ ID NO 79
<211> LENGTH: 1359
<212> TYPE: DNA
<213> ORGANISM: Artificial Sequence
<220> FEATURE:
<223> OTHER INFORMATION: caninized mouse antibody

<400> SEQUENCE: 79

```
gaggtgcagc tggtgcagag cggcggcgac ctggtgaagc ccggcggcag cgtgagactg      60
agctgcgtgg ccagcggcta caccttcacc agatacaaca tgcactgggt gagacaggcc     120
cccggcaagg gcctgcagtg gatcggcacc atctaccccg gctacggcga caccagctac     180
aaccagaagt tcaagggcaa ggccaccctg agcgtggaca tcgccaagaa caccgcctac     240
atgcagctga acagcctgag agccgaggac accgccgtgt acttctgcag cagagagttc     300
gccgacgact accccatccc ccccttcgac tactggggcc agggcacccc tggtgaccgtg     360 agcagcgcca gcaccaccgc ccccagcgtg ttccccctgg cccccagctg cggcagcacc     420
agcggcagca ccgtggccct ggcctgcctg gtgagcggct acttccccga gcccgtgacc     480
gtgagctgga acagcggcag cctgaccagc ggcgtgcaca ccttccccag cgtgctgcag     540
agcagcggcc tgcacagcct gagcagcatg gtgaccgtgc ccagcagcag atggcccagc     600
gagaccttca cctgcaacgt ggtgcacccc gccagcaaca ccaaggtgga caagcccgtg     660
ttcaacgagt gcagatgcac cgacaccccc cctgccccg tgcccgagcc cctgggcggc     720
cccagcgtgc tgatcttccc ccccaagccc aaggacatcc tgagaatcac cagaaccccc     780
gaggtgacct gcgtggtgct ggacctgggc agagaggacc ccgaggtgca gatcagctgg     840
ttcgtggacg gcaaggaggt gcacaccgcc aagacccaga gcagagagca gcagttcaac     900
ggcacctaca gagtggtgag cgtgctgccc atcgagcacc aggactggct gaccggcaag     960
gagttcaagt gcagagtgaa ccacatcgac ctgcccagcc catcgagag aaccatcagc    1020 aaggccagag gcagagccca aagcccagc gtgtacgtgc tgcccccag ccccaaggag    1080 ctgagcagca gcgacaccgt gagcatcacc tgcctgatca aggacttcta ccccccgac    1140 atcgacgtgg agtggcagag caacggccag caggagcccg agagaaagca cagaatgacc    1200 ccccccagc tggacgagga cggcagctac ttcctgtaca gcaagctgag cgtggacaag    1260
agcagatggc agcagggcga ccccttcacc tgcgccgtga tgcacgagac cctgcagaac    1320
cactacaccg acctgagcct gagccacagc cccggcaag                          1359
```

<210> SEQ ID NO 80
<211> LENGTH: 453
<212> TYPE: PRT
<213> ORGANISM: Artificial Sequence
<220> FEATURE:
<223> OTHER INFORMATION: caninized mouse antibody

<400> SEQUENCE: 80

```
Glu Val Gln Leu Val Gln Ser Gly Gly Asp Leu Val Lys Pro Gly Gly
1               5                   10                  15
```

```
Ser Val Arg Leu Ser Cys Val Ala Ser Gly Tyr Thr Phe Thr Arg Tyr
            20                  25                  30

Asn Met His Trp Val Arg Gln Ala Pro Gly Lys Gly Leu Gln Trp Ile
        35                  40                  45

Gly Thr Ile Tyr Pro Gly Tyr Gly Asp Thr Ser Tyr Asn Gln Lys Phe
    50                  55                  60

Lys Gly Lys Ala Thr Leu Ser Val Asp Ile Ala Lys Asn Thr Ala Tyr
65                  70                  75                  80

Met Gln Leu Asn Ser Leu Arg Ala Glu Asp Thr Ala Val Tyr Phe Cys
                85                  90                  95

Ser Arg Glu Phe Ala Asp Asp Tyr Pro Ile Pro Pro Phe Asp Tyr Trp
            100                 105                 110

Gly Gln Gly Thr Leu Val Thr Val Ser Ser Ala Ser Thr Thr Ala Pro
        115                 120                 125

Ser Val Phe Pro Leu Ala Pro Ser Cys Gly Ser Thr Ser Gly Ser Thr
    130                 135                 140

Val Ala Leu Ala Cys Leu Val Ser Gly Tyr Phe Pro Glu Pro Val Thr
145                 150                 155                 160

Val Ser Trp Asn Ser Gly Ser Leu Thr Ser Gly Val His Thr Phe Pro
                165                 170                 175

Ser Val Leu Gln Ser Ser Gly Leu His Ser Leu Ser Ser Met Val Thr
            180                 185                 190

Val Pro Ser Ser Arg Trp Pro Ser Glu Thr Phe Thr Cys Asn Val Val
        195                 200                 205

His Pro Ala Ser Asn Thr Lys Val Asp Lys Pro Val Phe Asn Glu Cys
    210                 215                 220

Arg Cys Thr Asp Thr Pro Pro Cys Pro Val Pro Glu Pro Leu Gly Gly
225                 230                 235                 240

Pro Ser Val Leu Ile Phe Pro Pro Lys Pro Lys Asp Ile Leu Arg Ile
                245                 250                 255

Thr Arg Thr Pro Glu Val Thr Cys Val Val Leu Asp Leu Gly Arg Glu
            260                 265                 270

Asp Pro Glu Val Gln Ile Ser Trp Phe Val Asp Gly Lys Glu Val His
        275                 280                 285

Thr Ala Lys Thr Gln Ser Arg Glu Gln Gln Phe Asn Gly Thr Tyr Arg
    290                 295                 300

Val Val Ser Val Leu Pro Ile Glu His Gln Asp Trp Leu Thr Gly Lys
305                 310                 315                 320

Glu Phe Lys Cys Arg Val Asn His Ile Asp Leu Pro Ser Pro Ile Glu
                325                 330                 335

Arg Thr Ile Ser Lys Ala Arg Gly Arg Ala His Lys Pro Ser Val Tyr
            340                 345                 350

Val Leu Pro Pro Ser Pro Lys Glu Leu Ser Ser Ser Asp Thr Val Ser
        355                 360                 365

Ile Thr Cys Leu Ile Lys Asp Phe Tyr Pro Pro Asp Ile Asp Val Glu
    370                 375                 380

Trp Gln Ser Asn Gly Gln Gln Glu Pro Glu Arg Lys His Arg Met Thr
385                 390                 395                 400

Pro Pro Gln Leu Asp Glu Asp Gly Ser Tyr Phe Leu Tyr Ser Lys Leu
                405                 410                 415

Ser Val Asp Lys Ser Arg Trp Gln Gln Gly Asp Pro Phe Thr Cys Ala
            420                 425                 430
```

Val Met His Glu Thr Leu Gln Asn His Tyr Thr Asp Leu Ser Leu Ser
        435                 440                 445

His Ser Pro Gly Lys
    450

<210> SEQ ID NO 81
<211> LENGTH: 1359
<212> TYPE: DNA
<213> ORGANISM: Artificial Sequence
<220> FEATURE:
<223> OTHER INFORMATION: caninized mouse antibody

<400> SEQUENCE: 81

```
gaggtgcagc tggtgcagag cggcggcgac ctggtgaagc ccggcggcag cgtgagactg      60
agctgcgtgg ccagcggcta caccttcacc agatacaaca tgcactgggt gagacaggcc     120
cccggcaagg gcctgcagtg gatcggcacc atctaccccg gctacggcga caccagctac     180
aaccagaagt tcaagggcaa ggccaccctg agcgtggaca tcgccaagaa caccgcctac     240
atgcagctga acagcctgag agccgaggac accgccgtgt acttctgcag cagagagttc     300
gccgacgact accccatccc ccccttcgac tactggggcc agggcaccct ggtgaccgtg     360
agcagcgcca gcaccaccgc ccccagcgtg ttccccctgg cccccagctg cggcagcacc     420
agcggcagca ccgtggccct ggcctgcctg gtgagcggct acttccccga gcccgtgacc     480
gtgagctgga acagcggcag cctgaccagc ggcgtgcaca ccttccccag cgtgctgcag     540
agcagcggcc tgtacagcct gagcagcacc gtgaccgtgc cagcagcag atggcccagc     600
gagaccttca cctgcaacgt ggtgcacccc gccagcaaca ccaaggtgga caagcccgtg     660
cccaaggaga gcacctgcaa gtgcatcagc ccctgccccg tgcccgagag cctgggcggc     720
cccagcgtgt tcatcttccc ccccaagccc aaggacatcc tgagaatcac cagaaccccc     780
gagatcacct gcgtggtgct ggacctgggc agagaggacc ccgaggtgca gatcagctgg     840
ttcgtggacg gcaaggaggt gcacaccgcc aagacccagc cagagagca gcagttcaac     900
agcacctaca gagtggtgag cgtgctgccc atcgagcacc aggactggct gaccggcaag     960
gagttcaagt gcagagtgaa ccacatcggc ctgcccagcc ccatcgagag aaccatcagc    1020
aaggccagag gccaggccca ccagcccagc gtgtacgtgc tgcccccag ccccaaggag    1080
ctgagcagca gcgacaccgt gaccctgacc tgcctgatca aggacttctt ccccccccgag    1140
atcgacgtgg agtggcagag caacggccag cccgagcccg agagcaagta ccacaccacc    1200
gccccccagc tggacgagga cggcagctac ttcctgtaca gcaagctgag cgtggacaag    1260
agcagatggc agcagggcga caccttcacc tgcgccgtga tgcacgaggc cctgcagaac    1320
cactacaccg acctgagcct gagccacagc cccggcaag                            1359
```

<210> SEQ ID NO 82
<211> LENGTH: 453
<212> TYPE: PRT
<213> ORGANISM: Artificial Sequence
<220> FEATURE:
<223> OTHER INFORMATION: caninized mouse antibody

<400> SEQUENCE: 82

Glu Val Gln Leu Val Gln Ser Gly Gly Asp Leu Val Lys Pro Gly Gly
1               5                   10                  15

Ser Val Arg Leu Ser Cys Val Ala Ser Gly Tyr Thr Phe Thr Arg Tyr
            20                  25                  30

Asn Met His Trp Val Arg Gln Ala Pro Gly Lys Gly Leu Gln Trp Ile

```
            35                  40                  45
Gly Thr Ile Tyr Pro Gly Tyr Gly Asp Thr Ser Tyr Asn Gln Lys Phe
 50                  55                  60
Lys Gly Lys Ala Thr Leu Ser Val Asp Ile Ala Lys Asn Thr Ala Tyr
 65                  70                  75                  80
Met Gln Leu Asn Ser Leu Arg Ala Glu Asp Thr Ala Val Tyr Phe Cys
                 85                  90                  95
Ser Arg Glu Phe Ala Asp Asp Tyr Pro Ile Pro Pro Phe Asp Tyr Trp
                100                 105                 110
Gly Gln Gly Thr Leu Val Thr Val Ser Ser Ala Ser Thr Thr Ala Pro
                115                 120                 125
Ser Val Phe Pro Leu Ala Pro Ser Cys Gly Ser Thr Ser Gly Ser Thr
130                 135                 140
Val Ala Leu Ala Cys Leu Val Ser Gly Tyr Phe Pro Glu Pro Val Thr
145                 150                 155                 160
Val Ser Trp Asn Ser Gly Ser Leu Thr Ser Gly Val His Thr Phe Pro
                165                 170                 175
Ser Val Leu Gln Ser Ser Gly Leu Tyr Ser Leu Ser Ser Thr Val Thr
                180                 185                 190
Val Pro Ser Ser Arg Trp Pro Ser Glu Thr Phe Thr Cys Asn Val Val
                195                 200                 205
His Pro Ala Ser Asn Thr Lys Val Asp Lys Pro Val Pro Lys Glu Ser
210                 215                 220
Thr Cys Lys Cys Ile Ser Pro Cys Pro Val Pro Glu Ser Leu Gly Gly
225                 230                 235                 240
Pro Ser Val Phe Ile Phe Pro Pro Lys Pro Lys Asp Ile Leu Arg Ile
                245                 250                 255
Thr Arg Thr Pro Glu Ile Thr Cys Val Val Leu Asp Leu Gly Arg Glu
                260                 265                 270
Asp Pro Glu Val Gln Ile Ser Trp Phe Val Asp Gly Lys Glu Val His
                275                 280                 285
Thr Ala Lys Thr Gln Pro Arg Glu Gln Gln Phe Asn Ser Thr Tyr Arg
290                 295                 300
Val Val Ser Val Leu Pro Ile Glu His Gln Asp Trp Leu Thr Gly Lys
305                 310                 315                 320
Glu Phe Lys Cys Arg Val Asn His Ile Gly Leu Pro Ser Pro Ile Glu
                325                 330                 335
Arg Thr Ile Ser Lys Ala Arg Gly Gln Ala His Gln Pro Ser Val Tyr
                340                 345                 350
Val Leu Pro Pro Ser Pro Lys Glu Leu Ser Ser Ser Asp Thr Val Thr
                355                 360                 365
Leu Thr Cys Leu Ile Lys Asp Phe Phe Pro Pro Glu Ile Asp Val Glu
                370                 375                 380
Trp Gln Ser Asn Gly Gln Pro Glu Pro Glu Ser Lys Tyr His Thr Thr
385                 390                 395                 400
Ala Pro Gln Leu Asp Glu Asp Gly Ser Tyr Phe Leu Tyr Ser Lys Leu
                405                 410                 415
Ser Val Asp Lys Ser Arg Trp Gln Gln Gly Asp Thr Phe Thr Cys Ala
                420                 425                 430
Val Met His Glu Ala Leu Gln Asn His Tyr Thr Asp Leu Ser Leu Ser
                435                 440                 445
His Ser Pro Gly Lys
450
```

<210> SEQ ID NO 83
<211> LENGTH: 666
<212> TYPE: DNA
<213> ORGANISM: Artificial Sequence
<220> FEATURE:
<223> OTHER INFORMATION: caninized mouse antibody

<400> SEQUENCE: 83

```
gacatcgtga tgacccagac ccccctgagc ctgcccgtga gcctgggcga gcccgccagc      60
atcagctgca gaagcagcca gaacatcgtg cacagcaacg gcaacaccta cctggagtgg     120
tacagacaga agcccggcca gagcccccag ctgctgatct acaaggtgag caacagattc     180
agcggcgtgc ccgacagatt cagcggcagc ggcagcggca ccgacttcac cctgagaatc     240
agcagagtgg aggccgacga cgccggcgtg tactactgct tccagggcag ccacgtgccc     300
tacaccttcg gccagggcac caaggtggag atcaagagag acgcccagcc cgccgtgtac     360
ctgttccagc ccagccccga ccagctgcac accggcagcg ccagcgtggt gtgcctgctg     420
aacagcttct accccaagga catcaacgtg aagtggaagg tggacggcgt gatccaggac     480
accggcatcc aggagagcgt gaccgagcag gacagcaagg acagcaccta cagcctgagc     540
agcacactga ccatgagcag caccgagtac ctgagccacg agctgtacag ctgcgagatc     600
acccacaaga gcctgcccag cacccctgatc aagagcttcc agagaagcga gtgccagaga     660
gtggac                                                                 666
```

<210> SEQ ID NO 84
<211> LENGTH: 222
<212> TYPE: PRT
<213> ORGANISM: Artificial Sequence
<220> FEATURE:
<223> OTHER INFORMATION: caninized mouse antibody

<400> SEQUENCE: 84

```
Asp Ile Val Met Thr Gln Thr Pro Leu Ser Leu Pro Val Ser Leu Gly
 1               5                  10                  15
Glu Pro Ala Ser Ile Ser Cys Arg Ser Ser Gln Asn Ile Val His Ser
            20                  25                  30
Asn Gly Asn Thr Tyr Leu Glu Trp Tyr Arg Gln Lys Pro Gly Gln Ser
        35                  40                  45
Pro Gln Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Arg Ile
65                  70                  75                  80
Ser Arg Val Glu Ala Asp Asp Ala Gly Val Tyr Tyr Cys Phe Gln Gly
                85                  90                  95
Ser His Val Pro Tyr Thr Phe Gly Gln Gly Thr Lys Val Glu Ile Lys
           100                 105                 110
Arg Asp Ala Gln Pro Ala Val Tyr Leu Phe Gln Pro Ser Pro Asp Gln
       115                 120                 125
Leu His Thr Gly Ser Ala Ser Val Val Cys Leu Leu Asn Ser Phe Tyr
   130                 135                 140
Pro Lys Asp Ile Asn Val Lys Trp Lys Val Asp Gly Val Ile Gln Asp
145                 150                 155                 160
Thr Gly Ile Gln Glu Ser Val Thr Glu Gln Asp Ser Lys Asp Ser Thr
               165                 170                 175
Tyr Ser Leu Ser Ser Thr Leu Thr Met Ser Ser Thr Glu Tyr Leu Ser
```

```
            180                 185                 190
His Glu Leu Tyr Ser Cys Glu Ile Thr His Lys Ser Leu Pro Ser Thr
        195                 200                 205

Leu Ile Lys Ser Phe Gln Arg Ser Glu Cys Gln Arg Val Asp
        210                 215                 220

<210> SEQ ID NO 85
<211> LENGTH: 1338
<212> TYPE: DNA
<213> ORGANISM: Artificial Sequence
<220> FEATURE:
<223> OTHER INFORMATION: caninized mouse antibody

<400> SEQUENCE: 85
gaggtgcagc tggtgcagag cggccccggc ctggtgaagc ccagccagag cctgagcctg      60
acctgcgtgg tgagcggctt cagcctgacc agctacggcg tgcactgggt gagacaggcc     120
cccggcaagg gcctgcagtg gatgggctgg atcaacatct acagcggcat ccccacctac     180
gccgacgact tcaagggcag attcaccttc agcctggaca ccgccaagaa caccgcctac     240
ctgcagctga gcagcctgag agccgaggac accgccgtgt actactgcgc cagattcgac     300
ggccccgact actggggcca gggcaccctg gtgaccgtga gcgccagcac caccgcc       360 cccagcgtgt tcccccctggc cccagctgc ggcagcacca gcggcagcac cgtggccctg     420
gcctgcctgg tgagcggcta cttccccgag cccgtgaccg tgagctggaa cagcggcagc     480
ctgaccagcg gcgtgcacac cttccccagc gtgctgcaga gcagcggcct gcacagcctg     540
agcagcatgg tgaccgtgcc cagcagcaga tggcccagcg agaccttcac ctgcaacgtg     600
gtgcaccccg ccagcaacac caaggtggac aagcccgtgt caacgagtg cagatgcacc     660 gacaccccccc cctgccccgt gcccgagccc tgggcggcc ccagcgtgct gatcttcccc     720
cccaagccca aggacatcct gagaatcacc agaaccccccg aggtgacctg cgtggtgctg     780
gacctgggca gagaggaccc cgaggtgcag atcagctggt tcgtggacgg caaggaggtg     840
cacaccgcca agacccagag cagagagcag cagttcaacg gcacctacag agtggtgagc     900
gtgctgccca tcgagcacca ggactggctg accggcaagg agttcaagtg cagagtgaac     960
cacatcgacc tgcccagccc catcgagaga accatcagca aggccagagg cagagcccac    1020
aagcccagcg tgtacgtgct gccccccagc cccaaggagc tgagcagcag cgacaccgtg    1080 agcatcaccct gcctgatcaa ggacttctac ccccccgaca tcgacgtgga gtggcagagc    1140
aacggccagc aggagcccga gagaaagcac agaatgaccc ccccccagct ggacgaggac    1200
ggcagctact tcctgtacag caagctgagc gtggacaaga gcagatggca gcagggcgac    1260
ccctccacct gcgccgtgat gcacgagacc ctgcagaacc actacaccga cctgagcctg    1320
agccacagcc ccggcaag                                                   1338

<210> SEQ ID NO 86
<211> LENGTH: 446
<212> TYPE: PRT
<213> ORGANISM: Artificial Sequence
<220> FEATURE:
<223> OTHER INFORMATION: caninized mouse antibody

<400> SEQUENCE: 86

Glu Val Gln Leu Val Gln Ser Gly Pro Gly Leu Val Lys Pro Ser Gln
1               5                   10                  15

Ser Leu Ser Leu Thr Cys Val Val Ser Gly Phe Ser Leu Thr Ser Tyr
            20                  25                  30
```

```
Gly Val His Trp Val Arg Gln Ala Pro Gly Lys Gly Leu Gln Trp Met
         35                  40                  45

Gly Trp Ile Asn Ile Tyr Ser Gly Ile Pro Thr Tyr Ala Asp Asp Phe
 50                  55                  60

Lys Gly Arg Phe Thr Phe Ser Leu Asp Thr Ala Lys Asn Thr Ala Tyr
 65                  70                  75                  80

Leu Gln Leu Ser Ser Leu Arg Ala Glu Asp Thr Ala Val Tyr Tyr Cys
                 85                  90                  95

Ala Arg Phe Asp Gly Pro Asp Tyr Trp Gly Gln Gly Thr Leu Val Thr
                100                 105                 110

Val Ser Ser Ala Ser Thr Thr Ala Pro Ser Val Phe Pro Leu Ala Pro
                115                 120                 125

Ser Cys Gly Ser Thr Ser Gly Ser Thr Val Ala Leu Ala Cys Leu Val
                130                 135                 140

Ser Gly Tyr Phe Pro Glu Pro Val Thr Val Ser Trp Asn Ser Gly Ser
145                 150                 155                 160

Leu Thr Ser Gly Val His Thr Phe Pro Ser Val Leu Gln Ser Ser Gly
                165                 170                 175

Leu His Ser Leu Ser Ser Met Val Thr Val Pro Ser Ser Arg Trp Pro
                180                 185                 190

Ser Glu Thr Phe Thr Cys Asn Val Val His Pro Ala Ser Asn Thr Lys
                195                 200                 205

Val Asp Lys Pro Val Phe Asn Glu Cys Arg Cys Thr Asp Thr Pro Pro
210                 215                 220

Cys Pro Val Pro Glu Pro Leu Gly Gly Pro Ser Val Leu Ile Phe Pro
225                 230                 235                 240

Pro Lys Pro Lys Asp Ile Leu Arg Ile Thr Arg Thr Pro Glu Val Thr
                245                 250                 255

Cys Val Val Leu Asp Leu Gly Arg Glu Asp Pro Glu Val Gln Ile Ser
                260                 265                 270

Trp Phe Val Asp Gly Lys Glu Val His Thr Ala Lys Thr Gln Ser Arg
            275                 280                 285

Glu Gln Gln Phe Asn Gly Thr Tyr Arg Val Val Ser Val Leu Pro Ile
            290                 295                 300

Glu His Gln Asp Trp Leu Thr Gly Lys Glu Phe Lys Cys Arg Val Asn
305                 310                 315                 320

His Ile Asp Leu Pro Ser Pro Ile Glu Arg Thr Ile Ser Lys Ala Arg
                325                 330                 335

Gly Arg Ala His Lys Pro Ser Val Tyr Val Leu Pro Pro Ser Pro Lys
                340                 345                 350

Glu Leu Ser Ser Ser Asp Thr Val Ser Ile Thr Cys Leu Ile Lys Asp
                355                 360                 365

Phe Tyr Pro Pro Asp Ile Asp Val Glu Trp Gln Ser Asn Gly Gln Gln
        370                 375                 380

Glu Pro Glu Arg Lys His Arg Met Thr Pro Gln Leu Asp Glu Asp
385                 390                 395                 400

Gly Ser Tyr Phe Leu Tyr Ser Lys Leu Ser Val Asp Lys Ser Arg Trp
                405                 410                 415

Gln Gln Gly Asp Pro Phe Thr Cys Ala Val Met His Glu Thr Leu Gln
                420                 425                 430

Asn His Tyr Thr Asp Leu Ser Leu Ser His Ser Pro Gly Lys
                435                 440                 445
```

<210> SEQ ID NO 87
<211> LENGTH: 1338
<212> TYPE: DNA
<213> ORGANISM: Artificial Sequence
<220> FEATURE:
<223> OTHER INFORMATION: caninized mouse antibody

<400> SEQUENCE: 87

| | | | | | |
|---|---|---|---|---|---|
| gaggtgcagc | tggtgcagag | cggccccggc | ctggtgaagc | ccagccagag | cctgagcctg | 60 |
| acctgcgtgg | tgagcggctt | cagcctgacc | agctacggcg | tgcactgggt | gagacaggcc | 120 |
| cccggcaagg | gcctgcagtg | gatgggctgg | atcaacatct | acagcggcat | ccccacctac | 180 |
| gccgacgact | tcaagggcag | attcaccttc | agcctggaca | ccgccaagaa | caccgcctac | 240 |
| ctgcagctga | gcagcctgag | agccgaggac | accgccgtgt | actactgcgc | cagattcgac | 300 |
| ggccccgact | actggggcca | gggcaccctg | gtgaccgtga | gcgccagcac | caccaccgcc | 360 |
| cccagcgtgt | tccccctggc | ccccagctgc | ggcagcacca | gcggcagcac | cgtggccctg | 420 |
| gcctgcctgg | tgagcggcta | cttccccgag | cccgtgaccg | tgagctggaa | cagcggcagc | 480 |
| ctgaccagcg | gcgtgcacac | cttccccagc | gtgctgcaga | gcagcggcct | gtacagcctg | 540 |
| agcagcaccg | tgaccgtgcc | cagcagcaga | tgggcccagc | gaccttcac | ctgcaacgtg | 600 |
| gtgcaccccg | ccagcaacac | caaggtggac | aagcccgtgc | caaggagag | cacctgcaag | 660 |
| tgcatcagcc | cctgccccgt | gcccgagagc | ctgggcggcc | ccagcgtgtt | catcttcccc | 720 |
| cccaagccca | aggacatcct | gagaatcacc | agaaccccccg | agatcacctg | cgtggtgctg | 780 |
| gacctgggca | gagaggaccc | cgaggtgcag | atcagctggt | tcgtggacgg | caaggaggtg | 840 |
| cacaccgcca | agacccagcc | cagagagcag | cagttcaaca | gcacctacag | agtggtgagc | 900 |
| gtgctgccca | tcgagcacca | ggactggctg | accggcaagg | agttcaagtg | cagagtgaac | 960 |
| cacatcggcc | tgcccagccc | catcgagaga | accatcagca | aggccagagg | ccaggcccac | 1020 |
| cagcccagcg | tgtacgtgct | gccccccagc | cccaaggagc | tgagcagcag | cgacaccgtg | 1080 |
| accctgacct | gcctgatcaa | ggacttcttc | cccccccgaga | tcgacgtgga | gtggcagagc | 1140 |
| aacggccagc | ccgagcccga | gagcaagtac | cacaccaccg | cccccccagct | ggacgaggac | 1200 |
| ggcagctact | tcctgtacag | caagctgagc | gtggacaaga | gcagatggca | gcagggcgac | 1260 |
| accttcacct | gcgccgtgat | gcacgaggcc | ctgcagaacc | actacaccga | cctgagcctg | 1320 |
| agccacagcc | ccggcaag | | | | | 1338 |

<210> SEQ ID NO 88
<211> LENGTH: 446
<212> TYPE: PRT
<213> ORGANISM: Artificial Sequence
<220> FEATURE:
<223> OTHER INFORMATION: caninized mouse antibody

<400> SEQUENCE: 88

Glu Val Gln Leu Val Gln Ser Gly Pro Gly Leu Val Lys Pro Ser Gln
1               5                   10                  15

Ser Leu Ser Leu Thr Cys Val Val Ser Gly Phe Ser Leu Thr Ser Tyr
            20                  25                  30

Gly Val His Trp Val Arg Gln Ala Pro Gly Lys Gly Leu Gln Trp Met
        35                  40                  45

Gly Trp Ile Asn Ile Tyr Ser Gly Ile Pro Thr Tyr Ala Asp Asp Phe
    50                  55                  60

Lys Gly Arg Phe Thr Phe Ser Leu Asp Thr Ala Lys Asn Thr Ala Tyr

```
                65                  70                  75                  80
Leu Gln Leu Ser Ser Leu Arg Ala Glu Asp Thr Ala Val Tyr Tyr Cys
                    85                  90                  95

Ala Arg Phe Asp Gly Pro Asp Tyr Trp Gly Gln Gly Thr Leu Val Thr
                100                 105                 110

Val Ser Ser Ala Ser Thr Thr Ala Pro Ser Val Phe Pro Leu Ala Pro
                115                 120                 125

Ser Cys Gly Ser Thr Ser Gly Ser Thr Val Ala Leu Ala Cys Leu Val
130                 135                 140

Ser Gly Tyr Phe Pro Glu Pro Val Thr Val Ser Trp Asn Ser Gly Ser
145                 150                 155                 160

Leu Thr Ser Gly Val His Thr Phe Pro Ser Val Leu Gln Ser Ser Gly
                165                 170                 175

Leu Tyr Ser Leu Ser Ser Thr Val Thr Val Pro Ser Ser Arg Trp Pro
                180                 185                 190

Ser Glu Thr Phe Thr Cys Asn Val Val His Pro Ala Ser Asn Thr Lys
                195                 200                 205

Val Asp Lys Pro Val Pro Lys Glu Ser Thr Cys Lys Cys Ile Ser Pro
210                 215                 220

Cys Pro Val Pro Glu Ser Leu Gly Gly Pro Ser Val Phe Ile Phe Pro
225                 230                 235                 240

Pro Lys Pro Lys Asp Ile Leu Arg Ile Thr Arg Thr Pro Glu Ile Thr
                245                 250                 255

Cys Val Val Leu Asp Leu Gly Arg Glu Asp Pro Glu Val Gln Ile Ser
                260                 265                 270

Trp Phe Val Asp Gly Lys Glu Val His Thr Ala Lys Thr Gln Pro Arg
                275                 280                 285

Glu Gln Gln Phe Asn Ser Thr Tyr Arg Val Val Ser Val Leu Pro Ile
                290                 295                 300

Glu His Gln Asp Trp Leu Thr Gly Lys Glu Phe Lys Cys Arg Val Asn
305                 310                 315                 320

His Ile Gly Leu Pro Ser Pro Ile Glu Arg Thr Ile Ser Lys Ala Arg
                325                 330                 335

Gly Gln Ala His Gln Pro Ser Val Tyr Val Leu Pro Pro Ser Pro Lys
                340                 345                 350

Glu Leu Ser Ser Ser Asp Thr Val Thr Leu Thr Cys Leu Ile Lys Asp
                355                 360                 365

Phe Phe Pro Pro Glu Ile Asp Val Glu Trp Gln Ser Asn Gly Gln Pro
                370                 375                 380

Glu Pro Glu Ser Lys Tyr His Thr Thr Ala Pro Gln Leu Asp Glu Asp
385                 390                 395                 400

Gly Ser Tyr Phe Leu Tyr Ser Lys Leu Ser Val Asp Lys Ser Arg Trp
                405                 410                 415

Gln Gln Gly Asp Thr Phe Thr Cys Ala Val Met His Glu Ala Leu Gln
                420                 425                 430

Asn His Tyr Thr Asp Leu Ser Leu Ser His Ser Pro Gly Lys
                435                 440                 445

<210> SEQ ID NO 89
<211> LENGTH: 672
<212> TYPE: DNA
<213> ORGANISM: Artificial Sequence
<220> FEATURE:
<223> OTHER INFORMATION: caninized mouse antibody
```

<400> SEQUENCE: 89

```
gacatcgtga tgacccagac cccctgagc ctgagcgtga gccccggcga gcccgccagc      60
atgagctgca agagcagcca gagcctgctg aacagcgtga accagaagaa ctacctggcc    120
tggtacagac agaagcccgg ccagagcccc caggtgctgg tgtacttcgc cagcaccaga    180
gtgagcggcg tgcccgacag attcatcggc agcggcagcg gcaccgactt caccctgaga    240
atcagcagag tggaggccga cgacctgggc gtgtactact gccagcagta cttcagcacc    300
cccctgacct tcggccaggg caccaagctg gagctgaaga gaaacgacgc ccagcccgcc    360
gtgtacctgt tccagcccag ccccgaccag ctgcacaccg gcagcgccag cgtggtgtgc    420
ctgctgaaca gcttctaccc caaggacatc aacgtgaagt ggaaggtgga cggcgtgatc    480
caggacaccg gcatccagga gagcgtgacc gagcaggaca gcaaggacag cacctacagc    540
ctgagcagca ccctgaccat gagcagcacc gagtacctga gccacgagct gtacagctgc    600
gagatcaccc acaagagcct gcccagcacc ctgatcaaga gcttccagag aagcgagtgc    660
cagagagtgg ac                                                        672
```

<210> SEQ ID NO 90
<211> LENGTH: 224
<212> TYPE: PRT
<213> ORGANISM: Artificial Sequence
<220> FEATURE:
<223> OTHER INFORMATION: caninized mouse antibody

<400> SEQUENCE: 90

```
Asp Ile Val Met Thr Gln Thr Pro Leu Ser Leu Ser Val Ser Pro Gly
1               5                   10                  15

Glu Pro Ala Ser Met Ser Cys Lys Ser Ser Gln Ser Leu Leu Asn Ser
            20                  25                  30

Val Asn Gln Lys Asn Tyr Leu Ala Trp Tyr Arg Gln Lys Pro Gly Gln
        35                  40                  45

Ser Pro Gln Val Leu Val Tyr Phe Ala Ser Thr Arg Val Ser Gly Val
    50                  55                  60

Pro Asp Arg Phe Ile Gly Ser Gly Ser Gly Thr Asp Phe Thr Leu Arg
65                  70                  75                  80

Ile Ser Arg Val Glu Ala Asp Asp Leu Gly Val Tyr Tyr Cys Gln Gln
                85                  90                  95

Tyr Phe Ser Thr Pro Leu Thr Phe Gly Gln Gly Thr Lys Leu Glu Leu
            100                 105                 110

Lys Arg Asn Asp Ala Gln Pro Ala Val Tyr Leu Phe Gln Pro Ser Pro
        115                 120                 125

Asp Gln Leu His Thr Gly Ser Ala Ser Val Val Cys Leu Leu Asn Ser
    130                 135                 140

Phe Tyr Pro Lys Asp Ile Asn Val Lys Trp Lys Val Asp Gly Val Ile
145                 150                 155                 160

Gln Asp Thr Gly Ile Gln Glu Ser Val Thr Glu Gln Asp Ser Lys Asp
                165                 170                 175

Ser Thr Tyr Ser Leu Ser Ser Thr Leu Thr Met Ser Ser Thr Glu Tyr
            180                 185                 190

Leu Ser His Glu Leu Tyr Ser Cys Glu Ile Thr His Lys Ser Leu Pro
        195                 200                 205

Ser Thr Leu Ile Lys Ser Phe Gln Arg Ser Glu Cys Gln Arg Val Asp
    210                 215                 220
```

<210> SEQ ID NO 91
<211> LENGTH: 1338
<212> TYPE: DNA
<213> ORGANISM: Artificial Sequence
<220> FEATURE:
<223> OTHER INFORMATION: caninized mouse antibody

<400> SEQUENCE: 91

```
gaggtgcagc tggtgcagag cggcgccgag gtgaagaagc ccggcgccag cgtgaaggtg      60
agctgcaagg ccagcggcta caccttcacc acctacggca tgagctgggt gagacaggcc     120
cccggcaagg gcctgcagtg gatgggctgg atcaacatct acagcggcat ccccacctac     180
gccgacgact tcaagggcag attcgccctg agcctggaca ccagcaccag caccgcctac     240
atggagctga acagcctgag agccgaggac accgccgtgt actactgcgc cagattcgac     300
ggccccgact actggggcca gggcaccctg gtgaccgtga gcagcgccag caccaccgcc     360
cccagcgtgt tccccctggc cccagctgc ggcagcacca gcggcagcac cgtggccctg     420
gcctgcctgg tgagcggcta cttccccgag ccgtgaccg tgagctggaa cagcggcagc     480
ctgaccagcg gcgtgcacac cttccccagc gtgctgcaga gcagcggcct gcacagcctg     540
agcagcatgg tgaccgtgcc agcagcaga tggcccagcg agaccttcac ctgcaacgtg     600
gtgcaccccg ccagcaacac caaggtggac aagcccgtgt caacgagtg cagatgcacc     660
gacaccccc cctgccccgt gcccgagccc ctgggcggcc ccagcgtgct gatcttcccc     720
cccaagccca aggacatcct gagaatcacc agaacccccg aggtgacctg cgtggtgctg     780
gacctgggca gagaggaccc cgaggtgcag atcagctggt tcgtggacgg caaggaggtg     840
cacaccgcca agacccagag cagagagcag cagttcaacg gcacctacag agtggtgagc     900
gtgctgccca tcgagcacca ggactggctg accggcaagg agttcaagtg cagagtgaac     960
cacatcgacc tgcccagccc catcgagaga accatcagca aggccagagg cagagcccac    1020
aagcccagcg tgtacgtgct gcccccagc cccaaggagc tgagcagcag cgacaccgtg    1080
agcatcacct gcctgatcaa ggacttctac ccccccgaca tcgacgtgga gtggcagagc    1140
aacggccagc aggagcccga gaaaagcac agaatgaccc ccccagct ggacgaggac    1200
ggcagctact tcctgtacag caagctgagc gtggacaaga cagatggca gcagggcgac    1260
cccttcacct gcgccgtgat gcacgagacc ctgcagaacc actacaccga cctgagcctg    1320
agccacagcc ccggcaag                                                  1338
```

<210> SEQ ID NO 92
<211> LENGTH: 446
<212> TYPE: PRT
<213> ORGANISM: Artificial Sequence
<220> FEATURE:
<223> OTHER INFORMATION: caninized mouse antibody

<400> SEQUENCE: 92

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
                20                  25                  30

Gly Met Ser Trp Val Arg Gln Ala Pro Gly Lys Gly Leu Gln Trp Met
            35                  40                  45

Gly Trp Ile Asn Ile Tyr Ser Gly Ile Pro Thr Tyr Ala Asp Asp Phe
        50                  55                  60

Lys Gly Arg Phe Ala Leu Ser Leu Asp Thr Ser Thr Ser Thr Ala Tyr
65                  70                  75                  80
```

Met Glu Leu Asn Ser Leu Arg Ala Glu Asp Thr Ala Val Tyr Tyr Cys
                85                  90                  95

Ala Arg Phe Asp Gly Pro Asp Tyr Trp Gly Gln Gly Thr Leu Val Thr
           100                 105                 110

Val Ser Ser Ala Ser Thr Thr Ala Pro Ser Val Phe Pro Leu Ala Pro
        115                 120                 125

Ser Cys Gly Ser Thr Gly Ser Thr Val Ala Leu Ala Cys Leu Val
130                 135                 140

Ser Gly Tyr Phe Pro Glu Pro Val Thr Val Ser Trp Asn Ser Gly Ser
145                 150                 155                 160

Leu Thr Ser Gly Val His Thr Phe Pro Ser Val Leu Gln Ser Ser Gly
                165                 170                 175

Leu His Ser Leu Ser Ser Met Val Thr Val Pro Ser Ser Arg Trp Pro
            180                 185                 190

Ser Glu Thr Phe Thr Cys Asn Val Val His Pro Ala Ser Asn Thr Lys
        195                 200                 205

Val Asp Lys Pro Val Phe Asn Glu Cys Arg Cys Thr Asp Thr Pro Pro
210                 215                 220

Cys Pro Val Pro Glu Pro Leu Gly Gly Pro Ser Val Leu Ile Phe Pro
225                 230                 235                 240

Pro Lys Pro Lys Asp Ile Leu Arg Ile Thr Arg Thr Pro Glu Val Thr
                245                 250                 255

Cys Val Val Leu Asp Leu Gly Arg Glu Asp Pro Glu Val Gln Ile Ser
            260                 265                 270

Trp Phe Val Asp Gly Lys Glu Val His Thr Ala Lys Thr Gln Ser Arg
        275                 280                 285

Glu Gln Gln Phe Asn Gly Thr Tyr Arg Val Val Ser Val Leu Pro Ile
290                 295                 300

Glu His Gln Asp Trp Leu Thr Gly Lys Glu Phe Lys Cys Arg Val Asn
305                 310                 315                 320

His Ile Asp Leu Pro Ser Pro Ile Glu Arg Thr Ile Ser Lys Ala Arg
                325                 330                 335

Gly Arg Ala His Lys Pro Ser Val Tyr Val Leu Pro Pro Ser Pro Lys
            340                 345                 350

Glu Leu Ser Ser Ser Asp Thr Val Ser Ile Thr Cys Leu Ile Lys Asp
        355                 360                 365

Phe Tyr Pro Pro Asp Ile Asp Val Glu Trp Gln Ser Asn Gly Gln Gln
370                 375                 380

Glu Pro Glu Arg Lys His Arg Met Thr Pro Gln Leu Asp Glu Asp
385                 390                 395                 400

Gly Ser Tyr Phe Leu Tyr Ser Lys Leu Ser Val Asp Lys Ser Arg Trp
                405                 410                 415

Gln Gln Gly Asp Pro Phe Thr Cys Ala Val Met His Glu Thr Leu Gln
            420                 425                 430

Asn His Tyr Thr Asp Leu Ser Leu Ser His Ser Pro Gly Lys
        435                 440                 445

<210> SEQ ID NO 93
<211> LENGTH: 1338
<212> TYPE: DNA
<213> ORGANISM: Artificial Sequence
<220> FEATURE:
<223> OTHER INFORMATION: caninized mouse antibody

<400> SEQUENCE: 93

```
gaggtgcagc tggtgcagag cggcgccgag gtgaagaagc ccggcgccag cgtgaaggtg    60
agctgcaagg ccagcggcta caccttcacc acctacggca tgagctgggt gagacaggcc   120
cccggcaagg gcctgcagtg gatgggctgg atcaacatct acagcggcat ccccacctac   180
gccgacgact tcaagggcag attcgccctg agcctggaca ccagcaccag caccgcctac   240
atggagctga acagcctgag agccgaggac accgccgtgt actactgcgc cagattcgac   300
ggccccgact actggggcca gggcaccctg gtgaccgtga gcgccagcac caccgcc     360 cccagcgtgt tccccctggc cccagctgc ggcagcacca gcggcagcac cgtggccctg   420
gcctgcctgg tgagcggcta cttccccgag cccgtgaccg tgagctggaa cagcggcagc   480
ctgaccagcg gcgtgcacac cttccccagc gtgctgcaga gcagcggcct gtacagcctg   540
agcagcaccg tgaccgtgcc cagcagcaga tggcccagcg agaccttcac ctgcaacgtg   600
gtgcaccccg ccagcaacac caaggtggac aagcccgtgc caaggagag cacctgcaag   660 tgcatcagcc cctgccccgt gcccgagagc ctgggcggcc ccagcgtgtt catcttcccc   720
cccaagccca aggacatcct gagaatcacc agaaccccc gatcacctg cgtggtgctg   780 gacctgggca gagaggaccc cgaggtgcag atcagctggt tcgtggacgg caaggaggtg   840
cacaccgcca agacccagcc cagagagcag cagttcaaca gcacctacag agtggtgagc   900
gtgctgccca tcgagcacca ggactggctg accggcaagg agttcaagtg cagagtgaac   960
cacatcggcc tgcccagccc catcgagaga accatcagca aggccagagg ccaggcccac  1020
cagcccagcg tgtacgtgct gccccccagc cccaaggagc tgagcagcag cgacaccgtg  1080
accctgacct gcctgatcaa ggacttcttc ccccccgaga tcgacgtgga gtggcagagc  1140
aacggccagc ccgagcccga gagcaagtac cacaccaccg cccccagct ggacgaggac  1200 ggcagctact tcctgtacag caagctgagc gtggacaaga gcagatggca gcagggcgac  1260
accttcacct gcgccgtgat gcacgaggcc ctgcagaacc actacaccga cctgagcctg  1320
agccacagcc ccggcaag                                                1338
```

<210> SEQ ID NO 94
<211> LENGTH: 446
<212> TYPE: PRT
<213> ORGANISM: Artificial Sequence
<220> FEATURE:
<223> OTHER INFORMATION: caninized mouse antibody

<400> SEQUENCE: 94

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Gly Met Ser Trp Val Arg Gln Ala Pro Gly Lys Gly Leu Gln Trp Met
        35                  40                  45

Gly Trp Ile Asn Ile Tyr Ser Gly Ile Pro Thr Tyr Ala Asp Asp Phe
    50                  55                  60

Lys Gly Arg Phe Ala Leu Ser Leu Asp Thr Ser Thr Ser Thr Ala Tyr
65                  70                  75                  80

Met Glu Leu Asn Ser Leu Arg Ala Glu Asp Thr Ala Val Tyr Tyr Cys
                85                  90                  95

Ala Arg Phe Asp Gly Pro Asp Tyr Trp Gly Gln Gly Thr Leu Val Thr
            100                 105                 110

Val Ser Ser Ala Ser Thr Thr Ala Pro Ser Val Phe Pro Leu Ala Pro
```

```
            115                 120                 125
Ser Cys Gly Ser Thr Ser Gly Ser Thr Val Ala Leu Ala Cys Leu Val
    130                 135                 140

Ser Gly Tyr Phe Pro Glu Pro Val Thr Val Ser Trp Asn Ser Gly Ser
145                 150                 155                 160

Leu Thr Ser Gly Val His Thr Phe Pro Ser Val Leu Gln Ser Ser Gly
                165                 170                 175

Leu Tyr Ser Leu Ser Ser Thr Val Thr Val Pro Ser Ser Arg Trp Pro
            180                 185                 190

Ser Glu Thr Phe Thr Cys Asn Val Val His Pro Ala Ser Asn Thr Lys
        195                 200                 205

Val Asp Lys Pro Val Pro Lys Glu Ser Thr Cys Lys Cys Ile Ser Pro
    210                 215                 220

Cys Pro Val Pro Glu Ser Leu Gly Gly Pro Ser Val Phe Ile Phe Pro
225                 230                 235                 240

Pro Lys Pro Lys Asp Ile Leu Arg Ile Thr Arg Thr Pro Glu Ile Thr
                245                 250                 255

Cys Val Val Leu Asp Leu Gly Arg Glu Asp Pro Glu Val Gln Ile Ser
            260                 265                 270

Trp Phe Val Asp Gly Lys Glu Val His Thr Ala Lys Thr Gln Pro Arg
        275                 280                 285

Glu Gln Gln Phe Asn Ser Thr Tyr Arg Val Val Ser Val Leu Pro Ile
290                 295                 300

Glu His Gln Asp Trp Leu Thr Gly Lys Glu Phe Lys Cys Arg Val Asn
305                 310                 315                 320

His Ile Gly Leu Pro Ser Pro Ile Glu Arg Thr Ile Ser Lys Ala Arg
                325                 330                 335

Gly Gln Ala His Gln Pro Ser Val Tyr Val Leu Pro Pro Ser Pro Lys
            340                 345                 350

Glu Leu Ser Ser Ser Asp Thr Val Thr Leu Thr Cys Leu Ile Lys Asp
        355                 360                 365

Phe Phe Pro Pro Glu Ile Asp Val Glu Trp Gln Ser Asn Gly Gln Pro
370                 375                 380

Glu Pro Glu Ser Lys Tyr His Thr Thr Ala Pro Gln Leu Asp Glu Asp
385                 390                 395                 400

Gly Ser Tyr Phe Leu Tyr Ser Lys Leu Ser Val Asp Lys Ser Arg Trp
                405                 410                 415

Gln Gln Gly Asp Thr Phe Thr Cys Ala Val Met His Glu Ala Leu Gln
            420                 425                 430

Asn His Tyr Thr Asp Leu Ser Leu Ser His Ser Pro Gly Lys
        435                 440                 445

<210> SEQ ID NO 95
<211> LENGTH: 672
<212> TYPE: DNA
<213> ORGANISM: Artificial Sequence
<220> FEATURE:
<223> OTHER INFORMATION: caninized mouse antibody

<400> SEQUENCE: 95
gacatcgtga tgacccagac cccccctgagc ctgagcgtga gccccggcga gcccgccagc      60
atgagctgca agagcagcca gagcctgctg aacagcgtga accagaagaa ctacctggcc     120
tggtacagac agaagcccgg ccagagcccc caggtgctgg tgtacttcgc cagcaccaga     180
gtgagcggcg tgcccgacag attcatcggc agcggcagcg gcaccgactt caccctgaga     240
```

```
atcagcagag tggaggccga cgacctgggc gtgtactact gccagcagta cttcagcacc    300
cccctgacct tcggccaggg caccaagctg gagctgaaga gaaacgacgc ccagcccgcc    360
gtgtacctgt tccagcccag ccccgaccag ctgcacaccg gcagcgccag cgtggtgtgc    420
ctgctgaaca gcttctaccc caaggacatc aacgtgaagt ggaaggtgga cggcgtgatc    480
caggacaccg gcatccagga gagcgtgacc gagcaggaca gcaaggacag cacctacagc    540
ctgagcagca ccctgaccat gagcagcacc gagtacctga ccacgagct gtacagctgc    600 gagatcaccc acaagagcct gcccagcacc ctgatcaaga gcttccagag aagcgagtgc    660
cagagagtgg ac                                                       672
```

<210> SEQ ID NO 96
<211> LENGTH: 224
<212> TYPE: PRT
<213> ORGANISM: Artificial Sequence
<220> FEATURE:
<223> OTHER INFORMATION: caninized mouse antibody

<400> SEQUENCE: 96

```
Asp Ile Val Met Thr Gln Thr Pro Leu Ser Leu Ser Val Ser Pro Gly
1               5                   10                  15

Glu Pro Ala Ser Met Ser Cys Lys Ser Ser Gln Ser Leu Leu Asn Ser
            20                  25                  30

Val Asn Gln Lys Asn Tyr Leu Ala Trp Tyr Arg Gln Lys Pro Gly Gln
        35                  40                  45

Ser Pro Gln Val Leu Val Tyr Phe Ala Ser Thr Arg Val Ser Gly Val
    50                  55                  60

Pro Asp Arg Phe Ile Gly Ser Gly Ser Gly Thr Asp Phe Thr Leu Arg
65                  70                  75                  80

Ile Ser Arg Val Glu Ala Asp Asp Leu Gly Val Tyr Tyr Cys Gln Gln
                85                  90                  95

Tyr Phe Ser Thr Pro Leu Thr Phe Gly Gln Gly Thr Lys Leu Glu Leu
            100                 105                 110

Lys Arg Asn Asp Ala Gln Pro Ala Val Tyr Leu Phe Gln Pro Ser Pro
        115                 120                 125

Asp Gln Leu His Thr Gly Ser Ala Ser Val Val Cys Leu Leu Asn Ser
    130                 135                 140

Phe Tyr Pro Lys Asp Ile Asn Val Lys Trp Lys Val Asp Gly Val Ile
145                 150                 155                 160

Gln Asp Thr Gly Ile Gln Glu Ser Val Thr Glu Gln Asp Ser Lys Asp
                165                 170                 175

Ser Thr Tyr Ser Leu Ser Ser Thr Leu Thr Met Ser Ser Thr Glu Tyr
            180                 185                 190

Leu Ser His Glu Leu Tyr Ser Cys Glu Ile Thr His Lys Ser Leu Pro
        195                 200                 205

Ser Thr Leu Ile Lys Ser Phe Gln Arg Ser Glu Cys Gln Arg Val Asp
    210                 215                 220
```

<210> SEQ ID NO 97
<211> LENGTH: 1353
<212> TYPE: DNA
<213> ORGANISM: Artificial Sequence
<220> FEATURE:
<223> OTHER INFORMATION: caninized mouse antibody

<400> SEQUENCE: 97

```
gaggtgcagc tggtgcagag cgtggccgag ctggtgaagc ccggcgccag cgtgaaggtg      60
agctgcaccg tgagcggctt caacatcaag aacacctaca tgcactgggt gagacaggcc     120
cccggcaagg gcctgcagtg gatcggcaga atcgaccccg ccaacgtgaa caccaagtac     180
gcccccaagt tccagggcag agccaccatc accgccgaca ccagcaccaa caccgcctac     240
atgcagctga gcagcctgag agccgaggac accgccgtgt actactgcgc cagaatcttc     300
tacgactacg acggcgacat cgacgtgtgg ggccagggca ccctggtgac cgtgagcagc     360
gccagcacca ccgcccccag cgtgttcccc ctggccccca gctgcggcag caccagcggc     420
agcaccgtgg ccctggcctg cctggtgagc ggctacttcc ccgagcccgt gaccgtgagc     480
tggaacagcg gcagcctgac cagcggcgtg cacaccttcc ccgccgtgct gcagagcagc     540
ggcctgcaca cctgagcag catggtgacc gtgcccagca gcagatggcc cagcgagacc     600
ttcacctgca cgtggtgca ccccgccagc aacaccaagg tggacaagcc cgtgttcaac     660
gagtgcagat gcaccgacac ccccccctgc cccgtgcccg agcccctggg cggccccagc     720
gtgctgatct tccccccccaa gcccaaggac atcctgagaa tcaccagaac ccccgaggtg     780
acctgcgtgg tgctggacct gggcagagag gaccccgagg tgcagatcag ctggttcgtg     840
gacggcaagg aggtgcacac cgccaagacc cagagcagag agcagcagtt caacggcacc     900
tacagagtgg tgagcgtgct gcccatcgag caccaggact ggctgaccgg caaggagttc     960
aagtgcaagg tgaaccacat cgacctgccc agccccatcg agaaccatc agcaaggcc      1020
agaggcagag cccacaagcc cagcgtgtac gtgctgcccc ccagccccaa ggagctgagc     1080
agcagcgaca ccgtgagcat cacctgcctg atcaaggact cctacccccc cgacatcgac     1140
gtggagtggc agagcaacgg ccagcaggag cccgagagaa agcacagaat gaccccccccc    1200
cagctggacg aggacggcag ctacttcctg tacagcaagc tgagcgtgga caagagcaga     1260
tggcagcagg gcgacccctt cacctgcgcc gtgatgcacg agaccctgca gaaccactac     1320
accgacctga gcctgagcca cagccccggc aag                                  1353
```

<210> SEQ ID NO 98
<211> LENGTH: 451
<212> TYPE: PRT
<213> ORGANISM: Artificial Sequence
<220> FEATURE:
<223> OTHER INFORMATION: caninized mouse antibody

<400> SEQUENCE: 98

```
Glu Val Gln Leu Val Gln Ser Val Ala Glu Leu Val Lys Pro Gly Ala
1               5                   10                  15

Ser Val Lys Val Ser Cys Thr Val Ser Gly Phe Asn Ile Lys Asn Thr
            20                  25                  30

Tyr Met His Trp Val Arg Gln Ala Pro Gly Lys Gly Leu Gln Trp Ile
        35                  40                  45

Gly Arg Ile Asp Pro Ala Asn Val Asn Thr Lys Tyr Ala Pro Lys Phe
    50                  55                  60

Gln Gly Arg Ala Thr Ile Thr Ala Asp Thr Ser Thr Asn Thr Ala Tyr
65                  70                  75                  80

Met Gln Leu Ser Ser Leu Arg Ala Glu Asp Thr Ala Val Tyr Tyr Cys
                85                  90                  95

Ala Arg Ile Phe Tyr Asp Tyr Asp Gly Asp Ile Asp Val Trp Gly Gln
            100                 105                 110

Gly Thr Leu Val Thr Val Ser Ser Ala Ser Thr Thr Ala Pro Ser Val
        115                 120                 125
```

```
Phe Pro Leu Ala Pro Ser Cys Gly Ser Thr Ser Gly Ser Thr Val Ala
    130                 135                 140

Leu Ala Cys Leu Val Ser Gly Tyr Phe Pro Glu Pro Val Thr Val Ser
145                 150                 155                 160

Trp Asn Ser Gly Ser Leu Thr Ser Gly Val His Thr Phe Pro Ser Val
                165                 170                 175

Leu Gln Ser Ser Gly Leu His Ser Leu Ser Ser Met Val Thr Val Pro
            180                 185                 190

Ser Ser Arg Trp Pro Ser Glu Thr Phe Thr Cys Asn Val Val His Pro
        195                 200                 205

Ala Ser Asn Thr Lys Val Asp Lys Pro Val Phe Asn Glu Cys Arg Cys
210                 215                 220

Thr Asp Thr Pro Pro Cys Pro Val Pro Glu Pro Leu Gly Gly Pro Ser
225                 230                 235                 240

Val Leu Ile Phe Pro Pro Lys Pro Lys Asp Ile Leu Arg Ile Thr Arg
                245                 250                 255

Thr Pro Glu Val Thr Cys Val Val Leu Asp Leu Gly Arg Glu Asp Pro
            260                 265                 270

Glu Val Gln Ile Ser Trp Phe Val Asp Gly Lys Glu Val His Thr Ala
        275                 280                 285

Lys Thr Gln Ser Arg Glu Gln Gln Phe Asn Gly Thr Tyr Arg Val Val
290                 295                 300

Ser Val Leu Pro Ile Glu His Gln Asp Trp Leu Thr Gly Lys Glu Phe
305                 310                 315                 320

Lys Cys Arg Val Asn His Ile Asp Leu Pro Ser Pro Ile Glu Arg Thr
                325                 330                 335

Ile Ser Lys Ala Arg Gly Arg Ala His Lys Pro Ser Val Tyr Val Leu
            340                 345                 350

Pro Pro Ser Pro Lys Glu Leu Ser Ser Ser Asp Thr Val Ser Ile Thr
        355                 360                 365

Cys Leu Ile Lys Asp Phe Tyr Pro Pro Asp Ile Asp Val Glu Trp Gln
370                 375                 380

Ser Asn Gly Gln Gln Glu Pro Glu Arg Lys His Arg Met Thr Pro Pro
385                 390                 395                 400

Gln Leu Asp Glu Asp Gly Ser Tyr Phe Leu Tyr Ser Lys Leu Ser Val
                405                 410                 415

Asp Lys Ser Arg Trp Gln Gln Gly Asp Pro Phe Thr Cys Ala Val Met
            420                 425                 430

His Glu Thr Leu Gln Asn His Tyr Thr Asp Leu Ser Leu Ser His Ser
        435                 440                 445

Pro Gly Lys
    450

<210> SEQ ID NO 99
<211> LENGTH: 1353
<212> TYPE: DNA
<213> ORGANISM: Artificial Sequence
<220> FEATURE:
<223> OTHER INFORMATION: caninized mouse antibody

<400> SEQUENCE: 99
gaggtgcagc tggtgcagag cgtggccgag ctggtgaagc ccggcgccag cgtgaaggtg      60
agctgcaccg tgagcggctt caacatcaag aacacctaca tgcactgggt gagacaggcc     120
cccggcaagg gcctgcagtg gatcggcaga atcgaccccg ccaacgtgaa caccaagtac     180
```

```
gcccccaagt tccagggcag agccaccatc accgccgaca ccagcaccaa caccgcctac    240
atgcagctga gcagcctgag agccgaggac ccgccgtgt actactgcgc cagaatcttc     300
tacgactacg acggcgacat cgacgtgtgg ggccagggca ccctggtgac cgtgagcagc    360
gccagcacca ccgcccccag cgtgttcccc ctggccccca gctgcggcag caccagcggc    420
agcaccgtgg ccctggcctg cctggtgagc ggctacttcc ccgagcccgt gaccgtgagc    480
tggaacagcg gcagcctgac cagcggcgtg cacaccttcc ccagcgtgct gcagagcagc    540
ggcctgtaca gcctgagcag caccgtgacc gtgcccagca gcagatggcc cagcgagacc    600
ttcacctgca acgtggtgca ccccgccagc aacaccaagg tggacaagcc cgtgcccaag    660
gagagcacct gcaagtgcat cagcccctgc cccgtgcccg agagcctggg cggccccagc    720
gtgttcatct ccccccccaa gcccaaggac atcctgagaa tcaccagaac ccccgagatc    780
acctgcgtgg tgctggacct gggcagagag gaccccgagg tgcagatcag ctggttcgtg    840
gacggcaagg aggtgcacac cgccaagacc cagcccagag agcagcagtt caacagcacc    900
tacagagtgg tgagcgtgct gcccatcgag caccaggact ggctgaccgg caaggagttc    960
aagtgcaagg tgaaccacat cggcctgccc agccccatcg agagaaccat cagcaaggcc    1020
agaggccagg cccaccagcc cagcgtgtac gtgctgcccc ccagccccaa ggagctgagc    1080
agcagcgaca ccgtgaccct gacctgcctg atcaaggact cttccccccc cgagatcgac    1140
gtggagtggc agagcaacgg ccagcccgag cccgagagca agtaccacac caccgccccc    1200
cagctggacg aggacggcag ctacttcctg tacagcaagc tgagcgtgga caagagcaga    1260
tggcagcagg gcgacaccct cacctgcgcc gtgatgcacg aggccctgca gaaccactac    1320
accgacctga gcctgagcca cagccccggc aag                                1353
```

<210> SEQ ID NO 100
<211> LENGTH: 451
<212> TYPE: PRT
<213> ORGANISM: Artificial Sequence
<220> FEATURE:
<223> OTHER INFORMATION: caninized mouse antibody

<400> SEQUENCE: 100

```
Glu Val Gln Leu Val Gln Ser Val Ala Glu Leu Val Lys Pro Gly Ala
1               5                   10                  15

Ser Val Lys Val Ser Cys Thr Val Ser Gly Phe Asn Ile Lys Asn Thr
            20                  25                  30

Tyr Met His Trp Val Arg Gln Ala Pro Gly Lys Gly Leu Gln Trp Ile
        35                  40                  45

Gly Arg Ile Asp Pro Ala Asn Val Asn Thr Lys Tyr Ala Pro Lys Phe
    50                  55                  60

Gln Gly Arg Ala Thr Ile Thr Ala Asp Thr Ser Thr Asn Thr Ala Tyr
65                  70                  75                  80

Met Gln Leu Ser Ser Leu Arg Ala Glu Asp Thr Ala Val Tyr Tyr Cys
                85                  90                  95

Ala Arg Ile Phe Tyr Asp Tyr Asp Gly Asp Ile Asp Val Trp Gly Gln
            100                 105                 110

Gly Thr Leu Val Thr Val Ser Ser Ala Ser Thr Thr Ala Pro Ser Val
        115                 120                 125

Phe Pro Leu Ala Pro Ser Cys Gly Ser Thr Ser Gly Ser Thr Val Ala
    130                 135                 140

Leu Ala Cys Leu Val Ser Gly Tyr Phe Pro Glu Pro Val Thr Val Ser
```

```
                145                 150                 155                 160
Trp Asn Ser Gly Ser Leu Thr Ser Gly Val His Thr Phe Pro Ser Val
                    165                 170                 175
Leu Gln Ser Ser Gly Leu Tyr Ser Leu Ser Ser Thr Val Thr Val Pro
                    180                 185                 190
Ser Ser Arg Trp Pro Ser Glu Thr Phe Thr Cys Asn Val His Pro
                195                 200                 205
Ala Ser Asn Thr Lys Val Asp Lys Pro Val Pro Lys Glu Ser Thr Cys
    210                 215                 220
Lys Cys Ile Ser Pro Cys Pro Val Pro Glu Ser Leu Gly Gly Pro Ser
225                 230                 235                 240
Val Phe Ile Phe Pro Pro Lys Pro Lys Asp Ile Leu Arg Ile Thr Arg
                    245                 250                 255
Thr Pro Glu Ile Thr Cys Val Val Leu Asp Leu Gly Arg Glu Asp Pro
                    260                 265                 270
Glu Val Gln Ile Ser Trp Phe Val Asp Gly Lys Glu Val His Thr Ala
                275                 280                 285
Lys Thr Gln Pro Arg Glu Gln Gln Phe Asn Ser Thr Tyr Arg Val Val
    290                 295                 300
Ser Val Leu Pro Ile Glu His Gln Asp Trp Leu Thr Gly Lys Glu Phe
305                 310                 315                 320
Lys Cys Arg Val Asn His Ile Gly Leu Pro Ser Pro Ile Glu Arg Thr
                    325                 330                 335
Ile Ser Lys Ala Arg Gly Gln Ala His Gln Pro Ser Val Tyr Val Leu
                    340                 345                 350
Pro Pro Ser Pro Lys Glu Leu Ser Ser Ser Asp Thr Val Thr Leu Thr
                355                 360                 365
Cys Leu Ile Lys Asp Phe Phe Pro Pro Glu Ile Asp Val Glu Trp Gln
    370                 375                 380
Ser Asn Gly Gln Pro Glu Pro Glu Ser Lys Tyr His Thr Thr Ala Pro
385                 390                 395                 400
Gln Leu Asp Glu Asp Gly Ser Tyr Phe Leu Tyr Ser Lys Leu Ser Val
                    405                 410                 415
Asp Lys Ser Arg Trp Gln Gln Gly Asp Thr Phe Thr Cys Ala Val Met
                    420                 425                 430
His Glu Ala Leu Gln Asn His Tyr Thr Asp Leu Ser Leu Ser His Ser
                435                 440                 445
Pro Gly Lys
    450

<210> SEQ ID NO 101
<211> LENGTH: 654
<212> TYPE: DNA
<213> ORGANISM: Artificial Sequence
<220> FEATURE:
<223> OTHER INFORMATION: caninized mouse antibody

<400> SEQUENCE: 101
gacatcgtga tgacccagac cccccctgagc ctgagcgtga gcctgggcga gccgccagc      60 atcagctgcc acgccagcca gaacatcaac gtgtggctga ctggtacag acagaagccc     120 ggccagatcc cccagctgct gatctacaag gccagcaacc tgcacaccgg cgtgcccgac     180
agattcagcg gcagcggcag cggcaccgac ttcaccctga gaatcagcag agtggaggcc     240
gacgacgccg gcgtgtacta ctgccagcag ggccagagct accccctgac cttcggccag     300
```

```
ggcaccaagg tggagatcaa gagaaacgac gcccagcccg ccgtgtacct gttccagccc      360
agccccgacc agctgcacac cggcagcgcc agcgtggtgt gcctgctgaa cagcttctac      420
cccaaggaca tcaacgtgaa gtggaaggtg acggcgtga tccaggacac cggcatccag       480
gagagcgtga ccgagcagga cagcaaggac agcaccctaca gcctgagcag caccctgacc    540
atgagcagca ccgagtacct gagccacgag ctgtacagct gcgagatcac ccacaagagc     600
ctgcccagca ccctgatcaa gagcttccag agaagcgagt gccagagagt ggac            654
```

<210> SEQ ID NO 102
<211> LENGTH: 218
<212> TYPE: PRT
<213> ORGANISM: Artificial Sequence
<220> FEATURE:
<223> OTHER INFORMATION: caninized mouse antibody

<400> SEQUENCE: 102

```
Asp Ile Val Met Thr Gln Thr Pro Leu Ser Leu Ser Val Ser Leu Gly
1               5                   10                  15

Glu Pro Ala Ser Ile Ser Cys His Ala Ser Gln Asn Ile Asn Val Trp
            20                  25                  30

Leu Ser Trp Tyr Arg Gln Lys Pro Gly Gln Ile Pro Gln Leu Leu Ile
        35                  40                  45

Tyr Lys Ala Ser Asn Leu His Thr Gly Val Pro Asp Arg Phe Ser Gly
    50                  55                  60

Ser Gly Ser Gly Thr Asp Phe Thr Leu Arg Ile Ser Arg Val Glu Ala
65                  70                  75                  80

Asp Asp Ala Gly Val Tyr Tyr Cys Gln Gln Gly Gln Ser Tyr Pro Leu
                85                  90                  95

Thr Phe Gly Gln Gly Thr Lys Val Glu Ile Lys Arg Asn Asp Ala Gln
            100                 105                 110

Pro Ala Val Tyr Leu Phe Gln Pro Ser Pro Asp Gln Leu His Thr Gly
        115                 120                 125

Ser Ala Ser Val Val Cys Leu Leu Asn Ser Phe Tyr Pro Lys Asp Ile
    130                 135                 140

Asn Val Lys Trp Lys Val Asp Gly Val Ile Gln Asp Thr Gly Ile Gln
145                 150                 155                 160

Glu Ser Val Thr Glu Gln Asp Ser Lys Asp Ser Thr Tyr Ser Leu Ser
                165                 170                 175

Ser Thr Leu Thr Met Ser Ser Thr Glu Tyr Leu Ser His Glu Leu Tyr
            180                 185                 190

Ser Cys Glu Ile Thr His Lys Ser Leu Pro Ser Thr Leu Ile Lys Ser
        195                 200                 205

Phe Gln Arg Ser Glu Cys Gln Arg Val Asp
    210                 215
```

<210> SEQ ID NO 103
<211> LENGTH: 1338
<212> TYPE: DNA
<213> ORGANISM: Artificial Sequence
<220> FEATURE:
<223> OTHER INFORMATION: caninized mouse antibody

<400> SEQUENCE: 103

```
gaggtgcagc tggtgcagag cggcgccgag gtgaagaagc ccggcgccag cgtgaaggtg      60
agctgcaagg ccagcggcta caccttcacc acctacggca tgagctgggt gagacaggcc     120
cccggcaagg gcctgcagtg gatgggctgg atcaacatct acagcggcat gcccacctac     180
```

```
gccgacgact tcaagggcag attcgccctg agcctggaca ccagcaccag caccgcctac    240
atggagctga acagcctgag agccgaggac accgccgtgt actactgcac cagattcgac    300
ggccccgact actggggcca gggcaccctg gtgaccgtga gcagcgccag caccaccgcc    360
cccagcgtgt tcccccctgg ccccagcctg ggcagcacca cggcagcac cgtggccctg    420 gcctgcctgg tgagcggcta cttccccgag cccgtgaccg tgagctggaa cagcggcagc    480
ctgaccagcg gcgtgcacac cttccccagc gtgctgcaga gcagcggcct gcacagcctg    540
agcagcatgg tgaccgtgcc cagcagcaga tggcccagcg agaccttcac ctgcaacgtg    600
gtgcaccccg ccagcaacac caaggtggac aagcccgtgt caacgagtg cagatgcacc    660 gacacccccc cctgccccgt gcccgagccc ctgggcggcc cagcgtgct gatcttcccc    720 cccaagccca aggacatcct gagaatcacc agaaccccg aggtgacctg cgtggtgctg    780
gacctgggca gagaggaccc cgaggtgcag atcagctggt tcgtggacgg caaggaggtg    840
cacaccgcca agacccagag cagagagcag cagttcaacg gcacctacag agtggtgagc    900
gtgctgccca tcgagcacca ggactggctg accggcaagg agttcaagtg cagagtgaac    960
cacatcgacc tgcccagccc catcgagaga accatcagca aggccagagg cagagcccac   1020
aagcccagcg tgtacgtgct gccccccagc cccaaggagc tgagcagcag cgacaccgtg   1080
agcatcacct gcctgatcaa ggacttctac cccccgaca tcgacgtgga gtggcagagc   1140
aacggccagc aggagcccga gagaaagcac agaatgaccc ccccccagct ggacgaggac   1200
ggcagctact cctgtacag caagctgagc gtggacaaga gcagatggca gcagggcgac   1260
cccttcacct gcgccgtgat gcacgagacc ctgcagaacc actacaccga cctgagcctg   1320
agccacagcc ccggcaag                                                  1338
```

<210> SEQ ID NO 104
<211> LENGTH: 446
<212> TYPE: PRT
<213> ORGANISM: Artificial Sequence
<220> FEATURE:
<223> OTHER INFORMATION: caninized mouse antibody

<400> SEQUENCE: 104

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Gly Met Ser Trp Val Arg Gln Ala Pro Gly Lys Gly Leu Gln Trp Met
        35                  40                  45

Gly Trp Ile Asn Ile Tyr Ser Gly Met Pro Thr Tyr Ala Asp Asp Phe
    50                  55                  60

Lys Gly Arg Phe Ala Leu Ser Leu Asp Thr Ser Thr Ser Thr Ala Tyr
65                  70                  75                  80

Met Glu Leu Asn Ser Leu Arg Ala Glu Asp Thr Ala Val Tyr Tyr Cys
                85                  90                  95

Thr Arg Phe Asp Gly Pro Asp Tyr Trp Gly Gln Gly Thr Leu Val Thr
            100                 105                 110

Val Ser Ser Ala Ser Thr Thr Ala Pro Ser Val Phe Pro Leu Ala Pro
        115                 120                 125

Ser Cys Gly Ser Thr Ser Gly Ser Thr Val Ala Leu Ala Cys Leu Val
    130                 135                 140

Ser Gly Tyr Phe Pro Glu Pro Val Thr Val Ser Trp Asn Ser Gly Ser
```

```
                    145                 150                 155                 160
Leu Thr Ser Gly Val His Thr Phe Pro Ser Val Leu Gln Ser Ser Gly
                165                 170                 175
Leu His Ser Leu Ser Ser Met Val Thr Val Pro Ser Ser Arg Trp Pro
                180                 185                 190
Ser Glu Thr Phe Thr Cys Asn Val Val His Pro Ala Ser Asn Thr Lys
                195                 200                 205
Val Asp Lys Pro Val Phe Asn Glu Cys Arg Cys Thr Asp Thr Pro Pro
            210                 215                 220
Cys Pro Val Pro Glu Pro Leu Gly Gly Pro Ser Val Leu Ile Phe Pro
225                 230                 235                 240
Pro Lys Pro Lys Asp Ile Leu Arg Ile Thr Arg Thr Pro Glu Val Thr
                245                 250                 255
Cys Val Val Leu Asp Leu Gly Arg Glu Asp Pro Glu Val Gln Ile Ser
                260                 265                 270
Trp Phe Val Asp Gly Lys Glu Val His Thr Ala Lys Thr Gln Ser Arg
                275                 280                 285
Glu Gln Gln Phe Asn Gly Thr Tyr Arg Val Val Ser Val Leu Pro Ile
            290                 295                 300
Glu His Gln Asp Trp Leu Thr Gly Lys Glu Phe Lys Cys Arg Val Asn
305                 310                 315                 320
His Ile Asp Leu Pro Ser Pro Ile Glu Arg Thr Ile Ser Lys Ala Arg
                325                 330                 335
Gly Arg Ala His Lys Pro Ser Val Tyr Val Leu Pro Pro Ser Pro Lys
                340                 345                 350
Glu Leu Ser Ser Ser Asp Thr Val Ser Ile Thr Cys Leu Ile Lys Asp
                355                 360                 365
Phe Tyr Pro Pro Asp Ile Asp Val Glu Trp Gln Ser Asn Gly Gln Gln
            370                 375                 380
Glu Pro Glu Arg Lys His Arg Met Thr Pro Pro Gln Leu Asp Glu Asp
385                 390                 395                 400
Gly Ser Tyr Phe Leu Tyr Ser Lys Leu Ser Val Asp Lys Ser Arg Trp
                405                 410                 415
Gln Gln Gly Asp Pro Phe Thr Cys Ala Val Met His Glu Thr Leu Gln
                420                 425                 430
Asn His Tyr Thr Asp Leu Ser Leu Ser His Ser Pro Gly Lys
                435                 440                 445
```

<210> SEQ ID NO 105
<211> LENGTH: 1338
<212> TYPE: DNA
<213> ORGANISM: Artificial Sequence
<220> FEATURE:
<223> OTHER INFORMATION: caninized mouse antibody

<400> SEQUENCE: 105

```
gaggtgcagc tggtgcagag cggcgccgag gtgaagaagc ccggcgccag cgtgaaggtg      60
agctgcaagg ccagcggcta caccttcacc acctacggca tgagctgggt gagacaggcc     120
cccggcaagg gcctgcagtg gatgggctgg atcaacatct acagcggcat gcccacctac     180
gccgacgact tcaagggcag attcgccctg agcctggaca ccagcaccag caccgcctac     240
atggagctga acagcctgag agccgaggac accgccgtgt actactgcac cagattcgac     300
ggccccgact actggggcca gggcaccctg gtgaccgtga gcagcgccag caccaccgcc     360
cccagcgtgt tcccctggc cccagctgc ggcagcacca gcggcagcac cgtggccctg     420
```

```
gcctgcctgg tgagcggcta cttccccgag cccgtgaccg tgagctggaa cagcggcagc    480
ctgaccagcg gcgtgcacac cttccccagc gtgctgcaga gcagcggcct gtacagcctg    540
agcagcaccg tgaccgtgcc cagcagcaga tggcccagcg agaccttcac ctgcaacgtg    600
gtgcaccccg ccagcaacac caaggtggac aagcccgtgc ccaaggagag cacctgcaag    660
tgcatcagcc cctgccccgt gcccgagagc ctgggcggcc ccagcgtgtt catcttcccc    720
cccaagccca aggacatcct gagaatcacc agaaccccg  agatcacctg cgtggtgctg    780
gacctgggca gagaggaccc cgaggtgcag atcagctggt tcgtggacgg caaggaggtg    840
cacaccgcca gacccagcc cagagagcag cagttcaaca gcacctacag agtggtgagc    900
gtgctgccca tcgagcacca ggactggctg accggcaagg agttcaagtg cagagtgaac    960
cacatcggcc tgcccagccc catcgagaga accatcagca aggccagagg ccaggcccac   1020
cagcccagcg tgtacgtgct gccccccagc cccaaggagc tgagcagcag cgacaccgtg   1080
accctgacct gcctgatcaa ggacttcttc ccccccgaga tcgacgtgga gtggcagagc   1140
aacggccagc ccgagcccga gagcaagtac cacaccaccg ccccccagct ggacgaggac   1200
ggcagctact cctgtacag  caagctgagc gtggacaaga gcagatggca gcagggcgac   1260
accttcacct gcgccgtgat gcacgaggcc ctgcagaacc actacaccga cctgagcctg   1320
agccacagcc ccggcaag                                                 1338
```

<210> SEQ ID NO 106
<211> LENGTH: 446
<212> TYPE: PRT
<213> ORGANISM: Artificial Sequence
<220> FEATURE:
<223> OTHER INFORMATION: caninized mouse antibody

<400> SEQUENCE: 106

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Gly Met Ser Trp Val Arg Gln Ala Pro Gly Lys Gly Leu Gln Trp Met
        35                  40                  45

Gly Trp Ile Asn Ile Tyr Ser Gly Met Pro Thr Tyr Ala Asp Asp Phe
    50                  55                  60

Lys Gly Arg Phe Ala Leu Ser Leu Asp Thr Ser Thr Ser Thr Ala Tyr
65                  70                  75                  80

Met Glu Leu Asn Ser Leu Arg Ala Glu Asp Thr Ala Val Tyr Tyr Cys
                85                  90                  95

Thr Arg Phe Asp Gly Pro Asp Tyr Trp Gly Gln Gly Thr Leu Val Thr
            100                 105                 110

Val Ser Ser Ala Ser Thr Thr Ala Pro Ser Val Phe Pro Leu Ala Pro
        115                 120                 125

Ser Cys Gly Ser Thr Ser Gly Ser Thr Val Ala Leu Ala Cys Leu Val
    130                 135                 140

Ser Gly Tyr Phe Pro Glu Pro Val Thr Val Ser Trp Asn Ser Gly Ser
145                 150                 155                 160

Leu Thr Ser Gly Val His Thr Phe Pro Ser Val Leu Gln Ser Ser Gly
                165                 170                 175

Leu Tyr Ser Leu Ser Ser Thr Val Thr Val Pro Ser Ser Arg Trp Pro
            180                 185                 190
```

```
Ser Glu Thr Phe Thr Cys Asn Val Val His Pro Ala Ser Asn Thr Lys
            195                 200                 205

Val Asp Lys Pro Val Pro Lys Glu Ser Thr Cys Lys Cys Ile Ser Pro
210                 215                 220

Cys Pro Val Pro Glu Ser Leu Gly Gly Pro Ser Val Phe Ile Phe Pro
225                 230                 235                 240

Pro Lys Pro Lys Asp Ile Leu Arg Ile Thr Arg Thr Pro Glu Ile Thr
                245                 250                 255

Cys Val Val Leu Asp Leu Gly Arg Glu Asp Pro Glu Val Gln Ile Ser
            260                 265                 270

Trp Phe Val Asp Gly Lys Glu Val His Thr Ala Lys Thr Gln Pro Arg
        275                 280                 285

Glu Gln Gln Phe Asn Ser Thr Tyr Arg Val Val Ser Val Leu Pro Ile
    290                 295                 300

Glu His Gln Asp Trp Leu Thr Gly Lys Glu Phe Lys Cys Arg Val Asn
305                 310                 315                 320

His Ile Gly Leu Pro Ser Pro Ile Glu Arg Thr Ile Ser Lys Ala Arg
                325                 330                 335

Gly Gln Ala His Gln Pro Ser Val Tyr Val Leu Pro Pro Ser Pro Lys
            340                 345                 350

Glu Leu Ser Ser Ser Asp Thr Val Thr Leu Thr Cys Leu Ile Lys Asp
        355                 360                 365

Phe Phe Pro Pro Glu Ile Asp Val Glu Trp Gln Ser Asn Gly Gln Pro
    370                 375                 380

Glu Pro Glu Ser Lys Tyr His Thr Thr Ala Pro Gln Leu Asp Glu Asp
385                 390                 395                 400

Gly Ser Tyr Phe Leu Tyr Ser Lys Leu Ser Val Asp Lys Ser Arg Trp
                405                 410                 415

Gln Gln Gly Asp Thr Phe Thr Cys Ala Val Met His Glu Ala Leu Gln
            420                 425                 430

Asn His Tyr Thr Asp Leu Ser Leu Ser His Ser Pro Gly Lys
        435                 440                 445

<210> SEQ ID NO 107
<211> LENGTH: 672
<212> TYPE: DNA
<213> ORGANISM: Artificial Sequence
<220> FEATURE:
<223> OTHER INFORMATION: caninized mouse antibody

<400> SEQUENCE: 107
gacatcgtga tgacccagac cccctgagc ctgagcgtga gccccggcga gcccgccagc      60
atgagctgca agagcagcca gagcctgctg aacagcgtga accagaagaa ctacctggcc     120
tggtacagac agaagcccgg ccagagcccc caggtgctgg tgtacttcgc cagcaccaga     180
atcagcggcg tgcccgacag attcatcggc agcggcagcg gcaccgactt cacccctgaga    240 atcagcagag tggaggccga cgacctgggc gtgtactact gccagcagta cttcagcacc     300
cccctgacct tcggccaggg caccaagctg gagctgaaga gaaacgacgc ccagcccgcc     360
gtgtacctgt tccagcccag ccccgaccag ctgcacaccg gcagcgccag cgtggtgtgc     420
ctgctgaaca gcttctaccc caaggacatc aacgtgaagt ggaaggtgga cggcgtgatc     480
caggacaccg gcatccagga gagcgtgacc gagcaggaca gcaaggacag cacctacagc     540
ctgagcagca ccctgaccat gagcagcacc gagtacctga ccacgagct gtacagctgc     600 gagatcaccc acaagagcct gcccagcacc ctgatcaaga gcttccagag aagcgagtgc     660
```
cagagagtgg ac                                                    672

<210> SEQ ID NO 108
<211> LENGTH: 224
<212> TYPE: PRT
<213> ORGANISM: Artificial Sequence
<220> FEATURE:
<223> OTHER INFORMATION: caninized mouse antibody

<400> SEQUENCE: 108

```
Asp Ile Val Met Thr Gln Thr Pro Leu Ser Leu Ser Val Ser Pro Gly
1               5                   10                  15

Glu Pro Ala Ser Met Ser Cys Lys Ser Ser Gln Ser Leu Leu Asn Ser
            20                  25                  30

Val Asn Gln Lys Asn Tyr Leu Ala Trp Tyr Arg Gln Lys Pro Gly Gln
        35                  40                  45

Ser Pro Gln Val Leu Val Tyr Phe Ala Ser Thr Arg Ile Ser Gly Val
    50                  55                  60

Pro Asp Arg Phe Ile Gly Ser Gly Ser Gly Thr Asp Phe Thr Leu Arg
65                  70                  75                  80

Ile Ser Arg Val Glu Ala Asp Asp Leu Gly Val Tyr Tyr Cys Gln Gln
                85                  90                  95

Tyr Phe Ser Thr Pro Leu Thr Phe Gly Gln Gly Thr Lys Leu Glu Leu
            100                 105                 110

Lys Arg Asn Asp Ala Gln Pro Ala Val Tyr Leu Phe Gln Pro Ser Pro
        115                 120                 125

Asp Gln Leu His Thr Gly Ser Ala Ser Val Val Cys Leu Leu Asn Ser
    130                 135                 140

Phe Tyr Pro Lys Asp Ile Asn Val Lys Trp Lys Val Asp Gly Val Ile
145                 150                 155                 160

Gln Asp Thr Gly Ile Gln Glu Ser Val Thr Glu Gln Asp Ser Lys Asp
                165                 170                 175

Ser Thr Tyr Ser Leu Ser Ser Thr Leu Thr Met Ser Ser Thr Glu Tyr
            180                 185                 190

Leu Ser His Glu Leu Tyr Ser Cys Glu Ile Thr His Lys Ser Leu Pro
        195                 200                 205

Ser Thr Leu Ile Lys Ser Phe Gln Arg Ser Glu Cys Gln Arg Val Asp
    210                 215                 220
```

<210> SEQ ID NO 109
<211> LENGTH: 17
<212> TYPE: PRT
<213> ORGANISM: Canis familiaris

<400> SEQUENCE: 109

```
Phe Asn Glu Cys Arg Cys Thr Asp Thr Pro Cys Pro Val Pro Glu
1               5                   10                  15

Pro
```

<210> SEQ ID NO 110
<211> LENGTH: 22
<212> TYPE: PRT
<213> ORGANISM: Canis familiaris

<400> SEQUENCE: 110

```
Pro Lys Arg Glu Asn Gly Arg Val Pro Arg Pro Pro Asp Cys Pro Lys
1               5                   10                  15
```

Cys Pro Ala Pro Glu Met
            20

<210> SEQ ID NO 111
<211> LENGTH: 20
<212> TYPE: PRT
<213> ORGANISM: Canis familiaris

<400> SEQUENCE: 111

Ala Lys Glu Cys Glu Cys Lys Cys Asn Cys Asn Asn Cys Pro Cys Pro
1               5                   10                  15

Gly Cys Gly Leu
            20

<210> SEQ ID NO 112
<211> LENGTH: 17
<212> TYPE: PRT
<213> ORGANISM: Artificial Sequence
<220> FEATURE:
<223> OTHER INFORMATION: modified canine

<400> SEQUENCE: 112

Pro Lys Glu Ser Thr Cys Lys Cys Ile Pro Pro Cys Pro Val Pro Glu
1               5                   10                  15

Ser

<210> SEQ ID NO 113
<211> LENGTH: 795
<212> TYPE: DNA
<213> ORGANISM: Canis familiaris

<400> SEQUENCE: 113
ctagactccc ctgacaggcc ctggagcccg ctcaccttct ccccggcgca gctcacggtg      60
caggagggag agaacgccac gttcacctgc agcctggccg acatccccga cagcttcgtg     120
ctcaactggt accgcctgag cccccgcaac cagacggaca agctggccgc cttccaggag     180
gaccgcatcg agccgggccg ggacaggcgc ttccgcgtca tgcggctgcc caacgggcgg     240
gacttccaca tgagcatcgt cgctgcgcgc ctcaacgaca gcggcatcta cctgtgcggg     300
gccatctacc tgcccccaa cacacagatc aacgagagtc cccgcgcaga gctctccgtg      360
acggagagaa ccctggagcc cccacacag agccccagcc cccacccag actcagcggc       420 cagttgcagg ggctggtcat cggcgtcacg agcgtgctgg tgggtgtcct gctactgctg     480
ctgctgacct gggtcctggc cgctgtcttc cccaggcca cccgaggtgc ctgtgtgtgc      540
gggagcgagg acgagcctct gaaggagggc cccgatgcag cgcccgtctt cacccctggac    600 tacggggagc tggacttcca gtggcgagag aagacgccgg agcccccggc gcctgtgcc     660 ccggagcaga ccgagtatgc caccatcgtc ttcccgggca ggcggcgtc cccgggccgc      720 agggcctcgg ccagcagcct gcagggagcc cagcctccga gccccgagga cggacccggc     780
ctgtggcccc tctga                                                      795

<210> SEQ ID NO 114
<211> LENGTH: 264
<212> TYPE: PRT
<213> ORGANISM: Canis familiaris

<400> SEQUENCE: 114

Leu Asp Ser Pro Asp Arg Pro Trp Ser Pro Leu Thr Phe Ser Pro Ala
1               5                   10                  15

Gln Leu Thr Val Gln Glu Gly Glu Asn Ala Thr Phe Thr Cys Ser Leu
            20                  25                  30

Ala Asp Ile Pro Asp Ser Phe Val Leu Asn Trp Tyr Arg Leu Ser Pro
        35                  40                  45

Arg Asn Gln Thr Asp Lys Leu Ala Ala Phe Gln Glu Asp Arg Ile Glu
    50                  55                  60

Pro Gly Arg Asp Arg Arg Phe Arg Val Met Arg Leu Pro Asn Gly Arg
65                  70                  75                  80

Asp Phe His Met Ser Ile Val Ala Ala Arg Leu Asn Asp Ser Gly Ile
                85                  90                  95

Tyr Leu Cys Gly Ala Ile Tyr Leu Pro Pro Asn Thr Gln Ile Asn Glu
            100                 105                 110

Ser Pro Arg Ala Glu Leu Ser Val Thr Glu Arg Thr Leu Glu Pro Pro
        115                 120                 125

Thr Gln Ser Pro Ser Pro Pro Arg Leu Ser Gly Gln Leu Gln Gly
    130                 135                 140

Leu Val Ile Gly Val Thr Ser Val Leu Val Gly Val Leu Leu Leu
145                 150                 155                 160

Leu Leu Thr Trp Val Leu Ala Ala Val Phe Pro Arg Ala Thr Arg Gly
            165                 170                 175

Ala Cys Val Cys Gly Ser Glu Asp Glu Pro Leu Lys Glu Gly Pro Asp
        180                 185                 190

Ala Ala Pro Val Phe Thr Leu Asp Tyr Gly Glu Leu Asp Phe Gln Trp
    195                 200                 205

Arg Glu Lys Thr Pro Glu Pro Pro Ala Pro Cys Ala Pro Glu Gln Thr
210                 215                 220

Glu Tyr Ala Thr Ile Val Phe Pro Gly Arg Pro Ala Ser Pro Gly Arg
225                 230                 235                 240

Arg Ala Ser Ala Ser Ser Leu Gln Gly Ala Gln Pro Pro Ser Pro Glu
            245                 250                 255

Asp Gly Pro Gly Leu Trp Pro Leu
            260

<210> SEQ ID NO 115
<211> LENGTH: 438
<212> TYPE: DNA
<213> ORGANISM: Canis familiaris

<400> SEQUENCE: 115
ctggattccc ccgacagacc ctggagccct ctcaccttct ccctgccca gctgaccgtc      60 caggaaggcg agaatgccac cttcacctgc agcctcgccg acatccccga cagcttcgtg     120
ctgaactggt acagactgag ccccaggaac cagaccgaca gctggccgc tttccaggag     180 gacaggatcg aacccggcag ggacaggagg tttagggtca tgaggctgcc caacggcagg     240
gacttccaca tgtccatcgt ggccgccaga ctgaacgact ccggcatcta cctgtgcggc     300
gctatctacc tgccccccaa cacccagatc aacgagagcc caggccga actgagcgtg      360 acagagagaa ccctggaacc tcccacccag agcccttccc ctcctcctag actgagcgga     420
cagctgcagg gcctggtg                                                   438

<210> SEQ ID NO 116
<211> LENGTH: 146
<212> TYPE: PRT
<213> ORGANISM: Canis familiaris

<400> SEQUENCE: 116

```
Leu Asp Ser Pro Asp Arg Pro Trp Ser Pro Leu Thr Phe Ser Pro Ala
1               5                   10                  15

Gln Leu Thr Val Gln Glu Gly Glu Asn Ala Thr Phe Thr Cys Ser Leu
            20                  25                  30

Ala Asp Ile Pro Asp Ser Phe Val Leu Asn Trp Tyr Arg Leu Ser Pro
        35                  40                  45

Arg Asn Gln Thr Asp Lys Leu Ala Ala Phe Gln Glu Asp Arg Ile Glu
    50                  55                  60

Pro Gly Arg Asp Arg Arg Phe Arg Val Met Arg Leu Pro Asn Gly Arg
65                  70                  75                  80

Asp Phe His Met Ser Ile Val Ala Ala Arg Leu Asn Asp Ser Gly Ile
                85                  90                  95

Tyr Leu Cys Gly Ala Ile Tyr Leu Pro Pro Asn Thr Gln Ile Asn Glu
            100                 105                 110

Ser Pro Arg Ala Glu Leu Ser Val Thr Glu Arg Thr Leu Glu Pro Pro
        115                 120                 125

Thr Gln Ser Pro Ser Pro Pro Arg Leu Ser Gly Gln Leu Gln Gly
    130                 135                 140

Leu Val
145

<210> SEQ ID NO 117
<211> LENGTH: 1128
<212> TYPE: DNA
<213> ORGANISM: Artificial Sequence
<220> FEATURE:
<223> OTHER INFORMATION: canine and human sequence

<400> SEQUENCE: 117
ctggattccc ccgacagacc ctggagccct ctcaccttct ccctgccca gctgaccgtc      60 caggaaggcg agaatgccac cttcacctgc agcctcgccg acatccccga cagcttcgtg     120
ctgaactggt acagactgag ccccaggaac cagaccgaca gctggccgc tttccaggag      180 gacaggatcg aacccggcag ggacaggagg tttagggtca tgaggctgcc aacggcagg      240 gacttccaca tgtccatcgt ggccgccaga ctgaacgact ccggcatcta cctgtgcggc     300
gctatctacc tgcccccaa cacccagatc aacgagagcc caggccga actgagcgtg       360 acagagagaa ccctggaacc tcccacccag agccccttccc ctcctcctag actgagcgga    420
cagctgcagg gcctggtggg taccgacaaa actcacacat gcccaccgtg cccagcacct    480
gaactcctgg ggggaccgtc agtcttcctc ttccccccaa aacccaagga caccctcatg    540
atctcccgga cccctgaggt cacatgcgtg gtggtggacg tgagccacga agaccctgag    600
gtcaagttca actggtacgt ggacggcgtg gaggtgcata atgccaagac aaagccgcgg    660
gaggagcagt acaacagcac gtaccgtgtg gtcagcgtcc tcaccgtcct gcaccaggac    720
tggctgaatg gcaaggagta caagtgcaag gtctccaaca aagccctccc agcccccatc    780
gagaaaacca tctccaaagc caagggcag ccccgagaac acaggtgta caccctgccc     840 ccatcccggg atgagctgac caagaaccag gtcagcctga cctgcctggt caaaggcttc    900
tatcccagcg acatcgccgt ggagtgggag agcaatgggc agccggagaa caactacaag    960
accacgcctc ccgtgctgga ctccgacggc tccttcttcc tctacagcaa gctcaccgtg   1020
gacaagagca ggtggcagca ggggaacgtc ttctcatgct ccgtgatgca tgaggctctg   1080
cacaaccact acacgcagaa gagcctctcc ctgtctccgg gtaaatga              1128
```

<210> SEQ ID NO 118
<211> LENGTH: 375
<212> TYPE: PRT
<213> ORGANISM: Artificial Sequence
<220> FEATURE:
<223> OTHER INFORMATION: canine and human sequence

<400> SEQUENCE: 118

```
Leu Asp Ser Pro Asp Arg Pro Trp Ser Pro Leu Thr Phe Ser Pro Ala
1               5                   10                  15
Gln Leu Thr Val Gln Glu Gly Glu Asn Ala Thr Phe Thr Cys Ser Leu
            20                  25                  30
Ala Asp Ile Pro Asp Ser Phe Val Leu Asn Trp Tyr Arg Leu Ser Pro
        35                  40                  45
Arg Asn Gln Thr Asp Lys Leu Ala Ala Phe Gln Glu Asp Arg Ile Glu
    50                  55                  60
Pro Gly Arg Asp Arg Arg Phe Arg Val Met Arg Leu Pro Asn Gly Arg
65                  70                  75                  80
Asp Phe His Met Ser Ile Val Ala Ala Arg Leu Asn Asp Ser Gly Ile
                85                  90                  95
Tyr Leu Cys Gly Ala Ile Tyr Leu Pro Pro Asn Thr Gln Ile Asn Glu
            100                 105                 110
Ser Pro Arg Ala Glu Leu Ser Val Thr Glu Arg Thr Leu Glu Pro Pro
        115                 120                 125
Thr Gln Ser Pro Ser Pro Pro Arg Leu Ser Gly Gln Leu Gln Gly
    130                 135                 140
Leu Val Gly Thr Asp Lys Thr His Thr Cys Pro Pro Cys Pro Ala Pro
145                 150                 155                 160
Glu Leu Leu Gly Gly Pro Ser Val Phe Leu Phe Pro Pro Lys Pro Lys
                165                 170                 175
Asp Thr Leu Met Ile Ser Arg Thr Pro Glu Val Thr Cys Val Val Val
            180                 185                 190
Asp Val Ser His Glu Asp Pro Glu Val Lys Phe Asn Trp Tyr Val Asp
        195                 200                 205
Gly Val Glu Val His Asn Ala Lys Thr Lys Pro Arg Glu Glu Gln Tyr
    210                 215                 220
Asn Ser Thr Tyr Arg Val Val Ser Val Leu Thr Val Leu His Gln Asp
225                 230                 235                 240
Trp Leu Asn Gly Lys Glu Tyr Lys Cys Lys Val Ser Asn Lys Ala Leu
                245                 250                 255
Pro Ala Pro Ile Glu Lys Thr Ile Ser Lys Ala Lys Gly Gln Pro Arg
            260                 265                 270
Glu Pro Gln Val Tyr Thr Leu Pro Pro Ser Arg Asp Glu Leu Thr Lys
        275                 280                 285
Asn Gln Val Ser Leu Thr Cys Leu Val Lys Gly Phe Tyr Pro Ser Asp
    290                 295                 300
Ile Ala Val Glu Trp Glu Ser Asn Gly Gln Pro Glu Asn Asn Tyr Lys
305                 310                 315                 320
Thr Thr Pro Pro Val Leu Asp Ser Asp Gly Ser Phe Phe Leu Tyr Ser
                325                 330                 335
Lys Leu Thr Val Asp Lys Ser Arg Trp Gln Gln Gly Asn Val Phe Ser
            340                 345                 350
Cys Ser Val Met His Glu Ala Leu His Asn His Tyr Thr Gln Lys Ser
        355                 360                 365
```

Leu Ser Leu Ser Pro Gly Lys
    370             375

<210> SEQ ID NO 119
<211> LENGTH: 816
<212> TYPE: DNA
<213> ORGANISM: Canis familiaris

<400> SEQUENCE: 119

| | | | | | |
|---|---|---|---|---|---|
| tttacgatca | cagtttctaa | ggacctgtat | gtggtagagt | atggtggcaa | tgtgacaatg | 60 |
| gaatgcaaat | tcccggtgga | aaaacagtta | aacttgtttg | cactaatcgt | ctactgggaa | 120 |
| atggaggata | aaaaaattat | acaatttgtg | aatggaaagg | aagacctgaa | agttcagcac | 180 |
| agcagctaca | gccagagggc | tcagctattg | aaggaccagc | tcttcttggg | gaaggctgcg | 240 |
| cttcagatca | cagatgtgag | attgcaggat | gcagggggttt | actgctgctt | gatcggctat | 300 |
| ggcggtgctg | actacaagcg | gattactttg | aaagttcatg | ccccgtaccg | caacatcagc | 360 |
| caaagaattt | ctgtggatcc | tgtcacctct | gaacatgaac | taatgtgtca | ggctgagggt | 420 |
| taccctgagg | ctgaagtcat | ctggacaagc | agtgaccacc | gagtcctgag | tggcaaaacc | 480 |
| accatcacta | attccaatag | ggaagagaag | cttttcaatg | tgaccagcac | gctgaacatc | 540 |
| aatgcaacag | ctaatgagat | tttctactgc | acttttcaaa | gatcaggtcc | tgaggaaaac | 600 |
| aatactgccg | agttggtcat | cccagaacga | ctgcccgttc | cagcaagtga | gaggactcat | 660 |
| ttcatgattc | tgggacctttt | cctgttgctt | cttggtgtag | tcctggcagt | cactttctgt | 720 |
| ctaaaaaaac | atgggagaat | gatggatgtg | gaaaaatgtt | gcacccgaga | taggaactca | 780 |
| aagaaacgaa | atgatataca | atttgaagag | acataa | | | 816 |

<210> SEQ ID NO 120
<211> LENGTH: 271
<212> TYPE: PRT
<213> ORGANISM: Canis familiaris

<400> SEQUENCE: 120

Phe Thr Ile Thr Val Ser Lys Asp Leu Tyr Val Val Glu Tyr Gly Gly
1               5                   10                  15

Asn Val Thr Met Glu Cys Lys Phe Pro Val Glu Lys Gln Leu Asn Leu
            20                  25                  30

Phe Ala Leu Ile Val Tyr Trp Glu Met Glu Asp Lys Lys Ile Ile Gln
        35                  40                  45

Phe Val Asn Gly Lys Glu Asp Leu Lys Val Gln His Ser Ser Tyr Ser
    50                  55                  60

Gln Arg Ala Gln Leu Leu Lys Asp Gln Leu Phe Leu Gly Lys Ala Ala
65                  70                  75                  80

Leu Gln Ile Thr Asp Val Arg Leu Gln Asp Ala Gly Val Tyr Cys Cys
                85                  90                  95

Leu Ile Gly Tyr Gly Gly Ala Asp Tyr Lys Arg Ile Thr Leu Lys Val
            100                 105                 110

His Ala Pro Tyr Arg Asn Ile Ser Gln Arg Ile Ser Val Asp Pro Val
        115                 120                 125

Thr Ser Glu His Glu Leu Met Cys Gln Ala Glu Gly Tyr Pro Glu Ala
    130                 135                 140

Glu Val Ile Trp Thr Ser Ser Asp His Arg Val Leu Ser Gly Lys Thr
145                 150                 155                 160

Thr Ile Thr Asn Ser Asn Arg Glu Glu Lys Leu Phe Asn Val Thr Ser
                165                 170                 175

Thr Leu Asn Ile Asn Ala Thr Ala Asn Glu Ile Phe Tyr Cys Thr Phe
            180                 185                 190

Gln Arg Ser Gly Pro Glu Glu Asn Thr Ala Glu Leu Val Ile Pro
        195                 200                 205

Glu Arg Leu Pro Val Pro Ala Ser Glu Arg Thr His Phe Met Ile Leu
210                 215                 220

Gly Pro Phe Leu Leu Leu Gly Val Val Leu Ala Val Thr Phe Cys
225                 230                 235                 240

Leu Lys Lys His Gly Arg Met Met Asp Val Glu Lys Cys Cys Thr Arg
                245                 250                 255

Asp Arg Asn Ser Lys Lys Arg Asn Asp Ile Gln Phe Glu Glu Thr
            260                 265                 270

<210> SEQ ID NO 121
<211> LENGTH: 660
<212> TYPE: DNA
<213> ORGANISM: Canis familiaris

<400> SEQUENCE: 121
tttaccatca ccgtgtccaa ggacctgtac gtggtcgagt acggcggcaa tgtgaccatg      60
gagtgcaagt tccccgtgga gaagcagctg aacctgttcg ccctcatcgt gtactgggag     120
atggaggaca gaagatcat ccagttcgtg aacggcaagg aggacctgaa ggtgcagcac      180
tccagctact cccagagagc ccagctgctg aaggaccagc tgttcctggg caaggccgcc     240
ctgcagatca ccgacgtgag actgcaggac gccggcgtgt attgctgcct gatcggctac     300
ggaggcgccg actacaagag gatcaccctg aaggtgcatg caccctacag gaacatcagc     360
cagaggatca gcgtcgatcc cgtgaccagc gagcacgagc tgatgtgcca agccgagggc     420
tatcccgagg ccgaagtgat ctggaccagc agcgaccaca gggtcctgag cggcaagacc     480
accatcacca cagcaacag ggaggagaag ctgttcaacg tgaccagcac cctcaacatc      540
aacgccaccg ccaacgagat cttctactgc accttccaga ggagcggccc cgaagagaac     600
aacaccgccg agctggtgat ccccgagaga ctgcctgtgc ctgccagcga gaggacccac     660

<210> SEQ ID NO 122
<211> LENGTH: 220
<212> TYPE: PRT
<213> ORGANISM: Canis familiaris

<400> SEQUENCE: 122

Phe Thr Ile Thr Val Ser Lys Asp Leu Tyr Val Val Glu Tyr Gly Gly
1               5                   10                  15

Asn Val Thr Met Glu Cys Lys Phe Pro Val Glu Lys Gln Leu Asn Leu
            20                  25                  30

Phe Ala Leu Ile Val Tyr Trp Glu Met Glu Asp Lys Lys Ile Ile Gln
        35                  40                  45

Phe Val Asn Gly Lys Glu Asp Leu Lys Val Gln His Ser Ser Tyr Ser
    50                  55                  60

Gln Arg Ala Gln Leu Leu Lys Asp Gln Leu Phe Leu Gly Lys Ala Ala
65                  70                  75                  80

Leu Gln Ile Thr Asp Val Arg Leu Gln Asp Ala Gly Val Tyr Cys Cys
                85                  90                  95

Leu Ile Gly Tyr Gly Gly Ala Asp Tyr Lys Arg Ile Thr Leu Lys Val
            100                 105                 110

His Ala Pro Tyr Arg Asn Ile Ser Gln Arg Ile Ser Val Asp Pro Val

```
            115                 120                 125
Thr Ser Glu His Glu Leu Met Cys Gln Ala Glu Gly Tyr Pro Glu Ala
    130                 135                 140

Glu Val Ile Trp Thr Ser Asp His Arg Val Leu Ser Gly Lys Thr
145                 150                 155                 160

Thr Ile Thr Asn Ser Asn Arg Glu Glu Lys Leu Phe Asn Val Thr Ser
                165                 170                 175

Thr Leu Asn Ile Asn Ala Thr Ala Asn Glu Ile Phe Tyr Cys Thr Phe
            180                 185                 190

Gln Arg Ser Gly Pro Glu Glu Asn Asn Thr Ala Glu Leu Val Ile Pro
        195                 200                 205

Glu Arg Leu Pro Val Pro Ala Ser Glu Arg Thr His
210                 215                 220
```

<210> SEQ ID NO 123
<211> LENGTH: 1350
<212> TYPE: DNA
<213> ORGANISM: Canis familiaris

<400> SEQUENCE: 123

```
tttaccatca ccgtgtccaa ggacctgtac gtggtcgagt acggcggcaa tgtgaccatg    60
gagtgcaagt tccccgtgga gaagcagctg aacctgttcg ccctcatcgt gactgggag    120
atggaggaca gaagatcat ccagttcgtg aacggcaagg aggacctgaa ggtgcagcac    180
tccagctact cccagagagc ccagctgctg aaggaccagc tgttcctggg caaggccgcc    240
ctgcagatca ccgacgtgag actgcaggac gccggcgtgt attgctgcct gatcggctac    300
ggaggcgccg actacaagag gatcaccctg aaggtgcatg caccctacag aacatcagc    360
cagaggatca gcgtcgatcc cgtgaccagc gagcacgagc tgatgtgcca gccgagggc    420
tatcccgagg ccgaagtgat ctggaccagc agcgaccaca gggtcctgag cggcaagacc    480
accatcacca cagcaacag ggaggagaag ctgttcaacg tgaccagcac cctcaacatc    540
aacgccaccg ccaacgagat cttctactgc accttccaga ggagcggccc cgaagagaac    600
aacaccgccg agctggtgat ccccgagaga ctgcctgtgc ctgccagcga gaggacccac    660
ggtaccgaca aaactcacac atgcccaccg tgcccagcac ctgaactcct ggggggaccg    720
tcagtcttcc tcttcccccc aaaacccaag gacaccctca tgatctcccg gacccctgag    780
gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccgtg tggtcagcgt cctcaccgtc ctgcaccagg actggctgaa tggcaaggag    960
tacaagtgca aggtctccaa caaagccctc ccagccccca tcgagaaaac catctccaaa    1020
gccaaagggc agccccgaga accacaggtg tacaccctgc ccccatcccg ggatgagctg    1080
accaagaacc aggtcagcct gacctgcctg gtcaaaggct tctatcccag cgacatcgcc    1140
gtggagtggg agagcaatgg gcagccggag aacaactaca agaccacgcc tcccgtgctg    1200
gactccgacg gctccttctt cctctacagc aagctcaccg tggacaagag caggtggcag    1260
caggggaacg tcttctcatg ctccgtgatg catgaggctc tgcacaacca ctacacgcag    1320
aagagcctct ccctgtctcc gggtaaatga                                    1350
```

<210> SEQ ID NO 124
<211> LENGTH: 449
<212> TYPE: PRT
<213> ORGANISM: Canis familiaris

<400> SEQUENCE: 124

```
Phe Thr Ile Thr Val Ser Lys Asp Leu Tyr Val Val Glu Tyr Gly Gly
1               5                   10                  15

Asn Val Thr Met Glu Cys Lys Phe Pro Val Glu Lys Gln Leu Asn Leu
            20                  25                  30

Phe Ala Leu Ile Val Tyr Trp Glu Met Glu Asp Lys Lys Ile Ile Gln
        35                  40                  45

Phe Val Asn Gly Lys Glu Asp Leu Lys Val Gln His Ser Ser Tyr Ser
    50                  55                  60

Gln Arg Ala Gln Leu Leu Lys Asp Gln Leu Phe Leu Gly Lys Ala Ala
65                  70                  75                  80

Leu Gln Ile Thr Asp Val Arg Leu Gln Asp Ala Gly Val Tyr Cys Cys
                85                  90                  95

Leu Ile Gly Tyr Gly Gly Ala Asp Tyr Lys Arg Ile Thr Leu Lys Val
            100                 105                 110

His Ala Pro Tyr Arg Asn Ile Ser Gln Arg Ile Ser Val Asp Pro Val
        115                 120                 125

Thr Ser Glu His Glu Leu Met Cys Gln Ala Glu Gly Tyr Pro Glu Ala
    130                 135                 140

Glu Val Ile Trp Thr Ser Ser Asp His Arg Val Leu Ser Gly Lys Thr
145                 150                 155                 160

Thr Ile Thr Asn Ser Asn Arg Glu Glu Lys Leu Phe Asn Val Thr Ser
                165                 170                 175

Thr Leu Asn Ile Asn Ala Thr Ala Asn Glu Ile Phe Tyr Cys Thr Phe
            180                 185                 190

Gln Arg Ser Gly Pro Glu Glu Asn Asn Thr Ala Glu Leu Val Ile Pro
        195                 200                 205

Glu Arg Leu Pro Val Pro Ala Ser Glu Arg Thr His Gly Thr Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
```

```
                405                 410                 415
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 125
<211> LENGTH: 648
<212> TYPE: DNA
<213> ORGANISM: Canis familiaris

<400> SEQUENCE: 125
ctgggcggcc ccagcgtgct gatcttcccc cccaagccca aggacatcct gagaatcacc      60 agaaccccccg aggtgacctg cgtggtgctg gacctgggca gagaggaccc cgaggtgcag    120
atcagctggt tcgtggacgg caaggaggtg cacaccgcca agacccagag cagagagcag    180
cagttcaacg gcacctacag agtggtgagc gtgctgccca tcgagcacca ggactggctg    240
accggcaagg agttcaagtg cagagtgaac cacatcgacc tgcccagccc catcgagaga    300
accatcagca aggccagagg cagagcccac aagcccagcg tgtacgtgct gcccccccagc    360 cccaaggagc tgagcagcag cgacaccgtg agcatcacct gcctgatcaa ggacttctac    420 cccccccgaca tcgacgtgga gtggcagagc aacggccagc aggagcccga gagaaagcac    480
agaatgaccc cccccccagct ggacgaggac ggcagctact cctgtacag caagctgagc    540 gtggacaaga gcagatggca gcagggcgac cccttcacct gcgccgtgat gcacgagacc    600
ctgcagaacc actacaccga cctgagcctg agccacagcc ccggcaag              648

<210> SEQ ID NO 126
<211> LENGTH: 216
<212> TYPE: PRT
<213> ORGANISM: Canis familiaris

<400> SEQUENCE: 126

Leu Gly Gly Pro Ser Val Leu Ile Phe Pro Pro Lys Pro Lys Asp Ile
1               5                   10                  15

Leu Arg Ile Thr Arg Thr Pro Glu Val Thr Cys Val Val Leu Asp Leu
            20                  25                  30

Gly Arg Glu Asp Pro Glu Val Gln Ile Ser Trp Phe Val Asp Gly Lys
        35                  40                  45

Glu Val His Thr Ala Lys Thr Gln Ser Arg Glu Gln Gln Phe Asn Gly
    50                  55                  60

Thr Tyr Arg Val Val Ser Val Leu Pro Ile Glu His Gln Asp Trp Leu
65                  70                  75                  80

Thr Gly Lys Glu Phe Lys Cys Arg Val Asn His Ile Asp Leu Pro Ser
                85                  90                  95

Pro Ile Glu Arg Thr Ile Ser Lys Ala Arg Gly Arg Ala His Lys Pro
            100                 105                 110

Ser Val Tyr Val Leu Pro Pro Ser Pro Lys Glu Leu Ser Ser Ser Asp
        115                 120                 125

Thr Val Ser Ile Thr Cys Leu Ile Lys Asp Phe Tyr Pro Pro Asp Ile
    130                 135                 140

Asp Val Glu Trp Gln Ser Asn Gly Gln Gln Glu Pro Glu Arg Lys His
145                 150                 155                 160

Arg Met Thr Pro Pro Gln Leu Asp Glu Asp Gly Ser Tyr Phe Leu Tyr
```

165                 170                 175
Ser Lys Leu Ser Val Asp Lys Ser Arg Trp Gln Gln Gly Asp Pro Phe
            180                 185                 190

Thr Cys Ala Val Met His Glu Thr Leu Gln Asn His Tyr Thr Asp Leu
            195                 200                 205

Ser Leu Ser His Ser Pro Gly Lys
    210                 215

<210> SEQ ID NO 127
<211> LENGTH: 648
<212> TYPE: DNA
<213> ORGANISM: Canis familiaris

<400> SEQUENCE: 127
ctgggcggcc ccagcgtgtt catcttcccc cccaagccca aggacatcct gagaatcacc    60 agaaccccg agatcacctg cgtggtgctg gacctgggca gagaggaccc cgaggtgcag   120
atcagctggt tcgtggacgg caaggaggtg cacaccgcca agacccagcc cagagagcag   180
cagttcaaca gcacctacag agtggtgagc gtgctgccca tcgagcacca ggactggctg   240
accggcaagg agttcaagtg cagagtgaac cacatcggcc tgcccagccc catcgagaga   300
accatcagca aggccagagg ccaggcccac cagcccagcg tgtacgtgct gcccccagc   360 cccaaggagc tgagcagcag cgacaccgtg accctgacct gcctgatcaa ggacttcttc   420
ccccccgaga tcgacgtgga gtggcagagc aacggccagc ccgagcccga gagcaagtac   480
cacaccaccg ccccccagct ggacgaggac ggcagctact cctgtacag caagctgagc   540 gtggacaaga gcagatggca gcagggcgac accttcacct gcgccgtgat gcacgaggcc   600
ctgcagaacc actacaccga cctgagcctg agccacagcc ccggcaag              648

<210> SEQ ID NO 128
<211> LENGTH: 216
<212> TYPE: PRT
<213> ORGANISM: Canis familiaris

<400> SEQUENCE: 128

Leu Gly Gly Pro Ser Val Phe Ile Phe Pro Pro Lys Pro Lys Asp Ile
1               5                   10                  15

Leu Arg Ile Thr Arg Thr Pro Glu Ile Thr Cys Val Val Leu Asp Leu
            20                  25                  30

Gly Arg Glu Asp Pro Glu Val Gln Ile Ser Trp Phe Val Asp Gly Lys
        35                  40                  45

Glu Val His Thr Ala Lys Thr Gln Pro Arg Glu Gln Gln Phe Asn Ser
    50                  55                  60

Thr Tyr Arg Val Val Ser Val Leu Pro Ile Glu His Gln Asp Trp Leu
65                  70                  75                  80

Thr Gly Lys Glu Phe Lys Cys Arg Val Asn His Ile Gly Leu Pro Ser
                85                  90                  95

Pro Ile Glu Arg Thr Ile Ser Lys Ala Arg Gly Gln Ala His Gln Pro
            100                 105                 110

Ser Val Tyr Val Leu Pro Pro Ser Pro Lys Glu Leu Ser Ser Ser Asp
        115                 120                 125

Thr Val Thr Leu Thr Cys Leu Ile Lys Asp Phe Phe Pro Pro Glu Ile
    130                 135                 140

Asp Val Glu Trp Gln Ser Asn Gly Gln Pro Glu Pro Glu Ser Lys Tyr
145                 150                 155                 160

His Thr Thr Ala Pro Gln Leu Asp Glu Asp Gly Ser Tyr Phe Leu Tyr
            165                 170                 175

Ser Lys Leu Ser Val Asp Lys Ser Arg Trp Gln Gln Gly Asp Thr Phe
        180                 185                 190

Thr Cys Ala Val Met His Glu Ala Leu Gln Asn His Tyr Thr Asp Leu
    195                 200                 205

Ser Leu Ser His Ser Pro Gly Lys
    210                 215

<210> SEQ ID NO 129
<211> LENGTH: 645
<212> TYPE: DNA
<213> ORGANISM: Canis familiaris

<400> SEQUENCE: 129
ctgggcggcc ccagcgtgtt catcttcccc cccaagccca aggacaccct gctgatcgcc      60 agaaccccg aggtgacctg cgtggtggtg gacctggacc ccgaggaccc cgaggtgcag     120
atcagctggt tcgtggacgg caagcagatg cagaccgcca agacccagcc cagagaggag     180
cagttcaacg gcacctacag agtggtgagc gtgctgccca tcggccacca ggactggctg     240
aagggcaagc agttcacctg caaggtgaac aacaaggccc tgcccagccc catcgagaga     300
accatcagca aggccagagg ccaggcccac cagcccagcg tgtacgtgct gccccccagc     360
agagaggagc tgagcaagaa caccgtgagc ctgacctgcc tgatcaagga cttcttcccc     420
cccgacatcg acgtggagtg gcagagcaac ggccagcagg agcccgagag caagtacaga     480 accaccccccc cccagctgga cgaggacggc agctacttcc tgtacagcaa gctgagcgtg     540
gacaagagca gatggcagag aggcgacacc ttcatctgcg ccgtgatgca cgaggccctg     600
cacaaccact acacccagga gagcctgagc cacagccccg gcaag                    645

<210> SEQ ID NO 130
<211> LENGTH: 215
<212> TYPE: PRT
<213> ORGANISM: Canis familiaris

<400> SEQUENCE: 130

Leu Gly Gly Pro Ser Val Phe Ile Phe Pro Pro Lys Pro Lys Asp Thr
1               5                   10                  15

Leu Leu Ile Ala Arg Thr Pro Glu Val Thr Cys Val Val Val Asp Leu
            20                  25                  30

Asp Pro Glu Asp Pro Glu Val Gln Ile Ser Trp Phe Val Asp Gly Lys
        35                  40                  45

Gln Met Gln Thr Ala Lys Thr Gln Pro Arg Glu Glu Gln Phe Asn Gly
    50                  55                  60

Thr Tyr Arg Val Val Ser Val Leu Pro Ile Gly His Gln Asp Trp Leu
65                  70                  75                  80

Lys Gly Lys Gln Phe Thr Cys Lys Val Asn Asn Lys Ala Leu Pro Ser
                85                  90                  95

Pro Ile Glu Arg Thr Ile Ser Lys Ala Arg Gly Gln Ala His Gln Pro
            100                 105                 110

Ser Val Tyr Val Leu Pro Pro Ser Arg Glu Glu Leu Ser Lys Asn Thr
        115                 120                 125

Val Ser Leu Thr Cys Leu Ile Lys Asp Phe Phe Pro Pro Asp Ile Asp
    130                 135                 140

Val Glu Trp Gln Ser Asn Gly Gln Gln Glu Pro Glu Ser Lys Tyr Arg
145                 150                 155                 160

```
Thr Thr Pro Pro Gln Leu Asp Glu Asp Gly Ser Tyr Phe Leu Tyr Ser
            165                 170                 175

Lys Leu Ser Val Asp Lys Ser Arg Trp Gln Arg Gly Asp Thr Phe Ile
        180                 185                 190

Cys Ala Val Met His Glu Ala Leu His Asn His Tyr Thr Gln Glu Ser
        195                 200                 205

Leu Ser His Ser Pro Gly Lys
    210                 215

<210> SEQ ID NO 131
<211> LENGTH: 645
<212> TYPE: DNA
<213> ORGANISM: Canis familiaris

<400> SEQUENCE: 131
ctgggcggcc ccagcgtgtt catcttcccc cccaagccca aggacatcct ggtgaccgcc      60
agaaccccca ccgtgacctg cgtggtggtg gacctggacc ccgagaaccc cgaggtgcag     120
atcagctggt tcgtggacag caagcaggtg cagaccgcca acacccagcc cagagaggag     180
cagagcaacg gcacctacag agtggtgagc gtgctgccca tcggccacca ggactggctg     240
agcggcaagc agttcaagtg caaggtgaac aacaaggccc tgcccagccc catcgaggag     300
atcatcagca gaccccccgg ccaggcccac cagcccaacg tgtacgtgct gccccccagc     360
agagacgaga tgagcaagaa caccgtgacc ctgacctgcc tggtgaagga cttcttcccc     420
cccgagatcg acgtggagtg gcagagcaac ggccagcagg agcccgagag caagtacaga     480
atgacccccc ccagctgga cgaggacggc agctacttcc tgtacagcaa gctgagcgtg     540
gacaagagca gatggcagag aggcgacacc ttcatctgcg ccgtgatgca cgaggccctg     600
cacaaccact acacccagat cagcctgagc cacagccccg gcaag                    645

<210> SEQ ID NO 132
<211> LENGTH: 215
<212> TYPE: PRT
<213> ORGANISM: Canis familiaris

<400> SEQUENCE: 132

Leu Gly Gly Pro Ser Val Phe Ile Phe Pro Pro Lys Pro Lys Asp Ile
1               5                   10                  15

Leu Val Thr Ala Arg Thr Pro Thr Val Thr Cys Val Val Val Asp Leu
            20                  25                  30

Asp Pro Glu Asn Pro Glu Val Gln Ile Ser Trp Phe Val Asp Ser Lys
        35                  40                  45

Gln Val Gln Thr Ala Asn Thr Gln Pro Arg Glu Glu Gln Ser Asn Gly
    50                  55                  60

Thr Tyr Arg Val Val Ser Val Leu Pro Ile Gly His Gln Asp Trp Leu
65                  70                  75                  80

Ser Gly Lys Gln Phe Lys Cys Lys Val Asn Asn Lys Ala Leu Pro Ser
                85                  90                  95

Pro Ile Glu Glu Ile Ile Ser Lys Thr Pro Gly Gln Ala His Gln Pro
            100                 105                 110

Asn Val Tyr Val Leu Pro Pro Ser Arg Asp Glu Met Ser Lys Asn Thr
        115                 120                 125

Val Thr Leu Thr Cys Leu Val Lys Asp Phe Phe Pro Pro Glu Ile Asp
    130                 135                 140

Val Glu Trp Gln Ser Asn Gly Gln Gln Glu Pro Glu Ser Lys Tyr Arg
```

```
               145                 150                 155                 160
Met Thr Pro Pro Gln Leu Asp Glu Asp Gly Ser Tyr Phe Leu Tyr Ser
                    165                 170                 175

Lys Leu Ser Val Asp Lys Ser Arg Trp Gln Arg Gly Asp Thr Phe Ile
                180                 185                 190

Cys Ala Val Met His Glu Ala Leu His Asn His Tyr Thr Gln Ile Ser
                195                 200                 205

Leu Ser His Ser Pro Gly Lys
                210                 215

<210> SEQ ID NO 133
<211> LENGTH: 867
<212> TYPE: DNA
<213> ORGANISM: Canis familiaris

<400> SEQUENCE: 133
atggggagcc ggcgggggcc ctggccgctc gtctgggccg tgctgcagct gggctggtgg      60
ccaggatggc tcctagactc ccctgacagg ccctggagcc cgctcacctt ctccccggcg     120
cagctcacgg tgcaggaggg agagaacgcc acgttcacct gcagcctggc cgacatcccc     180
gacagcttcg tgctcaactg gtaccgcctg agcccccgca accagacgga caagctggcc     240
gccttccagg aggaccgcat cgagccgggc cgggacaggc gcttccgcgt catgcggctg     300
cccaacgggc gggacttcca catgagcatc gtcgctgcgc cctcaacga cagcggcatc      360 tacctgtgcg ggccatcta cctgccccc aacacacaga tcaacgagag tccccgcgca      420
gagctctccg tgacggagag aaccctggag cccccacac agagcccag cccccaccc       480 agactcagcg gccagttgca ggggctggtc atcggcgtca cgagcgtgct ggtgggtgtc     540
ctgctactgc tgctgctgac ctgggtcctg gccgctgtct tccccagggc cacccgaggt    600
gcctgtgtgt gcgggagcga ggacgagcct ctgaaggagg ccccgatgc agcgcccgtc     660 ttcaccctgg actacgggga gctggacttc agtggcgag agaagacgcc ggagcccccg    720
gcgccctgtg ccccggagca gaccgagtat gccaccatcg tcttcccggg caggccggcg     780
tccccgggcc gcagggcctc ggccagcagc ctgcagggag cccagcctcc gagccccgag    840
gacggacccg gcctgtggcc cctctga                                        867

<210> SEQ ID NO 134
<211> LENGTH: 288
<212> TYPE: PRT
<213> ORGANISM: Canis familiaris

<400> SEQUENCE: 134

Met Gly Ser Arg Arg Gly Pro Trp Pro Leu Val Trp Ala Val Leu Gln
1               5                   10                  15

Leu Gly Trp Trp Pro Gly Trp Leu Leu Asp Ser Pro Asp Arg Pro Trp
                20                  25                  30

Ser Pro Leu Thr Phe Ser Pro Ala Gln Leu Thr Val Gln Glu Gly Glu
            35                  40                  45

Asn Ala Thr Phe Thr Cys Ser Leu Ala Asp Ile Pro Asp Ser Phe Val
        50                  55                  60

Leu Asn Trp Tyr Arg Leu Ser Pro Arg Asn Gln Thr Asp Lys Leu Ala
65                  70                  75                  80

Ala Phe Gln Glu Asp Arg Ile Glu Pro Gly Arg Asp Arg Arg Phe Arg
                85                  90                  95

Val Met Arg Leu Pro Asn Gly Arg Asp Phe His Met Ser Ile Val Ala
```

```
                100             105                110
Ala Arg Leu Asn Asp Ser Gly Ile Tyr Leu Cys Gly Ala Ile Tyr Leu
            115                 120             125

Pro Pro Asn Thr Gln Ile Asn Glu Ser Pro Arg Ala Glu Leu Ser Val
        130                 135             140

Thr Glu Arg Thr Leu Glu Pro Pro Thr Gln Ser Pro Ser Pro Pro Pro
145                 150             155                 160

Arg Leu Ser Gly Gln Leu Gln Gly Leu Val Ile Gly Val Thr Ser Val
                165             170             175

Leu Val Gly Val Leu Leu Leu Leu Leu Thr Trp Val Leu Ala Ala
            180             185                 190

Val Phe Pro Arg Ala Thr Arg Gly Ala Cys Val Cys Gly Ser Glu Asp
        195             200             205

Glu Pro Leu Lys Glu Gly Pro Asp Ala Ala Pro Val Phe Thr Leu Asp
        210             215             220

Tyr Gly Glu Leu Asp Phe Gln Trp Arg Glu Lys Thr Pro Glu Pro Pro
225             230             235                 240

Ala Pro Cys Ala Pro Glu Gln Thr Glu Tyr Ala Thr Ile Val Phe Pro
            245             250                 255

Gly Arg Pro Ala Ser Pro Gly Arg Arg Ala Ser Ala Ser Ser Leu Gln
            260             265             270

Gly Ala Gln Pro Pro Ser Pro Glu Asp Gly Pro Gly Leu Trp Pro Leu
            275             280             285
```

<210> SEQ ID NO 135
<211> LENGTH: 870
<212> TYPE: DNA
<213> ORGANISM: Canis familiaris

<400> SEQUENCE: 135

```
atgagaatgt ttagtgtctt tacattcatg gcctactgcc atttgctaaa agcatttacg      60
atcacagttt ctaaggacct gtatgtggta gagtatggtg caatgtgac aatggaatgc     120
aaattcccgg tggaaaaaca gttaaacttg tttgcactaa tcgtctactg ggaaatggag    180
gataaaaaaa ttatacaatt tgtgaatgga aaggaagacc tgaaagttca gcacagcagc    240
tacagccaga gggctcagct attgaaggac cagctcttct tggggaaggc tgcgcttcag    300
atcacagatg tgagattgca ggatgcaggg gtttactgct gcttgatcgg ctatggcggt    360
gctgactaca gcggattac tttgaaagtt catgccccgt accgcaacat cagccaaaga    420
atttctgtgg atcctgtcac ctctgaacat gaactaatgt gtcaggctga gggttaccct    480
gaggctgaag tcatctggac aagcagtgac caccgagtcc tgagtggcaa aaccaccatc    540
actaattcca atagggaaga aagcttttc aatgtgacca gcacgctgaa catcaatgca    600
acagctaatg agattttcta ctgcactttt caaagatcag gtcctgagga aacaatact    660
gccgagttgg tcatcccaga acgactgccc gttccagcaa gtgagaggac tcatttcatg    720
attctgggac ctttcctgtt gcttcttggt gtagtcctgg cagtcacttt ctgtctaaaa    780
aaacatggga gaatgatgga tgtggaaaaa tgttgcaccc gagataggaa ctcaaagaaa    840
cgaaatgata tacaatttga agagacataa                                    870
```

<210> SEQ ID NO 136
<211> LENGTH: 289
<212> TYPE: PRT
<213> ORGANISM: Canis familiaris

<400> SEQUENCE: 136

```
Met Arg Met Phe Ser Val Phe Thr Phe Met Ala Tyr Cys His Leu Leu
1               5                   10                  15

Lys Ala Phe Thr Ile Thr Val Ser Lys Asp Leu Tyr Val Val Glu Tyr
            20                  25                  30

Gly Gly Asn Val Thr Met Glu Cys Lys Phe Pro Val Glu Lys Gln Leu
        35                  40                  45

Asn Leu Phe Ala Leu Ile Val Tyr Trp Glu Met Glu Asp Lys Lys Ile
    50                  55                  60

Ile Gln Phe Val Asn Gly Lys Glu Asp Leu Lys Val Gln His Ser Ser
65                  70                  75                  80

Tyr Ser Gln Arg Ala Gln Leu Leu Lys Asp Gln Leu Phe Leu Gly Lys
                85                  90                  95

Ala Ala Leu Gln Ile Thr Asp Val Arg Leu Gln Asp Ala Gly Val Tyr
            100                 105                 110

Cys Cys Leu Ile Gly Tyr Gly Gly Ala Asp Tyr Lys Arg Ile Thr Leu
        115                 120                 125

Lys Val His Ala Pro Tyr Arg Asn Ile Ser Gln Arg Ile Ser Val Asp
    130                 135                 140

Pro Val Thr Ser Glu His Glu Leu Met Cys Gln Ala Glu Gly Tyr Pro
145                 150                 155                 160

Glu Ala Glu Val Ile Trp Thr Ser Ser Asp His Arg Val Leu Ser Gly
                165                 170                 175

Lys Thr Thr Ile Thr Asn Ser Asn Arg Glu Glu Lys Leu Phe Asn Val
            180                 185                 190

Thr Ser Thr Leu Asn Ile Asn Ala Thr Ala Asn Glu Ile Phe Tyr Cys
        195                 200                 205

Thr Phe Gln Arg Ser Gly Pro Glu Glu Asn Asn Thr Ala Glu Leu Val
    210                 215                 220

Ile Pro Glu Arg Leu Pro Val Pro Ala Ser Glu Arg Thr His Phe Met
225                 230                 235                 240

Ile Leu Gly Pro Phe Leu Leu Leu Gly Val Val Leu Ala Val Thr
                245                 250                 255

Phe Cys Leu Lys Lys His Gly Arg Met Met Asp Val Glu Lys Cys Cys
            260                 265                 270

Thr Arg Asp Arg Asn Ser Lys Lys Arg Asn Asp Ile Gln Phe Glu Glu
        275                 280                 285

Thr
```

<210> SEQ ID NO 137
<211> LENGTH: 401
<212> TYPE: PRT
<213> ORGANISM: Canis familiaris

<400> SEQUENCE: 137

```
Met Asn Phe Leu Leu Ser Trp Val His Trp Ser Leu Ala Leu Leu Leu
1               5                   10                  15

Tyr Leu His His Ala Lys Trp Ser Gln Ala Leu Asp Ser Pro Asp Arg
            20                  25                  30

Pro Trp Ser Pro Leu Thr Phe Ser Pro Ala Gln Leu Thr Val Gln Glu
        35                  40                  45

Gly Glu Asn Ala Thr Phe Thr Cys Ser Leu Ala Asp Ile Pro Asp Ser
    50                  55                  60

Phe Val Leu Asn Trp Tyr Arg Leu Ser Pro Arg Asn Gln Thr Asp Lys
```

```
            65                  70                  75                  80
Leu Ala Ala Phe Gln Glu Asp Arg Ile Glu Pro Gly Arg Asp Arg Arg
                85                  90                  95

Phe Arg Val Met Arg Leu Pro Asn Gly Arg Asp Phe His Met Ser Ile
            100                 105                 110

Val Ala Ala Arg Leu Asn Asp Ser Gly Ile Tyr Leu Cys Gly Ala Ile
            115                 120                 125

Tyr Leu Pro Pro Asn Thr Gln Ile Asn Glu Ser Pro Arg Ala Glu Leu
        130                 135                 140

Ser Val Thr Glu Arg Thr Leu Glu Pro Pro Thr Gln Ser Pro Ser Pro
145                 150                 155                 160

Pro Pro Arg Leu Ser Gly Gln Leu Gln Gly Leu Val Gly Thr Asp Lys
                165                 170                 175

Thr His Thr Cys Pro Pro Cys Pro Ala Pro Glu Leu Leu Gly Gly Pro
            180                 185                 190

Ser Val Phe Leu Phe Pro Pro Lys Pro Lys Asp Thr Leu Met Ile Ser
        195                 200                 205

Arg Thr Pro Glu Val Thr Cys Val Val Val Asp Val Ser His Glu Asp
210                 215                 220

Pro Glu Val Lys Phe Asn Trp Tyr Val Asp Gly Val Glu Val His Asn
225                 230                 235                 240

Ala Lys Thr Lys Pro Arg Glu Glu Gln Tyr Asn Ser Thr Tyr Arg Val
                245                 250                 255

Val Ser Val Leu Thr Val Leu His Gln Asp Trp Leu Asn Gly Lys Glu
            260                 265                 270

Tyr Lys Cys Lys Val Ser Asn Lys Ala Leu Pro Ala Pro Ile Glu Lys
        275                 280                 285

Thr Ile Ser Lys Ala Lys Gly Gln Pro Arg Glu Pro Gln Val Tyr Thr
        290                 295                 300

Leu Pro Pro Ser Arg Asp Glu Leu Thr Lys Asn Gln Val Ser Leu Thr
305                 310                 315                 320

Cys Leu Val Lys Gly Phe Tyr Pro Ser Asp Ile Ala Val Glu Trp Glu
                325                 330                 335

Ser Asn Gly Gln Pro Glu Asn Asn Tyr Lys Thr Thr Pro Pro Val Leu
            340                 345                 350

Asp Ser Asp Gly Ser Phe Phe Leu Tyr Ser Lys Leu Thr Val Asp Lys
        355                 360                 365

Ser Arg Trp Gln Gln Gly Asn Val Phe Ser Cys Ser Val Met His Glu
    370                 375                 380

Ala Leu His Asn His Tyr Thr Gln Lys Ser Leu Ser Leu Ser Pro Gly
385                 390                 395                 400

Lys

<210> SEQ ID NO 138
<211> LENGTH: 15
<212> TYPE: PRT
<213> ORGANISM: Canis familiaris
<220> FEATURE:
<221> NAME/KEY: misc_feature
<222> LOCATION: (9)..(9)
<223> OTHER INFORMATION: Xaa can be Met or Thr

<400> SEQUENCE: 138

Gly Arg Asp Arg Arg Phe Arg Val Xaa Arg Leu Pro Asn Gly Arg
1               5                   10                  15
```

```
<210> SEQ ID NO 139
<211> LENGTH: 15
<212> TYPE: PRT
<213> ORGANISM: Canis familiaris
<220> FEATURE:
<221> NAME/KEY: MISC_FEATURE
<222> LOCATION: (14)..(14)
<223> OTHER INFORMATION: Xaa can be Met or Thr

<400> SEQUENCE: 139

Asp Arg Ile Glu Pro Gly Arg Asp Arg Arg Phe Arg Val Xaa Arg
1               5                   10                  15

<210> SEQ ID NO 140
<211> LENGTH: 25
<212> TYPE: PRT
<213> ORGANISM: Canis familiaris
<220> FEATURE:
<221> NAME/KEY: MISC_FEATURE
<222> LOCATION: (5)..(5)
<223> OTHER INFORMATION: Xaa can be Met or Thr

<400> SEQUENCE: 140

Arg Phe Arg Val Xaa Arg Leu Pro Asn Gly Arg Asp Phe His Met Ser
1               5                   10                  15

Ile Val Ala Ala Arg Leu Asn Asp Ser
            20                  25

<210> SEQ ID NO 141
<211> LENGTH: 26
<212> TYPE: PRT
<213> ORGANISM: Canis familiaris
<220> FEATURE:
<221> NAME/KEY: MISC_FEATURE
<222> LOCATION: (20)..(20)
<223> OTHER INFORMATION: Xaa can be Met or Thr

<400> SEQUENCE: 141

Leu Ala Ala Phe Gln Glu Asp Arg Ile Glu Pro Gly Arg Asp Arg Arg
1               5                   10                  15

Phe Arg Val Xaa Arg Leu Pro Asn Gly Arg
            20                  25

<210> SEQ ID NO 142
<211> LENGTH: 31
<212> TYPE: PRT
<213> ORGANISM: Canis familiaris
<220> FEATURE:
<221> NAME/KEY: MISC_FEATURE
<222> LOCATION: (15)..(15)
<223> OTHER INFORMATION: Xaa can be Met or Thr

<400> SEQUENCE: 142

Glu Asp Arg Ile Glu Pro Gly Arg Asp Arg Arg Phe Arg Val Xaa Arg
1               5                   10                  15

Leu Pro Asn Gly Arg Asp Phe His Met Ser Ile Val Ala Ala Arg
            20                  25                  30

<210> SEQ ID NO 143
<211> LENGTH: 31
<212> TYPE: PRT
<213> ORGANISM: Canis familiaris
<220> FEATURE:
<221> NAME/KEY: MISC_FEATURE
<222> LOCATION: (25)..(25)
<223> OTHER INFORMATION: Xaa can be Met or Thr
```

```
<400> SEQUENCE: 143

Asn Gln Thr Asp Lys Leu Ala Ala Phe Gln Glu Asp Arg Ile Glu Pro
1               5                   10                  15

Gly Arg Asp Arg Arg Phe Arg Val Xaa Arg Leu Pro Asn Gly Arg
            20                  25                  30

<210> SEQ ID NO 144
<211> LENGTH: 45
<212> TYPE: PRT
<213> ORGANISM: Canis familiaris
<220> FEATURE:
<221> NAME/KEY: MISC_FEATURE
<222> LOCATION: (25)..(25)
<223> OTHER INFORMATION: Xaa can be Met or Thr

<400> SEQUENCE: 144

Asn Gln Thr Asp Lys Leu Ala Ala Phe Gln Glu Asp Arg Ile Glu Pro
1               5                   10                  15

Gly Arg Asp Arg Arg Phe Arg Val Xaa Arg Leu Pro Asn Gly Arg Asp
            20                  25                  30

Phe His Met Ser Ile Val Ala Ala Arg Leu Asn Asp Ser
        35                  40                  45

<210> SEQ ID NO 145
<211> LENGTH: 20
<212> TYPE: PRT
<213> ORGANISM: Canis familiaris
<220> FEATURE:
<221> NAME/KEY: MISC_FEATURE
<222> LOCATION: (14)..(14)
<223> OTHER INFORMATION: Xaa can be Met or Thr

<400> SEQUENCE: 145

Asp Arg Ile Glu Pro Gly Arg Asp Arg Arg Phe Arg Val Xaa Arg Leu
1               5                   10                  15

Pro Asn Gly Arg
            20

<210> SEQ ID NO 146
<211> LENGTH: 11
<212> TYPE: PRT
<213> ORGANISM: Mus musculus

<400> SEQUENCE: 146

Ile Phe Tyr Asp Tyr Asp Gly Asp Ile Asp Val
1               5                   10
```